United States Patent
Chin et al.

(10) Patent No.: US 11,052,087 B2
(45) Date of Patent: Jul. 6, 2021

(54) ANTI-HIV COMPOUNDS

(71) Applicant: Gilead Sciences, Inc., Foster City, CA (US)

(72) Inventors: Elbert Chin, San Mateo, CA (US); Darryl Kato, San Francisco, CA (US); John O. Link, San Francisco, CA (US); Nathan Shapiro, Belmont, CA (US); Zheng-Yu Yang, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 16/525,203

(22) Filed: Jul. 29, 2019

(65) Prior Publication Data

US 2020/0030327 A1 Jan. 30, 2020

Related U.S. Application Data

(60) Provisional application No. 62/711,768, filed on Jul. 30, 2018.

(51) Int. Cl.
| | | |
|---|---|---|
| *A61K 31/506* | (2006.01) | |
| *A61K 31/4995* | (2006.01) | |
| *C07D 487/08* | (2006.01) | |
| *A61P 31/18* | (2006.01) | |

(52) U.S. Cl.
CPC ........ *A61K 31/506* (2013.01); *A61K 31/4995* (2013.01); *A61P 31/18* (2018.01); *C07D 487/08* (2013.01)

(58) Field of Classification Search
CPC .............. C07D 487/08; A61K 31/4995; A61K 31/506; A61P 31/18
See application file for complete search history.

(56) References Cited

U.S. PATENT DOCUMENTS

| | | | |
|---|---|---|---|
| 3,845,770 | A | 11/1974 | Theeuwes et al. |
| 4,326,525 | A | 4/1982 | Swanson et al. |
| 4,902,514 | A | 2/1990 | Barclay et al. |
| 4,992,445 | A | 2/1991 | Lawter et al. |
| 5,001,139 | A | 3/1991 | Lawter et al. |
| 5,023,252 | A | 6/1991 | Hseih |
| 5,461,067 | A | 10/1995 | Norbeck et al. |
| 5,616,345 | A | 4/1997 | Geoghegan et al. |
| 5,679,688 | A | 10/1997 | Grobelny |
| 5,753,652 | A | 5/1998 | Fassler et al. |
| 5,849,911 | A | 12/1998 | Fassler et al. |
| 10,294,234 | B2 | 5/2019 | Bacon et al. |
| 10,752,636 | B2 | 8/2020 | Bacon et al. |
| 2005/0159469 | A1 | 7/2005 | Randolph et al. |
| 2009/0076097 | A1 | 3/2009 | Czarnik |
| 2010/0143301 | A1 | 6/2010 | Desai et al. |
| 2013/0165489 | A1 | 6/2013 | Cocklin et al. |
| 2013/0289067 | A1 | 10/2013 | Ghosh et al. |
| 2014/0221356 | A1 | 8/2014 | Jin et al. |
| 2014/0221378 | A1 | 8/2014 | Miyazaki et al. |
| 2014/0221380 | A1 | 8/2014 | Miyazaki et al. |
| 2018/0258097 | A1 | 9/2018 | Bacon et al. |
| 2019/0308983 | A1 | 10/2019 | Bacon et al. |

FOREIGN PATENT DOCUMENTS

| | | |
|---|---|---|
| AU | 2003200066 | 4/2003 |
| EP | 521827 | 1/1993 |
| EP | 604368 | 6/1994 |
| EP | 2003120 | 12/2008 |
| IN | 2008CH01037 | 4/2016 |
| WO | WO9318006 | 9/1993 |
| WO | WO9419332 | 9/1994 |
| WO | WO9719055 | 5/1997 |
| WO | WO9740029 | 10/1997 |

(Continued)

OTHER PUBLICATIONS

Lv et al. HIV/AIDS—Research and Palliative Care 2015:7 95-104.*
Australian Office Action in AU Appln. No. 2018215546, dated Dec. 19, 2019, 3 pages.
Colombian Notice of Opposition in CO Appln. No. NC2019/0008531, dated Feb. 11, 2020, 14 pages (with English translation).
European Office Action in EP Application No. 18706072, dated Sep. 25, 2019, 13 pages.
Indian Office Action in IN Appln. No. 201917032272, dated Mar. 4, 2020, 4 pages (with English translation).
International Search Report and Written Opinion in International Application No. PCT/US2018/016893, dated Apr. 24, 2018, 12 pages.

(Continued)

*Primary Examiner* — Rebecca L Anderson
(74) *Attorney, Agent, or Firm* — Fish & Richardson P.C.

(57) ABSTRACT

The invention provides compounds having Formula (I):

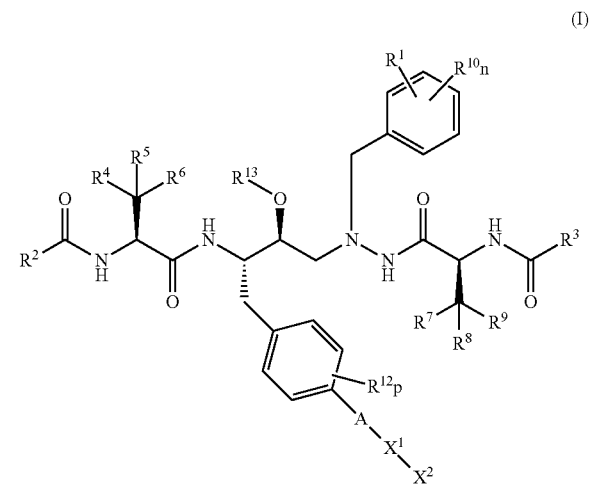

or a pharmaceutically acceptable salt thereof, as well as pharmaceutical compositions comprising the same, processes for their preparation, and methods of treating and preventing HIV infection by their administration.

86 Claims, No Drawings

(56) References Cited

FOREIGN PATENT DOCUMENTS

| | | |
|---|---|---|
| WO | WO9746514 | 12/1997 |
| WO | WO9803476 | 1/1998 |
| WO | WO200104120 | 1/2001 |
| WO | WO200146120 | 6/2001 |
| WO | WO2002094768 | 11/2002 |
| WO | WO2003020370 | 3/2003 |
| WO | WO2003078438 | 9/2003 |
| WO | WO2004096286 | 11/2004 |
| WO | WO2005061487 | 7/2005 |
| WO | WO2006014282 | 2/2006 |
| WO | WO2006015261 | 2/2006 |
| WO | WO2006110157 | 10/2006 |
| WO | WO2007002172 | 1/2007 |
| WO | WO2008011116 | 1/2008 |
| WO | WO2008011117 | 1/2008 |
| WO | WO2008118849 | 10/2008 |
| WO | WO2008156632 | 12/2008 |
| WO | WO2009062285 | 5/2009 |
| WO | WO2009114151 | 9/2009 |
| WO | WO2009136365 | 11/2009 |
| WO | WO2010032852 | 3/2010 |
| WO | WO2010077317 | 7/2010 |
| WO | WO2010130034 | 10/2010 |
| WO | WO2011026781 | 3/2011 |
| WO | WO2011080562 | 7/2011 |
| WO | WO2012003497 | 1/2012 |
| WO | WO2012003498 | 1/2012 |
| WO | WO2012031237 | 3/2012 |
| WO | WO2012092168 | 7/2012 |
| WO | WO2012092188 | 7/2012 |
| WO | WO2012145728 | 10/2012 |
| WO | WO2012170792 | 12/2012 |
| WO | WO2013006738 | 1/2013 |
| WO | WO2013006792 | 1/2013 |
| WO | WO2013091096 | 6/2013 |
| WO | WO2013159064 | 10/2013 |
| WO | WO2014100323 | 6/2014 |
| WO | WO2015097667 | 7/2015 |
| WO | WO2015175994 | 11/2015 |
| WO | WO2016033243 | 3/2016 |
| WO | WO2018145021 | 8/2018 |

OTHER PUBLICATIONS

Taiwanese Office Action in TW Application No. 107103968, dated Dec. 3, 2019, 7 pages (with English translation).
Taiwanese Office Action in TW Application No. 107103968, dated Jan. 29, 2019, 9 pages.
Taiwanese Office Action in TW Appln. No. 108124043, dated May 11, 2020, 7 pages (with English translation).
Third Party Observation in International Application No. PCT/US2018/016893, dated Jun. 7, 2019, 10 pages.
"Transporter Certified Hepatocytes" Qualyst Transporter Solutions, 2012, LLC:1-2.
Berge et al., "Pharmaceutical salts," J. Pharma Sci., 1977, 66(1):1-19.
Choiu et al., "In Vitro OATP1 B1 and OATP1 B3 Inhibition is Associated With Observations of Benign Clinical Unconjugated Hyperbilirubinemia," Xenobiotica, Informa Healthcare, 2014, 44(3):276-282.
Chu et al. "Species Differences in Drug Transporters and Implications for Translating Preclinical Findings to Humans," Expert Opinion Drug Metabolism Toxicology, 2013, 9(3):237-252.
Cihlar et al., "Suppression of HIV-1 Protease Inhibitor Resistance by Phosphonemediated Solvent Anchoring," Journal of Molecular Biology, 2006, 363:635-647.
Croom et al., "Atazanavir—a review of its use in the management of HIV-1 infection," Drugs, 2009, 69(8):1107-1140.
Foster, "Deuterium Isotope Effects in Studies of Drug Metabolism," Trends Pharmacol. Sci., 5(12):524-527 (1984).
Giacomini et al., "Membrane Transporters in Drug Development," Nature Reviews Drug Development, 2010, 9:215-236.
Gillis, E. et al., "Applications of Fluorine in Medicinal Chemistry", Journal of Medicinal Chemistry, Feb. 2013, 58(21):8315-8359.
Link et al., "Novel HIV P1 With High Resistance Barrier and Potential for Unboosted OD Oral dosing", Abstract, CROI—Conference on Retroviruses and Opportunistic Infections, Seattle, WA: Jan. 3, 2017.
Link et al., "Novel HIV P1 With High Resistance Barrier and Potential for Unboosted OD Oral Dosing," CROI—Conference on the Retroviruses and Opportunistic Infections, Poster:1-3, 2017.
Link et al., "Novel HIV P1 with High Resistance Barrier and Potential for Unboosted OD Oral Dosing," Poster; CROI—Conference on Retroviruses and Opportunistic Infections; Poster, 2017, 433: 1-6.
Lv et al., "HIV protease inhibitors: a review of molecular selectivity and toxicity," HIV/AIDS—Research and Palliative Care, 2015, 7:95-104.
Poonam Shah and Andrew D. Westwell, "The role of fluorine in medicinal chemistry", Journal of Enzyme Inhibition and Medicinal Chemistry, Oct. 2007; 22(5): 527-540.
Swift et al., "Sandwich-Cultured Hepatocytes: An In Vitro Model to Evaluate Hepatobiliary Transporter-Based Drug Interactions and Hepatotoxicity," Drug Metabolism Review, 2010, 42(3):1-45.
Chilean Office Action in CL Appln. No. 201902204, dated Jun. 15, 2020, 24 pages (with English translation).
Gulf Coop Council Office Action in GC Appln. No. 2019-37997, dated Jul. 28, 2020, 4 pages.
Chilean Office Action in CL Appln. No. 201902204, dated Nov. 16, 2020, 25 pages.
Eurasian Office Action in EA Appln. No. 201991684/28, dated Oct. 1, 2020, 5 pages (with English translation).
Gulf Coop Council Office Action in GC Appln. No. 2019-37997, dated Nov. 29, 2020, 3 pages.
Japanese Office Action in JP Appln. No. 2019-542392, dated Oct. 6, 2020, 6 pages (with English translation).
New Zealand Office Action in NZ Appln. No. 755929, dated Nov. 13, 2020, 5 pages.
PCT International Preliminary Report on Patentability in International Appln. No. PCT/US2019/043965, dated Feb. 2, 2021, 7 pages.
PCT Third Party Observation in International Appln. No. PCT/US2019/043965, dated Nov. 30, 2020, 9 pages.
Rouquayrol et al., "Transepithelial transport of prodrugs of the HIV protease inhibitors Sanquinavir, Indinavir, and Nelfinavir across CaCo-2 cell monolayers," Pharmaceutical Research, 2002,. 19(11):1704-1712.
Stella et al., "Prodrugs: Challenges and Rewards Part 1," Biotechnology: Pharmaceutical Aspects, 2007, 5:33-52.
Subbaiah et al., "Design strategies in the prodrugs of HIV-1 protease inhibitors to improve pharmaceutical properties," European Journal of Medicinal Chemistry, 2017, 139:865-883.
Taiwanese Office Action in TW Appln. No. 108124043, dated Oct. 6, 2020, 5 pages (with English translation).
Ukrainian Office Action in UA Appln. No. a2019 09440, dated Sep. 21, 2020, 5 pages (with English translation).
Eurasian Office Action in EA Application No. 201991684, dated Mar. 18, 2021, 2 pages (with English translation).
Korean Office Action in KR Appln. No. 10-2019-7025847, dated Feb. 26, 2021, 10 pages (with English translation).
Canadian Office Action in CA Application No. 3,051,588, dated Apr. 30, 2021, 3 pages.

* cited by examiner

ANTI-HIV COMPOUNDS

CROSS REFERENCE TO RELATED APPLICATIONS

This application claims the benefit of U.S. Provisional Application 62/711,768 filed on Jul. 30, 2018. The entire contents of this application are incorporated herein by reference in its entirety.

FIELD

The present disclosure relates to compounds for use in the treatment of a Retroviridae viral infection including an infection caused by the HIV virus. The present disclosure also relates to intermediates for their preparation and to pharmaceutical compositions containing those compounds.

BACKGROUND

Human immunodeficiency virus (HIV) infection and related diseases are a major public health problem worldwide. Human immunodeficiency virus type 1 (HIV-1) encodes three enzymes which are required for viral replication: reverse transcriptase, protease, and integrase. Several protease inhibitors (PI) are presently approved for use in AIDS or HIV. Others are in development. See for example, the compounds of U.S. App. No. 62/455,348.

Yet many protease inhibitors suffer from high rates of hepatic metabolism, which may require co-administration of a booster or more frequent dosing. Furthermore, viral resistance remains a problem. Accordingly, there is a need for new agents that inhibit the replication of HIV.

SUMMARY

The present disclosure provides compounds and methods for the treatment of an HIV infection. The compounds of the invention may be metabolized in vivo to form one or more of the therapeutic compounds described in U.S. App. No. 62/455,348. Accordingly, the invention provides a compound of Formula (I):

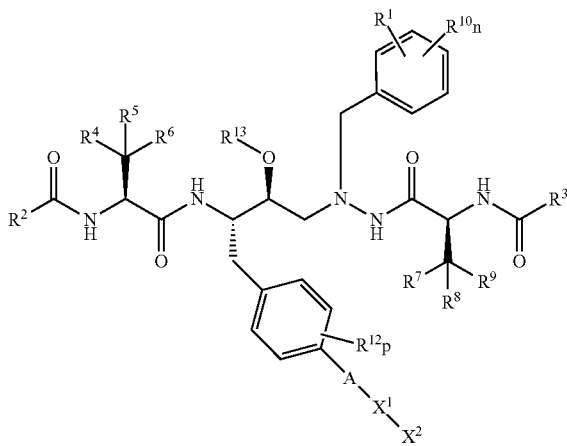

or a pharmaceutically acceptable salt thereof, wherein:
$R^1$ is a 5 to 10-membered heterocycle having 1 to 5 heteroatoms selected from N, O, and S, or a 5 to 10-membered heteroaryl having 1 to 5 heteroatoms selected from N, O, and S, wherein the 5 to 10-membered heterocycle or 5 to 10-membered heteroaryl is optionally substituted with 1 to 5 $R^a$ groups;
$R^2$ and $R^3$ are each independently $C_{1-4}$ alkyl, $C_{3-6}$ cycloalkyl, O—$R^{2A}$, $C_{1-2}$ alkyl-O—$R^{2A}$, N—$(R^{3A})_2$, or $C_{1-2}$ alkyl-N—$(R^{3A})_2$,
wherein each $R^{2A}$ is independently $C_{1-4}$ alkyl, $C_{3-6}$ cycloalkyl, or a 4 to 10-membered heterocyclyl having 1 to 5 heteroatoms selected from N, O, and S,
wherein each $R^{3A}$ is independently hydrogen, $C_{1-4}$ alkyl, $C_{3-6}$ cycloalkyl, or COO($R^e$), wherein each $R^e$ is independently hydrogen or $C_{1-4}$ alkyl,
and wherein each $C_{3-6}$ cycloalkyl or 4 to 10-membered heterocyclyl is optionally substituted by 1 to 3 $R^f$ groups, wherein each $R^f$ is independently $C_{1-2}$ alkyl or halogen; $R^4$ is hydrogen, halo, $C_{1-4}$ alkyl, $C_{1-4}$ haloalkyl, $C_{3-6}$ cycloalkyl, $C_{1-4}$ alkoxy, or $C_{1-4}$ haloalkoxy;
$R^7$ is hydrogen, halo, $C_{1-4}$ alkyl, $C_{1-4}$ haloalkyl, $C_{3-6}$ cycloalkyl, $C_{1-4}$ alkoxy, or $C_{1-4}$ haloalkoxy;
$R^5$, $R^6$, $R^8$, and $R^9$ are each independently hydrogen, halo, $C_{1-2}$ alkyl, $C_{1-2}$ haloalkyl, or $C_{3-6}$ cycloalkyl;
and wherein two or more of $R^4$, $R^5$ and $R^6$ or two or more of $R^7$, $R^8$, and $R^9$ optionally join together to form one or more $C_{3-6}$ cycloalkyl groups that are optionally substituted with 1 to 4 groups selected from halogen, $C_{1-2}$ alkyl, and $C_{1-2}$ haloalkyl;
each $R^{10}$ is independently halogen, cyano, $C_{1-4}$ alkoxy, $C_{1-6}$ alkyl, or $C_{3-6}$ cycloalkyl;
n is 0 to 4;
each $R^a$ is independently halogen, $C_{1-4}$ alkyl, $C_{1-4}$ alkyl with 1 to 2 groups selected from hydroxyl and $C_{1-4}$ alkoxy, $C_{1-4}$ haloalkyl, $C_{1-4}$ alkoxy, $C_{3-6}$ cycloalkyl, 4 to 10-membered heterocyclyl having 1 to 5 heteroatoms selected from N, O, and S which is optionally substituted with $R^{a1}$, or O—$R^{3B}$,
wherein $R^{3B}$ is $C_{3-6}$ cycloalkyl optionally substituted with $R^{a1}$ or a 4 to 10-membered heterocyclyl having 1 to 5 heteroatoms selected from N, O, and S optionally substituted with $R^{a1}$,
wherein each $R^{a1}$ is independently $C_{1-4}$ alkyl, $C_{3-6}$ cycloalkyl, $C_{1-4}$ haloalkyl, or 4 to 8-membered heterocyclyl having 1 to 3 heteroatoms selected from N, O, and S;
A is ethynyl or a bond;
$X^1$ is a 6 to 10-membered aryl or a 5 to 10-membered heteroaryl having 1 to 3 heteroatoms selected from N, O, and S, wherein each 6 to 10-membered aryl or 5 to 10-membered heteroaryl is optionally substituted with 1 to 4 $R^b$ groups;
$X^2$ is hydrogen or a 4 to 10-membered heterocyclyl having 1 to 5 heteroatoms selected from N, O, and S, wherein the 4 to 10-membered heterocyclyl is optionally substituted with one $R^{11}$ and optionally substituted with 1 to 5 $R^b$ groups;
$R^{11}$ is C=O($R^c$), $CH_2(R^d)$, $S(O)_{1-2}(C_{1-4}$ alkyl), $S(O)_{1-2}C_{3-6}$ cycloalkyl, a 4 to 10-membered heterocyclyl having 1 to 5 heteroatoms selected from N, O, and S, or a 5 to 9-membered heteroaryl having 1 to 5 heteroatoms selected from N, O, and S, wherein each 4 to 10-membered heterocyclyl or 5 to 9-membered heteroaryl is optionally substituted with 1 to 5 $R^b$ groups;
each $R^b$ is independently halogen, oxo, $C_{1-4}$ alkyl, $C_{1-4}$ alkyl with 1 to 2 groups selected from hydroxyl and $C_{1-4}$ alkoxy, $C_{1-4}$ haloalkyl, $C_{1-4}$ alkoxy, or COO($R^e$);
$R^c$ is $C_{1-4}$ alkyl, $C_{1-4}$ haloalkyl, $C_{1-4}$ alkoxy, $N(R^e)_2$, $C_{3-6}$ cycloalkyl, or a 4 to 6-membered heterocyclyl having 1 to 3 heteroatoms selected from N, O, and S, wherein the $C_{3-6}$ cycloalkyl and the 4 to 6-membered heterocyclyl are optionally substituted by 1 to 5 $R^b$ groups;

$R^d$ is $COO(R^e)$, $N(R^e)_2$, $C_{3-6}$ cycloalkyl, or a 4 to 6-membered heterocyclyl having 1 to 3 heteroatoms selected from N, O, and S, wherein the $C_{3-6}$ cycloalkyl and the 4 to 6-membered heterocyclyl is optionally substituted by 1 to 5 $R^b$ groups;

each $R^{12}$ is $C_{1-2}$ alkyl, halo, $-OC_{1-2}$ alkyl, or cyano;

each p is 0 to 4;

$R^{13}$ is $-C(=O)R^{g1}$, $-C(=O)OR^{g2}$, or $-P(=O)(OR^h)_2$;

$R^{g1}$ is H, $C_{1-6}$ alkyl, $C_{3-6}$ cycloalkyl, or 5- to 6-membered heteroaryl having 1 to 3 heteroatoms selected from N, O, and S;

wherein the $C_{1-6}$ alkyl of $R^{g1}$ is optionally substituted with 1, 2, 3, or 4 substituents independently selected from halogen, $C_{1-4}$ alkoxy, $-N(R^i)_2$, $-C_{1-4}$ alkyl-$N(R^i)_2$, $-N(R^i)_3^+$, and 4- to 6-membered heterocyclyl having 1 to 3 heteroatoms selected from N, O, and S that is optionally substituted with 1, 2, 3, or 4 substituents independently selected from halogen, $C_{1-4}$ alkyl, $C_{1-4}$ alkoxy, $-N(R^i)_2$, and $-C_{1-4}$ alkyl-$N(R^1)_2$; and wherein the 5- to 6-membered heteroaryl and $C_{3-6}$ cycloalkyl of $R^{g1}$ are each optionally substituted with 1, 2, 3, or 4 substituents independently selected from halogen, $C_{1-6}$ alkyl, $C_{1-4}$ alkoxy, $-N(R^i)_2$, and $-C_{1-4}$ alkyl-$N(R^i)_2$;

$R^{g2}$ is $C_{1-6}$ alkyl optionally substituted with 1, 2, 3, or 4 substituents independently selected from halogen, $C_{1-6}$ alkyl, $C_{1-4}$ alkoxy, $-N(R^i)_2$, $-C_{1-4}$ alkyl-$N(R^i)_2$, and $-O-P(=O)(OR^h)_2$; and $R^h$ and $R^i$ are each independently selected from H and $C_{1-3}$ alkyl.

In certain embodiments of the compound of Formula (I):

$R^1$ is a 5 to 10-membered heteroaryl having 1 to 3 heteroatoms selected from N, O, and S, optionally substituted with 1 to 2 $R^a$ groups, wherein each $R^a$ is independently $C_{1-4}$ haloalkyl;

$R^2$ and $R^3$ are each independently $O-R^{2A}$, wherein each $R^{2A}$ is independently $C_{1-4}$ alkyl;

$R^4$ is $C_{1-4}$ alkyl or $C_{1-4}$ haloalkyl;

$R^7$ is $C_{1-4}$ alkyl or $C_{1-4}$ haloalkyl;

$R^5$, $R^6$, $R^8$, and $R^9$ are each independently $C_{1-2}$ alkyl or $C_{1-2}$ haloalkyl;

each $R^{10}$ is independently halogen;

n is 0, 1 or 2;

A is ethynyl;

$X^1$ is a 5 to 10-membered heteroaryl having 1 to 3 heteroatoms selected from N, O, and S;

$X^2$ is a 4 to 10-membered heterocyclyl having 1 to 3 heteroatoms selected from N, O, and S, optionally substituted with one $R^{11}$ group, wherein $R^{11}$ is a 4 to 10-membered heterocyclyl having 1 to 2 heteroatoms selected from N, O, and S;

p is 0;

$R^{13}$ is $-C(=O)R^{g1}$, $-C(=O)OR^{g2}$, or $-P(=O)(OR^h)_2$;

$R^{g1}$ is H, $C_{1-6}$ alkyl, $C_{3-6}$ cycloalkyl, or 5- to 6-membered heteroaryl having 1 to 3 heteroatoms selected from N, O, and S;

wherein the $C_{1-6}$ alkyl of $R^{g1}$ is optionally substituted with 1, 2, 3, or 4 substituents independently selected from halogen, $C_{1-4}$ alkoxy, $-N(R^i)_2$, $-C_{1-4}$ alkyl-$N(R^i)_2$, $-N(R^i)_3^+$, and 4- to 6-membered heterocyclyl having 1 to 3 heteroatoms selected from N, O, and S that is optionally substituted with 1, 2, 3, or 4 substituents independently selected from halogen, $C_{1-4}$ alkyl, $C_{1-4}$ alkoxy, $-N(R^i)_2$, and $-C_{1-4}$ alkyl-$N(R^i)_2$; and wherein the 5- to 6-membered heteroaryl and $C_{3-6}$ cycloalkyl of $R^{g1}$ are each optionally substituted with 1, 2, 3, or 4 substituents independently selected from halogen, $C_{1-6}$ alkyl, $C_{1-4}$ alkoxy, $-N(R^i)_2$, and $-C_{1-4}$ alkyl-$N(R^1)_2$;

$R^{g2}$ is $C_{1-6}$ alkyl optionally substituted with 1, 2, 3, or 4 substituents independently selected from halogen, $C_{1-6}$ alkyl, $C_{1-4}$ alkoxy, $-N(R^i)_2$, $-C_{1-4}$ alkyl-$N(R^i)_2$, and $-O-P(=O)(OR^h)_2$; and $R^h$ and $R^W$ are each independently selected from H and $C_{1-3}$ alkyl.

In certain embodiments of the compound of Formula (I):

$R^1$ is a 5-membered heteroaryl having 2 heteroatoms that are each N, substituted with 1 $R^a$ group, wherein $R^a$ is $-CHF_2$;

$R^2$ and $R^3$ are each independently $O-R^{2A}$, wherein each $R^{2A}$ is methyl;

$R^4$ is $CF_3$;

$R^7$ is $CF_3$;

$R^5$, $R^6$, $R^8$, and $R^9$ are each methyl;

each $R^{10}$ is F;

n is 2;

A is ethynyl;

$X^1$ is a 6-membered heteroaryl having 2 heteroatoms that are each N;

$X^2$ is an 8-membered bridged heterocyclyl having 2 heteroatoms that are each N, substituted with one $R^{11}$ group, wherein $R^{11}$ is a 4-membered heterocyclyl having 1 heteroatom that is O;

p is 0;

$R^{13}$ is $-C(=O)R^{g1}$, $-C(=O)OR^{g2}$, or $-P(=O)(OH)_2$;

$R^{g1}$ is H, $C_{1-6}$ alkyl, or a 6-membered heteroaryl having 1 heteroatom that is N;

wherein the $C_{1-6}$ alkyl of $R^{g1}$ is optionally substituted with 1 or 2 substituents independently selected from $-N(R^i)_2$, $-C_{1-4}$ alkyl-$N(R^i)_2$, $-N(R^i)_3^+$, and a 6-membered heterocyclyl having 1 to 2 heteroatoms selected from N and O;

$R^{g2}$ is $C_{1-2}$ alkyl substituted with $-O-P(=O)(OH)_2$; and $R^i$ are each independently selected from H and $C_{1-3}$ alkyl.

In certain embodiments, the compound of Formula (I) is a compound of Formula (II):

(II)

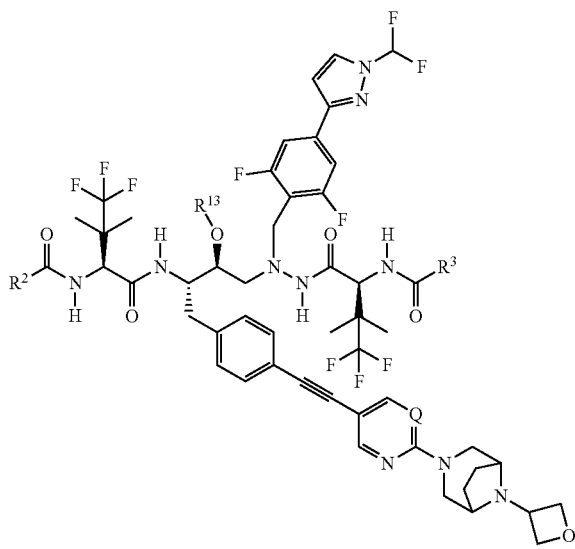

or a pharmaceutically acceptable salt thereof, wherein $R^2$, $R^3$, and $R^{13}$ are as defined herein and Q is N or CH.

Also provided is a pharmaceutical composition comprising a therapeutically effective amount of a compound disclosed herein, or a pharmaceutically acceptable salt thereof, and a pharmaceutically acceptable excipient. In certain embodiments, the pharmaceutical composition further comprises one, two, three, or four additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, compounds targeting the HIV capsid (e.g., HIV capsid polymerization inhibitors), and other drugs for treating HIV, and combinations thereof.

Also provided is method of treating or preventing a Retroviridae viral infection (e.g., a human immunodeficiency virus (HIV) infection) comprising administering a therapeutically effective amount of a compound disclosed herein, or a pharmaceutically acceptable salt thereof, to a subject in need thereof. In some embodiments, provided herein is a method for treating or preventing an HIV infection in a mammal (e.g., a human), comprising administering to the mammal in need thereof a therapeutically effective amount of a compound of formula I and/or II, or a pharmaceutically acceptable salt thereof, in combination with a therapeutically effective amount of one, two, three, or four additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, compounds targeting the HIV capsid (e.g., HIV capsid polymerization inhibitors), and other drugs for treating HIV, and combinations thereof.

In certain embodiments, the current disclosure relates to an article of manufacture comprising a unit dosage of a compound disclosed herein, or a pharmaceutically acceptable salt thereof.

Also provided is a compound disclosed herein, or a pharmaceutically acceptable salt thereof, for use in medical therapy (e.g., for use in treating or preventing a Retroviridae viral infection (e.g., an HIV viral infection) or the proliferation of the HIV virus or AIDS or delaying the onset of AIDS or ARC symptoms in a mammal (e.g., a human)).

A compound disclosed herein, or a pharmaceutically acceptable salt thereof, for use in a method of treating or preventing a Retroviridae viral infection, a human immunodeficiency virus (HIV) infection or AIDS comprising administering a therapeutically effective amount of the compound to a subject in need thereof, is also provided.

DETAILED DESCRIPTION

The following is a list of abbreviations and acronyms used throughout the application:

| Abbreviation | Meaning |
|---|---|
| ° C. | Degree Celsius |
| ATP | Adenosine-5'-triphosphate |
| AcOH | Acetic acid |
| d | Doublet |
| dd | Doublet of doublets |
| DCE | 1,2-dichloroethane |
| DCM | Dichloromethane |
| DIPEA | N,N-diisopropylethylamine |
| DME | 1,2-dimethoxyethane |
| DMF | Dimethylformamide |
| DMSO | Dimethylsulfoxide |
| dppf | 1,1'-Bis(diphenylphosphino)ferrocene |
| EGTA | Ethylene glycol tetraacetic acid |
| ETOAC | Ethyl acetate |
| equiv/eq | Equivalents |
| ESI | Electrospray ionization |
| Ac | Acetate |
| Et | Ethyl |
| g | Grams |
| HATU | 2-(7-Aza-1H-Benzotriazole-1-yl)-1,1,3,3-tetramethyluronium hexafluorophosphate |
| hERG | human Ether-à-go-go Related Gene |
| HPLC | High-performance liquid chromatography |
| h/hr | Hours |
| Hz | Hertz |
| $IC_{50}$ | The half maximal inhibitory concentration |
| J | Coupling constant |
| Kg | Kilogram |
| M | Molar |
| m | multiplet |
| m/z | mass-to-charge ratio |
| M+ | Mass peak |
| M + H | Mass peak plus hydrogen |
| Me | Methyl |
| MeOH | Methyl alcohol/methanol |
| mg | Milligram |
| MHz | Megahertz |
| min/m | Minute |
| mL/mL | Milliliter |
| mM | Millimolar |
| mmol | Millimole |
| MS | Mass spectroscopy |
| mw | Microwave |
| N | Normal |
| mol | Mole |
| NMP | N-methylpyrrolidinone |
| NMR | Nuclear magnetic resonance |
| Ph | Phenyl |
| ppm | Parts per million |
| prep | Preparative |
| Rf | Retention factor |
| RP | Reverse phase |
| RT/rt | Room temperature |
| s | Second |
| s | Singlet |
| t | Triplet |

-continued

| Abbreviation | Meaning |
|---|---|
| TEA | Triethylamine |
| TFA | Trifluoroacetic acid |
| TLC | Thin layer chromatography |
| TMS | trimethylsilyl |
| WT | Wild type |
| δ | Chemical shift |
| μg | Microgram |
| μL/μl | Microliter |
| μM | Micromolar |
| μm | Micrometer |
| μmol | Micromole |

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

A dash at the front or end of a chemical group is a matter of convenience; chemical groups may be depicted with or without one or more dashes without losing their ordinary meaning. A wavy line drawn through a line in a structure indicates a point of attachment of a group, e.g.:

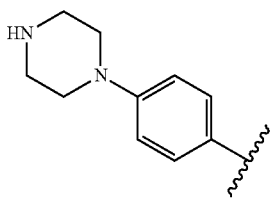 [SMILES: *c1ccc(N2CCNCC2)cc1]

A dashed line indicates an optional bond. Where multiple substituent groups are identified the point of attachment is at the terminal substituent (e.g., for "alkylaminocarbonyl" the point of attachment is at the carbonyl substituent).

The prefix "$C_{x-y}$" indicates that the following group has from x (e.g., 1) to y (e.g., 6) carbon atoms, one or more of which, in certain groups (e.g., heteroalkyl, heteroaryl, heteroarylalkyl, etc.), may be replaced with one or more heteroatoms or heteroatomic groups. For example, "$C_{1-6}$ alkyl" indicates that the alkyl group has from 1 to 6 carbon atoms. Likewise, the term "x-y membered" rings, wherein x and y are numerical ranges, such as "3 to 12-membered heterocyclyl", refers to a ring containing x-y atoms (e.g., 3-12), of which up to 80% may be heteroatoms, such as N, O, S, P, and the remaining atoms are carbon.

Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"A compound disclosed herein" or "a compound of the present disclosure" refers to the compounds of Formula (I). Also included are the specific compounds of Examples 1-13.

"Alkyl" refers to any group derived from a linear or branched saturated hydrocarbon. Alkyl groups include, but are not limited to, methyl, ethyl, propyl such as propan-1-yl, propan-2-yl (iso-propyl), butyls such as butan-1-yl, butan-2-yl (sec-butyl), 2-methyl-propan-1-yl (iso-butyl), 2-methyl-propan-2-yl (t-butyl), pentyls, hexyls, octyls, dectyls, and the like. Unless otherwise specified, an alkyl group has from 1 to 10 carbon atoms, for example from 1 to 6 carbon atoms, for example from 1 to 4 carbon atoms.

"Alkenyl" refers to any group derived from a straight or branched hydrocarbon with at least one carbon-carbon double bond. Alkenyl groups include, but are not limited to, ethenyl (vinyl), propenyl (allyl), 1-butenyl, 1,3-butadienyl, and the like. Unless otherwise specified, an alkenyl group has from 2 to 10 carbon atoms, for example from 2 to 6 carbon atoms, for example from 2 to 4 carbon atoms.

"Alkynyl" refers to any group derived from a straight or branched hydrocarbon with at least one carbon-carbon triple bond and includes those groups having one triple bond and one double bond. Examples of alkynyl groups include, but are not limited to, ethynyl (—C≡C—), propargyl (—CH$_2$C≡C—), (E)-pent-3-en-1-ynyl, and the like. Unless otherwise specified, an alkynyl group has from 2 to 10 carbon atoms, for example from 2 to 6 carbon atoms, for example from 2 to 4 carbon atoms.

"Amino" refers to —NH$_2$. Amino groups may also be substituted as described herein, such as with alkyl, carbonyl or other amino groups. The term "alkylamino" refers to an amino group substituted with one or two alkyl substituents (e.g., dimethylamino or propylamino).

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1, 2, 3, 4-tetrahydronaphthyl. Aryl groups include, but are not limited to, those groups derived from acenaphthylene, anthracene, azulene, benzene, chrysene, a cyclopentadienyl anion, naphthalene, fluoranthene, fluorene, indane, perylene, phenalene, phenanthrene, pyrene and the like. Non-limiting examples of aryl groups include, but are not limited to, phenyl, indenyl, naphthyl, 1, 2, 3, 4-tetrahydronaphthyl, anthracenyl, and the like.

"Bridged" refers to a ring fusion wherein non-adjacent atoms on a ring are joined by a divalent substituent, such as an alkylenyl or heteroalkylenyl group or a single heteroatom. Quinuclidinyl and adamantanyl are examples of bridged ring systems.

The term "cycloalkyl" refers to a single saturated or partially unsaturated all carbon ring having 3 to 20 annular carbon atoms (i.e., $C_{3-20}$ cycloalkyl), for example from 3 to 12 annular atoms, for example from 3 to 10 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocycles such as a bicyclic carbocycles (e.g., bicyclic carbocycles having about 6 to 12 annular carbon atoms such as bicyclo [3.1.0]hexane and bicyclo[2.1.1]hexane), and polycyclic carbocycles (e.g., tricyclic and tetracyclic carbocycles with up to about 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, spiro [3.3]heptane, and 1-cyclohex-3-enyl.

"Halo" and "halogen" refer to fluoro, chloro, bromo and iodo.

"Haloalkyl" refers to an alkyl wherein one or more hydrogen atoms are each replaced by a halogen. Examples include, but are not limited to, —$CH_2Cl$, —$CH_2F$, —$CH_2Br$, —CFClBr, —$CH_2CH_2Cl$, —$CH_2CH_2F$, —$CF_3$, —$CH_2CF_3$, —$CH_2CCl_3$, and the like, as well as alkyl groups such as perfluoroalkyl in which all hydrogen atoms are replaced by fluorine atoms.

"Alkoxy" or "alkoxyl" refers to a moiety of the formula —O-alkyl, wherein the alkyl portion is as defined above. For example, $C_{1-4}$ alkoxy refers to a moiety having 1-4 carbon alkyl group attached to the oxygen. "Haloalkoxy" or "haloalkoxyl" refers to a moiety of the formula —O-haloalkyl, wherein the haloalkyl portion is as defined above. For example, $C_{1-4}$ alkoxy refers to a moiety having 1-4 carbon halo alkyl group attached to the oxygen.

"Heteroalkyl" refers to an alkyl in which one or more of the carbon atoms (and any associated hydrogen atoms) are each independently replaced with the same or different heteroatom or heteroatomic group. Heteroatoms include, but are not limited to, N, P, O, S, etc. Heteroatomic groups include, but are not limited to, —NR—, —O—, —S—, —PH—, —$P(O)_2$—, —S(O)—, —$S(O)_2$—, and the like, where R is H, alkyl, aryl, cycloalkyl, heteroalkyl, heteroaryl or cycloheteroalkyl. Heteroalkyl groups include, but are not limited to, —$OCH_3$, —$CH_2OCH_3$, —$SCH_3$, —$CH_2SCH_3$, —$NRCH_3$, —$CH_2NRCH_3$, —$CH_2OH$ and the like, where R is hydrogen, alkyl, aryl, arylalkyl, heteroalkyl, or heteroaryl, each of which may be optionally substituted. A heteroalkyl group comprises from 1 to 10 carbon and up to four three hetero atoms, e.g., from 1 to 6 carbon and from 1 to 2 hetero atoms.

"Heteroaryl" refers to mono or multicyclic aryl group in which one or more of the aromatic carbon atoms (and any associated hydrogen atoms) are independently replaced with the same or different heteroatom or heteroatomic group, as defined above. Multicyclic ring systems are included in heteroaryl and may be attached at the ring with the heteroatom or the aryl ring. Heteroaryl groups include, but are not limited to, groups derived from acridine, benzoimidazole, benzothiophene, benzofuran, benzoxazole, benzothiazole, carbazole, carboline, cinnoline, furan, imidazole, imidazopyridine, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyridone, pyrimidine, pyrrole, pyrrolizine, quinazoline, quinoline, quinolizine, quinoxaline, tetrazole, thiadiazole, thiazole, thiophene, triazole, xanthene, and the like. Heteroaryl groups may have 5-12 members, 5-10 members, or 5-6 members.

The term "heterocyclyl" or "heterocycle" as used herein refers to a single saturated or partially unsaturated non-aromatic ring or a non-aromatic multiple ring system that has at least one heteroatom in the ring (i.e., at least one annular heteroatom selected from oxygen, nitrogen, and sulfur). Unless otherwise specified, a heterocyclyl group has from 5 to about 20 annular atoms, for example from 3 to 12 annular atoms, for example from 3 to 10 annular atoms, for example from 5 to 10 annular atoms or for example from 5 to 6 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The rings of the multiple condensed ring (e.g., bicyclic heterocyclyl) system can be connected to each other via fused, spiro and bridged bonds when allowed by valency requirements. Heterocycles include, but are not limited to, groups derived from azetidine, aziridine, imidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, tetrahydro-2H-thiopyran 1,1-dioxide, quinuclidine, N-bromopyrrolidine, N-chloropiperidine, and the like. Heterocycles include spirocycles, such as, for example, aza or oxo-spiroheptanes. Heterocyclyl groups also include partially unsaturated ring systems containing one or more double bonds, including fused ring systems with one aromatic ring and one non-aromatic ring, but not fully aromatic ring systems. Examples include dihydroquinolines, e.g., 3,4-dihydroquinoline, dihydroisoquinolines, e.g., 1,2-dihydroisoquinoline, dihydroimidazole, tetrahydroimidazole, etc., indoline, isoindoline, isoindolones (e.g., isoindolin-1-one), isatin, dihydrophthalazine, quinolinone, spiro[cyclopropane-1,1'-isoindolin]-3'-one, and the like. Additional examples of heterocycles include 3,8-diazabicyclo[3.2.1] octanyl, 2,5-diazabicyclo[2.2.1]heptanyl, 3,6-diazabicyclo [3.1.1]heptanyl, 3-oxa-7,9-diazabicyclo[3.3.1]nonanyl, and hexahydropyrazino[2,1-c][1,4]oxazinyl, for example.

"Hydroxyl" and "hydroxy" are used interchangeably and refer to —OH. "Oxo" refers to

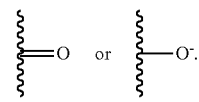

Where tautomeric forms of the compound exist, hydroxyl and oxo groups are interchangeable.

It is understood that combinations of chemical groups may be used and will be recognized by persons of ordinary skill in the art. For instance, the group "hydroxyalkyl" would refer to a hydroxyl group attached to an alkyl group. A great number of such combinations may be readily envisaged. Additional examples of substituent combinations used herein include: $C_{1-6}$ alkylaminocarbonyl (e.g., $CH_3CH_2NHC(O)$—) $C_{1-6}$ alkoxycarbonyl (e.g., $CH_3O$—C (O)—), 5-7 membered heterocyclyl-$C_{1-6}$ alkyl (e.g., piperazinyl-$CH_2$—), $C_{1-6}$ alkylsulfonyl-5-7 membered heterocyclyl (e.g., $CH_3S(O)_2$-morpholinyl-), 5-7 membered heterocyclyl $C_{1-6}$ alkoxy 5-7 membered heterocyclyloxy, (4-7 membered heterocyclyl)-4-7 membered heterocyclyl (e.g., oxetanyl-pyrrolidinyl-), $C_{3-6}$ cycloalkylaminocarbonyl (e.g., cyclopropyl-NH—C(O)—), 5-7 membered heterocyclyl-$C_{2-6}$ alkynyl (e.g., N-piperazinyl-$CH_2C\equiv CCH_2$—), and $C_{6-10}$ arylaminocarbonyl (e.g., phenyl-NH—C(O)—).

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents. When substituents (R-groups) join together (e.g., when $R^7$ and $R^8$ join together) they may be taken from the same point of attachment to form a spiro ring.

The phrase "meta (3) position with respect to the point of attachment of the A ring", refers to the position on the ring where the substituent (e.g., —CN) is adjoined and is shown below with an arrow, wherein z represents a carbon atom or nitrogen:

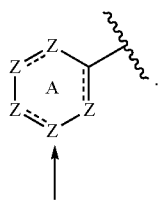

Similarly, para (4) position substitution refers to attachment of a substituent at the position indicated below, with respect to the point of attachment (e.g., of the B ring):

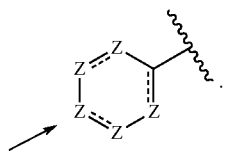

Similarly, ortho or 2-position refers to attachment of a substituent at the position indicated below, with respect to the point of attachment:

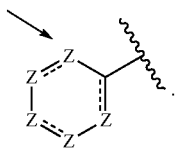

The compounds described herein include isomers, stereoisomers and the like. As used herein, the term "isomers" refers to different compounds that have the same molecular formula but differ in arrangement and configuration of the atoms. Also as used herein, the term "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound.

The term "fused" refers to a ring which is bound to an adjacent ring.

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures. Optically active (R)— and (S)— isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included. To the extent that compounds depicted herein are represented as having a particular stereochemistry, it is understood by one of skill in the art that such compounds may contain some detectable or undetectable levels of compounds sharing the same structure, but having different stereochemistry.

"$IC_{95}$" or "$EC_{95}$" refers to the inhibitory concentration required to achieve 95% of the maximum desired effect, which in many cases here is the inhibition of the HIV virus. This term is obtained using an in vitro assay evaluating the concentration-dependent inhibition of wild type HIV virus.

"$IC_{50}$" or "$EC_{50}$" refers to the inhibitory concentration required to achieve 50% of the maximum desired effect, which in many cases here is the inhibition of the HIV virus. This term is obtained using an in vitro assay evaluating the concentration-dependent inhibition of wild type HIV virus.

"IQ" or "inhibitory quotient" refers to the ratio between the trough drug concentration ($C_{tau}$) and level of drug resistance of the HIV isolate as determined by the $IC_{95}$ (i.e. $C_{tau}/IC_{95}$).

"Pharmaceutically acceptable" refers to compounds, salts, compositions, dosage forms and other materials which are useful in preparing a pharmaceutical composition that is suitable for veterinary or human pharmaceutical use.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-naphthalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

"Subject" and "subjects" refers to humans, domestic animals (e.g., dogs and cats), farm animals (e.g., cattle, horses, sheep, goats and pigs), laboratory animals (e.g., mice, rats, hamsters, guinea pigs, pigs, pocket pets, rabbits, dogs, and monkeys), and the like.

As used herein, "treatment" or "treating" is an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and/or c) relieving the disease or condition, e.g., causing the regression of clinical symptoms, ameliorating the disease state, delaying the progression of the disease, increasing the quality of life, and/or prolonging survival.

As used herein, "delaying" development of a disease or condition means to defer, hinder, slow, retard, stabilize and/or postpone development of the disease or condition. This delay can be of varying lengths of time, depending on the history of the disease and/or subject being treated. As is evident to one skilled in the art, a sufficient or significant delay can, in effect, encompass prevention, in that the subject does not develop the disease or condition. For example, a method that "delays" development of AIDS is a method that reduces the probability of disease development in a given time frame and/or reduces extent of the disease in a given time frame, when compared to not using the method. Such comparisons may be based on clinical studies, using a statistically significant number of subjects. For example, the development of AIDS can be detected using known methods, such as confirming a subject's $HIV^+$ status and assessing the subject's T-cell count or other indication of AIDS development, such as extreme fatigue, weight loss, persistent diarrhea, high fever, swollen lymph nodes in the neck, armpits or groin, or presence of an opportunistic condition that is known to be associated with AIDS (e.g., a condition that is generally not present in subjects with functioning immune systems but does occur in AIDS patients). Development may also refer to disease progression that may be initially undetectable and includes occurrence, recurrence and onset.

As used herein, "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable infectious agent (e.g., virus) in the subject). The subject may be an individual at risk of developing the disease or disorder, such as an individual who has one or more risk factors known to be associated with development or onset of the disease or disorder. Thus, the term "preventing HIV infection" refers to administering to a subject who does not have a detectable HIV infection an anti-HIV therapeutic substance. It is understood that the subject for anti-HIV preventative therapy may be an individual at risk of contracting the HIV virus. Further, it is understood that prevention may not result in complete protection against onset of the disease or disorder. In some instances, prevention includes reducing the risk of developing the disease or disorder. The reduction of the risk may not result in complete elimination of the risk of developing the disease or disorder.

As used herein, an "at risk" individual is an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). For example, individuals at risk for AIDS are those having HIV.

As used herein, the term "therapeutically effective amount" or "effective amount" refers to an amount that is effective to elicit the desired biological or medical response, including the amount of a compound that, when administered to a subject for treating a disease, is sufficient to effect such treatment for the disease or to an amount that is effective to protect against the contracting or onset of a disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment outcome. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

The compounds of the invention include solvates, hydrates, tautomers, stereoisomers and salt forms thereof.

Provided are also compounds in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds exhibit may increase resistance to metabolism, and thus may be useful for increasing the half-life of the compounds when administered to a mammal. See, e.g., Foster, "Deuterium Isotope Effects in Studies of Drug Metabolism," Trends Pharmacol. Sci., 5(12):524-527

(1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I), can generally be prepared by conventional techniques known to those skilled in the art or by processes analogous to those described in the Examples as set out below using an appropriate isotopically-labeled reagent in place of the non-labeled reagent previously employed.

As referenced herein, darunavir is a HIV protease inhibitor having the structure:

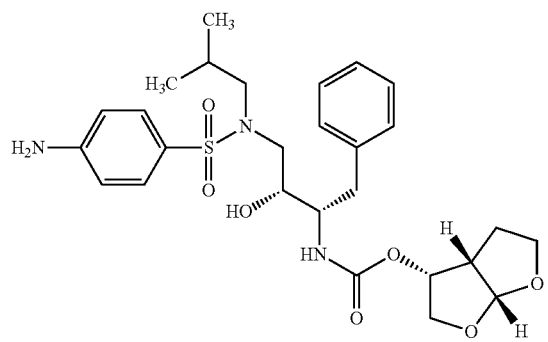 [SMILES: CC(C)CN(C[C@@H](O)[C@H](Cc1ccccc1)NC(=O)O[C@H]1CO[C@H]2OCC[C@H]21)S(=O)(=O)c1ccc(N)cc1]

and having the IUPAC name [(3aS,4R,6aR)-2,3,3a,4,5,6a-hexahydrofuro[2,3-b]furan-4-yl]N-[(2S,3R)-4-[(4-aminophenyl)sulfonyl-(2-methylpropyl)amino]-3-hydroxy-1-phenylbutan-2-yl]carbamate. Darunavir (DRV) is marketed under the brand name PREZISTA®.

As referenced herein, atazanavir is a HIV protease inhibitor having the structure:

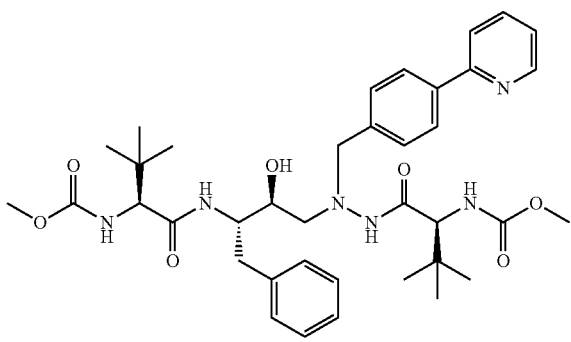

and having the IUPAC name methyl N-[(2S)-1-[2-[(2S,3S)-2-hydroxy-3-[[(2S)-2-(methoxycarbonylamino)-3,3-dimethylbutanoyl]amino]-4-phenylbutyl]-2-[(4-pyridin-2-ylphenyl)methyl]hydrazinyl]-3,3-dimethyl-1-oxobutan-2-yl]carbamate. Atazanavir (ATV) is marked under the brand name REYATAZ®.

Compounds

The compounds disclosed herein can be used to treat or prevent, for example, HIV infection. In some embodiments, the compounds of the invention are prodrugs, which upon administration to the human body are converted to compounds having biological activity.

In certain embodiments, the compound of the invention is a compound of Formula (I):

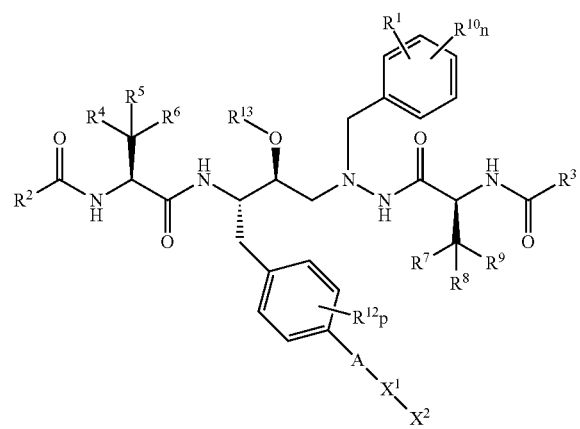

or a pharmaceutically acceptable salt thereof, wherein:

$R^1$ is a 5 to 10-membered heterocycle having 1 to 5 heteroatoms selected from N, O, and S, or a 5 to 10-membered heteroaryl having 1 to 5 heteroatoms selected from N, O, and S, wherein the 5 to 10-membered heterocycle or 5 to 10-membered heteroaryl is optionally substituted with 1 to 5 $R^a$ groups;

$R^2$ and $R^3$ are each independently $C_{1-4}$ alkyl, $C_{3-6}$ cycloalkyl, O—$R^{2A}$, $C_{1-2}$ alkyl-O—$R^{2A}$, N—$(R^{3A})_2$, or $C_{1-2}$ alkyl-N—$(R^{3A})_2$, wherein each $R^{2A}$ is independently $C_{1-4}$ alkyl, $C_{3-6}$ cycloalkyl, or a 4 to 10-membered heterocyclyl having 1 to 5 heteroatoms selected from N, O, and S, wherein each $R^{3A}$ is independently hydrogen, $C_{1-4}$ alkyl, $C_{3-6}$ cycloalkyl, or COO($R^e$), wherein each $R^e$ is independently hydrogen or $C_{1-4}$ alkyl, and wherein each $C_{3-6}$ cycloalkyl or 4 to 10-membered heterocyclyl is optionally substituted by 1 to 3 $R^f$ groups, wherein each $R^f$ is independently $C_{1-2}$ alkyl or halogen;

$R^4$ is hydrogen, halo, $C_{1-4}$ alkyl, $C_{1-4}$ haloalkyl, $C_{3-6}$ cycloalkyl, $C_{1-4}$ alkoxy, or $C_{1-4}$ haloalkoxy;

$R^7$ is hydrogen, halo, $C_{1-4}$ alkyl, $C_{1-4}$ haloalkyl, $C_{3-6}$ cycloalkyl, $C_{1-4}$ alkoxy, or $C_{1-4}$ haloalkoxy;

$R^5$, $R^6$, $R^8$, and $R^9$ are each independently hydrogen, halo, $C_{1-2}$ alkyl, $C_{1-2}$ haloalkyl, or $C_{3-6}$ cycloalkyl;

and wherein two or more of $R^4$, $R^5$ and $R^6$ or two or more of $R^7$, $R^8$, and $R^9$ optionally join together to form one or more $C_{3-6}$ cycloalkyl groups that are optionally substituted with 1 to 4 groups selected from halogen, $C_{1-2}$ alkyl, and $C_{1-2}$ haloalkyl;

each $R^{10}$ is independently halogen, cyano, $C_{1-4}$ alkoxy, $C_{1-6}$ alkyl, or $C_{3-6}$ cycloalkyl;

n is 0 to 4;

each $R^a$ is independently halogen, $C_{1-4}$ alkyl, $C_{1-4}$ alkyl with 1 to 2 groups selected from hydroxyl and $C_{1-4}$ alkoxy, $C_{1-4}$ haloalkyl, $C_{1-4}$ alkoxy, $C_{3-6}$ cycloalkyl, 4 to 10-membered heterocyclyl having 1 to 5 heteroatoms selected from N, O, and S which is optionally substituted with $R^{a1}$, or O—$R^{3B}$, wherein $R^{3B}$ is $C_{3-6}$ cycloalkyl optionally substituted with $R^{a1}$ or a 4 to 10-membered heterocyclyl having 1 to 5 heteroatoms selected from N, O, and S optionally substituted with $R^{a1}$, wherein each $R^{a1}$ is independently $C_{1-4}$ alkyl, $C_{3-6}$ cycloalkyl, $C_{1-4}$ haloalkyl, or 4 to 8-membered heterocyclyl having 1 to 3 heteroatoms selected from N, O, and S;

A is ethynyl or a bond;

$X^1$ is a 6 to 10-membered aryl or a 5 to 10-membered heteroaryl having 1 to 3 heteroatoms selected from N, O, and S, wherein each 6 to 10-membered aryl or 5 to 10-membered heteroaryl is optionally substituted with 1 to 4 $R^b$ groups;

$X^2$ is hydrogen or a 4 to 10-membered heterocyclyl having 1 to 5 heteroatoms selected from N, O, and S, wherein the 4 to 10-membered heterocyclyl is optionally substituted with one $R^{11}$ and optionally substituted with 1 to 5 $R^b$ groups;

$R^{11}$ is C=O($R^c$), $CH_2(R^d)$, $S(O)_{1-2}(C_{1-4}$ alkyl), $S(O)_{1-2}C_{3-6}$ cycloalkyl, a 4 to 10-membered heterocyclyl having 1 to 5 heteroatoms selected from N, O, and S, or a 5 to 9-membered heteroaryl having 1 to 5 heteroatoms selected from N, O, and S, wherein each 4 to 10-membered heterocyclyl or 5 to 9-membered heteroaryl is optionally substituted with 1 to 5 $R^b$ groups;

each $R^b$ is independently halogen, oxo, $C_{1-4}$ alkyl, $C_{1-4}$ alkyl with 1 to 2 groups selected from hydroxyl and $C_{1-4}$ alkoxy, $C_{1-4}$ haloalkyl, $C_{1-4}$ alkoxy, or COO($R^e$);

$R^c$ is $C_{1-4}$ alkyl, $C_{1-4}$ haloalkyl, $C_{1-4}$ alkoxy, $N(R^e)_2$, $C_{3-6}$ cycloalkyl, or a 4 to 6-membered heterocyclyl having 1 to 3 heteroatoms selected from N, O, and S, wherein the $C_{3-6}$ cycloalkyl and the 4 to 6-membered heterocyclyl are optionally substituted by 1 to 5 $R^b$ groups;

$R^d$ is COO($R^e$), $N(R^e)_2$, $C_{3-6}$ cycloalkyl, or a 4 to 6-membered heterocyclyl having 1 to 3 heteroatoms selected from N, O, and S, wherein the $C_{3-6}$ cycloalkyl and the 4 to 6-membered heterocyclyl is optionally substituted by 1 to 5 $R^b$ groups;

each $R^{12}$ is $C_{1-2}$ alkyl, halo, —$OC_{1-2}$ alkyl, or cyano;

each p is 0 to 4;

$R^{13}$ is —C(=O)$R^{g1}$, —C(=O)O$R^{g2}$, or —P(=O)(O$R^h$)$_2$;

$R^{g1}$ is H, $C_{1-6}$ alkyl, $C_{3-6}$ cycloalkyl, or 5- to 6-membered heteroaryl having 1 to 3 heteroatoms selected from N, O, and S;

wherein the $C_{1-6}$ alkyl of $R^{g1}$ is optionally substituted with 1, 2, 3, or 4 substituents independently selected from halogen, $C_{1-4}$ alkoxy, —N($R^i$)$_2$, —$C_{1-4}$ alkyl-N($R^i$)$_2$, —N($R^i$)$_3^+$, and 4- to 6-membered heterocyclyl having 1 to 3 heteroatoms selected from N, O, and S that is optionally substituted with 1, 2, 3, or 4 substituents independently selected from halogen, $C_{1-4}$ alkyl, $C_{1-4}$ alkoxy, —N($R^i$)$_2$, and —$C_{1-4}$ alkyl-N($R^i$)$_2$; and wherein the 5- to 6-membered heteroaryl and $C_{3-6}$ cycloalkyl of $R^{g1}$ are each optionally substituted with 1, 2, 3, or 4 substituents independently selected from halogen, $C_{1-6}$ alkyl, $C_{1-4}$ alkoxy, —N($R^i$)$_2$, and —$C_{1-4}$ alkyl-N($R^i$)$_2$;

$R^{g2}$ is $C_{1-6}$ alkyl optionally substituted with 1, 2, 3, or 4 substituents independently selected from halogen, $C_{1-6}$ alkyl, $C_{1-4}$ alkoxy, —N($R^i$)$_2$, —$C_{1-4}$ alkyl-N($R^i$)$_2$, and —O—P(=O)(O$R^h$)$_2$; and $R^h$ and $R^i$ are each independently selected from H and $C_{1-3}$ alkyl.

In certain embodiments of the compound of Formula (I):

$R^1$ is a 5 to 10-membered heteroaryl having 1 to 3 heteroatoms selected from N, O, and S, optionally substituted with 1 to 2 $R^a$ groups, wherein each $R^a$ is independently $C_{1-4}$ haloalkyl;

$R^2$ and $R^3$ are each independently O—$R^{2A}$, wherein each $R^{2A}$ is independently $C_{1-4}$ alkyl;

$R^4$ is $C_{1-4}$ alkyl or $C_{1-4}$ haloalkyl;

$R^7$ is $C_{1-4}$ alkyl or $C_{1-4}$ haloalkyl;

$R^5$, $R^6$, $R^8$, and $R^9$ are each independently $C_{1-2}$ alkyl or $C_{1-2}$ haloalkyl;

each $R^{10}$ is independently halogen;

n is 0, 1 or 2;

A is ethynyl;

$X^1$ is a 5 to 10-membered heteroaryl having 1 to 3 heteroatoms selected from N, O, and S;

$X^2$ is a 4 to 10-membered heterocyclyl having 1 to 3 heteroatoms selected from N, O, and S, optionally substituted with one $R^{11}$ group, wherein $R^{11}$ is a 4 to 10-membered heterocyclyl having 1 to 2 heteroatoms selected from N, O, and S;

p is 0;

$R^{13}$ is —C(=O)$R^{g1}$, —C(=O)O$R^{g2}$, or —P(=O)(O$R^h$)$_2$;

$R^{g1}$ is H, $C_{1-6}$ alkyl, $C_{3-6}$ cycloalkyl, or 5- to 6-membered heteroaryl having 1 to 3 heteroatoms selected from N, O, and S;

wherein the $C_{1-6}$ alkyl of $R^{g1}$ is optionally substituted with 1, 2, 3, or 4 substituents independently selected from halogen, $C_{1-4}$ alkoxy, —N($R^i$)$_2$, —$C_{1-4}$ alkyl-N($R^i$)$_2$, —N($R^i$)$_3^+$, and 4- to 6-membered heterocyclyl having 1 to 3 heteroatoms selected from N, O, and S that is optionally substituted with 1, 2, 3, or 4 substituents independently selected from halogen, $C_{1-4}$ alkyl, $C_{1-4}$ alkoxy, —N($R^i$)$_2$, and —$C_{1-4}$ alkyl-N($R^i$)$_2$; and wherein the 5- to 6-membered heteroaryl and $C_{3-6}$ cycloalkyl of $R^{g1}$ are each optionally substituted with 1, 2, 3, or 4 substituents independently selected from halogen, $C_{1-6}$ alkyl, $C_{1-4}$ alkoxy, —N($R^i$)$_2$, and —$C_{1-4}$ alkyl-N($R^i$)$_2$;

$R^{g2}$ is $C_{1-6}$ alkyl optionally substituted with 1, 2, 3, or 4 substituents independently selected from halogen, $C_{1-6}$ alkyl, $C_{1-4}$ alkoxy, —N($R^i$)$_2$, —$C_{1-4}$ alkyl-N($R^i$)$_2$, and —O—P(=O)(O$R^h$)$_2$; and $R^h$ and $R^i$ are each independently selected from H and $C_{1-3}$ alkyl.

In certain embodiments of the compound of Formula (I):

$R^1$ is a 5-membered heteroaryl having 2 heteroatoms that are each N, substituted with 1 $R^a$ group, wherein $R^a$ is —CHF$_2$;

$R^2$ and $R^3$ are each independently O—$R^{2A}$, wherein each $R^{2A}$ is methyl;

$R^4$ is CF$_3$;

$R^7$ is CF$_3$;

$R^5$, $R^6$, $R^8$, and $R^9$ are each methyl;

each $R^{10}$ is F;

n is 2;

A is ethynyl;

$X^1$ is a 6-membered heteroaryl having 2 heteroatoms that are each N;

$X^2$ is an 8-membered bridged heterocyclyl having 2 heteroatoms that are each N, substituted with one $R^{11}$ group, wherein $R^{11}$ is a 4-membered heterocyclyl having 1 heteroatom that is O;

p is 0;

$R^{13}$ is —C(=O)$R^{g1}$, —C(=O)O$R^{g2}$, or —P(=O)(OH)$_2$;

$R^{g1}$ is H, $C_{1-6}$ alkyl, or a 6-membered heteroaryl having 1 heteroatom that is N;

wherein the $C_{1-6}$ alkyl of $R^{g1}$ is optionally substituted with 1 or 2 substituents independently selected from —N($R^i$)$_2$, —$C_{1-4}$ alkyl-N($R^i$)$_2$, —N($R^i$)$_3^+$, and a 6-membered heterocyclyl having 1 to 2 heteroatoms selected from N and O;

$R^{g2}$ is $C_{1-2}$ alkyl substituted with —O—P(=O)(OH)$_2$; and $R^i$ are each independently selected from H and $C_{1-3}$ alkyl.

In certain embodiments of a compound of Formula (I), $R^4$ and $R^7$ may be the same or different. In certain embodiments of a compound of Formula (I), $R^4$ is hydrogen, $C_{1-4}$ alkyl, or $C_{1-4}$ haloalkyl. In certain embodiments, $R^4$ is $C_{1-4}$ haloalkyl. In certain embodiments of a compound of Formula (I), $R^4$ is $CF_3$. In certain embodiments of a compound of Formula (I), $R^7$ is hydrogen, $C_{1-4}$ alkyl, or $C_{1-4}$ haloalkyl. In certain embodiments, $R^7$ is $C_{1-4}$ haloalkyl. In certain embodiments, $R^7$ is $CF_3$. In certain embodiments of a compound of Formula (I), $R^4$ and $R^7$ are $CF_3$ or methyl. In certain embodiments of a compound of Formula (I), $R^4$ and $R^7$ are both $CF_3$. In certain embodiments of a compound of Formula (I), $R^5$, $R^6$, $R^8$, and $R^9$ may be the same or different. In certain embodiments of a compound of Formula (I), $R^5$, $R^6$, $R^8$, and $R^9$ are each independently hydrogen, halo, $C_{1-2}$ alkyl, $C_{1-2}$ haloalkyl, or $C_{3-6}$ cycloalkyl. In certain embodiments of a compound of Formula (I), $R^5$, $R^6$, $R^8$, and $R^9$ are hydrogen, methyl, or fluoro. In certain embodiments of a compound of Formula (I), $R^5$ and $R^6$ are $C_{1-2}$ alkyl. In certain embodiments of a compound of Formula (I), $R^5$ and $R^6$ are methyl. In certain embodiments of a compound of Formula (I), $R^8$ and $R^9$ are $C_{1-2}$ alkyl. In certain embodiments of a compound of Formula (I), $R^8$ and $R^9$ are methyl. In certain embodiments of a compound of Formula (I), $R^5$, $R^6$, $R^8$, and $R^9$ are methyl. In certain embodiments of a compound of Formula (I), two or more of $R^4$, $R^5$, and $R^6$ or $R^7$, $R^8$, and $R^9$ may join together to form one or more $C_{3-6}$ cycloalkyl groups that are optionally substituted with halogen.

In certain embodiments of a compound of Formula (I), $R^1$ is a 5 to 6-membered heterocycle having 1 to 3 heteroatoms selected from N, O, and S, or a 5 to 6-membered heteroaryl having 1 to 3 heteroatoms selected from N, O, and S, wherein the 5 to 6-membered heterocycle or 5 to 6-membered heteroaryl is optionally substituted with 1 to 3 $R^a$ groups. In certain embodiments of a compound of Formula (I), $R^1$ is a 5 to 6-membered heterocycle having 1 to 3 heteroatoms selected from N, O, and S and is optionally substituted with 1 to 3 $R^a$ groups. In certain embodiments of a compound of Formula (I), $R^1$ is:

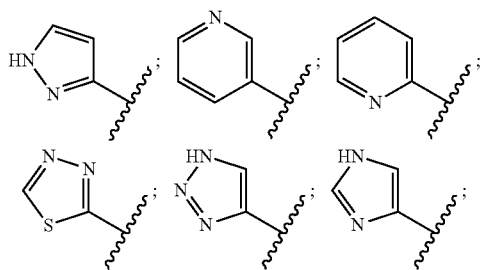

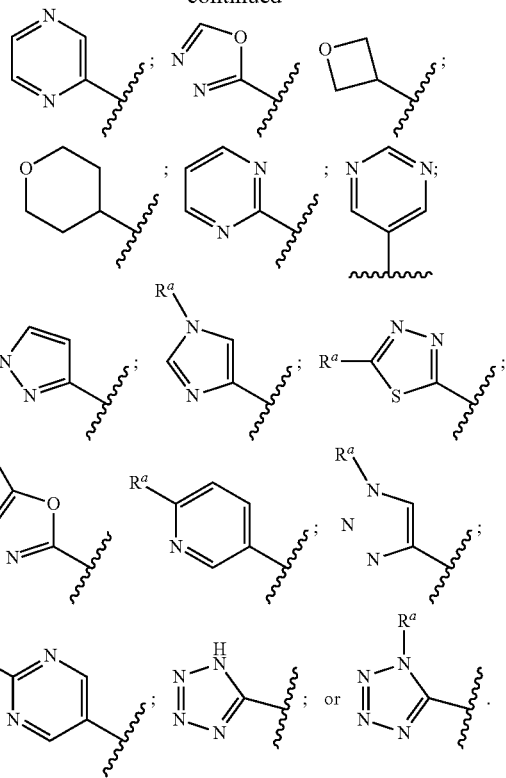

In certain embodiments, $R^1$ is

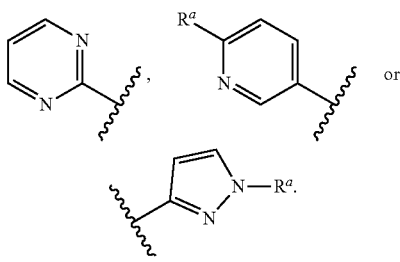

In certain embodiments, $R^1$ is:

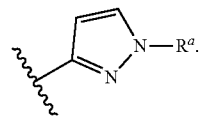

In certain embodiments of a compound of Formula (I), $R^a$ is independently $C_{1-4}$ alkyl, $C_{1-4}$ alkyl with 1 to 2 groups selected from hydroxyl and $C_{1-4}$ alkoxy, $C_{1-4}$ haloalkyl, or a 4 to 8-membered heterocyclyl having 1 to 3 heteroatoms selected from N, O, and S optionally substituted with $R^{a1}$. In certain embodiments of a compound of Formula (I), $R^a$ is independently $C_{1-4}$ alkyl, $C_{1-4}$ alkyl with 1 to 2 groups selected from hydroxyl and $C_{1-4}$ alkoxy, $C_{1-4}$ haloalkyl, furanyl, oxetanyl, or 3,8-diazabicyclo[3.2.1]octanyl optionally substituted with $R^{a1}$. In certain embodiments of a compound of Formula (I), $R^a$ is independently $C_{1-4}$ alkyl, $C_{1-4}$ alkyl with 1 to 2 groups selected from hydroxyl and $C_{1-4}$ alkoxy, or $C_{1-4}$ haloalkyl. In certain embodiments of a compound of Formula (I), $R^a$ is:

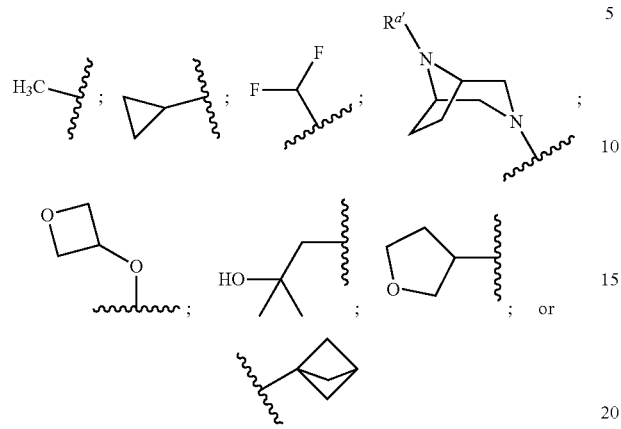

In certain embodiments of a compound of Formula (I), $R^a$ is $C_{1-4}$ haloalkyl. In certain embodiments of a compound of Formula (I), $R^a$ is:

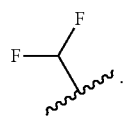

In certain embodiments of a compound of Formula (I), $R^a$ may be substituted by $R^{a1}$. In certain embodiments of a compound of Formula (I), $R^a$ is substituted with one $R^{a1}$ group. In certain embodiments of a compound of Formula (I), $R^a$ is $C_{1-4}$ alkyl, $C_{3-6}$ cycloalkyl, $C_{1-4}$ haloalkyl, or 4 to 8-membered heterocyclyl having 1 to 3 heteroatoms selected from N, O, and S. In certain embodiments of a compound of Formula (I), the 4 to 8-membered heterocyclyl contains 1 to 2 nitrogen heteroatoms or 1 to 2 oxygen atoms.

In certain embodiments of a compound of Formula (I), $X^1$ is a 6-membered aryl or a 5 to 6-membered heteroaryl having 1 to 3 heteroatoms selected from N, O, and S, wherein each 6-membered aryl or 5 to 6-membered heteroaryl is optionally substituted with 1 to 4 $R^b$ groups. In certain embodiments of a compound of Formula (I), $X^1$ is pyrimidine or pyridine optionally substituted with 1 to 4 $R^b$ groups. In certain embodiments of a compound of Formula (I), $X^1$ is pyrimidine or pyridine. In certain embodiments of a compound of Formula (I), $X^1$ is:

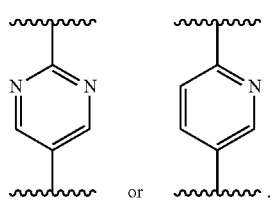 [SMILES: *c1cnc(*)nc1 ; *c1ccc(*)nc1]

In certain embodiments of a compound of Formula (I), $X^1$ is

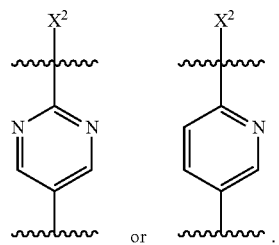

In certain embodiments of a compound of Formula (I), $X^1$ is

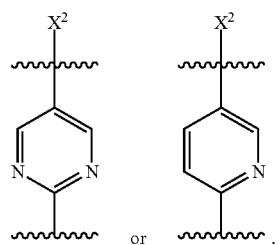

In certain embodiments of a compound of Formula (I), $X^1$ is

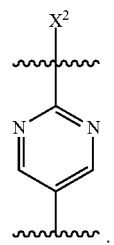

In certain embodiments of a compound of Formula (I), $X^2$ is a 4 to 10-membered heterocyclyl having 1 to 3 heteroatoms selected from N, O, and S and is optionally substituted with one $R^{11}$ and optionally substituted with 1 to 5 $R^b$ groups. In certain embodiments, $X^2$ may be substituted by $R^{11}$ and $R^b$. In certain embodiments of a compound of Formula (I), $X^2$ is:

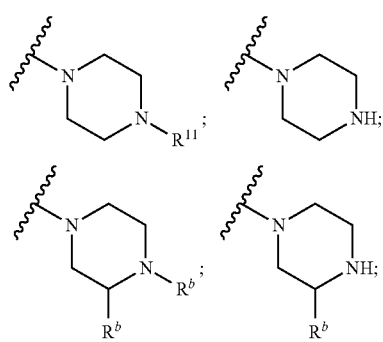

-continued

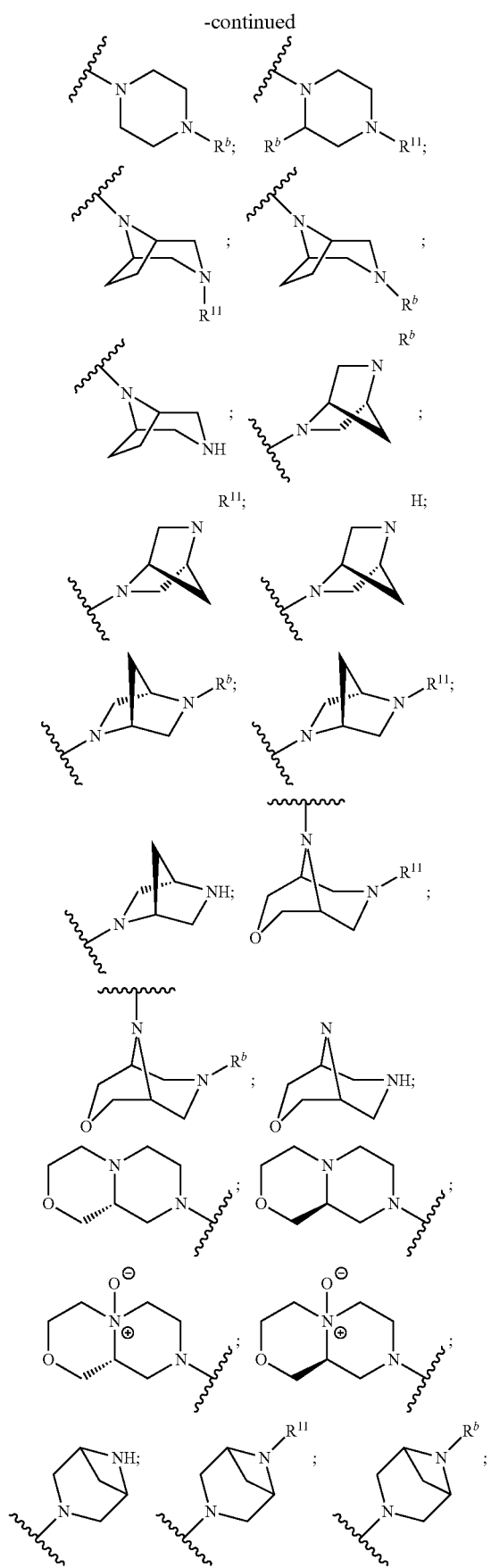

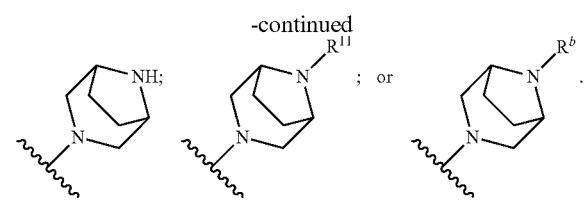

In certain embodiments of a compound of Formula (I), $X^2$ is:

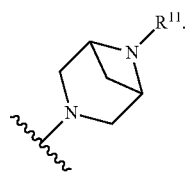

In certain embodiments of a compound of Formula (I), $X^2$ is:

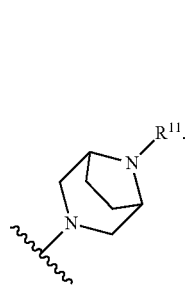

In certain embodiments of a compound of Formula (I), $X^2$ is

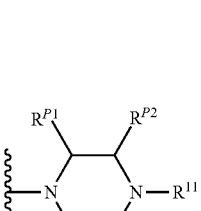

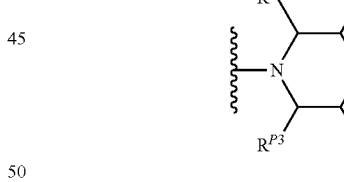

wherein:
a) $R^{P1}$, $R^{P2}$, $R^{P3}$, and $R^{P4}$ are each hydrogen;
b) $R^{P1}$ and $R^{P3}$ are taken together to form a —CH$_2$— or —CH$_2$CH$_2$— group and $R^{P2}$ and $R^{P4}$ are each hydrogen;
c) $R^{P2}$ and $R^{P4}$ are taken together to form a —CH$_2$— or —CH$_2$CH$_2$— group and $R^{P1}$ and $R^{P3}$ are each hydrogen.
d) $R^{P1}$ and $R^{P4}$ are taken together to form a —CH$_2$— group and $R^{P2}$ and $R^{P3}$ are each hydrogen; or
e) $R^{P2}$ and $R^{P3}$ are taken together to form a —CH$_2$— group and $R^{P1}$ and $R^{P4}$ are each hydrogen.

In certain embodiments of a compound of Formula (I), $X^2$ is

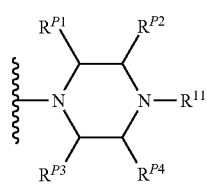

wherein:
$R^{P1}$ and $R^{P3}$ are taken together to form a —CH$_2$— or —CH$_2$CH$_2$— group and $R^{P2}$ and $R^{P4}$ are each hydrogen; or
$R^{P2}$ and $R^{P4}$ are taken together to form a —CH$_2$— or —CH$_2$CH$_2$— group and $R^{P1}$ and $R^{P3}$ are each hydrogen.

In certain embodiments of a compound of Formula (I), $X^2$ is optionally substituted by $R^{11}$. In certain embodiments of a compound of Formula (I), $R^{11}$ is 4 to 10-membered heterocyclyl having 1 to 3 heteroatoms selected from N, O, and S. In certain embodiments of a compound of Formula (I), $R^{11}$ is a 4 to 6-membered heterocycle having one oxygen. In certain embodiments of a compound of Formula (I), $R^{11}$ is oxetanyl, tetrahydrofuranyl, or tetrahydropyranyl. In certain embodiments of a compound of Formula (I), $R^{11}$ is oxetan-3-yl, tetrahydrofuran-3-yl, or tetrahydropyran-4-yl. In certain embodiments of a compound of Formula (I), $R^{11}$ is oxetan-3-yl.

In certain embodiments of a compound of Formula (I), $R^2$ and $R^3$ may be the same or different. In certain embodiments of a compound of Formula (I), $R^2$ and $R^3$ are each independently $C_{1-4}$ alkyl, $C_{3-6}$ cycloalkyl, or O—$R^{2A}$, wherein $R^{2A}$ is $C_{1-4}$ alkyl, $C_{3-6}$ cycloalkyl, or a 4 to 10-membered heterocyclyl having 1 to 5 heteroatoms selected from N, O, and S. In certain embodiments of a compound of Formula (I), $R^2$ and $R^3$ are each independently

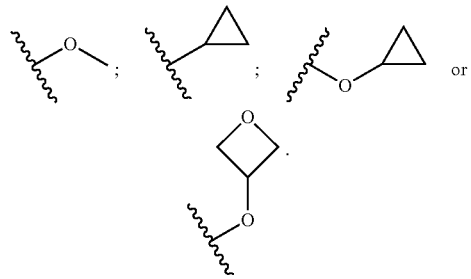

In certain embodiments of a compound of Formula (I), $R^2$ and $R^3$ are each methoxy.

In certain embodiments of a compound of Formula (I), each $R^{10}$ may be the same or different when n is greater than one. In some embodiments of a compound of Formula (I), n=0, 1, or 2. In some embodiments of a compound of Formula (I), n is 2. In certain embodiments of a compound of Formula (I), each $R^{10}$ is halogen. In certain embodiments, each $R^{10}$ is chloro or fluoro. In certain embodiments, each $R^{10}$ is fluoro. In certain embodiments of a compound of Formula (I), n is 2 and each $R^{10}$ is fluoro.

In certain embodiments of a compound of Formula (I), A is ethynyl. In certain embodiments of a compound of Formula (I), A is a bond.

In certain embodiments, whenever present, each of $X^1$ and $X^2$ may be substituted by one or more $R^b$ groups. In certain embodiments, each $R^b$ is independently halogen, oxo, $C_{1-4}$ alkyl, $C_{1-4}$ alkyl with 1 to 2 groups selected from hydroxyl and $C_{1-4}$ alkoxy, $C_{1-4}$ haloalkyl, $C_{1-4}$ alkoxy, or COO($R^e$). In certain embodiments, each $R^b$ is independently oxo or halo.

In certain embodiments of a compound of Formula (I), whenever present, each $R^{12}$ is $C_{1-2}$ alkyl, halo, —O$C_{1-2}$ alkyl or cyano. In some embodiments of a compound of Formula (I), p is 0, 1, 2, 3, or 4. In some embodiments of a compound of Formula (I), p is 0. In certain embodiments of a compound of Formula (I), $R^{12}$ is fluoro, chloro, or methyl. In certain embodiments of a compound of Formula (I), $R^{12}$ is absent.

In certain embodiments of a compound of Formula (I), $R^{13}$ is —C(=O)$R^{g1}$, —C(=O)O$R^{g2}$, or —P(=O)(O$R^h$)$_2$. In certain embodiments of a compound of Formula (I), $R^{13}$ is —C(=O)$R^{g1}$. In some embodiments, $R^{13}$ is —C(=O)$R^{g1}$ and $R^{g1}$ is H, $C_{1-6}$ alkyl, or 5- to 6-membered heteroaryl having 1 to 3 heteroatoms selected from N, O, and S; wherein the $C_{1-6}$ alkyl of $R^{g1}$ is optionally substituted with 1, 2, 3, or 4 substituents independently selected from —N($R^i$)$_2$, —N($R^i$)$_3^+$, and 4- to 6-membered heterocyclyl having 1 to 3 heteroatoms selected from N, O, and S.

In some embodiments, $R^{13}$ is —C(=O)$R^{g1}$, wherein $R^{g1}$ is (i) H, (ii) a 6-membered heteroaryl having 1 or 2 nitrogen atoms, or (iii) $C_{1-6}$ alkyl optionally substituted with 1 or 2 substituents independently selected from NH$_2$, N(CH$_3$)$_2$, N(CH$_3$)$_3^+$, and a 6-membered heterocyclyl having 1 to 2 heteroatoms selected from N and O.

In some embodiments, $R^{13}$ is —C(=O)$R^{g1}$ and $R^{g1}$ is H; methyl;

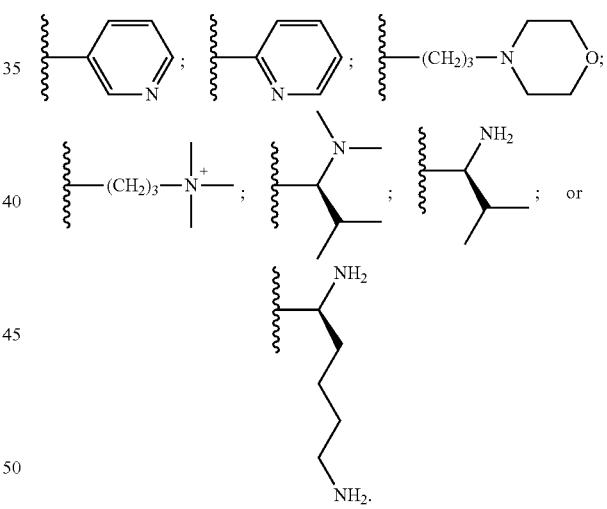

In certain embodiments of a compound of Formula (I), $R^{13}$ is —C(=O)O$R^{g2}$ or —P(=O)(OH)$_2$, wherein $R^{g2}$ is $C_{1-3}$ alkyl optionally substituted with —O—P(=O)(OH)$_2$. In certain embodiments of a compound of Formula (I), $R^{g2}$ is $C_{1-6}$ alkyl substituted with —O—P(=O)(O$R^h$)$_2$. In certain embodiments of a compound of Formula (I), $R^{g2}$ is

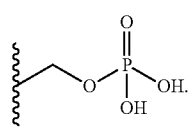 [SMILES: *COP(=O)(O)O]

In certain embodiments of a compound of Formula (I), $R^{13}$ is —P(=O)(OR$^h$)$_2$.

In certain embodiments of a compound of Formula (I), each $R^h$ is independently H. In certain embodiments of a compound of Formula (I), or a pharmaceutically acceptable salt thereof, $R^{13}$ is:

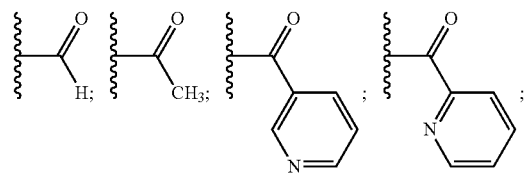

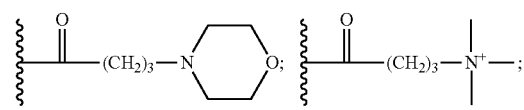

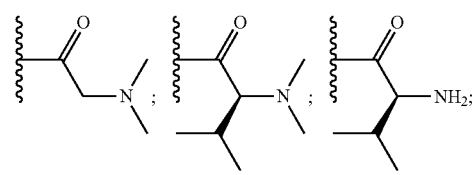

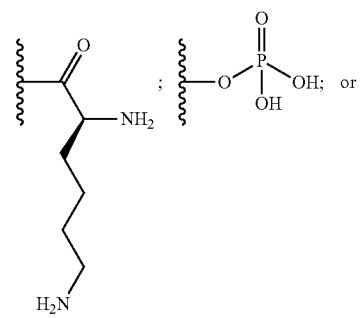

In certain embodiments of a compound of Formula (I), or a pharmaceutically acceptable salt thereof, $R^{13}$ is:

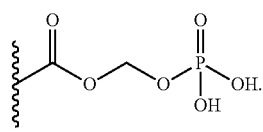 [SMILES: *C(=O)OCOP(=O)(O)O]

In certain embodiments, the compound of Formula (I) is a compound of Formula (II):

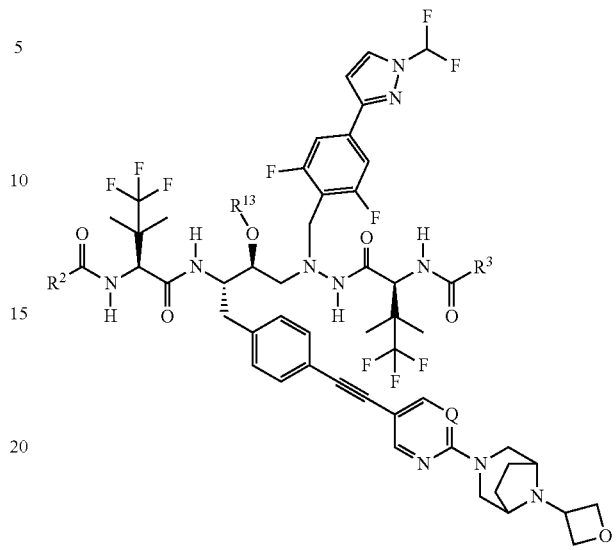

(II)

or a pharmaceutically acceptable salt thereof, wherein $R^2$, $R^3$, and $R^{13}$ are as defined herein and Q is N or CH.

In certain embodiments of a compound of Formula (II), or a pharmaceutically acceptable salt thereof, $R^2$ and $R^3$ are each independently $C_{1-4}$ alkyl, $C_{3-6}$ cycloalkyl, or O—$R^{2A}$, wherein $R^{2A}$ is $C_{1-4}$ alkyl, $C_{3-6}$ cycloalkyl, or a 4 to 10-membered heterocyclyl having 1 to 5 heteroatoms selected from N, O, and S. In certain embodiments of a compound of Formula (II), $R^2$ and $R^3$ are each independently:

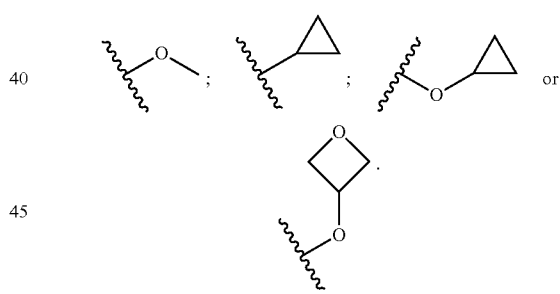

In certain embodiments of a compound of Formula (II), $R^2$ and $R^3$ are each methoxy.

In certain embodiments of a compound of Formula (II), or a pharmaceutically acceptable salt thereof, $R^{13}$ is:

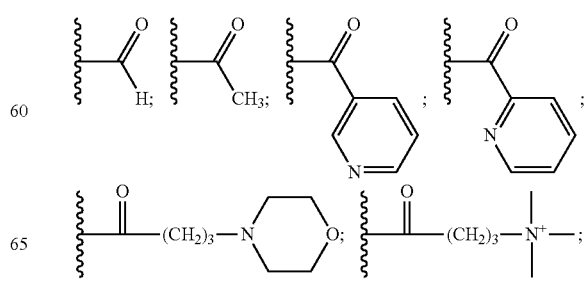

-continued

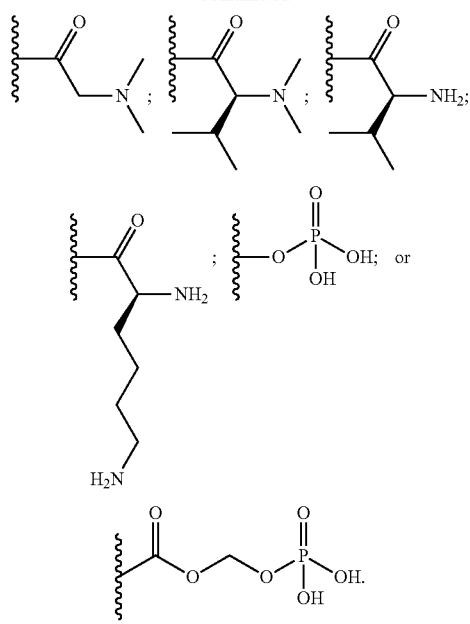

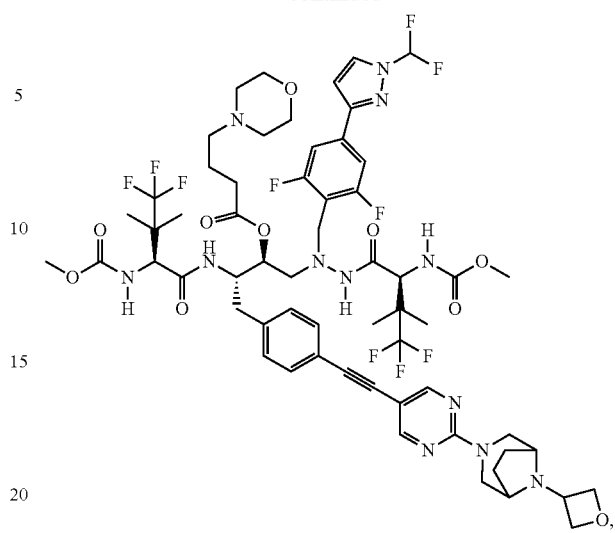

In certain embodiments of a compound of Formula (II), or a pharmaceutically acceptable salt thereof, $R^{13}$ is:

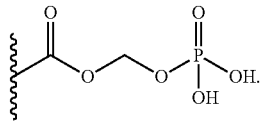 [SMILES: *C(=O)OCOP(=O)(O)O]

As disclosed above, any of the definitions for the variables provided (e.g., A, $R^1$, $R^2$, $R^3$, $R^4$, $R^5$, $R^6$, $R^7$, $R^8$, $R^9$, $R^{10}$, $R^{10a}$, $R^{10b}$, $Z^1$, $Z^2$, $X^1$, and $X^2$) may be combined and grouped with other variables, whether or not specifically recited together.

In certain embodiments, the compound is:

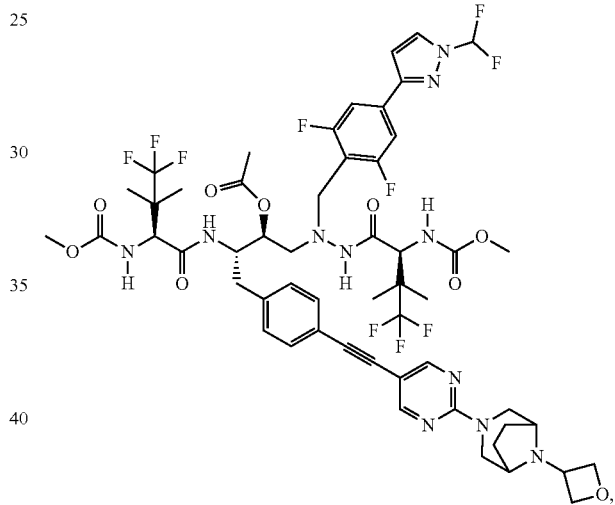

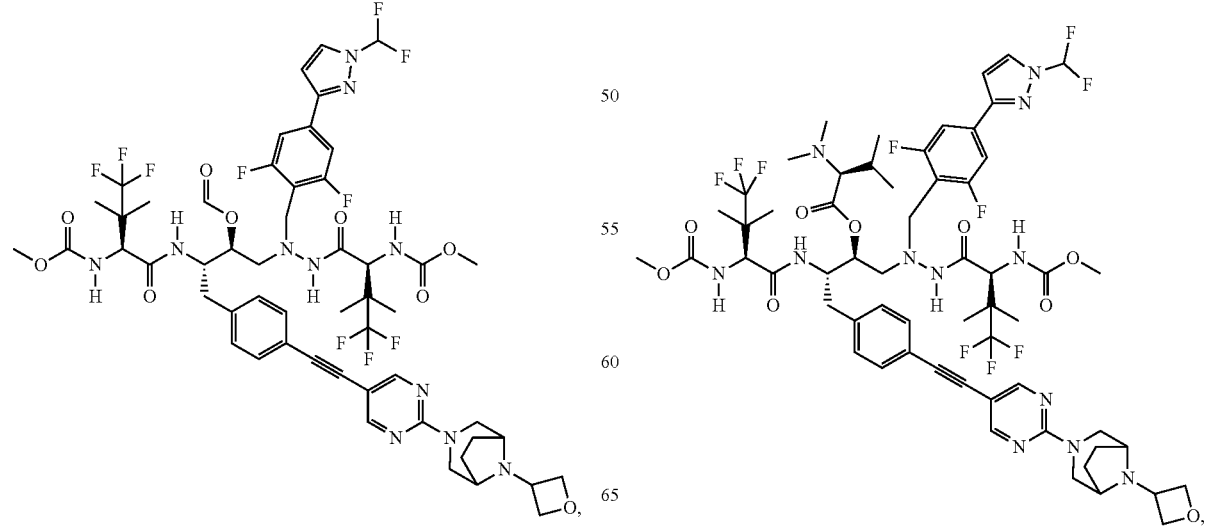

31
-continued
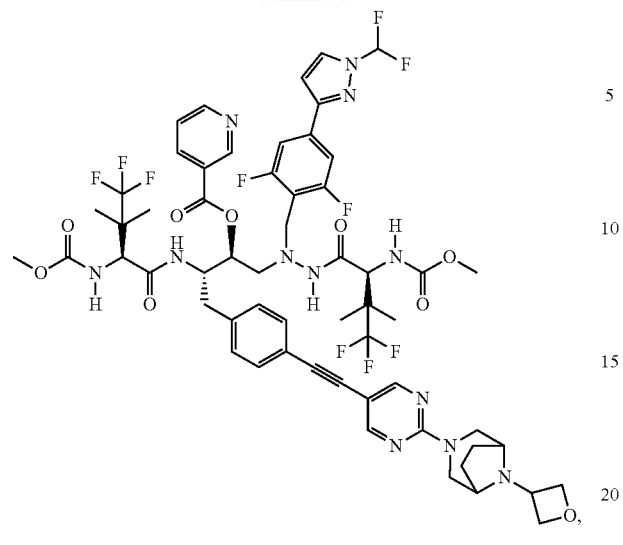
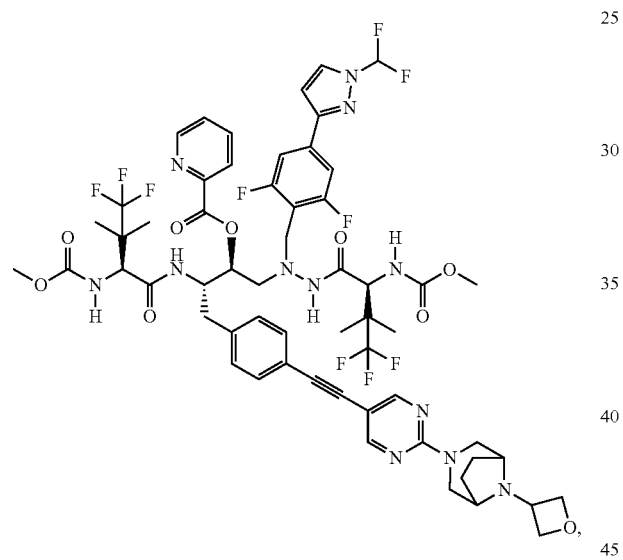
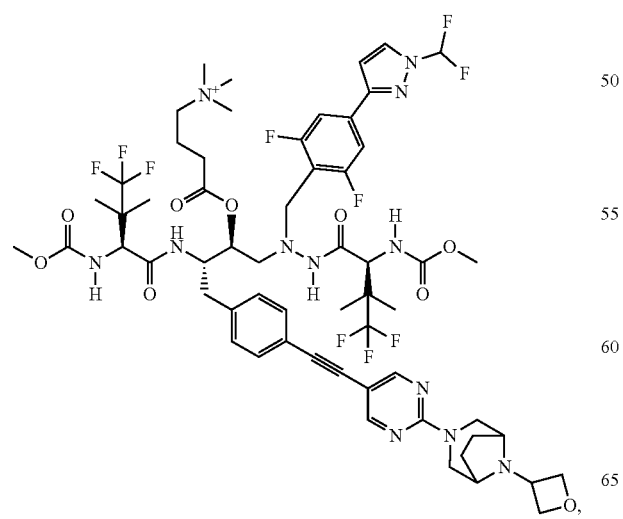
32
-continued
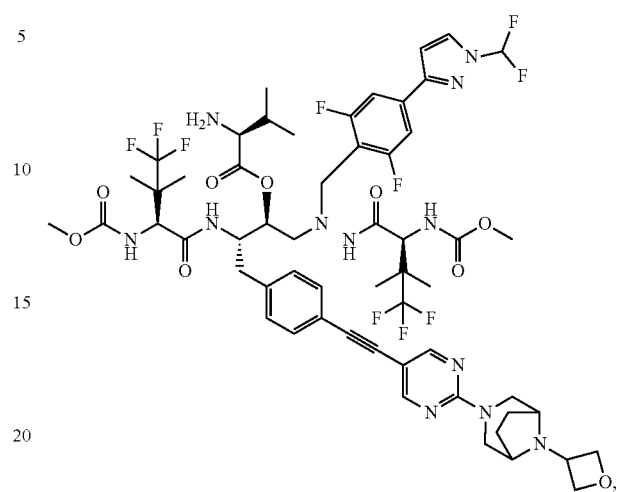
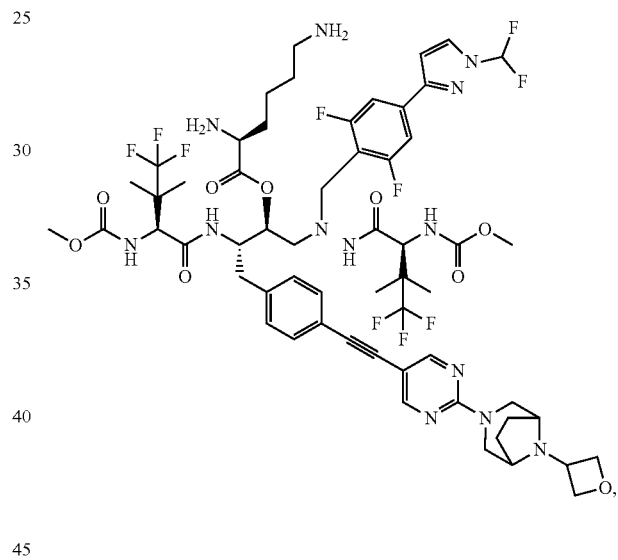
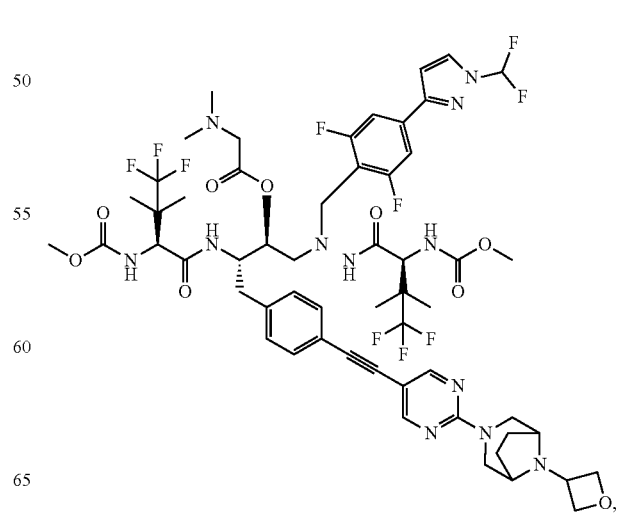

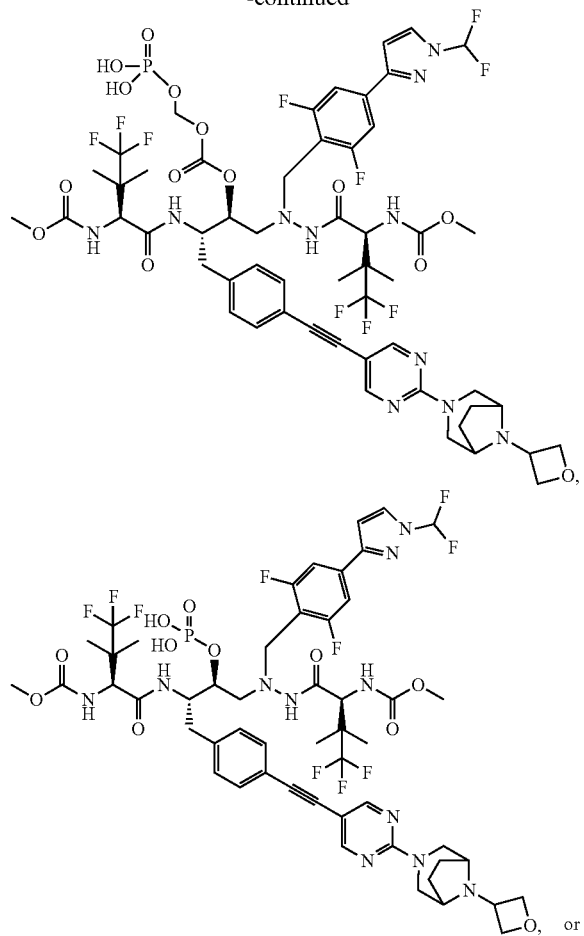

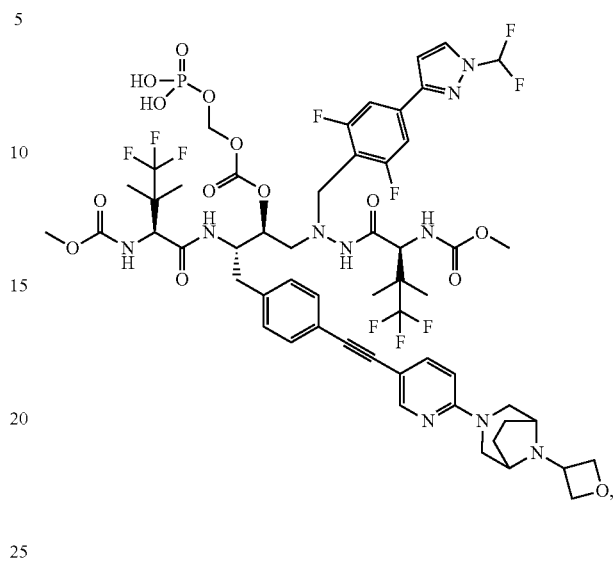

or a pharmaceutically acceptable salt thereof.

In certain embodiments, the compound is a compound of any of Examples 1-13, or a pharmaceutically acceptable salt thereof.

In certain embodiments, the compound is a compound of Example 14, or a pharmaceutically acceptable salt thereof.

In certain embodiments, the compound is

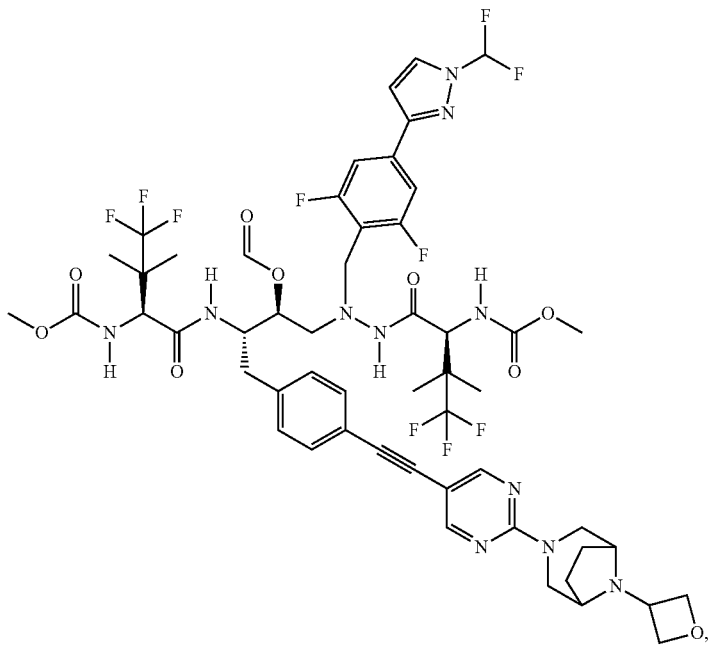 [SMILES: COC(=O)N[C@H](C(=O)N[C@@H](Cc1ccc(C#Cc2cnc(N3CC4CCC(C3)N4C3COC3)nc2)cc1)[C@H](CN(Cc1c(F)cc(-c2ccn(C(F)F)n2)cc1F)NC(=O)[C@@H](NC(=O)OC)C(C)(C)C(F)(F)F)OC=O)C(C)(C)C(F)(F)F]

or a pharmaceutically acceptable salt thereof.

In certain embodiments, the compound is
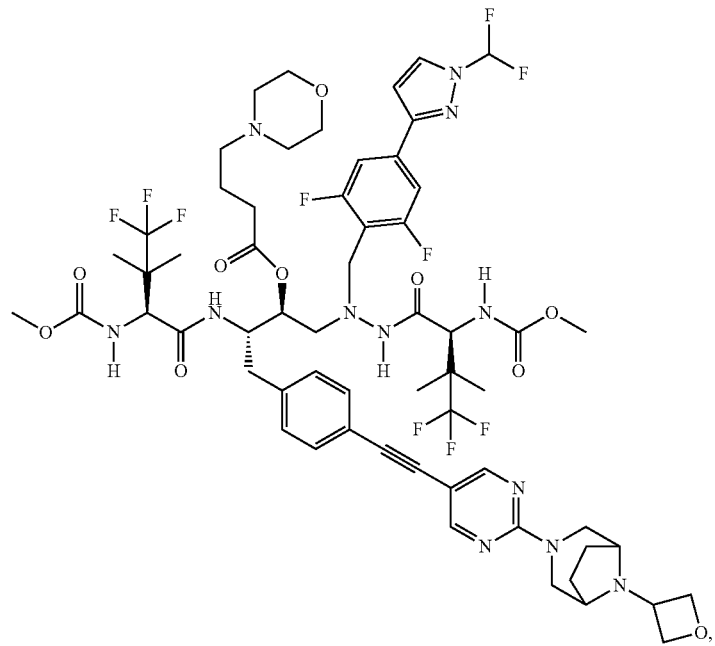 [SMILES: COC(=O)N[C@H](C(=O)N[C@@H](Cc1ccc(C#Cc2cnc(N3CC4CCC(C3)N4C3COC3)nc2)cc1)[C@H](CN(Cc1c(F)cc(-c2ccn(C(F)F)n2)cc1F)NC(=O)[C@@H](NC(=O)OC)C(C)(C)C(F)(F)F)OC(=O)CCCN1CCOCC1)C(C)(C)C(F)(F)F]
or a pharmaceutically acceptable salt thereof.
In certain embodiments, the compound is
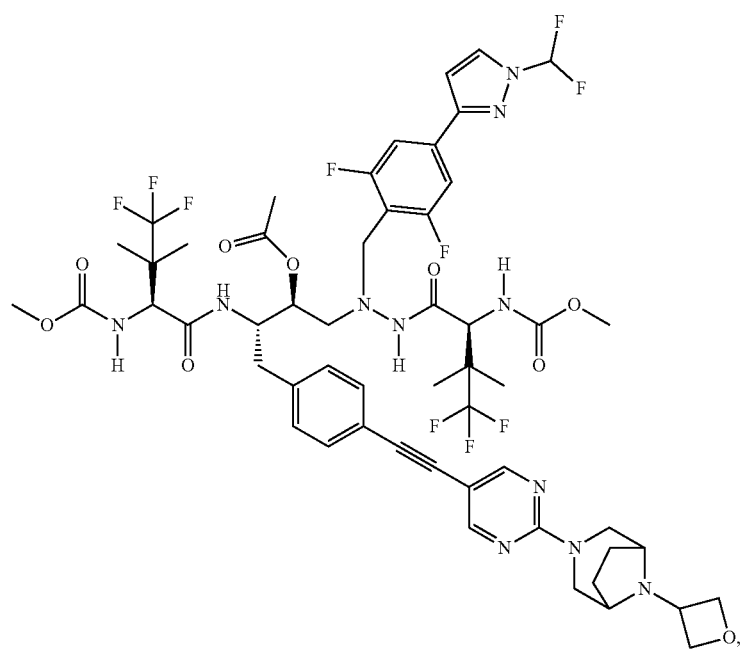 [SMILES: COC(=O)N[C@H](C(=O)N[C@@H](Cc1ccc(C#Cc2cnc(N3CC4CCC(C3)N4C3COC3)nc2)cc1)[C@H](CN(Cc1c(F)cc(-c2ccn(C(F)F)n2)cc1F)NC(=O)[C@@H](NC(=O)OC)C(C)(C)C(F)(F)F)OC(C)=O)C(C)(C)C(F)(F)F]
or a pharmaceutically acceptable salt thereof.

In certain embodiments, the compound is
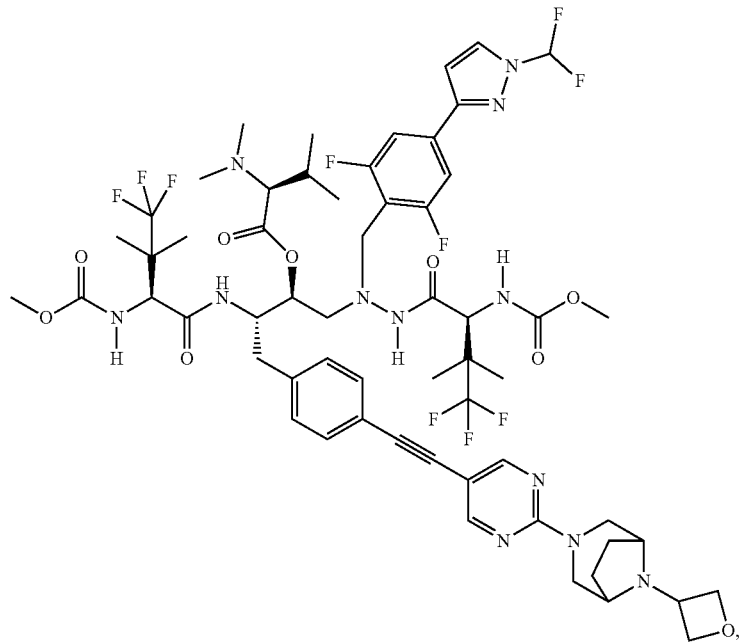 [SMILES: COC(=O)N[C@H](C(=O)N[C@@H](Cc1ccc(C#Cc2cnc(N3CC4CCC(C3)N4C3COC3)nc2)cc1)[C@H](CN(Cc1c(F)cc(-c2ccn(C(F)F)n2)cc1F)NC(=O)[C@@H](NC(=O)OC)C(C)(C)C(F)(F)F)OC(=O)[C@H](C(C)C)N(C)C)C(C)(C)C(F)(F)F]
or a pharmaceutically acceptable salt thereof.
In certain embodiments, the compound is
In certain embodiments, the compound is
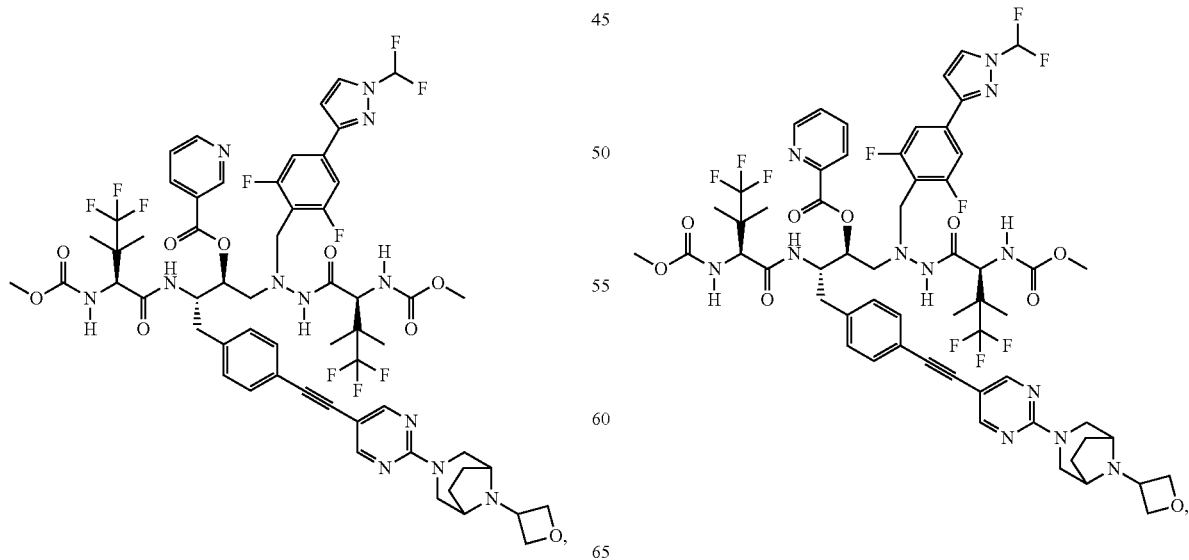
or a pharmaceutically acceptable salt thereof.
or a pharmaceutically acceptable salt thereof.

In certain embodiments, the compound is

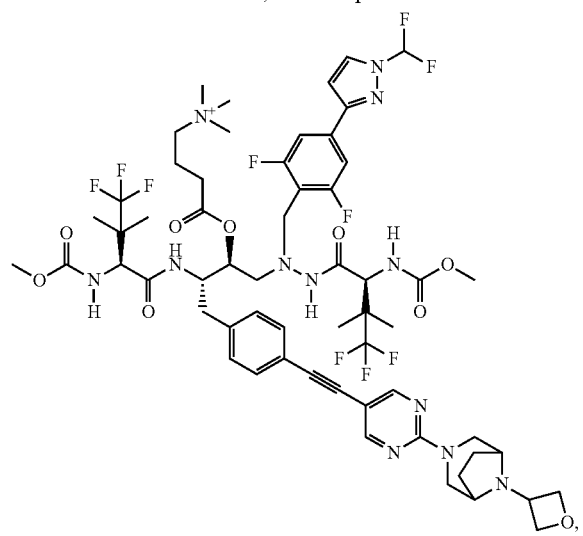

or a pharmaceutically acceptable salt thereof.
In certain embodiments, the compound is

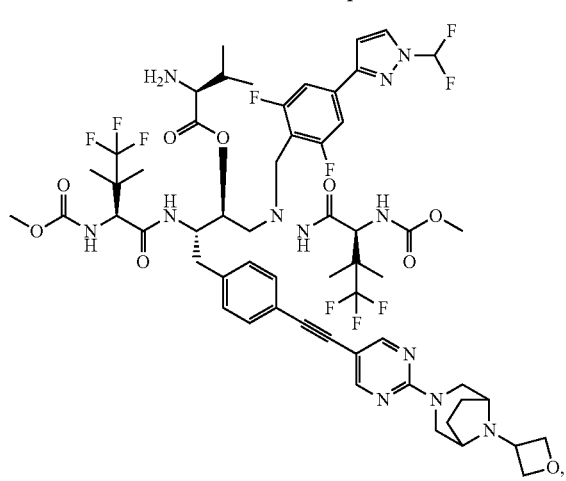

or a pharmaceutically acceptable salt thereof.
In certain embodiments, the compound is

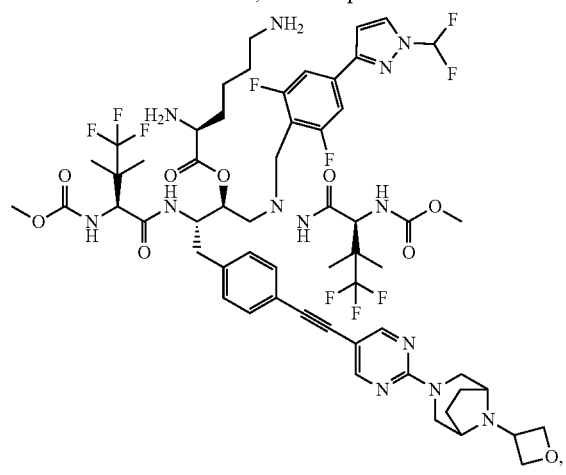

or a pharmaceutically acceptable salt thereof.

In certain embodiments, the compound is

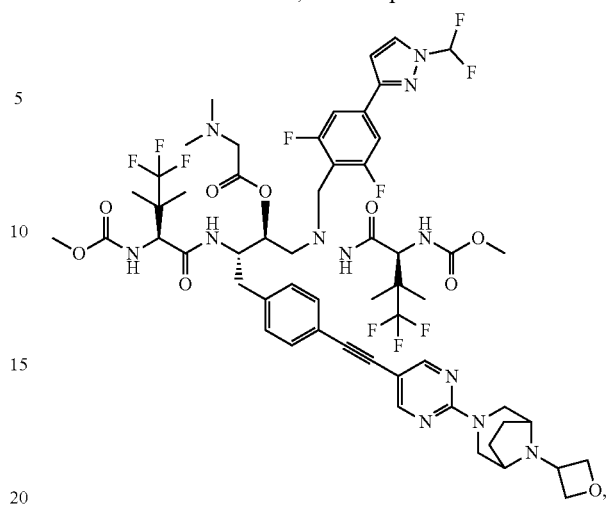

or a pharmaceutically acceptable salt thereof.
In certain embodiments, the compound is

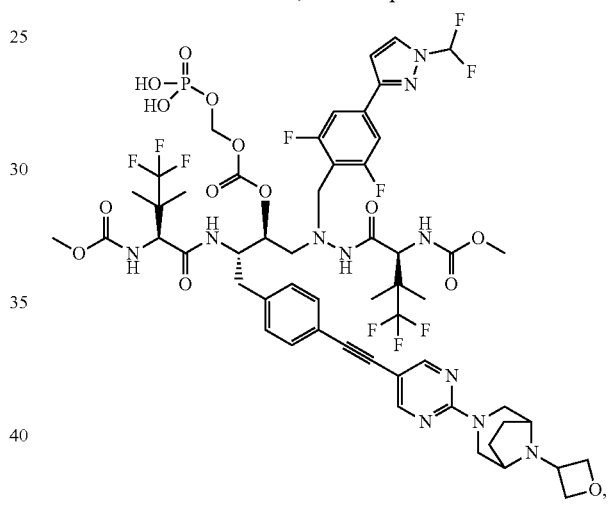

or a pharmaceutically acceptable salt thereof.
In certain embodiments, the compound is

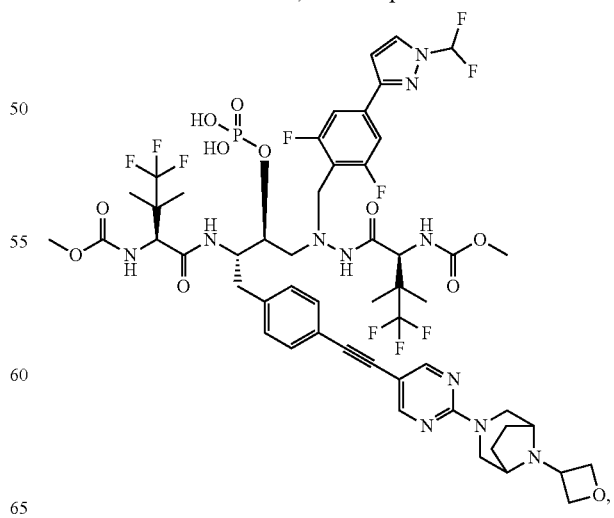

or a pharmaceutically acceptable salt thereof.

In certain embodiments, the compound is

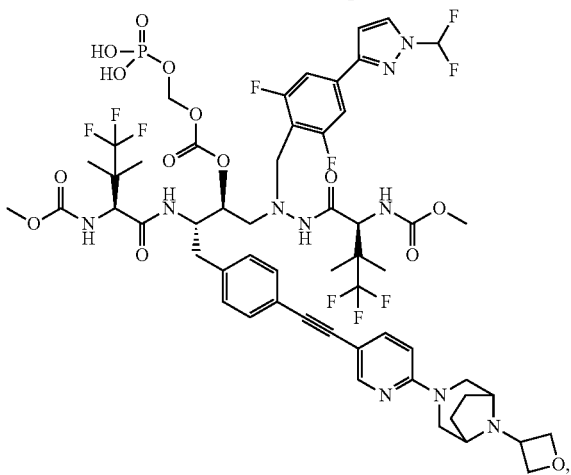 [SMILES: COC(=O)N[C@H](C(=O)N[C@@H](Cc1ccc(C#Cc2ccc(N3CC4CCC(C3)N4C3COC3)nc2)cc1)[C@H](CN(Cc1c(F)cc(-c2ccn(C(F)F)n2)cc1F)NC(=O)[C@@H](NC(=O)OC)C(C)(C)C(F)(F)F)OC(=O)OCOP(=O)(O)O)C(C)(C)C(F)(F)F]

or a pharmaceutically acceptable salt thereof.

In certain embodiments, the compound is

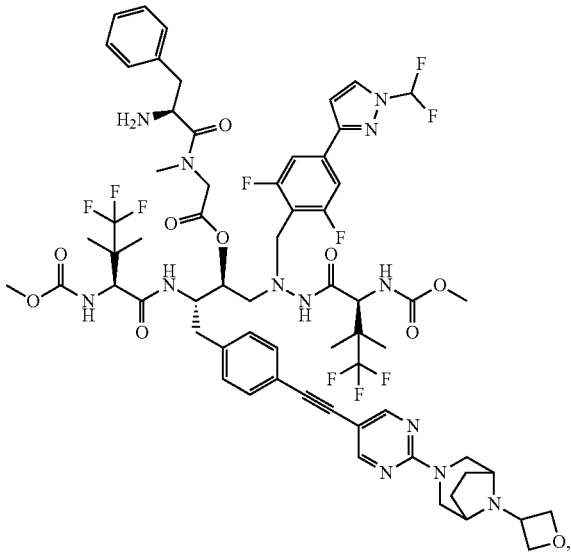 [SMILES: COC(=O)N[C@H](C(=O)N[C@@H](Cc1ccc(C#Cc2cnc(N3CC4CCC(C3)N4C3COC3)nc2)cc1)[C@H](CN(Cc1c(F)cc(-c2ccn(C(F)F)n2)cc1F)NC(=O)[C@@H](NC(=O)OC)C(C)(C)C(F)(F)F)OC(=O)CN(C)C(=O)[C@@H](N)Cc1ccccc1)C(C)(C)C(F)(F)F]

or a pharmaceutically acceptable salt thereof.

In some embodiments, the compounds provided herein are prodrugs of compounds having the formula:

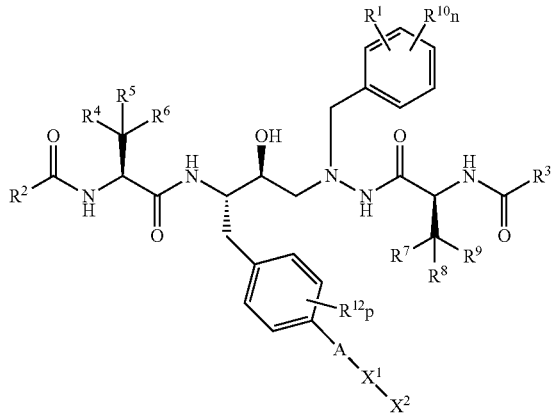

as described in U.S. App. No. 62/455,348.

Methods of Treatment

The pharmaceutical compositions of compounds of Formula (I) and/or Formula (II) may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

In one aspect, the compounds described herein may be administered orally. Oral administration may be via, for example, capsule or enteric coated tablets. In making the pharmaceutical compositions that include at least one compound of Formula (I) and/or Formula (II), or a pharmaceutically acceptable salt, is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound of Formula (I) and/or Formula (II), or a pharmaceutically acceptable salt, can be formulated so as to provide quick, sustained or delayed release of the active ingredient after administration to the subject by employing procedures known in the art. Controlled-release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions may, in some embodiments, be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, for oral administration, each dosage unit contains from about 10 mg to about 1000 mg of a compound described herein, for example from about 50 mg to about 500 mg, for example about 50 mg, about 75 mg, about 100 mg, about 150 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg. In other embodiments, for parenteral administration, each dosage unit contains from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, and the severity of the subject's symptoms.

In certain embodiments, dosage levels may be from 0.1 mg to 100 mg per kilogram of body weight per day, for example from about 1 mg to about 50 mg per kilogram, for example from about 5 mg to about 30 mg per kilogram. Such dosage levels may, in certain instances, be useful in the treatment of the above-indicated conditions. In other embodiments, dosage levels may be from about 10 mg to about 2000 mg per subject per day. The amount of active ingredient that may be combined with the vehicle to produce a single dosage form will vary depending upon the host treated and the particular mode of administration. Dosage unit forms may contain from 1 mg to 1000 mg of an active ingredient.

The compounds disclosed herein, or a pharmaceutically acceptable salt thereof, may be administered to a subject in accordance with an effective dosing regimen for a desired period of time or duration, such as at least about one day, at least about one week, at least about one month, at least about 2 months, at least about 3 months, at least about 4 months, at least about 6 months, or at least about 12 months or longer. In one variation, the compound is administered on a daily or intermittent schedule. In one variation, the compound is administered on a monthly schedule. In one variation, the compound is administered every two months. In one variation, the compound is administered every three months. In one variation, the compound is administered every four months. In one variation, the compound is administered every five months. In one variation, the compound is administered every 6 months.

The dosage or dosing frequency of a compound disclosed herein, or a pharmaceutically acceptable salt thereof, may be adjusted over the course of the treatment, based on the judgment of the administering physician. The compound may be administered to a subject (e.g., a human) in an effective amount. In certain embodiments, the compound is administered once daily.

For preparing solid compositions such as tablets, the principal active ingredient may be mixed with a pharmaceutical excipient to form a solid preformulation composition containing a homogeneous mixture of a compound of Formula (I) and/or Formula (II), or a pharmaceutically acceptable salt, thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

In some embodiments, formulations suitable for parenteral administration (e.g., intramuscular (IM) and subcutaneous (SC) administration) will include one or more excipients. Excipients should be compatible with the other ingredients of the formulation and physiologically innocuous to the recipient thereof. Examples of suitable excipients are well known to the person skilled in the art of parenteral formulation and may be found e.g., in Handbook of Pharmaceutical Excipients (eds. Rowe, Sheskey & Quinn), 6th edition 2009.

In some embodiments, the compounds described herein, or a pharmaceutically acceptable salt thereof, may be administered with a syringe. In some embodiments, the syringe is disposable. In some embodiments, the syringe is reusable. In some embodiments, the syringe is pre-filled with a compound described herein, or a pharmaceutically acceptable salt thereof.

In some embodiments, the compounds described herein, or a pharmaceutically acceptable salt thereof, may be administered with an auto-injector comprising a syringe. In some embodiments, the syringe is disposable. In some embodiments, the syringe is reusable. In some embodiments, the syringe is pre-filled with a compound described herein, or a pharmaceutically acceptable salt thereof.

In certain embodiments, a method of treating or preventing a Retroviridae viral infection (e.g., a human immunodeficiency virus (HIV) infection) comprising administering a therapeutically effective amount of a compound disclosed herein, or a pharmaceutically acceptable salt thereof, to a subject in need thereof, is provided. In certain embodiments, a method of treating a human immunodeficiency virus (HIV) infection comprising administering a therapeutically effective amount of a compound disclosed herein, or a pharmaceutically acceptable salt thereof, to a subject in need thereof, is provided. In certain embodiments, the method comprises administering a compound disclosed herein, or a pharmaceutically acceptable salt thereof, in combination with one, two, three, or four additional therapeutic agents. In certain embodiments, the subject is at risk of contracting the HIV virus, such as a subject who has one or more risk factors known to be associated with contracting the HIV virus. In certain embodiments, the subject may have not previously received antiviral treatment (treatment naïve). In certain embodiments, the subject may have previously received antiviral treatment (treatment experienced). In certain embodiments, the subject may have previously received antiviral treatment and developed resistance to the previously received antiviral treatment.

In certain embodiments, a method of treating or preventing a Retroviridae viral infection (e.g., a human immunodeficiency virus (HIV) infection) comprising administering a therapeutically effective amount of a compound disclosed herein, or a pharmaceutically acceptable salt thereof, to a subject in need thereof, in combination with a therapeutically effective amount of one or more (e.g., one, two, three, or four; or one or two; or one to three; or one to four) additional therapeutic agents selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof, is provided. In certain embodiments, the one or more (e.g., one, two, three, or four; or one or two; or one to three; or one to four) additional therapeutic agents are selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or any combinations thereof. In certain embodiments, the one or more additional therapeutic agent does not include a pharmacokinetic enhancer.

In certain embodiments, a method for inhibiting the replication of the HIV virus, treating AIDS or delaying the onset of AIDS in a subject (e.g., a human), comprising administering a compound disclosed herein, or a pharmaceutically acceptable salt thereof, to the subject is disclosed.

In certain embodiments, a compound of disclosed herein, or a pharmaceutically acceptable salt thereof for use in medical therapy of an HIV infection (e.g., HIV-1 or the replication of the HIV virus (e.g., HIV-1) or AIDS or delaying the onset of AIDS in a subject (e.g., a human)) is disclosed.

In certain embodiments, a compound disclosed herein, or a pharmaceutically acceptable salt thereof for use in the manufacture of a medicament for treating an HIV infection or the replication of the HIV virus or AIDS or delaying the onset of AIDS in a subject (e.g., a human) is disclosed. One embodiment relates to a compound disclosed herein, or a pharmaceutically acceptable salt thereof, for use in the prophylactic or therapeutic treatment of an HIV infection or AIDS or for use in the therapeutic treatment or delaying the onset of AIDS.

In certain embodiments, the use of a compound disclosed herein, or a pharmaceutically acceptable salt thereof, for the manufacture of a medicament for an Retroviridae viral infection (e.g., an HIV infection) in a subject (e.g., a human) is disclosed. In certain embodiments, a compound disclosed herein, or a pharmaceutically acceptable salt thereof, for use in the prophylactic or therapeutic treatment of an HIV infection is disclosed.

In certain embodiments, in the methods of use, the administration is to a subject (e.g., a human) in need of the treatment. In certain embodiments, in the methods of use, the administration is to a subject (e.g., a human) who is at risk of developing AIDS.

The compounds disclosed herein, or a pharmaceutically acceptable salt thereof, for use in therapy is provided. In one embodiment, a compound disclosed herein, or a pharmaceutically acceptable salt thereof, is for use in a method of treating or preventing an HIV infection or the replication of the HIV virus or AIDS or delaying the onset of AIDS in a subject (e.g., a human).

The compounds disclosed herein, or a pharmaceutically acceptable salt thereof, for use in a method of treating or preventing a Retroviridae viral infection (e.g., an HIV infection) in a subject in need thereof is provided. In certain embodiments, a compound disclosed herein, or a pharmaceutically acceptable salt thereof, for use in a method of treating HIV infection in a subject in need thereof is provided. In certain embodiments, the subject in need thereof is a human who has been infected with HIV. In certain embodiments, the subject in need thereof is a human who has been infected with HIV but who has not developed AIDS. In certain embodiments, the subject in need thereof is a subject at risk for developing AIDS. In certain embodiments, the subject in need thereof is a human who has been infected with HIV and who has developed AIDS.

In one embodiment, a compound disclosed herein, or a pharmaceutically acceptable salt thereof, in combination with one or more (e.g., one, two, three, or four; or one or two; or one to three; or one to four) additional therapeutic agents as described herein for use in a method of treating or preventing HIV infection in a subject in need thereof is provided. In one embodiment, the additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof. In certain embodiments, the additional therapeutic agents are selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or any combinations thereof.

In one embodiment, a compound disclosed herein, or a pharmaceutically acceptable salt thereof, in combination with a first additional therapeutic agent selected from the group consisting of tenofovir alafenamide fumarate, tenofovir alafenamide, and tenofovir alafenamide hemifumarate, and a second additional therapeutic agent, wherein the second additional therapeutic agent is emtricitabine, is provided for use in a method of treating or preventing HIV infection in a subject in need thereof. In a particular embodiment, a compound disclosed herein, or a pharmaceutically acceptable salt thereof, in combination with a first additional therapeutic agent selected from the group consisting of tenofovir disoproxil fumarate, tenofovir disoproxil, and tenofovir disoproxil hemifumarate, and a second additional therapeutic agent, wherein the second additional therapeutic agent is emtricitabine, is provided for use in a method of treating or preventing HIV infection in a subject in need thereof.

In a particular embodiment, a compound disclosed herein or a pharmaceutically acceptable salt thereof, are provided for use to prevent HIV infection from taking hold if the individual is exposed to the virus and/or to keep the virus from establishing a permanent infection and/or to prevent the appearance of symptoms of the disease and/or to prevent the virus from reaching detectable levels in the blood, for example for pre-exposure prophylaxis (PrEP) or post-exposure prophylaxis (PEP). Accordingly, in certain embodiments, methods for reducing the risk of acquiring HIV (e.g., HIV-1 and/or HIV-2) are provided. For example, methods for reducing the risk of acquiring HIV (e.g., HIV-1 and/or HIV-2) comprise administration of a compound disclosed herein, or a pharmaceutically acceptable salt thereof. In certain embodiments, methods for reducing the risk of acquiring HIV (e.g., HIV-1 and/or HIV-2) comprise administration of a compound disclosed herein, or a pharmaceutically acceptable salt thereof, in combination with one or more additional therapeutic agents. In certain embodiments, methods for reducing the risk of acquiring HIV (e.g., HIV-1 and/or HIV-2) comprise administration of a pharmaceutical composition comprising a therapeutically effective amount of the compound disclosed herein, or pharmaceutically acceptable salt thereof, and a pharmaceutically acceptable excipient.

In certain embodiments, methods for reducing the risk of acquiring HIV (e.g., HIV-1 and/or HIV-2) comprise administration of a compound of disclosed herein, or a pharmaceutically acceptable salt thereof, in combination with safer sex practices. In certain embodiments, methods for reducing the risk of acquiring HIV (e.g., HIV-1 and/or HIV-2) comprise administration to an individual at risk of acquiring HIV. Examples of individuals at high risk for acquiring HIV include, without limitation, an individual who is at risk of sexual transmission of HIV.

In certain embodiments, the reduction in risk of acquiring HIV is at least about 40%, 50%, 60%, 70%, 80%, 90%, or 95%. In certain embodiments, the reduction in risk of acquiring HIV is at least about 75%. In certain embodiments, the reduction in risk of acquiring HIV is about 80%, 85%, or 90%.

In another embodiment, the use of a compound disclosed herein, or a pharmaceutically acceptable salt thereof, for the manufacture of a medicament for the treatment of an HIV infection in a human being having or at risk of having the infection is disclosed.

Also disclosed herein is a compound disclosed herein, or a pharmaceutically acceptable salt thereof, for use in the therapeutic treatment or delaying the onset of AIDS.

Also disclosed herein is a compound disclosed herein, or a pharmaceutically acceptable salt thereof, for use in the prophylactic or therapeutic treatment of an HIV infection.

In certain embodiments, a compound disclosed herein, or a pharmaceutically acceptable salt thereof can be used as a research tool (e.g., to study the inhibition of HIV reverse transcriptase in a subject or in vitro).

Kits that include a compound of Formula (I), or a pharmaceutically acceptable salt, thereof, and suitable packaging are provided. In one embodiment, a kit further includes instructions for use. In one aspect, a kit includes a compound of Formula (I), or a pharmaceutically acceptable salt thereof, and instructions for use of the compounds in the treatment of the diseases or conditions described herein.

Articles of manufacture that include a compound of Formula (I), or a pharmaceutically acceptable salt thereof, in a suitable container are provided. The container may be a vial, jar, ampoule, preloaded syringe, and intravenous bag.

Administration of HIV Combination Therapy

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and the one or more additional therapeutic agents are both present in the body of the patient. When administered sequentially, the combination may be administered in two or more administrations.

Co-administration includes administration of unit dosages of the compounds disclosed herein before or after administration of unit dosages of one or more additional therapeutic agents. For example, the compound disclosed herein may be administered within seconds, minutes, or hours of the administration of the one or more additional therapeutic agents. In some embodiments, a unit dose of a compound disclosed herein is administered first, followed within seconds or minutes by administration of a unit dose of one or more additional therapeutic agents. Alternatively, a unit dose of one or more additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments, a compound of Formula (I) is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In some embodiments, a compound of Formula (I) is formulated as a tablet, which may optionally contain one or more other compounds useful for treating HIV. In certain embodiments, the tablet can contain another active ingredient for treating HIV, such as compounds that target the HIV capsid, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In some embodiments, the compounds that target the HIV capsid are selected from the group consisting of:

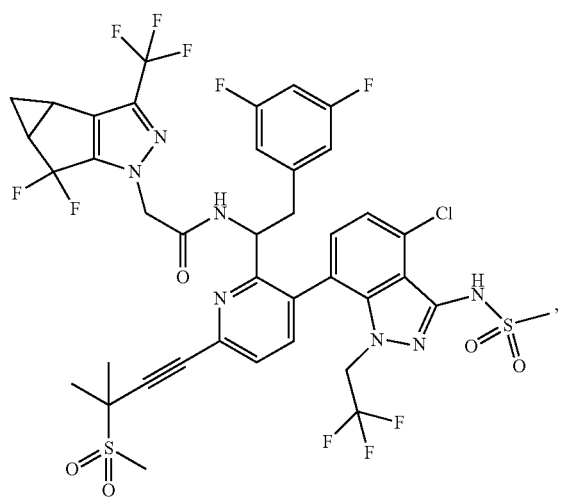

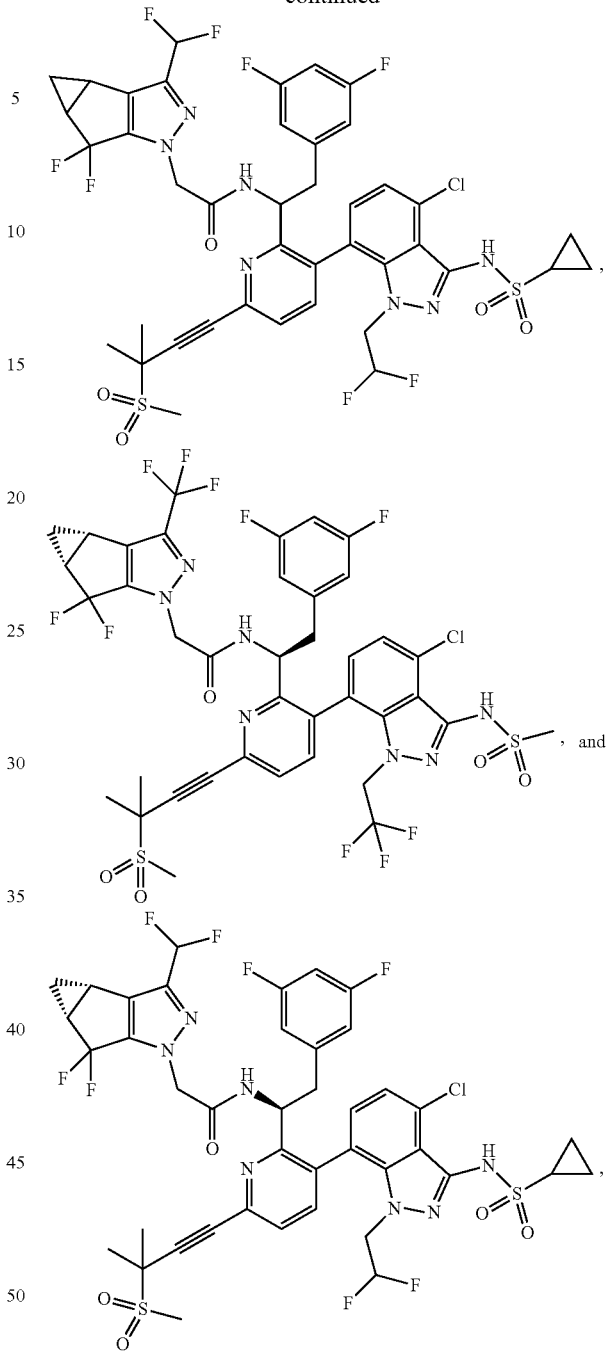

or a pharmaceutically acceptable salt thereof.

In certain embodiments, such tablets are suitable for once daily dosing.

HIV Combination Therapy

In some embodiments, provided herein is a method for preventing or treating an HIV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HIV infection.

In the above embodiments, the additional therapeutic agent may be an anti-HIV agent. For example, in some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent is selected from immunomodulators, immunotherapeutic agents, antibody-drug conjugates, gene modifiers, gene editors (such as CRISPR/Cas9, zinc finger nucleases, homing nucleases, synthetic nucleases, TALENs), and cell therapies such as chimeric antigen receptor T-cell, CAR-T (e.g., YESCARTA® (axicabtagene ciloleucel)), and engineered T cell receptors, TCR-T.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine; Vacc-4x and romidepsin; and APH-0812.

Other HIV Drugs

Examples of other drugs for treating HIV include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, AIC-292, KM-023, and VM-1500.

In some embodiments, examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, AIC-292, KM-023, PC-1005, and VM-1500.

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddl), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include cenicriviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs.

Examples of gp120 inhibitors include Radha-108 (receptol) 3B3-PE38, BanLec, bentonite-based nanomedicine, fostemsavir tromethamine, IQP-0831, and BMS-663068.

Examples of CXCR4 inhibitors include plerixafor, ALT-1188, N15 peptide, and vMIP (Haimipu).

HIV Maturation Inhibitors

Examples of HIV maturation inhibitors include BMS-955176 and GSK-2838232.

Latency Reversing Agents

Examples of latency reversing agents include histone deacetylase (HDAC) inhibitors, proteasome inhibitors such as velcade, protein kinase C (PKC) activators, BET-bromodomain 4 (BRD4) inhibitors, ionomycin, PMA, SAHA (suberanilohydroxamic acid, or suberoyl, anilide, and hydroxamic acid), IL-15, JQ1, disulfram, amphotericin B, and ubiquitin inhibitors such as largazole analogs, and GSK-343.

Examples of HDAC inhibitors include romidepsin, vorinostat, and panobinostat.

Examples of PKC activators include indolactam, prostratin, ingenol B, and DAG-lactones.

HIV Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, AVI-621, AVI-101, AVI-201, AVI-301, and AVI-CAN1-15 series;

In some embodiments, examples of capsid inhibitors include:

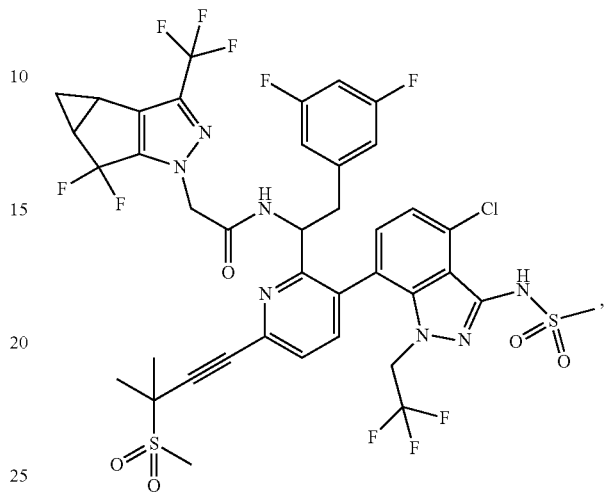

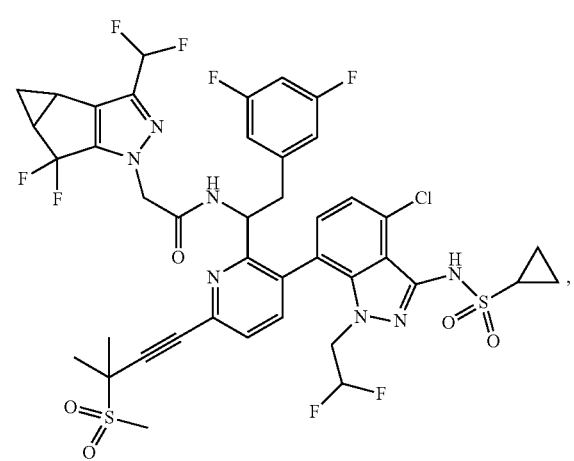

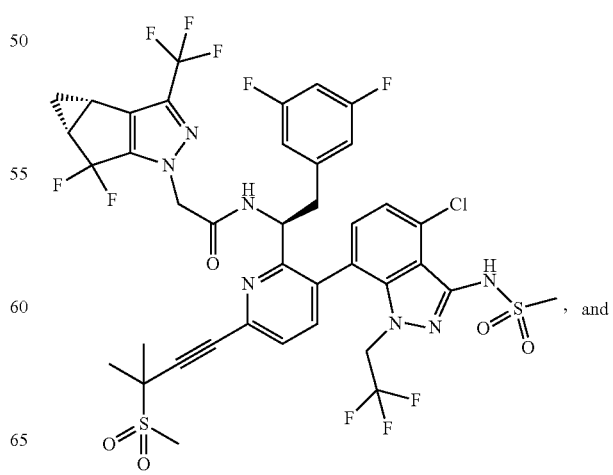

, and

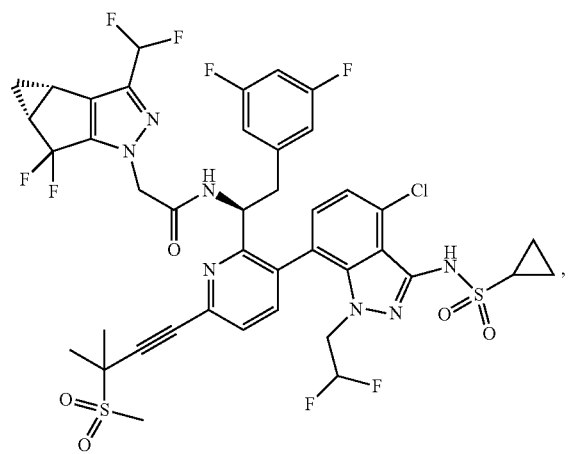 [SMILES: CC(C)(C#Cc1ccc(-c2ccc(Cl)c3c(NS(=O)(=O)C4CC4)nn(CC(F)F)c23)c([C@H](Cc2cc(F)cc(F)c2)NC(=O)Cn2nc(C(F)F)c3c2C(F)(F)[C@@H]2C[C@H]32)n1)S(C)(=O)=O]

or a pharmaceutically acceptable salt thereof.

In some embodiments, the capsid inhibitor is selected from:

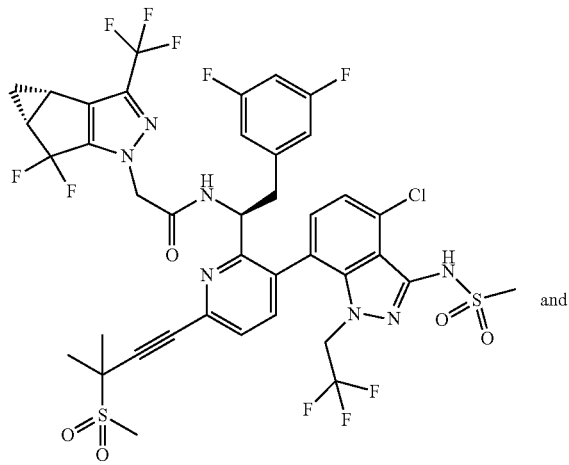

and

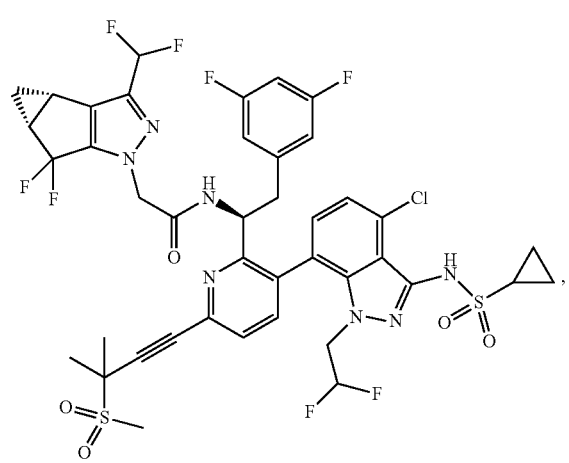 [SMILES: CC(C)(C#Cc1ccc(-c2ccc(Cl)c3c(NS(=O)(=O)C4CC4)nn(CC(F)F)c23)c([C@H](Cc2cc(F)cc(F)c2)NC(=O)Cn2nc(C(F)F)c3c2C(F)(F)[C@@H]2C[C@H]32)n1)S(C)(=O)=O]

or a pharmaceutically acceptable salt thereof.

In some embodiments, the capsid inhibitor is:

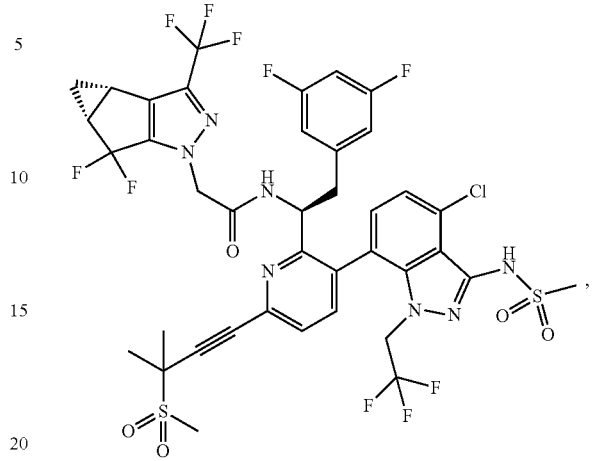

or a pharmaceutically acceptable salt thereof.

In some embodiments, the capsid inhibitor is:

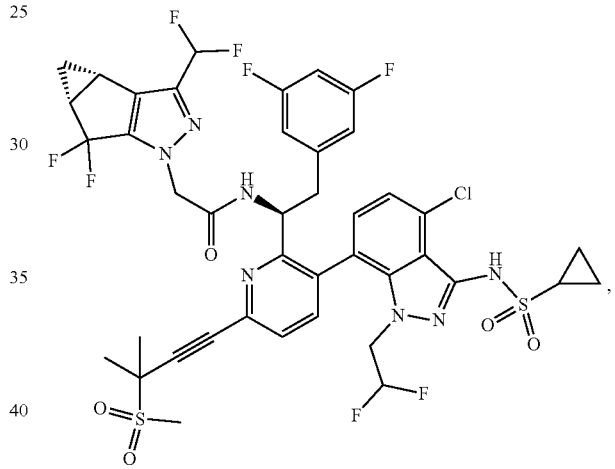

or a pharmaceutically acceptable salt thereof.

Immune-Based Therapies

Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 agonists; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107, interleukin-15/Fc fusion protein, normferon, peginterferon alfa-2a, peginterferon alfa-2b, recombinant interleukin-15, RPI-MN, GS-9620, and IR-103.

In some embodiments, examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 agonists; DermaVir; interleukin-7; plaquenil (hydroxychloroquine); proleukin (aldesleukin, IL-2); interferon alfa;

interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107, interleukin-15/Fc fusion protein, normferon, peginterferon alfa-2a, peginterferon alfa-2b, recombinant interleukin-15, RPI-MN, GS-9620, STING modulators, RIG-I modulators, NOD2 modulators, and IR-103.

Phosphatidylinositol 3-kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4/Beta-7 Antagonists

Examples of Integrin alpha-4/beta-7 antagonists include PTG-100, TRK-170, abrilumab, etrolizumab, carotegrast methyl, and vedolizumab.

HIV Antibodies, Bispecific Antibodies, and "Antibody-Like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bnABs (broadly neutralizing HIV-1 antibodies), BMS-936559, TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, MB-66.

In some embodiments, examples of those targeting HIV in such a manner include bavituximab, UB-421, C2F5, C2G12, C4E10, C2F5+C2G12+C4E10, 3-BNC-117, PGT145, PGT121, MDX010 (ipilimumab), VRCO1, A32, 7B2, 10E8, VRC-07-523, VRC-HIVMAB080-00-AB, MGD-014 and VRC07.

In some embodiments, examples of those targeting HIV in such a manner include bavituximab, UB-421, C2F5, 2G12, C4E10, C2F5+C2G12+C4E10, 8ANC195, 3BNC117, 3BNC60, 10-1074, PGT145, PGT121, PGT-151, PGT-133, MDXO10 (ipilimumab), DH511, N6, VRC01 PGDM1400, A32, 7B2, 10E8, 10E8v4, CAP256-VRC26.25, DRVIA7, VRC-07-523, VRC-HIVMAB080-00-AB, VRC-HIVMAB060-00-AB, MGD-014 and VRC07. Example of HIV bispecific antibodies includes MGD014.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

In some embodiments, examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), Pennvax-G, Pennvax-GP, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV 1-PG9DP, GOVX-B11, GOVX-B21, TVI-HIV-1, Ad-4 (Ad4-env Clade C+Ad4-mGag), EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS 1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine, DNA.HTI and MVA.HTI.

HIV Combination Therapy

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with GS-9131, abacavir sulfate, bictegravir, tenofovir, tenofovir disoproxil, tenofovir disoproxil fumarate, tenofovir disoproxil hemifumarate, tenofovir alafenamide, tenofovir alafenamide hemifumarate, or a combination thereof.

In a particular embodiment, a compound disclosed herein, or a pharmaceutically acceptable salt thereof, is combined with GS-9131, bictegravir, tenofovir, tenofovir disoproxil, tenofovir disoproxil fumarate, tenofovir alafenamide, or tenofovir alafenamide hemifumarate, or a combination thereof.

In a particular embodiment, a compound disclosed herein, or a pharmaceutically acceptable salt thereof, is combined with a first additional therapeutic agent selected from the group consisting of GS-9131, abacavir sulfate, bictegravir, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

In some embodiments, a compound disclosed herein, or a pharmaceutically acceptable salt thereof, is combined with a capsid inhibitor(s) (e.g., capsid polymerization inhibitors and/or capsid disrupting compounds).

In some embodiments, a compound disclosed herein, or a pharmaceutically acceptable salt thereof, is combined with (about 10 to about 1000 mg) of a capsid inhibitor selected from:

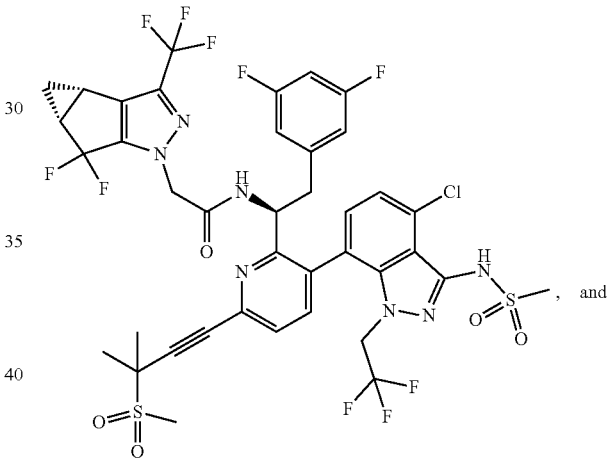

, and

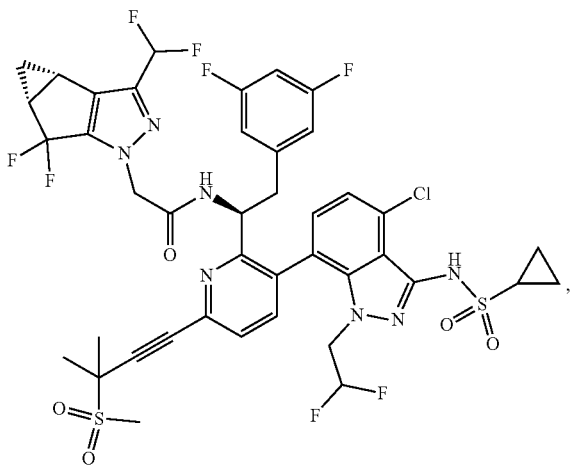 [SMILES: CC(C)(C#Cc1ccc(-c2ccc(Cl)c3c(NS(=O)(=O)C4CC4)nn(CC(F)F)c23)c([C@H](Cc2cc(F)cc(F)c2)NC(=O)Cn2nc(C(F)F)c3c2C(F)(F)[C@@H]2C[C@H]32)n1)S(C)(=O)=O]

, or a pharmaceutically acceptable salt thereof.

In some embodiments, a compound disclosed herein, or a pharmaceutically acceptable salt thereof, is combined with:

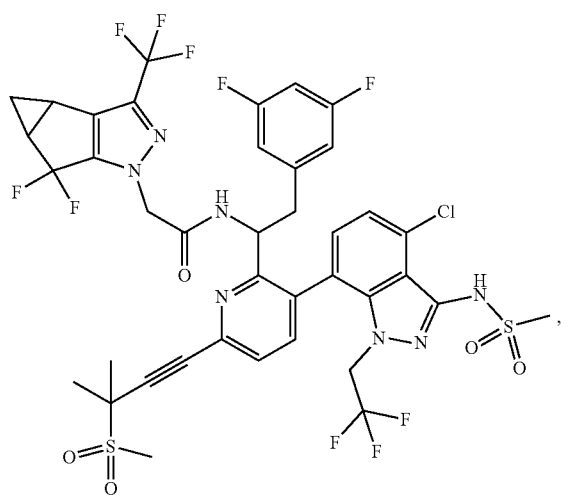
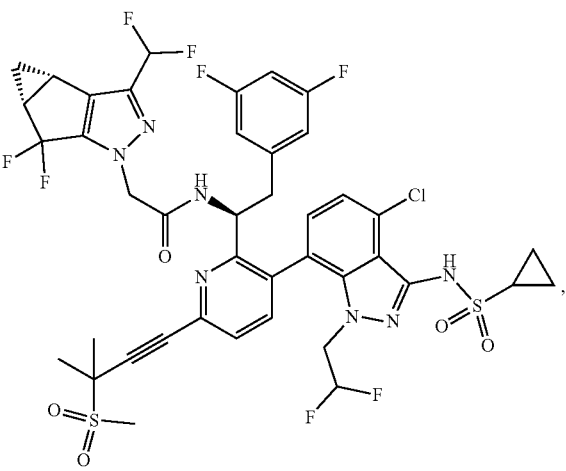 [SMILES: CC(C)(C#Cc1ccc(-c2ccc(Cl)c3c(NS(=O)(=O)C4CC4)nn(CC(F)F)c23)c([C@H](Cc2cc(F)cc(F)c2)NC(=O)Cn2nc(C(F)F)c3c2C(F)(F)[C@@H]2C[C@H]32)n1)S(C)(=O)=O]
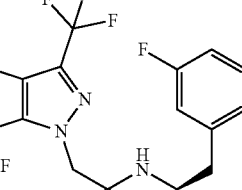
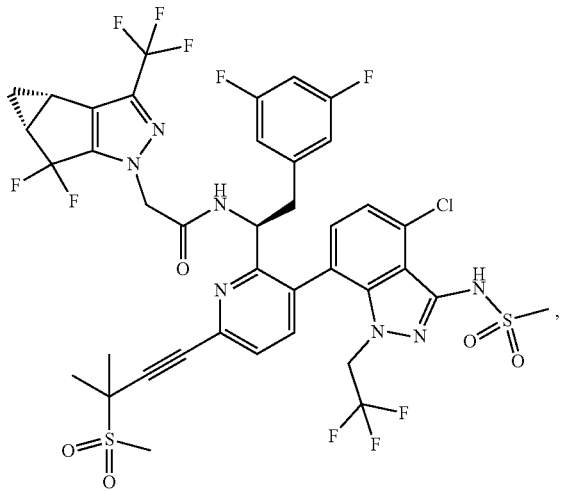 [SMILES: CC(C)(C#Cc1ccc(-c2ccc(Cl)c3c(NS(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]
or a pharmaceutically acceptable salt thereof.
In some embodiments, a compound disclosed herein, or a pharmaceutically acceptable salt thereof, is combined with a capsid inhibitor selected from:
or a pharmaceutically acceptable salt thereof.
In some embodiments, a compound disclosed herein, or a pharmaceutically acceptable salt thereof, is combined with:

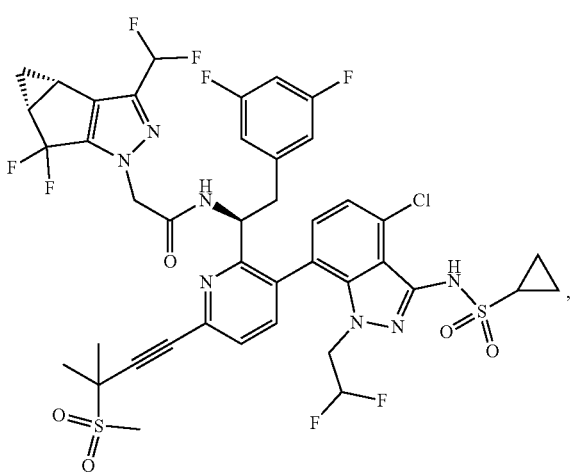 [SMILES: CC(C)(C#Cc1ccc(-c2ccc(Cl)c3c(NS(=O)(=O)C4CC4)nn(CC(F)F)c23)c([C@H](Cc2cc(F)cc(F)c2)NC(=O)Cn2nc(C(F)F)c3c2C(F)(F)[C@@H]2C[C@H]32)n1)S(C)(=O)=O]

or a pharmaceutically acceptable salt thereof.

A compound as disclosed herein (e.g., any compound of Formula (I) and/or Formula (II)) may be combined with one or more additional therapeutic agents in any dosage amount of the compound of Formula (I) and/or Formula (II) (e.g., from 1 mg to 1000 mg of compound).

In some embodiments, a compound disclosed herein, or a pharmaceutically acceptable salt thereof, is combined with 25-75 mg of bictegravir. In some embodiments, a compound disclosed herein, or a pharmaceutically acceptable salt thereof, is combined with 50 mg of bictegravir (equivalent to 52.5 mg of bictegravir sodium). In some embodiments, a compound disclosed herein, or a pharmaceutically acceptable salt thereof, is combined with 10-70 mg of GS-9131. In some embodiments, a compound disclosed herein, or a pharmaceutically acceptable salt thereof, is combined with 60 mg of GS-9131. In certain embodiments, a compound disclosed herein, or a pharmaceutically acceptable salt thereof, is combined with 5-30 mg tenofovir alafenamide, in the form of tenofovir alafenamide fumarate, tenofovir alafenamide hemifumarate, or tenofovir alafenamide, or any salt of solvate form of tenofovir alafenamide. In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein (e.g., a compound of formula (I)) may be combined with the agents provided herein in any dosage amount of the compound (e.g., from 1 mg to 1000 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein (e.g., a compound of formula (I)) may be combined with the agents provided herein in any dosage amount of the compound (e.g., from 1 mg to 1000 mg of compound) the same as if each combination of dosages were specifically and individually listed.

In certain embodiments, a compound disclosed herein, or a pharmaceutically acceptable salt thereof, is combined with a HIV nucleoside or nucleotide inhibitor and an integrase inhibitor. In certain embodiments, a compound disclosed herein, or a pharmaceutically acceptable salt thereof, is combined with GS-9131 and bictegravir.

In one embodiment, kits comprising a compound disclosed herein, or a pharmaceutically acceptable salt thereof, in combination with one or more (e.g., one, two, three, one or two, or one to three) additional therapeutic agents are provided.

Birth Control (Contraceptive) Combination Therapy

Therapeutic agents used for birth control (contraceptive) include cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

Gene Therapy and Cell Therapy

Gene Therapy and Cell Therapy including the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Examples of dendritic cell therapy include AGS-004.

Gene Editors

The genome editing system is selected from the group consisting of: a CRISPR/Cas9 system, a zinc finger nuclease system, a TALEN system, a homing endonucleases system, and a meganuclease system.

Examples of HIV targeting CRISPR/Cas9 systems include EBT101.

CAR-T Cell Therapy

A population of immune effector cells engineered to express a chimeric antigen receptor (CAR), wherein the CAR comprises an HIV antigen-binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T cell or an NK cell. In some embodiments, the T cell is a CD4+ T cell, a CD8+ T cell, or a combination thereof.

Examples of HIV CAR-T include VC-CAR-T.

TCR-T Cell Therapy

TCR-T cells are engineered to target HIV derived peptides present on the surface of virus-infected cells.

Certain embodiments of the methods disclosed herein exclude the administration of a pharmacokinetic enhancer. For example, in certain methods disclosed herein, the subject is not administered a pharmacokinetic enhancer, such as cobicistat or ritonavir, during the treatment with a compound disclosed herein, or a pharmaceutically acceptable salt thereof. Thus, in certain embodiments, a method of treating or preventing a human immunodeficiency virus (HIV) infection is provided, comprising administering a therapeutically effective amount of a compound disclosed herein, or a pharmaceutically acceptable salt thereof, to a subject in need thereof, wherein the treatment does not comprise administration of a pharmacokinetic enhancer. In certain embodiments, a method of treating or preventing a human immunodeficiency virus (HIV) infection is provided, comprising administering a therapeutically effective amount of a compound disclosed herein, or a pharmaceutically acceptable salt thereof, once daily to a subject in need thereof, wherein the treatment does not comprise administration of a pharmacokinetic enhancer.

The present disclosure also provides all of the P, S, A and I intermediates described in the Examples section below.

EXAMPLES

Methods for preparing the novel compounds described herein will be apparent to those of skill in the art with suitable procedures being described, for example, in the reaction schemes and examples below.

Section 1 shows preparation of Intermediates P (Section 1.1), Intermediates S (Section 1.2), Intermediates A (Section 1.3), and Intermediates I (Section 1.4), and Compound D as used herein. Section 2 provides example syntheses and compounds. Section 3 shows biological activity.

1.1 Synthesis of Intermediates P

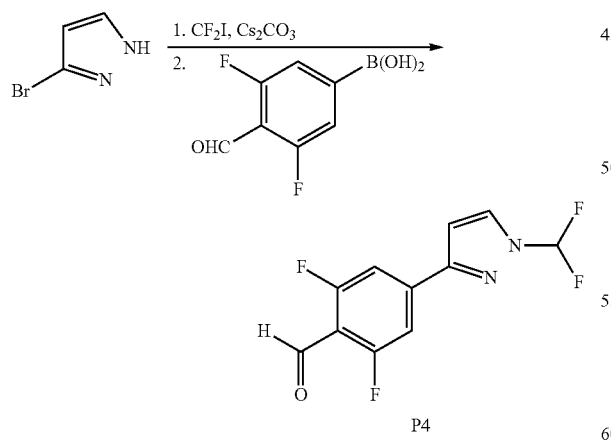

Synthesis of 4-(1-(difluoromethyl)-1H-pyrazol-3-yl)-2, 6-difluorobenzaldehyde (P4)

In a 150 mL pressure vessel, a suspension of 3-bromo-1H-pyrazole (8 g, 54.43 mmol) cesium carbonate (53.2 g, 163.29 mmol), and difluoroiodomethane (10% wt. in THF, 200 mL, 106.23 mmol) was heated at 45° C. overnight. The reaction mixture was cooled to room temperature and then filtered through Celite. The filter cake was washed with Et$_2$O (3×150 mL). The filtrate was washed with brine, dried over sodium sulfate and carefully concentrated (20° C. bath, 100 mb vacuum) to give ~17 g of a 1.5:1 ratio of regioisomers and solvent still present. This crude material was combined with 3,5-difluoro-4-formylphenylboronic acid (12.65 g, 68.03 mmol), palladium acetate (0.31 g, 1.381 mmol), butyl di-1-adamantylphosphine (1.171 g, 3.265 mmol) and potassium carbonate (22.80 g, 164.96 mmol) in dioxane (150 mL) and water (50 mL) the mixture was degassed for 10 min with argon, then heated at 100° C. overnight. The reaction mixture was cooled to room temperature, concentrated under reduce pressure, the residue was diluted with EtOAc and washed with brine 2× then dried over Na$_2$SO$_4$, filtered and concentrated under reduced pressure. The crude residue was purified by silica column chromatography (5% to 15% EtOAc/Hex). Mixed fractions were recrystallized (5:1 Hex/EtOAc) and the combined pure product afforded P4. $^1$H NMR (400 MHz, Chloroform-d) δ 10.35 (d, J=1.0 Hz, 1H), 7.92 (d, J=2.8 Hz, 1H), 7.46 (d, J=9.6 Hz, 2H), 7.24 (t, J=60.5 Hz, 1H), 6.80 (d, J=2.8 Hz, 1H).

1.2 Synthesis of Intermediates S

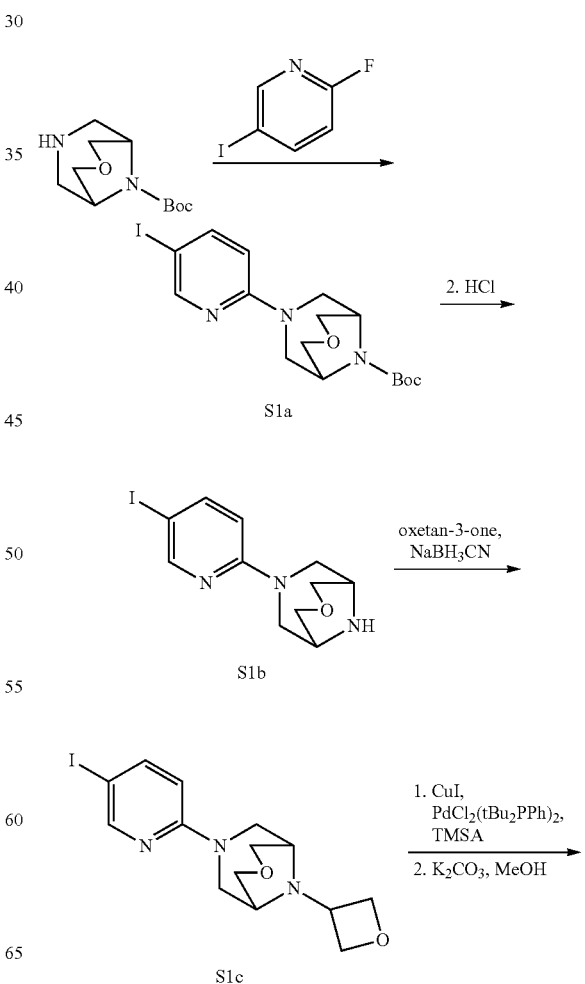

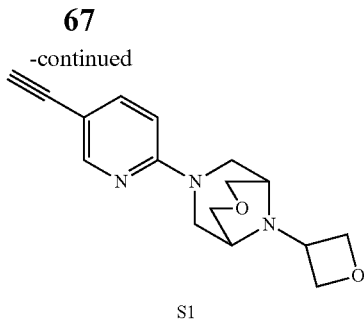

S1

Synthesis of tert-butyl 7-(5-iodopyridin-2-yl)-3-oxa-7,9-diazabicyclo[3.3.1]nonane-9-carboxylate (S1a)

A solution of tert-butyl 3-oxa-7,9-diazabicyclo[3.3.1]nonane-9-carboxylate (1 g, 4.38 mmol) 2-fluoro-5-iodopyridine (1.12 g, 5.04 mmol), and sodium carbonate (0.84 g, 7.88 mmol) in 1-methyl-2-pyrrolidinone (4 mL) was heated at 85° C. overnight. The mixture was cooled to room temperature, diluted with water and extracted into DCM. The organic extract was dried over $Na_2SO_4$ filtered and concentrated under reduced pressure. The residue was purified by silica chromatography to yield S1a (1.57 g, 62.3%). MS (ESI) m/z 431.9 [M+H]$^+$. $^1$H NMR (400 MHz, Chloroform-d) δ 8.30 (dd, J=2.4, 0.7 Hz, 1H), 7.66 (dd, J=9.0, 2.3 Hz, 1H), 6.44 (d, J=9.0 Hz, 1H), 4.25 (d, J=12.7 Hz, 1H), 4.21-4.00 (m, 3H), 3.97-3.86 (m, 2H), 3.80 (t, J=11.9 Hz, 2H), 3.26 (t, J=15.1 Hz, 2H), 1.48 (s, 9H).

Synthesis of 7-(5-iodopyridin-2-yl)-3-oxa-7,9-diazabicyclo[3.3.1]nonane (S1b)

To a solution of S1a (1.57 g, 0.004 mol) in DCM (15 mL) in a water bath at room temperature was added was added HCl (4.0M in dioxane, 4.6 mL). The reaction was stirred at room temperature overnight. The reaction was concentrated to dryness. MS (ESI) m/z 332.0 [M+H]$^+$. $^1$H NMR (400 MHz, Methanol-d4) δ 8.26 (dd, J=2.2, 0.7 Hz, 1H), 8.22 (ddd, J=9.5, 2.2, 1.0 Hz, 1H), 7.27 (d, J=9.7 Hz, 1H), 4.60 (d, J=14.4 Hz, 2H), 4.21 (dt, J=13.5, 0.9 Hz, 2H), 4.08 (dt, J=13.3, 2.4 Hz, 2H), 3.88 (d, J=14.6 Hz, 2H), 3.81 (s, 2H).

Synthesis of 7-(5-iodopyridin-2-yl)-9-(oxetan-3-yl)-3-oxa-7,9-diazabicyclo[3.3.1]nonane (S1c)

To S1b (0.62 g, 8.62 mmol) suspended in NMP (6 mL), was added Et$_3$N (0.12 mL, 0.8 mmol), oxetan-3-one (0.51 mL, 8.5 mmol), and sodium cyanoborohydride (2.62 g, 41.72 mmol) was added and the reaction mixture was stirred for 5 min then more Et$_3$N (0.18 mL, 0.1 mmol), stirred at room temperature for 4 h, then warmed up to 30° C. After 2 h the reaction was cooled to room temperature, diluted with EtOAc and washed with brine. The organic extract was dried over Na$_2$SO$_4$ filtered and concentrated under reduced pressure to afford S1c (0.84 g, 95%). MS (ESI) m/z 388.1 [M+H]$^+$.

Synthesis of 7-(5-ethynylpyridin-2-yl)-9-(oxetan-3-yl)-3-oxa-7,9-diazabicyclo[3.3.1]nonane (S1)

A solution of S1c (0.84 g, 0 mol), CuI (24.73 mg, 0.13 mmol) PdCl$_2$(tBu$_2$PPh)$_2$ (45.7 mg, 0.06 mmol), trimethylsilylacetylene (0.92 mL, 0.01 mol), in a 3:1 mixture of CH$_3$CN (9 mL)/Et$_3$N (3 mL) was degassed with Argon for 10 min. The reaction mixture was heated to 40° C. for 90 min. The reaction was diluted with EtOAc and washed with NaHCO$_3$ solution and dried over Na$_2$SO$_4$, filtered and concentrated under reduced pressure. The crude residue was dissolved in MeOH (5 mL) and potassium carbonate (0.45 g, 3.0 mmol) were added, the mixture was stirred at room temperature. After 15 min the reaction was concentrated to dryness, then diluted with DCM and washed with brine. The organic extract was dried over Na$_2$SO$_4$ to give S1 (300 mg 48%). MS (ESI) m/z 286.2 [M+H]$^+$. $^1$H NMR (400 MHz, Chloroform-d) δ 8.17 (dd, J=2.3, 0.8 Hz, 1H), 7.40 (dd, J=8.9, 2.3 Hz, 1H), 6.35 (dd, J=8.9, 0.8 Hz, 1H), 4.55 (t, J=6.2 Hz, 2H), 4.42 (t, J=5.9 Hz, 2H), 4.25 (p, J=6.2 Hz, 1H), 3.84 (dt, J=11.3, 2.2 Hz, 2H), 3.78 (d, J=12.9 Hz, 2H), 3.71 (dt, J=11.5, 0.9 Hz, 2H), 3.24 (ddd, J=12.9, 4.9, 2.0 Hz, 2H), 2.92 (s, 1H), 2.65-2.52 (m, 2H).

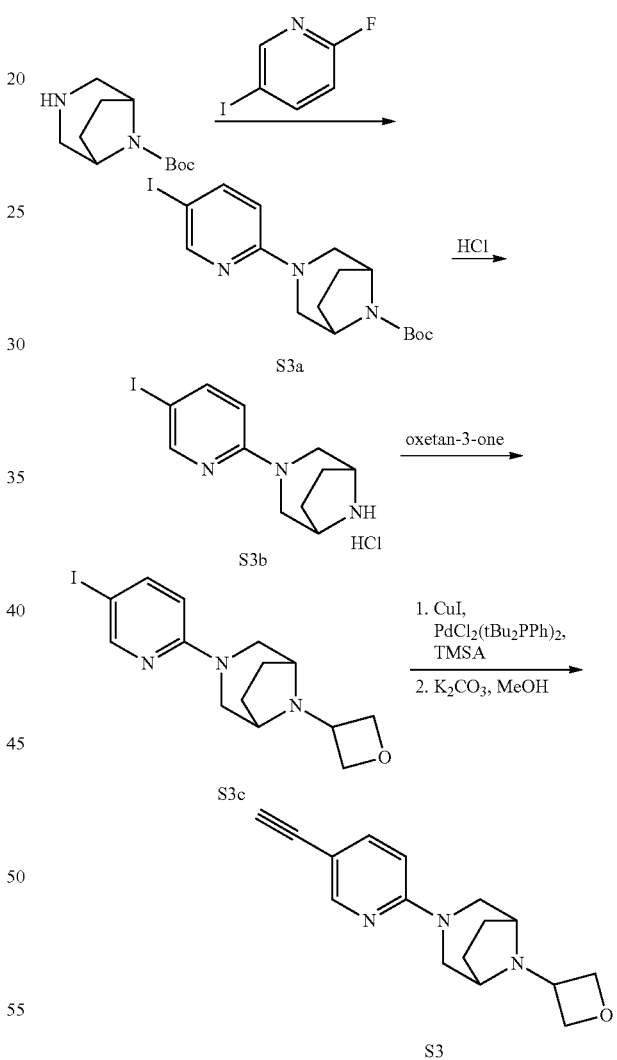

Synthesis of tert-butyl 3-(5-iodopyridin-2-yl)-3,8-diazabicyclo[3.2.1]octane-8-carboxylate (S3a)

The title compound S3a was prepared according to the method presented for the synthesis of compound S1a but instead utilizing tert-butyl 3,8-diazabicyclo[3.2.1]octane-8-carboxylate. MS (ESI) m/z 415.8 [M+H]$^+$. $^1$H NMR (400 MHz, Chloroform-d) δ 8.36-8.26 (m, 1H), 7.65 (dd, J=9.0, 2.4 Hz, 1H), 6.40 (d, J=9.0 Hz, 1H), 4.33 (s, 2H), 3.82 (d, J=40.5 Hz, 2H), 3.05 (s, 2H), 1.94 (dd, J=8.7, 4.6 Hz, 2H), 1.73 (d, J=7.3 Hz, 2H), 1.47 (s, 9H).

Synthesis of 3-(5-iodopyridin-2-yl)-3,8-diazabicyclo[3.2.1]octane hydrochloride (S3b)

The title compound S3b was prepared according to the method presented for the synthesis of compound S1b but instead utilizing S3a. MS (ESI) m/z 316.1 [M+H]⁺.

Synthesis of 3-(5-iodopyridin-2-yl)-8-(oxetan-3-yl)-3,8 diazabicyclo[3.2.1]octane (S3c)

The title compound S3c was prepared according to the method presented for the synthesis of compound S1c but instead utilizing S3b. MS (ESI) m/z 372.1 [M+H]⁺. ¹H NMR (400 MHz, Chloroform-d) δ 8.22 (d, J=2.3 Hz, 1H), 7.57 (dd, J=8.9, 2.4 Hz, 1H), 6.30 (d, J=9.0 Hz, 1H), 4.65 (t, J=6.3 Hz, 2H), 4.52 (t, J=5.8 Hz, 2H), 3.70 (dd, J=11.8, 2.4 Hz, 2H), 3.23-3.08 (m, 2H), 3.04 (dd, J=11.7, 2.2 Hz, 2H), 1.87-1.70 (m, 2H), 1.63 (d, J=7.5 Hz, 2H).

Synthesis of 3-(5-ethynylpyridin-2-yl)-8-(oxetan-3-yl)-3,8-diazabicyclo[3.2.1]octane (S3)

The title compound S3 was prepared according to the method presented for the synthesis of compound S1c but instead utilizing S3c. MS (ESI) m/z 244.0 [M+H]⁺. ¹H NMR (400 MHz, Methanol-d4) δ 8.16 (d, J=2.3 Hz, 1H), 7.55 (dd, J=8.9, 2.3 Hz, 1H), 6.66 (d, J=8.9 Hz, 1H), 4.76 (t, J=6.4 Hz, 3H), 4.57 (t, J=5.8 Hz, 3H), 3.88 (dd, J=12.2, 2.4 Hz, 3H), 3.78 (ddd, J=11.9, 6.5, 5.4 Hz, 1H), 3.43 (s, 1H), 3.29 (dd, J=6.9, 1.7 Hz, 4H), 3.10 (dd, J=11.9, 2.2 Hz, 3H), 1.93 (dd, J=8.7, 4.4 Hz, 2H), 1.68 (t, J=6.9 Hz, 2H).

Synthesis of 3-(5-iodopyrimidin-2-yl)-8-(oxetan-3-yl)-3,8-diazabicyclo[3.2.1]octane (S7a)

The title compound S7a was prepared according to the method presented for the synthesis of compound S1c but instead utilizing 2-chloro-5-iodopyrimidine. MS (ESI) m/z 373.0 [M+H]⁺. ¹H NMR (400 MHz, Chloroform-d) δ 8.37 (s, 2H), 4.71 (t, J=6.3 Hz, 2H), 4.59 (s, 2H), 4.21 (d, J=12.4 Hz, 2H), 3.68 (s, 1H), 3.15 (s, 4H), 1.83 (s, 2H), 1.62 (s, 2H).

Synthesis of 3-(5-ethynylpyrimidin-2-yl)-8-(oxetan-3-yl)-3,8-diazabicyclo[3.2.1]octane (S7)

The title compound S7 was prepared according to the method presented for the synthesis of compound S1 but instead utilizing S7a. MS (ESI) m/z 271.1[M+H]⁺. ¹H NMR (400 MHz, Chloroform-d) δ 8.38 (s, 1H), 4.71 (t, J=6.2 Hz, 2H), 4.67-4.46 (m, 2H), 4.40-4.24 (m, 2H), 3.69 (p, J=6.1 Hz, 1H), 3.29-3.10 (m, 4H), 1.89-1.73 (m, 2H), 1.74-1.47 (m, 2H).

1.3 Synthesis of Intermediates A

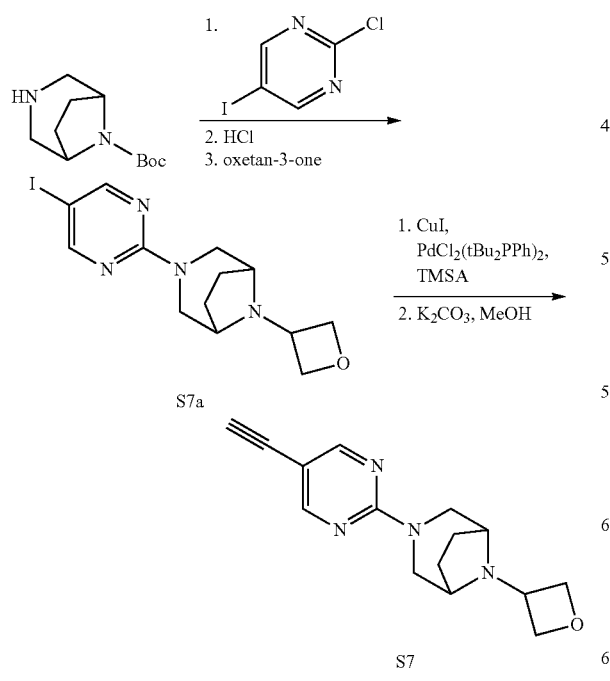

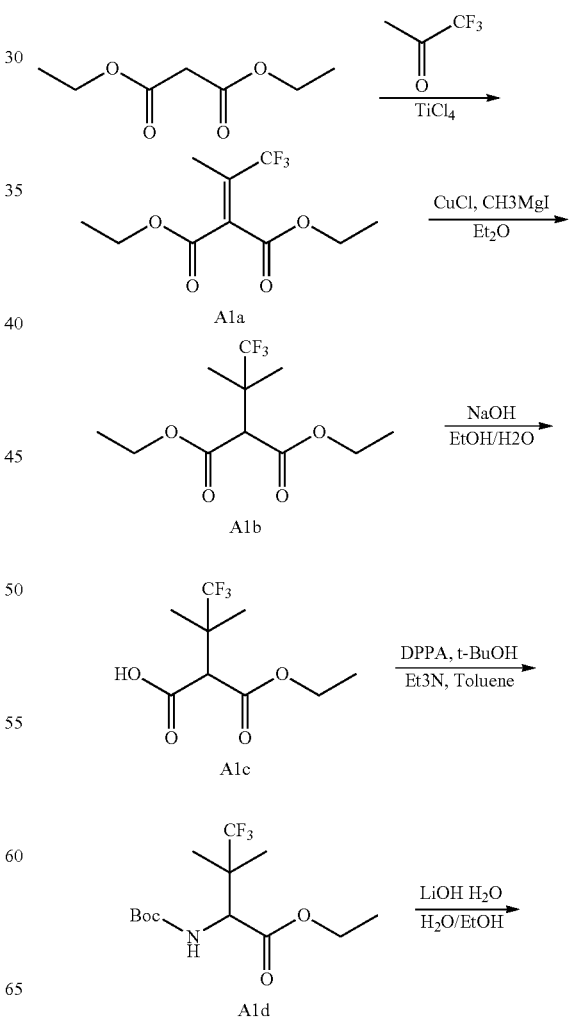

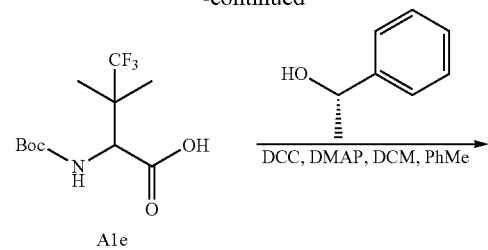

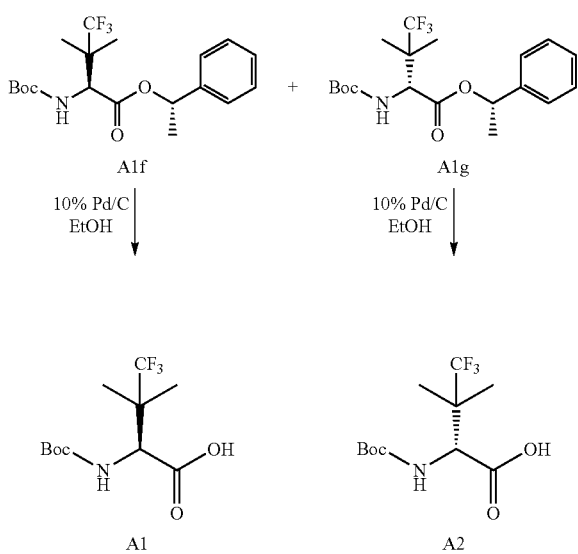

Synthesis of ethyl 2-(1,1,1-trifluoropropan-2-ylidene)malonate (A1a)

A mixture of dry THF (5000 mL) and dry CCl$_4$ (600 mL) was cooled to 0° C. and treated with TiCl$_4$ (275 mL, 2.50 mol). The resulting yellow suspension was stirred at 0° C. for 5 min, treated sequentially with 1,1,1-trifluoropropan-2-one (140 g, 1.25 mol) and freshly distilled diethyl malonate (200 g, 1.25 mol), and then stirred at 0° C. for 0.5 hour. The reaction mixture was then treated with a solution of dry pyridine (400 mL) in dry THF (500 mL) and stirred at 0° C. for 1 hour and then at room temperature overnight. The reaction mixture was quenched with water and extracted with EtOAc (1 L×3). The combined organic extracts were washed with brine and saturated NaHCO$_3$, dried (MgSO$_4$), filtered, and concentrated under reduced pressure. The residue was purified by column chromatography on silica gel (EtOAc:PE=1:50) to give the title compound A1a (298 g, 94%). $^1$H NMR (CDCl$_3$, 300 MHz): δ 4.32-4.23 (m, 4H), 2.20 (s, 3H), 1.33-1.24 (m, 6H).

Synthesis of diethyl 2-(1,1,1-trifluoro-2-methylpropan-2-yl)malonate (A1b)

A mixture of methylmagnesium iodide (3.0 mol/L in ether, 10 L, 30 mol) and cuprous chloride (3.5 g, 35 mmol) was stirred at 0° C., treated with a solution of compound A1a (178 g, 700 mmol) in dry Et$_2$O (1000 mL) over 30 min, and stirred at RT for 30 min and then quenched with the dropwise addition of ice-water (1.5 L) followed by HCl aq (3 mol/L, 350 mL). The mixture was then extracted with Et$_2$O (1 L×3). The combined organic extracts were washed with NaOH aq (1 N), water and brine, dried (MgSO$_4$), filtered and evaporated. The residue crude compound A1b (90 g, 47%) was used directly in the next step without further purification. MS (ESI) m/z 271 [M+H]$^+$. $^1$H NMR (CDCl$_3$, 300 MHz): δ 4.22-4.15 (m, 4H), 3.64 (s, 1H), 1.38 (s, 6H), 1.30-1.24 (m, 6H).

Synthesis of 2-(ethoxycarbonyl)-4,4,4-trifluoro-3,3-dimethylbutanoic acid (A1c)

A solution of compound A1b (144 g, 0.53 mol) in a mixture of EtOH (500 mL) and water (500 mL) was treated with NaOH (19 g, 0.48 mmol) in portions at 0° C., and stirred at room temperature for 5 hours. The reaction mixture was evaporated to a syrup, dissolved in water (1 L), and extracted with Et$_2$O (2 L). The aqueous phase was acidified with 1 M HCl to pH=2.0 and extracted with EtOAc (1 L×3). The combined organic extracts were washed with brine, dried (MgSO$_4$), filtered and evaporated to give the title compound A1c (107 g, 84%), which was used directly in the next step without further purification. MS (ESI) m/z 241 [M+H]$^+$. $^1$H NMR (CDCl$_3$, 300 MHz): δ 4.23 (q, J=5.4 Hz, 2H), 3.69 (s, 1H), 1.40 (s, 6H), 1.27 (t, J=5.1 Hz, 3H).

Synthesis of ethyl 2-((tert-butoxycarbonyl)amino)-4,4,4-trifluoro-3,3-dimethylbutanoate (A1d)

A solution of compound A1c (110 g, 454 mmol) in dry toluene (600 mL) was treated with triethylamine (45.4 g, 454 mmol) and diphenylphosphoryl azide (125 g, 454 mmol), the reaction mixture was refluxed for 1 hour, then t-BuOH (46.7 g, 630 mmol) was added in. The mixture was refluxed overnight. Cooled to RT, the solvent was evaporated and the residue was dissolved in EtOAc (1 L), washed with 5% NaHCO$_3$ solution, dried (MgSO$_4$), filtered and evaporated. The remainder was purified by column chromatography on silica gel (EtOAc:PE=1:9) to give crude compound A1d (60 g, 46%), which was used directly in next step without further purification. MS (ESI) m/z 313 [M+H]$^+$. $^1$H NMR (CDCl$_3$, 300 MHz): δ 5.20 (d, J=5.7 Hz, 1H), 4.44 (d, J=10.8 Hz, 1H), 4.25-4.16 (m, 2H), 1.44 (s, 9H), 1.39-1.26 (m, 6H), 1.19 (m, 3H).

Synthesis of 2-((tert-butoxycarbonyl)amino)-4,4,4-trifluoro-3,3-dimethylbutanoic acid (A1e)

To a solution of compound A1d (380 g, 1214 mmol) in water (2000 mL) and ethanol (2000 mL) was added LiOH.H$_2$O (134 g, 3166 mmol). The mixture was stirred overnight, then diluted with EtOAc, acidified to pH=2, and extracted with EtOAc (2000 mL×3). The organic layer was washed with brine, dried over MgSO$_4$, and concentrated to afford compound A1e (300 g, 86%) as a white solid. $^1$H NMR (CDCl$_3$, 300 MHz): δ 5.20 (d, J=10.2 Hz, 1H), 4.48 (d, J=10.2 Hz, 1H), 1.45 (s, 9H), 1.30 (s, 3H), 1.25 (s, 3H).

Synthesis of (S)—(S)-1-phenylethyl 2-((tert-butoxycarbonyl)amino)-4,4,4-trifluoro-3,3-dimethylbutanoate (A1g)

The acid A1e (300 g, 1052 mmol) and (N,N'-dicyclohexylcarbodiimide (325 g, 1578 mmol) were combined in DCM (250 mL) and PhMe (4000 mL). The solution was cooled to 0° C., and then 4-(dimethylamino)pyridine (128 g, 1052 mmol) and (S)-(−)-1-Phenylethanol (128 g, 1052 mmol) were added and the mixture was allowed to warm to room temperature and stirred overnight. The mixture was concentrated, and then the residue was taken up in EtOAc/water, and extracted with EtOAc (2000 mL×3). The combined organic layers were washed with brine, dried over MgSO$_4$ and concentrated. The crude concentrate was purified by column chromatography on silica gel (0-8% EtOAc/PE) to get two compounds. The mixture of diastereomers was separated by chiral column (IA; heptane; IPA (70:30)). The first peak was collected to get the compound A1f (105 g, 25%) and the second peak was collected to get the compound A1g (80 g, 19%). $^1$H NMR of compound A1f (CDCl$_3$, 300 MHz): δ 7.38-7.31 (m, 5H), 5.90 (q, J=6.3 Hz, 1H), 5.18 (d, J=9.6 Hz, 1H), 4.48 (d, J=9.6 Hz, 1H), 1.56 (d, J=6.9 Hz, 3H), 1.44 (s, 9H), 1.31 (s, 3H), 1.21 (s, 3H). $^1$H NMR of compound A1g (CDCl$_3$, 300 MHz): δ 7.34-7.30 (m, 5H), 5.92 (q, J=6.3 Hz, 1H), 5.20 (d, J=9.6 Hz, 1H), 4.44 (d, J=9.6 Hz, 1H), 1.58 (d, J=6.9 Hz, 3H), 1.45 (s, 9H), 1.21 (s, 3H), 1.11 (s, 3H).

Synthesis of (S)-2-((tert-butoxycarbonyl)amino)-4,4,4-trifluoro-3,3-dimethylbutanoic acid (A1)

The compound A1f (83 g, 214 mmol) was diluted with ethanol (1000 mL). Pd/C (10%, wet, 17 g) was added and the atmosphere was replaced with hydrogen. After stirring for 5 hours, the mixture was filtered over celite, washed with EtOAc and the filtrate was concentrated to get product A1 (50 g, 82%). MS (ESI) m/z 186 [M-Boc+1]$^+$. $^1$H NMR (300 MHz, DMSO-d6): δ 12.98 (br s, 1H), 7.18 (d, J=9.6 Hz, 1H), 4.27 (d, J=9.9 Hz, 1H), 1.36 (s, 9H), 1.14 (s, 6H).

Synthesis of (R)-2-((tert-butoxycarbonyl)amino)-4,4,4-trifluoro-3,3-dimethylbutanoic acid (A2)

The compound A1g (80 g, 205 mmol) was diluted with ethanol (800 mL). Pd/C (10%, wet, 15 g) was added and the atmosphere was replaced with hydrogen. After stirring for 5 hours, the mixture was filtered over celite, washed with EtOAc and the filtrate was concentrated to get product A2 (45 g, 77%). MS (ESI) m/z 186 [M-Boc+1]+. $^1$H NMR (300 MHz, DMSO-d6): δ7.18 (d, J=9.6 Hz, 1H), 4.25 (d, J=9.9 Hz, 1H), 1.36 (s, 9H), 1.14 (s, 6H).

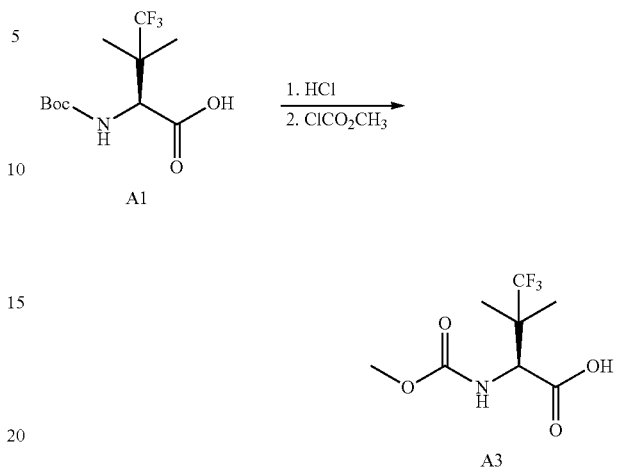

Synthesis of (S)-4, 4, 4-trifluoro-2-((methoxycarbonyl) amino)-3, 3-dimethylbutanoic acid (A3)

To a solution of A1 (10 g, 35.06 mmol) in DCM (160 mL) and MeOH (40 mL), was added HCl (4.0 M in dioxane, 40 mL). The reaction was stirred at room temperature overnight. The reaction was concentrated to dryness (foamy). The residue was dissolved in a mixture of dioxane and 2 M NaOH (90 mL), stirred for 5 min, and then add methyl chloroformate (5.7 mL, 73.33 mmol). After 4 h the reaction was extracted with 2×100 mL DCM (discard organics) and the aqueous layer was adjusted to pH ~2 with 4M HCl (~50 mL). The aqueous layer was extracted with 2×150 mL EtOAc, the combined EtOAc layers were dried over sodium sulfate, filtered, and concentrated to give A3 (8.54 g, 100%). MS (ESI) m/z 244.0 [M+H]$^+$. $^1$H NMR (400 MHz, Methanol-d4) δ 4.57-4.41 (m, 1H), 3.66 (d, J=2.1 Hz, 5H), 1.25 (d, J=10.0 Hz, 7H).

1.4 Synthesis of Intermediates I

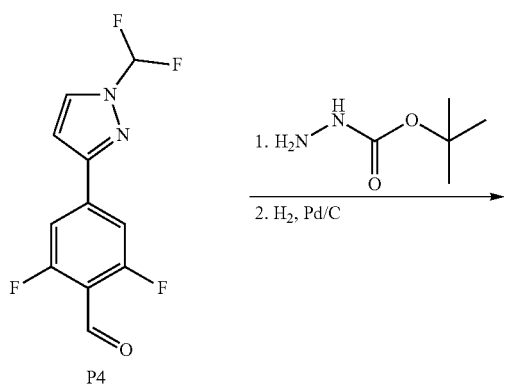

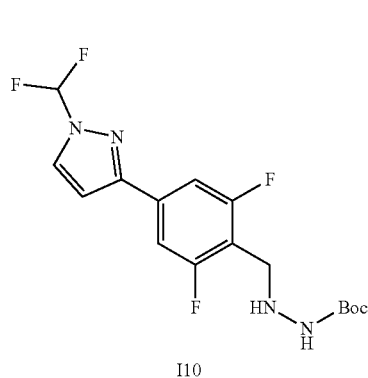
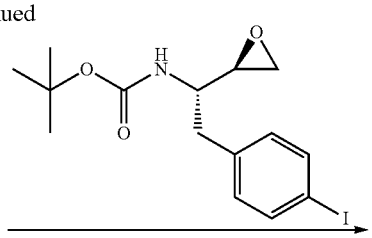
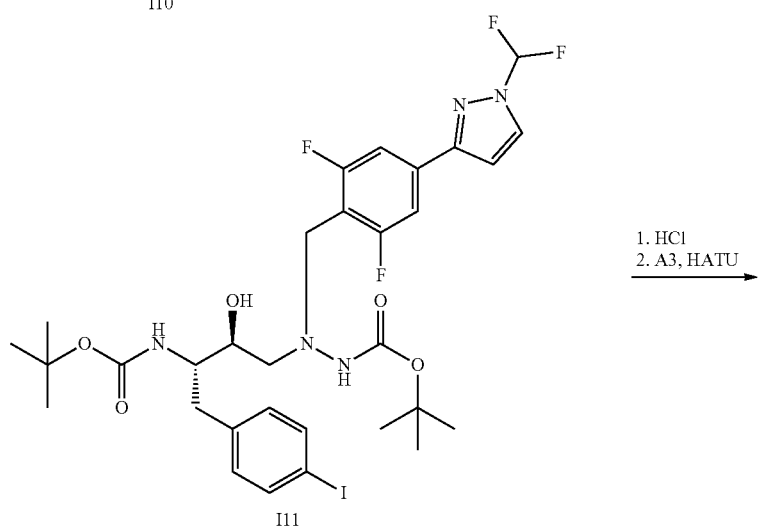
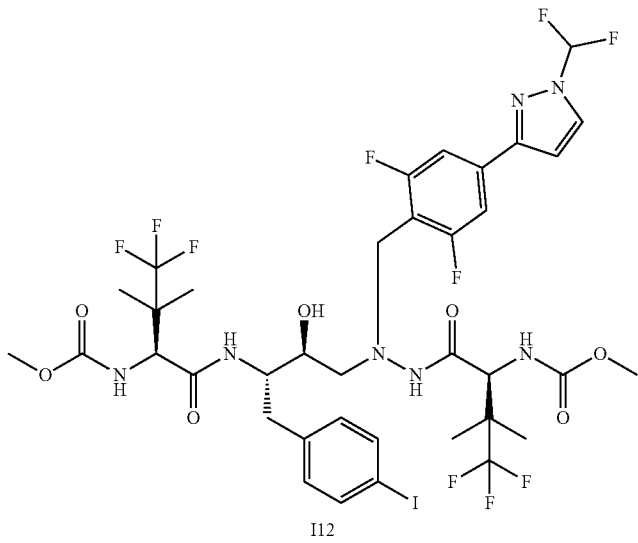

Synthesis of tert-butyl 2-(4-(1-(difluoromethyl)-1H-pyrazol-3-yl)-2,6-difluorobenzyl)hydrazine-1-carboxylate (I10)

P4 (29.9 g, 0.116 mol) and tert-butyl hydrazinecarboxylate (16.4 g, 0.124 mol) were stirred in 2-MeTHF (150 mL) and acetic acid (0.66 mL, 12 mmol) at 40° C. for 18 hours after which point LCMS analysis showed complete conversion to the intermediate hydrazine. The mixture was concentrated to dryness. Palladium on carbon (10 wt %, wet, 3.4 g) and ethanol (200 mL) were added and the mixture was degassed with argon, then stirred under a balloon of hydrogen gas for 4.5 hours. The hydrogen balloon was removed and the reaction was flushed with nitrogen gas. Celite (10 g) was added and the slurry was filtered through a small pad of additional celite (~1"), eluting with EtOAc (2×200 mL). The solvent was evaporated in vacuo and the resulting crude solids were redissolved in EtOAc (130 mL) at reflux. Hexanes (172 mL) was added slowly, and the solution was allowed to slowly cool to room temperature. No solids precipitated following the procedure, so 140 mL of solvent was removed in vacuo (110 mbar). Additional hexanes (172 mL) was added slowly, then 200 mL solvent was removed in vacuo (345 mbar), then additional hexanes was added (130 mL) and the solution was cooled to 5° C. and stirred for 1 hour. The resulting thick slurry was filtered, the solids were rinsed with cold 9:1 hexanes:EtOAc, and dried to provide 110. MS (ESI) m/z 318.9 [M-tBu]+.

Synthesis of tert-butyl 2-((2S,3S)-3-((tert-butoxycarbonyl)amino)-2-hydroxy-4-(4-iodophenyl)butyl)-2-(4-(1-(difluoromethyl)-1H-pyrazol-3-yl)-2,6-difluorobenzyl)hydrazine-1-carboxylate (I11)

I10 (34.7 g, 92.6 mmol) and tert-butyl ((S)-2-(4-iodophenyl)-1-((R)-oxiran-2-yl)ethyl)carbamate (45.1 g, 116 mmol) were combined in isopropanol (150 mL) and heptanes (250 mL) and stirred at reflux overnight. An additional portion of tert-butyl ((S)-2-(4-iodophenyl)-1-((R)-oxiran-2-yl)ethyl)carbamate (2.5 g) was added and 50 mL of the solvent mixture was distilled off. The remaining reaction mixture was stirred at reflux overnight, then slowly cooled to room temperature. The resulting precipitated solids were filtered, rinsing with 1:2 isopropanol:hexanes (70 mL), then 1:4 isopropanol:hexanes (70 mL), then hexanes (140 mL). The solids were dried in a vacuum oven to provide I11 which was used without further purification. MS (ESI) m/z 764.0 [M+H]+.

Synthesis of methyl ((5S,10S,11S,14S)-8-(4-(1-(difluoromethyl)-1H-pyrazol-3-yl)-2,6-difluorobenzyl)-16,16,16-trifluoro-10-hydroxy-11-(4-iodobenzyl)-15,15-dimethyl-3,6,13-trioxo-5-(1,1,1-trifluoro-2-methylpropan-2-yl)-2-oxa-4,7,8,12-tetraazahexadecan-14-yl)carbamate (I12)

I11 (19.2 g, 25.1 mmol) was dissolved in DCM (500 mL) at 5° C. and 4M HCl in dioxane (50 mL, 200 mmol) was added. The reaction was stirred overnight, allowing to slowly warm to room temperature after which point LCMS analysis showed complete conversion. The reaction was concentrated to dryness and the resulting material was redissolved in DCM (200 mL). A3 (13.2 g, 54 mmol) was added followed by HATU (20.1 g, 53 mmol). After 5 minutes, the mixture was cooled to 10° C. and DIPEA (24 mL, 0.14 mol) was added over 15 minutes. The cooling bath was removed and the mixture was allowed warm to room temperature. After 100 minutes, the reaction was quenched with 1M NaOH (150 mL), and stirred 5 minutes. The resulting white precipitate was removed by filtration. The organic layer was separated and the aqueous layer was extracted with an additional portion of DCM (50 mL). The combined organic layers were rinsed again with 1M NaOH (100 mL), followed by ½ saturated aqueous ammonium chloride (150 mL). The organic layer was then dried over $Na_2SO_4$, filtered and purified by flash column chromatography (35%-80% ethyl acetate in hexanes) to provide 112. MS (ESI) m/z 1014.4 [M+H]+.

1.5 Synthesis of Compound D

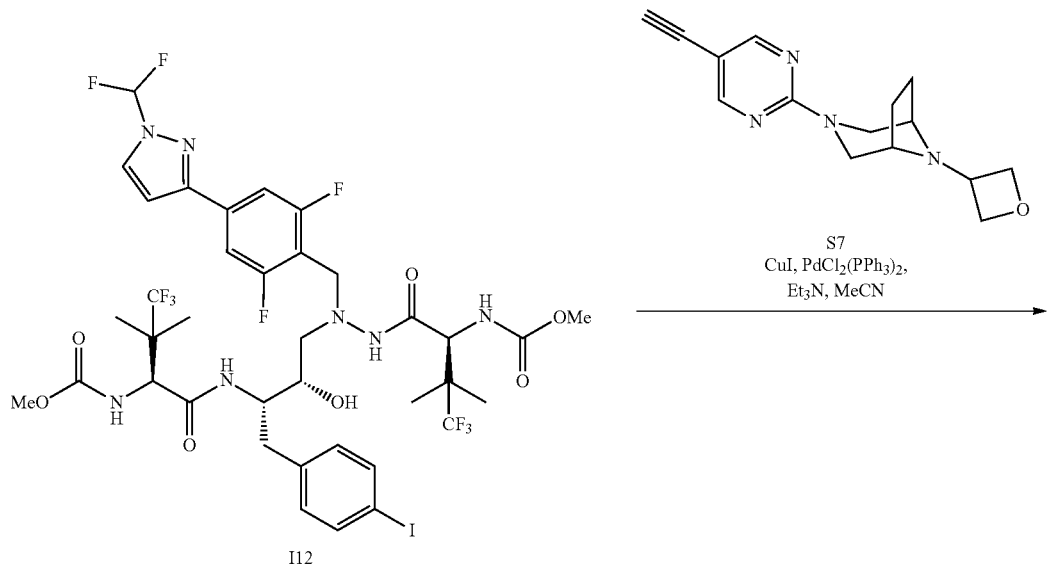

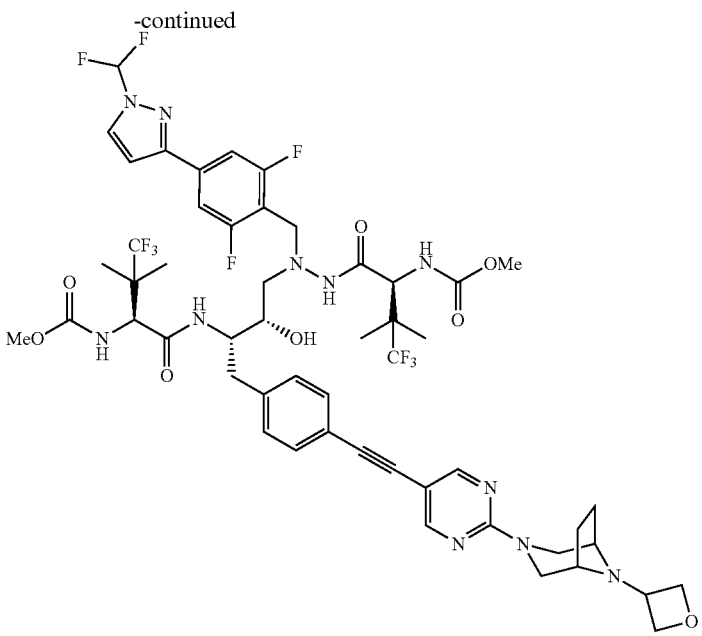

Synthesis of methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (D)

Intermediate 112 (3.3 g, 3.3 mmol) was combined with intermediate S7 (1.4 g, 5.2 mmol) and triethylamine (15 mL) in acetonitrile (45 mL). The solution was degassed with argon, followed by addition of PdCl$_2$($^t$Bu$_2$PPh)$_2$ (92 mg, 0.13 mmol) and CuI (62 mg, 0.33 mmol). The mixture was stirred at 50° C. under argon until LCMS showed complete conversion (~1.5 hours). The reaction was cooled to room temperature and quenched with thiol-linked silica (7 g), followed by filtration through a plug of celite (~1" thick), eluting with 95:5 EtOAc:MeOH. The mixture was concentrated to dryness and purified by flash column chromatography (45% to 0% hexanes in 98:1:1 ethyl acetate:triethylamine:methanol to 95:4:1 ethyl acetate:triethylamine:methanol) to provide compound D. MS (ESI) m/z 1156.4 [M+H]+. $^1$H NMR (400 MHz, Methanol-d4) δ 8.43 (s, 2H), 8.08 (d, J=9.4 Hz, 1H), 8.01 (d, J=2.8 Hz, 1H), 7.44 (d, J=59.8 Hz, 1H), 7.35 (d, J=8.2 Hz, 2H), 7.25 (d, J=7.9 Hz, 2H), 7.14 (d, J=8.1 Hz, 2H), 7.03 (d, J=9.9 Hz, 1H), 6.84 (d, J=2.7 Hz, 1H), 6.71 (d, J=9.9 Hz, 1H), 4.87 (t, J=7.6 Hz, 2H), 4.72 (dd, J=8.2, 4.9 Hz, 2H), 4.67 (s, 1H), 4.42-4.29 (m, 1H), 4.25-4.18 (m, 1H), 4.11-3.98 (m, 4H), 3.85 (d, J=13.1 Hz, 1H), 3.69-3.62 (m, 2H), 3.59 (s, 3H), 3.57 (s, 3H), 3.41-3.28 (m, 2H), 2.87-2.75 (m, 3H), 2.68 (dd, J=12.6, 9.1 Hz, 1H), 2.18-2.06 (m, 2H), 1.95-1.83 (m, 2H), 1.07 (s, 3H), 1.05 (s, 3H), 1.02 (s, 3H), 0.93 (s, 3H).

Compound D

2. Example Compounds, Synthesis, and Characterization

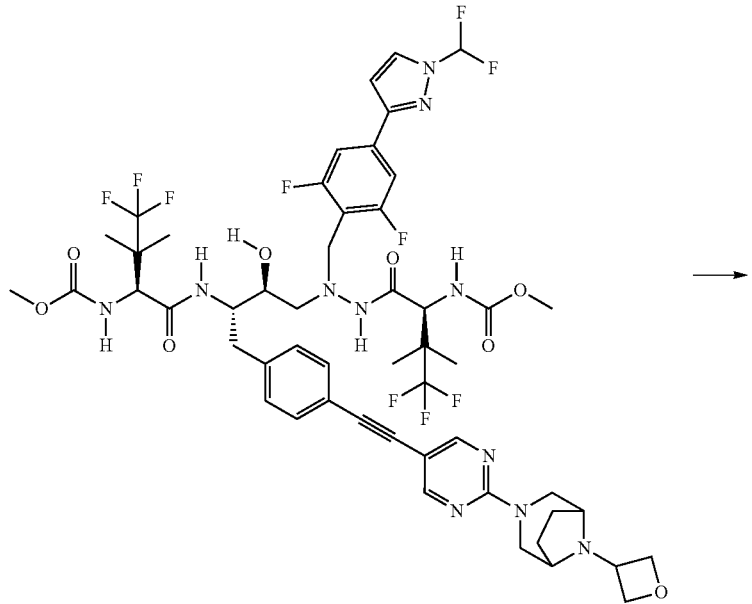

D

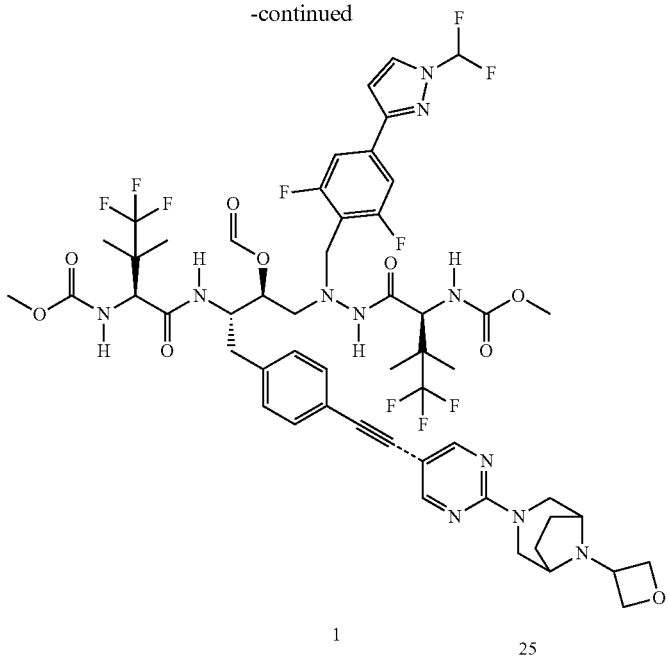

1

Example 1

Synthesis of (5S,10S,11S,14S)-8-(4-(1-(difluoromethyl)-1H-pyrazol-3-yl)-2,6-difluorobenzyl)-11-(4-((2-(8-(oxetan-3-yl)-3,8-diazabicyclo[3.2.1]octan-3-yl)pyrimidin-5-yl)ethynyl)benzyl)-3,6,13,16-tetraoxo-5,14-bis(1,1,1-trifluoro-2-methylpropan-2-yl)-2,17-dioxa-4,7,8,12,15-pentaazaoctadecan-10-yl formate (1)

Acetic anhydride (15 μL, 0.16 mmol) and formic acid (61 μL, 1.6 mmol) were combined in DCM (1 mL). To this mixture was added the trifluoroacetic acid salt of methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (compound D) (75 mg, 54 μmol). The mixture was then cooled to 5° C. and pyridine (0.17 mL, 2.2 mmol) was added dropwise. The mixture was then stirred while allowing it to slowly warm to room temperature. After 4 hours, the mixture was quenched with aq NaHCO₃, the organic layer was removed, dried over Na₂SO₄, filtered, concentrated and purified by HPLC to afford 1. MS (ESI) m/z 1184.4 [M+H]⁺. ¹H NMR (400 MHz, Methanol-d4) δ 8.43 (s, 2H), 8.27 (d, J=9.7 Hz, 1H), 8.12 (s, 1H), 8.01 (d, J=2.7 Hz, 1H), 7.44 (t, J=59.6 Hz, 1H), 7.36 (d, J=8.3 Hz, 2H), 7.25 (d, J=8.0 Hz, 2H), 7.13 (d, J=8.1 Hz, 2H), 6.95 (d, J=9.9 Hz, 1H), 6.85 (d, J=2.8 Hz, 1H), 6.68 (d, J=10.2 Hz, 1H), 4.97 (s, 1H), 4.86 (t, J=7.6 Hz, 2H), 4.70 (dd, J=8.2, 5.1 Hz, 2H), 4.35 (d, J=10.0 Hz, 1H), 4.25-4.13 (m, 2H), 4.02 (s, 2H), 3.92 (d, J=13.4 Hz, 1H), 3.59 (s, 3H), 3.57 (s, 3H), 3.42-3.29 (m, 3H), 2.91-2.74 (m, 2H), 2.66-2.54 (m, 1H), 2.20-2.04 (m, 2H), 1.95-1.83 (m, 2H), 1.11 (s, 3H), 1.06 (s, 3H), 1.04 (s, 3H), 0.97 (s, 3H).

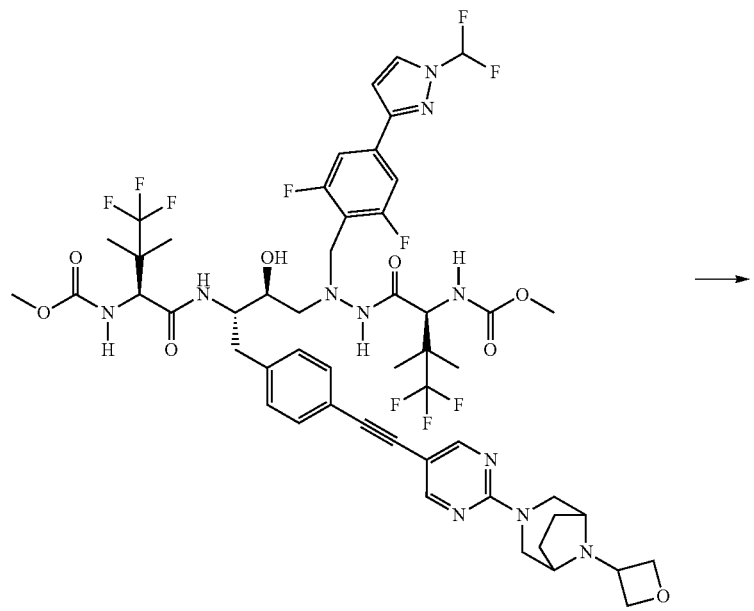

D

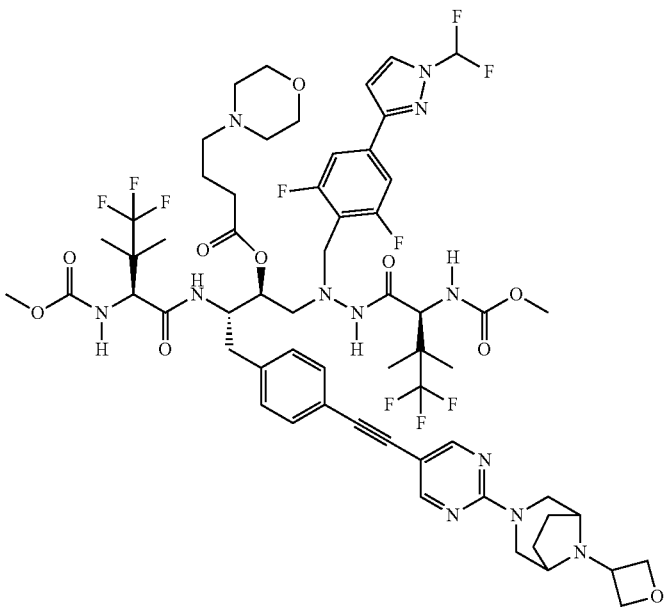

2

Example 2

Synthesis of (5S,10S,11S,14S)-8-(4-(1-(difluoromethyl)-1H-pyrazol-3-yl)-2,6-difluorobenzyl)-11-(4-((2-(8-(oxetan-3-yl)-3,8-diazabicyclo[3.2.1]octan-3-yl)pyrimidin-5-yl)ethynyl)benzyl)-3,6,13,16-tetraoxo-5,14-bis(1,1,1-trifluoro-2-methylpropan-2-yl)-2,17-dioxa-4,7,8,12,15-pentaazaoctadecan-10-yl 4-morpholinobutanoate (2)

To a stirring solution of methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (compound D) (30 mg, 26 μmol) in DCM (1 mL) at room temperature was added pyridine (63 μL) followed by 4-morpholinobutanoyl chloride hydrochloride (18 mg, 79 μmol). After 1 hour, an additional portion of 4-morpholinobutanoyl chloride hydrochloride (18 mg, 79 μmol) was added. After 2 hours, the mixture was quenched with methanol, concentrated to dryness and purified by HPLC to provide 2. MS (ESI) m/z 1311.6 [M+H]$^+$. $^1$H NMR (400 MHz, Methanol-d4) δ 8.43 (s, 2H), 8.14 (d, J=9.4 Hz, 1H), 8.03 (d, J=2.7 Hz, 1H), 7.45 (t, J=59.8 Hz, 1H), 7.38 (d, J=8.3 Hz, 2H), 7.25 (d, J=8.0 Hz, 2H), 7.11 (d, J=8.0 Hz, 2H), 6.89 (d, J=10.0 Hz, 1H), 6.85 (d, J=2.7 Hz, 1H), 6.75 (d, J=9.9 Hz, 1H), 5.17-5.09 (m, 1H), 4.87 (t, J=7.3 Hz, 1H), 4.72 (dd, J=8.3, 5.0 Hz, 2H), 4.67 (s, 1H), 4.33 (d, J=10.0 Hz, 1H), 4.19 (d, J=10.0 Hz, 1H), 4.12 (d, J=13.1 Hz, 1H), 4.07-4.01 (m, 2H), 3.97 (d, J=13.2 Hz, 1H), 3.88 (d, J=13.1 Hz, 1H), 3.71-3.62 (m, 2H), 3.60 (s, 3H), 3.58 (s, 3H), 3.46 (d, J=12.6 Hz, 1H), 3.37 (d, J=14.6 Hz, 2H), 3.13-3.06 (m, 1H), 2.88-2.74 (m, 2H), 2.60-2.45 (m, 2H), 2.16-2.08 (m, 2H), 2.06-1.96 (m, 1H), 1.94 (s, 1H), 1.92-1.84 (m, 2H), 1.11 (s, 3H), 1.03 (s, 3H), 1.02 (s, 3H), 1.01 (s, 3H).

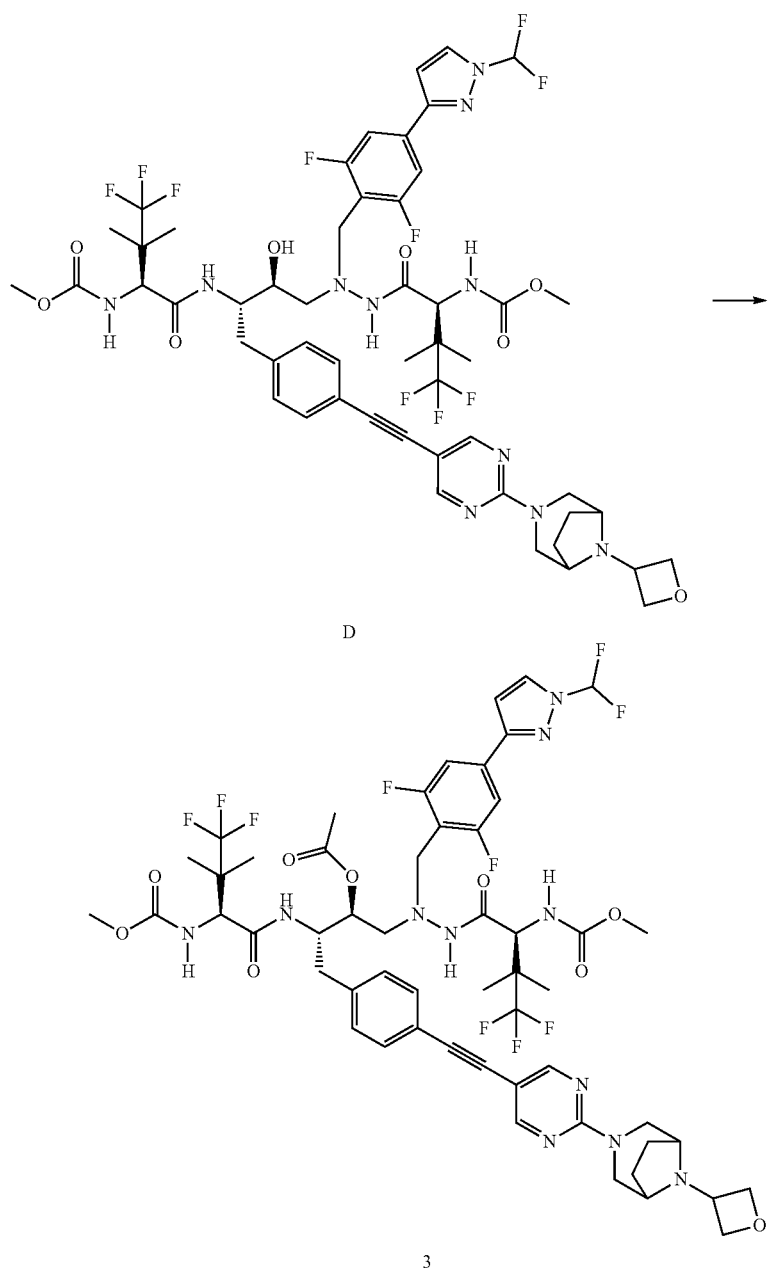

D

3

Example 3

Synthesis of (5S,10S,11S,14S)-8-(4-(1-(difluoromethyl)-1H-pyrazol-3-yl)-2,6-difluorobenzyl)-11-(4-((2-(8-(oxetan-3-yl)-3,8-diazabicyclo[3.2.1]octan-3-yl)pyrimidin-5-yl)ethynyl)benzyl)-3,6,13,16-tetraoxo-5,14-bis(1,1,1-trifluoro-2-methylpropan-2-yl)-2,17-dioxa-4,7,8,12,15-pentaazaoctadecan-10-yl acetate (3)

To a stirring solution of methyl ((5 S,8S,9 S,14S)-11-(4-(1-(difluoromethyl)-1H-pyrazol-3-yl)-2,6-difluorobenzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (compound D) (80 mg, 69 μmol) in DCM (1 mL) at room temperature was added 4-(dimethylamino)pyridine (25 mg, 0.21 mmol), and N-ethyldiisopropylamine (0.12 mL, 0.69 mmol) followed by acetic anhydride (39 μL, 0.41 mmol). After 15 minutes, the mixture was quenched with methanol, concentrated to dryness and purified by HPLC to provide 3. MS (ESI) m/z 1199.0 [M+H]$^+$. $^1$H NMR (400 MHz, Methanol-d4) δ 8.52 (s, 2H), 8.22 (d, J=9.4 Hz, 1H), 8.09 (d, J=2.8 Hz, 1H), 7.52 (t, J=60.0, 59.6 Hz, 1H), 7.44 (d, J=8.2 Hz, 2H), 7.34 (d, J=7.9 Hz, 2H), 7.21 (d, J=8.2 Hz, 2H), 6.97 (d, J=10.1 Hz, 1H), 6.93 (d, J=2.7 Hz, 1H), 6.77 (d, J=10.1 Hz, 1H), 5.00 (s, 1H), 4.95 (t, J=7.6 Hz, 2H), 4.81-4.73 (m, 3H), 4.63-4.53 (m, 2H), 4.49 (d, J=9.9 Hz, 1H), 4.32-4.22 (m, 2H), 4.16-4.09 (m, 2H), 4.02 (d, J=13.2 Hz, 1H), 3.69 (s, 3H), 3.66 (s, 3H), 3.46 (d, J=14.5 Hz, 2H), 3.17 (dd, J=13.2, 6.1 Hz, 1H), 2.88 (td, J=12.9, 6.0 Hz, 2H), 2.72-2.61 (m, 1H), 2.26-2.17 (m, 2H), 2.11 (s, 3H), 2.04-1.93 (m, 2H), 1.20 (s, 3H), 1.17 (s, 3H), 1.14 (s, 3H), 1.05 (s, 3H).

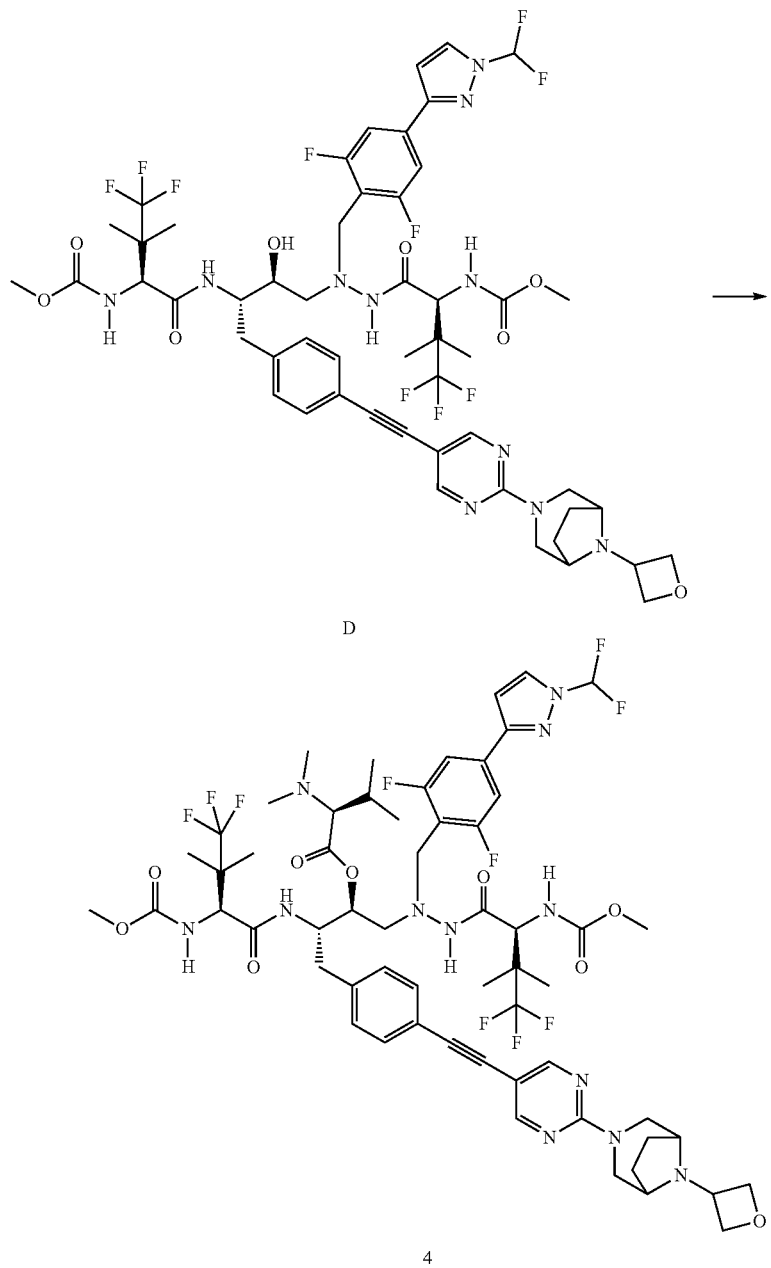

D

4

Example 4

Synthesis of (2S,3S)-1-(1-(4-(1-(difluoromethyl)-1H-pyrazol-3-yl)-2,6-difluorobenzyl)-2-((S)-4,4,4-trifluoro-2-((methoxycarbonyl)amino)-3,3-dimethylbutanoyl)hydrazinyl)-4-(4-((2-(8-(oxetan-3-yl)-3,8-diazabicyclo[3.2.1]octan-3-yl)pyrimidin-5-yl)ethynyl)phenyl)-3-((S)-4,4,4-trifluoro-2-((methoxycarbonyl)amino)-3,3-dimethylbutanamido)butan-2-yl dimethyl-L-valinate (4)

To a solution of dimethyl-L-valine (100 mg, 0.69 mmol) and triethylamine (0.19 mL) in DCM at 5° C. was added pivaloyl chloride (68 μL, 0.56 mmol). The mixture was stirred for 20 minutes, then methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (compound D) (80 mg, 69 μmol) and 4-(dimethylamino)pyridine (51 mg, 0.42 mmol) were added and the mixture was allowed to warm to room temperature. After 10 minutes the mixture was warmed to 35° C., after an additional 45 minutes the mixture was warmed to 45° C., after an additional 80 minutes the mixture was warmed to 55° C. (sealed vial). After an additional 100 minutes, the mixture was cooled to room temperature, quenched with methanol, concentrated to dryness and purified by HPLC to provide 4. MS (ESI) m/z 1284.0 [M+H]$^+$. $^1$H NMR (400 MHz, Methanol-d4) δ 8.43 (s, 2H), 8.03 (d, J=2.7 Hz, 1H), 7.44 (t, J=60.2, 59.7 Hz, 1H), 7.39 (d, J=8.3 Hz, 2H), 7.27 (d, J=8.0 Hz, 2H), 7.09 (d, J=8.1 Hz, 2H), 6.92 (d, J=9.9 Hz, 1H), 6.85 (d, J=2.8 Hz, 1H), 6.82 (d, J=10.0 Hz, 1H), 5.44 (d, J=9.2 Hz, 1H), 4.86 (t, J=7.6 Hz, 2H), 4.74-4.64 (m, 4H), 4.45-4.28 (m, 3H), 4.21 (d, J=10.0 Hz, 1H), 4.11-3.98 (m, 3H), 3.86 (d, J=13.1 Hz, 1H), 3.80 (d, J=7.5 Hz, 1H), 3.59 (s, 3H), 3.58 (s, 3H), 3.41-3.32 (m, 2H), 3.01 (s, 6H), 2.96-2.79 (m, 1H), 2.61-2.47 (m, 1H), 2.45-2.33 (m, 1H), 2.21-2.07 (m, 2H), 1.93-1.83 (m, 2H), 1.14 (d, J=6.8 Hz, 3H), 1.10 (s, 3H), 1.08-1.01 (m, 12H).
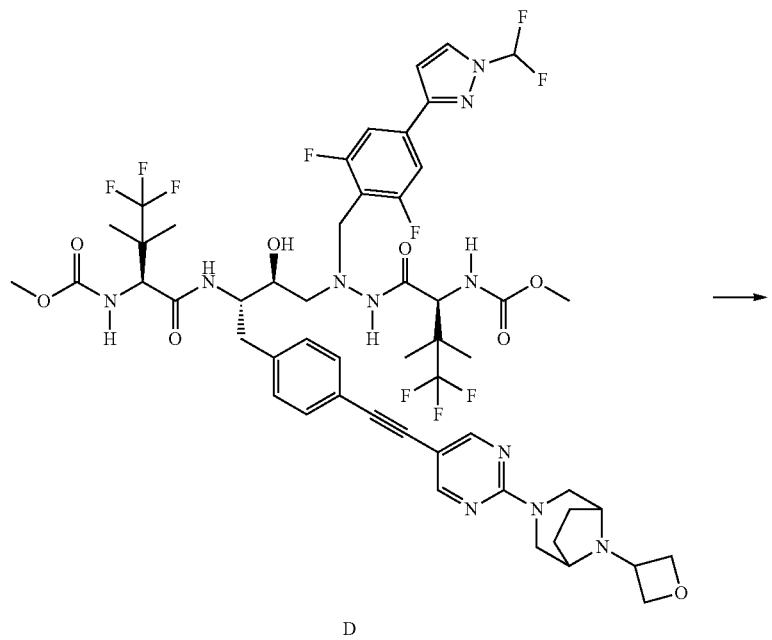
D
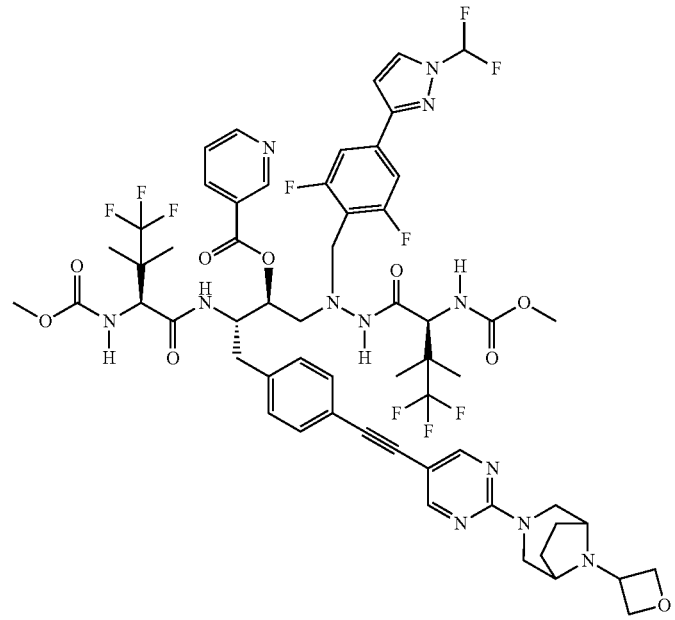
5

Example 5

Synthesis of (5S,10S,11S,14S)-8-(4-(1-(difluoromethyl)-1H-pyrazol-3-yl)-2,6-difluorobenzyl)-11-(4-((2-(8-(oxetan-3-yl)-3,8-diazabicyclo[3.2.1]octan-3-yl)pyrimidin-5-yl)ethynyl)benzyl)-3,6,13,16-tetraoxo-5,14-bis(1,1,1-trifluoro-2-methylpropan-2-yl)-2,17-dioxa-4,7,8,12,15-pentaazaoctadecan-10-yl nicotinate (5)

To a stirring solution of methyl ((5 S, 8S, 9 S,14S)-11-(4-(1-(difluoromethyl)-1H-pyrazol-3-yl)-2,6-difluorobenzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (compound D) (130 mg, 110 μmol) and pyridine (0.1 mL) in DCM (1 mL) at room temperature was added nicotinoyl chloride hydrochloride (60 mg, 0.34 mmol). After 15 minutes, HATU (63 mg, 0.166 mmol) and N-ethyldiisopropylamine (0.1 mL) were added. After an additional 15 minutes, 4-(dimethylamino)pyridine (50 mg) was added and the mixture was warmed to 40° C. After 3.5 hours, LCMS analysis showed complete conversion. The reaction was quenched with methanol, concentrated to dryness, and purified by HPLC to provide 5. MS (ESI) m/z 1262.2 [M+H]$^+$. $^1$H NMR (400 MHz, Methanol-d4) δ 9.24-9.15 (m, 1H), 8.79 (d, J=5.0 Hz, 1H), 8.56-8.44 (m, 3H), 8.34 (d, J=9.2 Hz, 1H), 8.10 (d, J=2.7 Hz, 1H), 7.65 (dd, J=8.0, 5.1 Hz, 1H), 7.53 (t, J=59.8, 59.4 Hz, 1H), 7.33 (t, J=7.6 Hz, 4H), 7.22 (d, J=8.2 Hz, 2H), 7.05 (d, J=10.0 Hz, 1H), 6.95-6.83 (m, 2H), 5.31 (s, 1H), 4.96 (t, J=7.6 Hz, 2H), 4.83 (dd, J=8.2, 5.1 Hz, 2H), 4.78 (d, J=14.8 Hz, 2H), 4.66 (s, 1H), 4.52-4.44 (m, 1H), 4.36-4.30 (m, 1H), 4.27 (d, J=13.2 Hz, 1H), 4.14 (d, J=3.8 Hz, 2H), 4.09 (d, J=13.2 Hz, 1H), 3.68 (d, J=1.4 Hz, 6H), 3.48 (d, J=14.4 Hz, 2H), 3.42 (dd, J=13.5, 5.2 Hz, 1H), 3.00 (ddd, J=23.0, 13.7, 6.6 Hz, 2H), 2.76 (dd, J=13.9, 9.5 Hz, 1H), 2.26-2.16 (m, 2H), 2.01-1.94 (m, 2H), 1.20 (s, 3H), 1.17 (s, 3H), 1.13 (s, 3H), 1.09 (s, 3H).

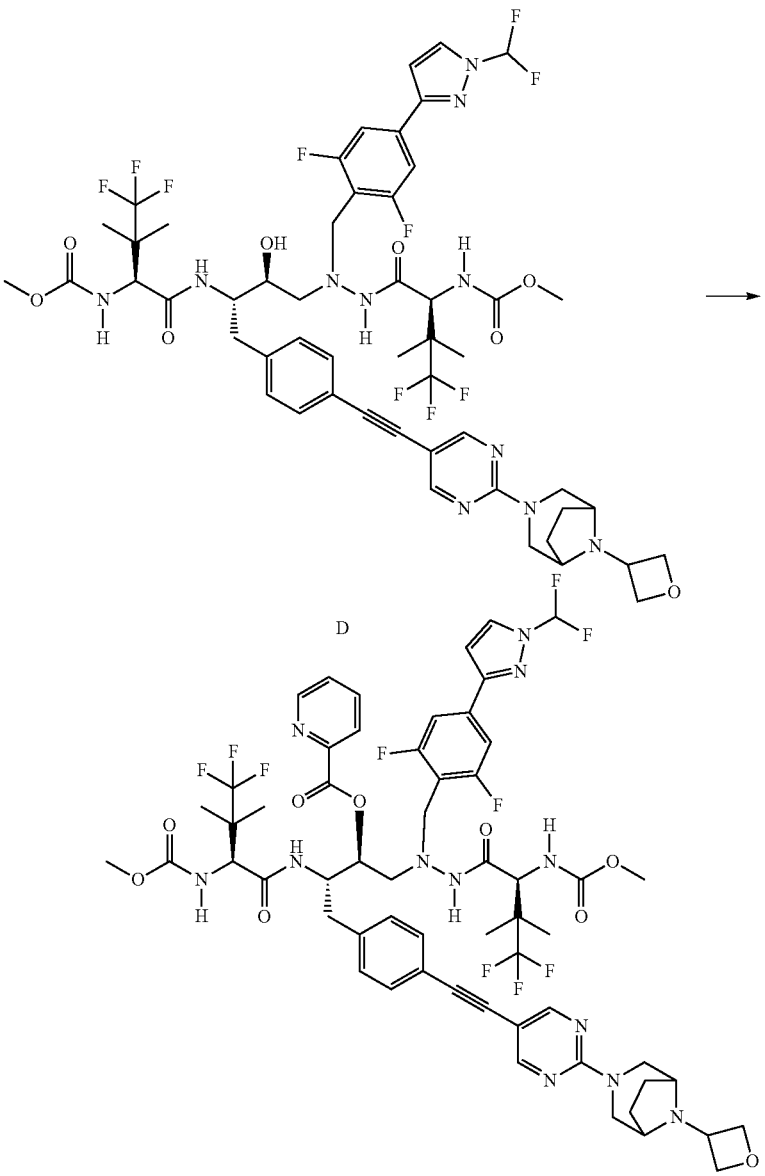

Example 6

Synthesis of (5S,10S,11S,14S)-8-(4-(1-(difluoromethyl)-1H-pyrazol-3-yl)-2,6-difluorobenzyl)-11-(4-((2-(8-(oxetan-3-yl)-3,8-diazabicyclo[3.2.1]octan-3-yl)pyrimidin-5-yl)ethynyl)benzyl)-3,6,13,16-tetraoxo-5,14-bis(1,1,1-trifluoro-2-methylpropan-2-yl)-2,17-dioxa-4,7,8,12,15-pentaazaoctadecan-10-yl picolinate (6)

To a stirring solution of picolinic acid (95 mg, 0.77 mmol) and triethylamine (0.31 mL) in DCM at 5° C. was slowly added pivaloyl chloride (81 μL, 0.66 mmol). After 10 minutes, the mixture was warmed to room temperature and methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (compound D) (127 mg, 110 μmol) and 4-(dimethylamino)pyridine (27 mg, 0.22 mmol) were added. After 5 minutes, LCMS analysis showed complete conversion. The reaction was quenched with aqueous ammonium chloride, concentrated to dryness, and purified by HPLC to provide 6. MS (ESI) m/z 1262.1 [M+H]$^+$. $^1$H NMR (400 MHz, Methanol-d4) δ 9.03 (d, J=9.3 Hz, 1H), 8.64-8.55 (m, 1H), 8.43 (s, 2H), 8.18 (d, J=7.9 Hz, 1H), 8.05-7.94 (m, 2H), 7.63-7.58 (m, 1H), 7.45 (t, J=60.0, 59.6 Hz, 1H), 7.24 (d, J=7.9 Hz, 2H), 7.17 (d, J=8.2 Hz, 2H), 7.11 (d, J=8.0 Hz, 2H), 7.00 (d, J=10.0 Hz, 1H), 6.82-6.75 (m, 2H), 5.19 (t, J=6.5 Hz, 1H), 4.87 (t, J=7.6 Hz, 2H), 4.73 (dd, J=8.3, 5.1 Hz, 2H), 4.67 (s, 1H), 4.52 (d, J=7.8 Hz, 1H), 4.49-4.44 (m, 1H), 4.28-4.21 (m, 1H), 4.14-3.98 (m, 4H), 3.59 (s, 3H), 3.58 (s, 3H), 3.38 (d, J=14.5 Hz, 2H), 2.88 (dd, J=13.4, 7.1 Hz, 1H), 2.71 (qd, J=13.6, 7.5 Hz, 2H), 2.23-2.04 (m, 2H), 1.98-1.81 (m, 2H), 1.14 (s, 3H), 1.11 (s, 3H), 1.11 (s, 3H), 0.97 (s, 3H).

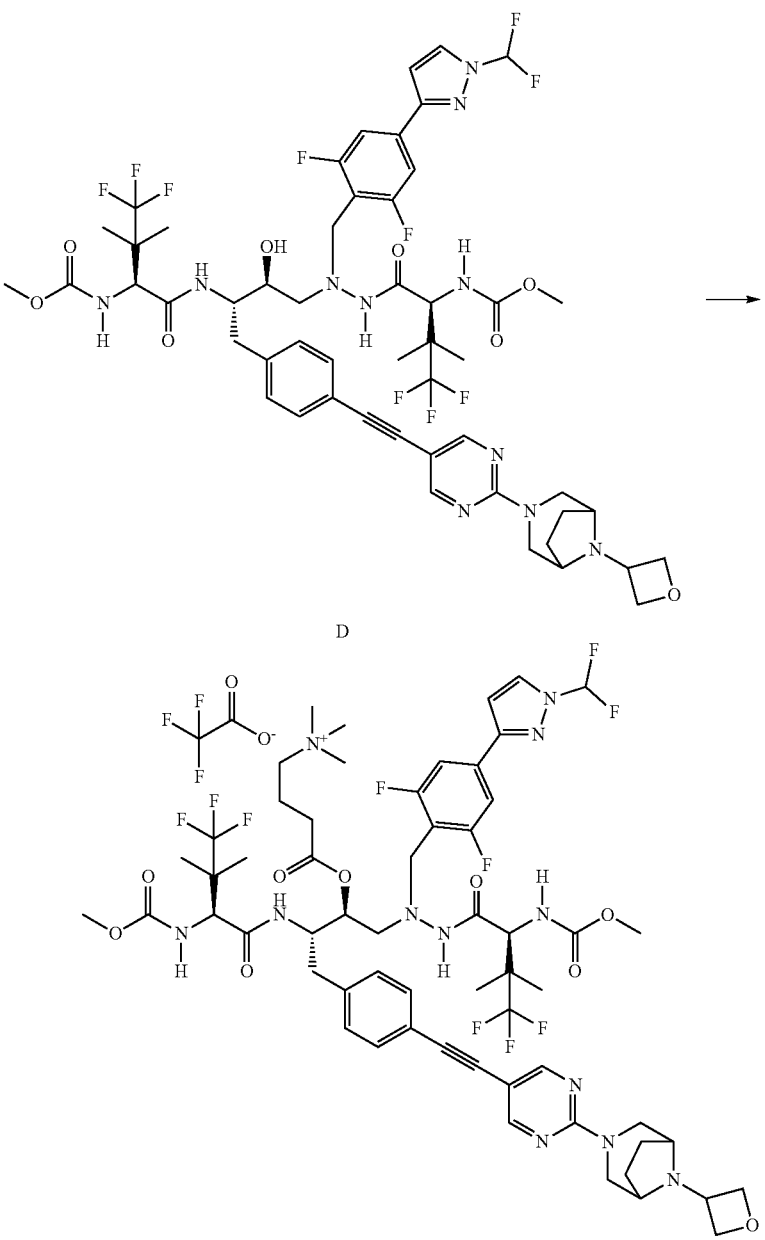

D

Example 7

Synthesis of (5S,10S)-8-(4-(1-(difluoromethyl)-1H-pyrazol-3-yl)-2,6-difluorobenzyl)-N,N,N-trimethyl-10-((1 S)-2-(4-((2-(8-(oxetan-3-yl)-3,8-diazabicyclo[3.2.1]octan-3-yl)pyrimidin-5-yl)ethynyl)phenyl)-1-((S)-4,4,4-trifluoro-2-((methoxycarbonyl)amino)-3,3-dimethylbutanamido)ethyl)-3,6,2-trioxo-5-(1,1,1-trifluoro-2-methylpropan-2-yl)-2,11-dioxa-4,7,8-triazapentadecan-15-aminium 2,2,2-trifluoroacetate (7)

Synthesized analogously to example 6, but using (3-carboxypropyl)trimethylammonium chloride in place of picolinic acid. MS (ESI) m/z 1283.6 [M+H]⁺. ¹H NMR (400 MHz, Methanol-d4) δ 8.52 (s, 1H), 8.21 (d, J=9.5 Hz, 1H), 8.11 (d, J=2.7 Hz, 1H), 7.53 (t, J=60.4, 59.5 Hz, 1H), 7.47 (d, J=8.3 Hz, 2H), 7.34 (d, J=7.9 Hz, 2H), 7.20 (d, J=7.9 Hz, 2H), 6.97 (d, J=10.0 Hz, 1H), 6.93 (d, J=2.7 Hz, 1H), 6.82 (d, J=9.9 Hz, 1H), 5.24 (d, J=8.7 Hz, 1H), 4.95 (t, J=7.6 Hz, 2H), 4.85-4.80 (m, 2H), 4.77 (d, J=14.7 Hz, 2H), 4.41 (d, J=10.0 Hz, 2H), 4.28 (d, J=9.9 Hz, 1H), 4.18 (d, J=13.2 Hz, 1H), 4.16-4.08 (m, 2H), 3.96 (d, J=13.0 Hz, 1H), 3.68 (s, 3H), 3.67 (s, 3H), 3.63-3.52 (m, 1H), 3.48 (d, J=14.7 Hz, 2H), 3.45-3.39 (m, 1H), 2.99-2.86 (m, 2H), 2.69-2.47 (m, 3H), 2.27-2.05 (m, 3H), 2.04-1.94 (m, 2H), 1.19 (s, 3H), 1.11 (s, 6H), 1.09 (s, 3H).

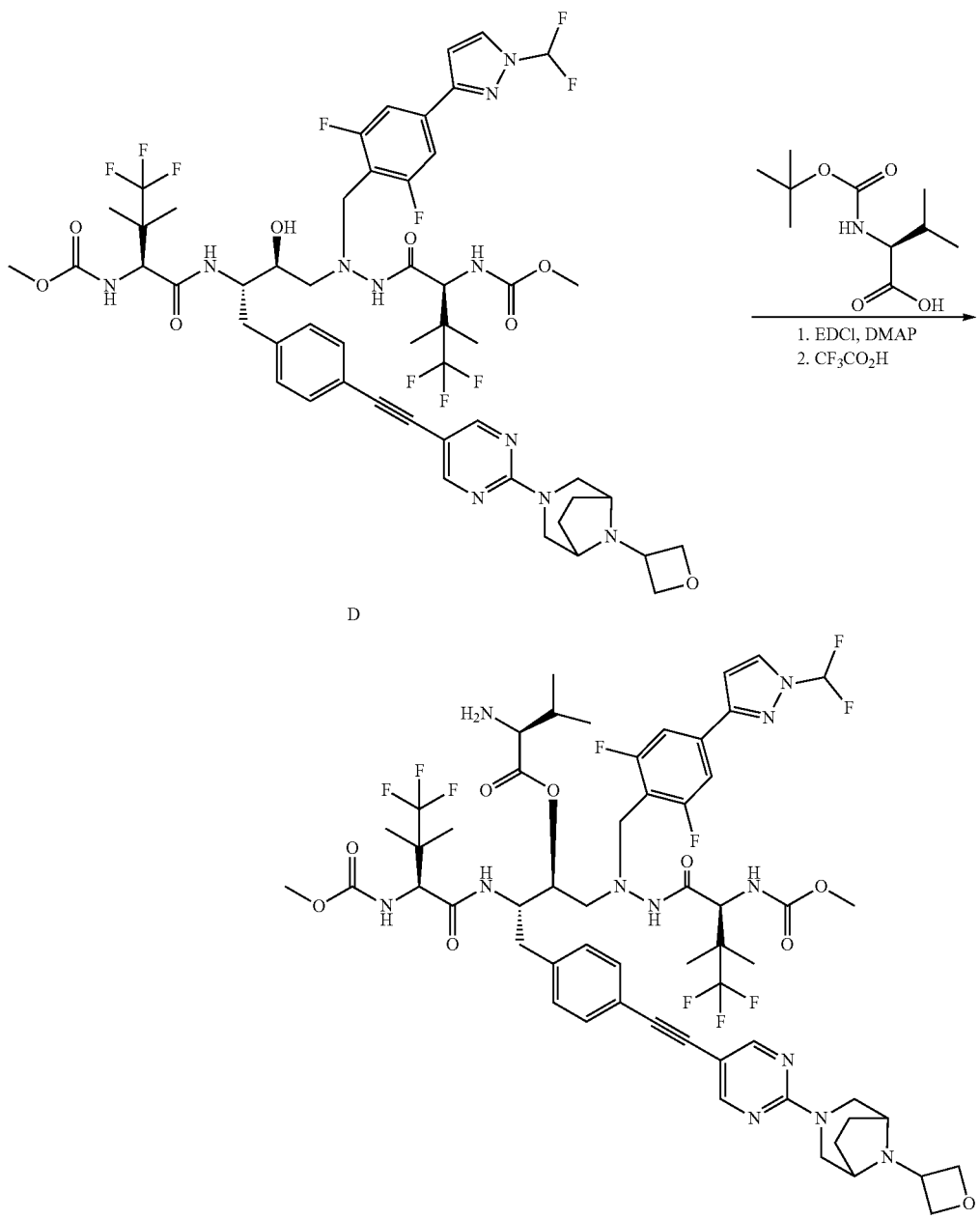

Example 8

(2S,3S)-1-(1-(4-(1-(difluoromethyl)-1H-pyrazol-3-yl)-2,6-difluorobenzyl)-2-((S)-4,4,4-trifluoro-2-((methoxycarbonyl)amino)-3,3-dimethylbutanoyl)hydrazinyl)-4-(4-((2-(8-(oxetan-3-yl)-3,8-diazabicyclo[3.2.1]octan-3-yl)pyrimidin-5-yl)ethynyl)phenyl)-3-((S)-4,4,4-trifluoro-2-((methoxycarbonyl)amino)-3,3-dimethylbutanamido)butan-2-yl L-valinate (8)

To a solution of compound D (150 mg, 0.130 mmol) in DMF (3 mL) at rt, was added Boc-L-valine (85 mg, 0.391 mmol), N-(3-dimethylaminopropyl)-N'-ethylcarbodiimide hydrochloride (124 mg, 0.647 mmol) and 4-(dimethylamino)-pyridine (79 mg, 0.647 mmol). The reaction was stirred at room temperature overnight. The reaction was diluted with EtOAc and washed with brine. The organic extract was dried over sodium sulfate, filtered, and concentrated. The crude residue was dissolved in DCM (2 mL) and TFA (1 mL) was added. The reaction was stirred for 4 hr, then purified by HPLC to afford 8. MS (ESI) m/z 1255.2 [M+H]$^+$. $^1$H NMR (400 MHz, Methanol-d4) δ 8.52 (s, 2H), 8.11 (d, J=2.7 Hz, 1H), 7.53 (t, J=59.7 Hz, 1H), 7.47 (d, J=8.3 Hz, 2H), 7.36 (d, J=8.0 Hz, 2H), 7.22 (s, 1H), 6.99 (d, J=10.0 Hz, 1H), 6.94 (d, J=2.7 Hz, 1H), 6.89 (d, J=10.0 Hz, 1H), 5.22 (s, 1H), 4.95 (t, J=7.6 Hz, 2H), 4.82-4.72 (m, 2H), 4.66-4.47 (m, 1H), 4.41 (d, J=9.9 Hz, 1H), 4.29 (s, OH), 4.20 (d, J=13.2 Hz, 1H), 4.13 (s, 2H), 4.02 (d, J=13.1 Hz, 1H), 3.90 (d, J=5.8 Hz, 1H), 3.69 (s, 3H), 3.67 (s, 3H), 3.48 (d, J=14.5 Hz, 2H), 3.24-2.92 (m, 3H), 2.70 (t, J=12.3 Hz, 1H), 2.35 (h, J=6.7 Hz, 1H), 2.25-2.16 (m, 2H), 1.99 (t, J=7.1 Hz, 2H), 1.34-1.27 (m, 1H), 1.20-1.08 (m, 15H), 1.03 (s, 3H). $^{19}$F NMR (376 MHz, Methanol-d4) δ −77.26, −77.62, −77.76, −97.02 (dd, J=59.8, 8.9 Hz), −114.69 (d, J=8.5 Hz).

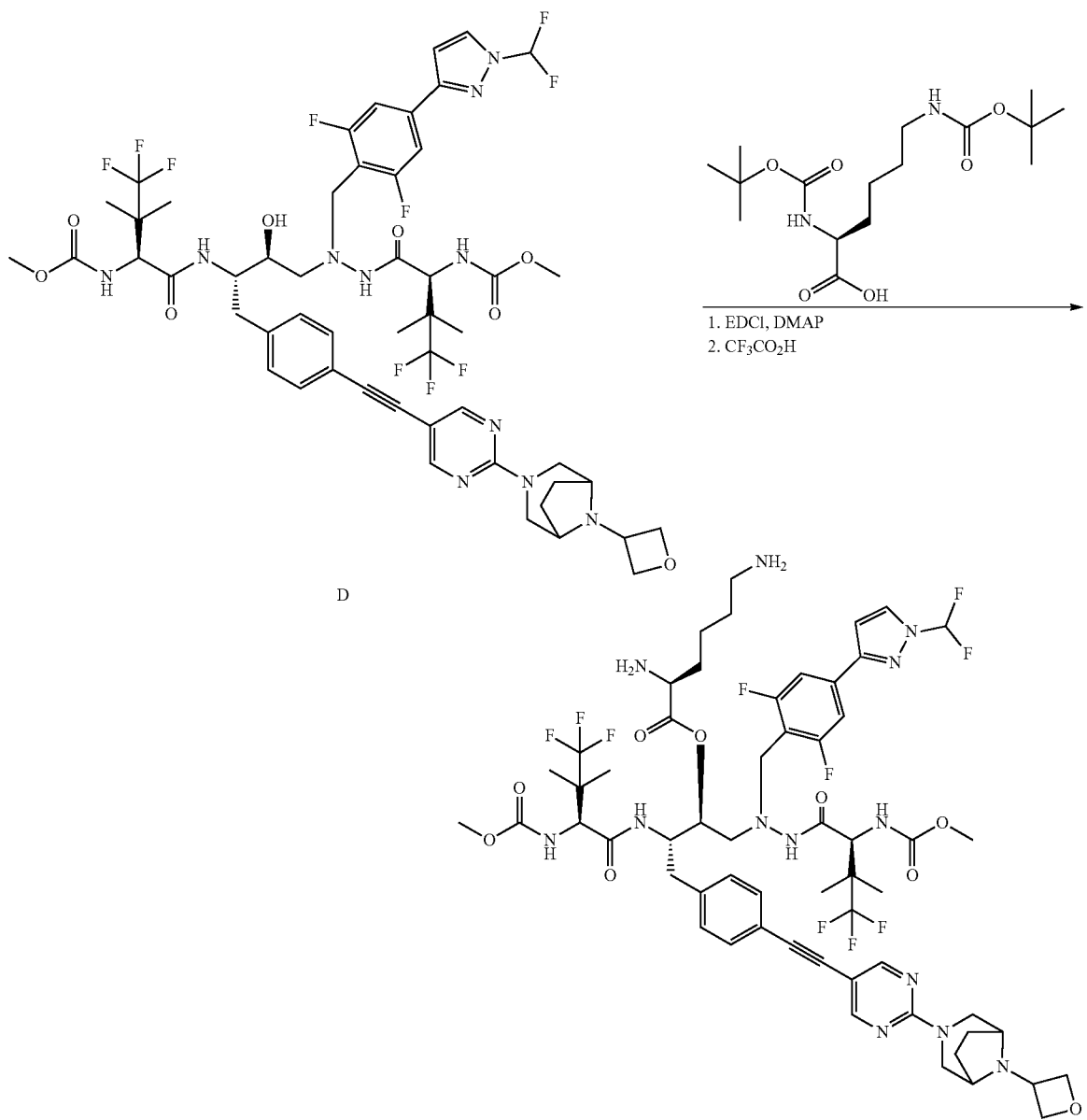

Example 9

(2S,3S)-1-(1-(4-(1-(difluoromethyl)-1H-pyrazol-3-yl)-2,6-difluorobenzyl)-2-((S)-4,4,4-trifluoro-2-((methoxycarbonyl)amino)-3,3-dimethylbutanoyl)hydrazinyl)-4-(4-((2-(8-(oxetan-3-yl)-3,8-diazabicyclo[3.2.1]octan-3-yl)pyrimidin-5-yl)ethynyl)phenyl)-3-((S)-4,4,4-trifluoro-2-((methoxycarbonyl)amino)-3,3-dimethylbutanamido)butan-2-yl L-lysinate (9)

To a solution of compound D (150 mg, 0.130 mmol) in DMF (3 mL) at RT, was added N2,N6-bis(tert-butoxycarbonyl)-L-lysine (135 mg, 0.390 mmol), N-(3-dimethylaminopropyl)-N'-ethylcarbodiimide hydrochloride (124 mg, 0.647 mmol) and 4-(dimethylamino)-pyridine (79 mg, 0.647 mmol). The reaction was stirred at room temperature for 6 hr. The reaction was diluted with EtOAc and washed with brine. The organic extract was dried over sodium sulfate, filtered, and concentrated. The crude residue was dissolved in DCM (2 mL) and TFA (1 mL) was added. The reaction was stirred for 3 hr, then purified by HPLC to afford 9. MS (ESI) m/z 1284.41 [M+H]$^+$. $^1$H NMR (400 MHz, Methanol-d4) δ 8.53 (s, 2H), 8.13 (d, J=2.7 Hz, 1H), 7.54 (t, J=59.7 Hz, 1H), 7.49 (d, J=8.4 Hz, 2H), 7.37 (d, J=8.0 Hz, 2H), 7.22 (d, J=8.0 Hz, 2H), 7.05 (d, J=10.0 Hz, 1H), 7.02-6.85 (m, 2H), 5.26 (s, 1H), 4.94 (d, J=7.4 Hz, 1H), 4.86-4.69 (m, 3H), 4.49 (s, 1H), 4.39-4.31 (m, 1H), 4.28 (d, J=9.9 Hz, 1H), 4.11 (d, J=12.2 Hz, 4H), 4.00 (d, J=13.0 Hz, 1H), 3.69 (d, J=6.8 Hz, 6H), 3.51-3.40 (m, 2H), 3.21-2.88 (m, 5H), 2.67 (t, J=12.4 Hz, 1H), 2.25-2.15 (m, 3H), 1.97 (d, J=8.8 Hz, 2H), 1.77 (d, J=11.7 Hz, 2H), 1.65 (q, J=7.3, 6.6 Hz, 2H), 1.15 (s, 3H), 1.10-1.03 (m, 9H). $^{19}$F NMR (377 MHz, Methanol-d4) δ −77.36, −77.52 (d, J=8.6 Hz), −96.99 (dd, J=59.6, 10.2 Hz), −114.69 (d, J=8.6 Hz).

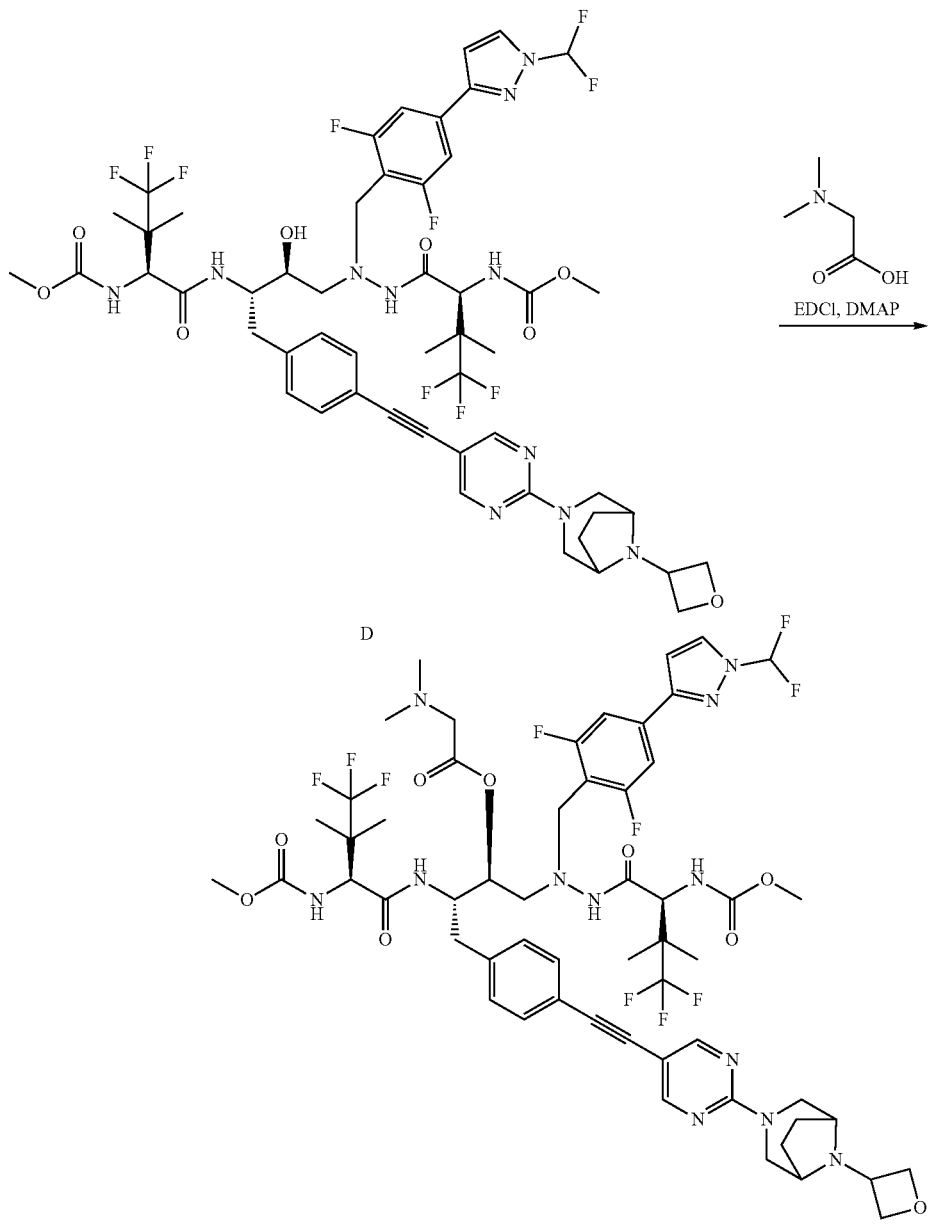

Example 10

(2S,3S)-1-(1-(4-(1-(difluoromethyl)-1H-pyrazol-3-yl)-2,6-difluorobenzyl)-2-((S)-4,4,4-trifluoro-2-((methoxycarbonyl)amino)-3,3-dimethylbutanoyl)hydrazinyl)-4-(4-((2-(8-(oxetan-3-yl)-3,8-diazabicyclo[3.2.1]octan-3-yl)pyrimidin-5-yl)ethynyl)phenyl)-3-((S)-4,4,4-trifluoro-2-((methoxycarbonyl)amino)-3,3-dimethylbutanamido)butan-2-yl dimethylglycinate (10)

To a solution of compound D (105 mg, 0.091 mmol) in DMF (3 mL) at RT, was added dimethylglycine (33.5 mg, 0.325 mmol), N-(3-dimethylaminopropyl)-N'-ethylcarbodiimide hydrochloride (87.7 mg, 0.457 mmol) and 4-(dimethylamino)pyridine (54 mg, 0.44 mmol). The reaction was stirred at room temperature overnight. Dimethylglycine (33.5 mg, 0.325 mmol), N-(3-dimethylaminopropyl)-N'-ethylcarbodiimide hydrochloride (87.7 mg, 0.457 mmol), and 4-(dimethylamino)-pyridine (54 mg, 0.44 mmol) were added. The reaction was stirred at room temperature overnight. The reaction was diluted with EtOAc and washed with brine. The organic extract was dried over sodium sulfate, filtered, and concentrated. Purification by HPLC afforded 10. MS (ESI) m/z 1241.3 [M+H]$^+$. $^1$H NMR (400 MHz, Methanol-d4) δ 8.52 (s, 2H), 8.11 (s, 1H), 7.71-7.43 (m, 3H), 7.42-7.30 (m, 3H), 7.21 (d, J=8.0 Hz, 3H), 7.04 (d, J=9.9 Hz, 1H), 6.94 (s, 1H), 6.89 (d, J=9.9 Hz, 1H), 5.32 (s, 1H), 5.02-4.91 (m, 16H), 4.81 (d, J=9.6 Hz, 7H), 4.46 (s, 2H), 4.38 (d, J=9.3 Hz, 1H), 4.26 (d, J=16.8 Hz, 3H), 4.16 (d, J=21.3 Hz, 3H), 3.97 (d, J=13.0 Hz, 1H), 3.76-3.63 (m, 8H), 3.47 (d, J=14.5 Hz, 3H), 3.07 (s, 8H), 2.95 (d, J=13.1 Hz, 2H), 2.68 (t, J=12.4 Hz, 1H), 2.20 (s, 2H), 1.98 (d, J=9.5 Hz, 3H), 1.18 (s, 3H), 1.09 (d, J=8.7 Hz, 12H). $^{19}$F NMR (377 MHz, Methanol-d4) δ −76.01, −77.60 (m), −96.00 (d, J=62.3 Hz), −113.66.

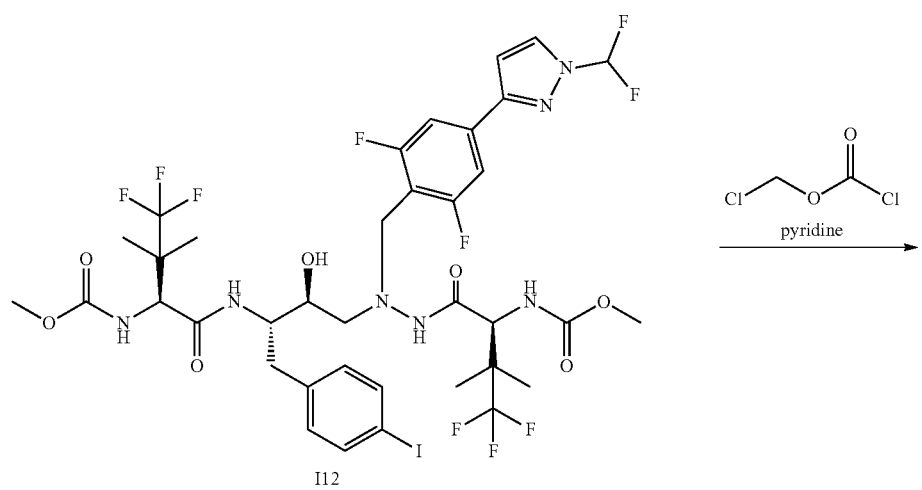

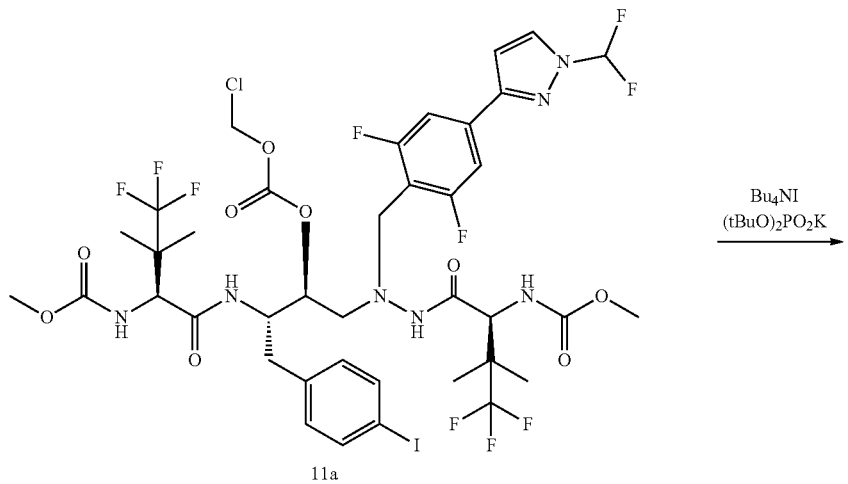

-continued
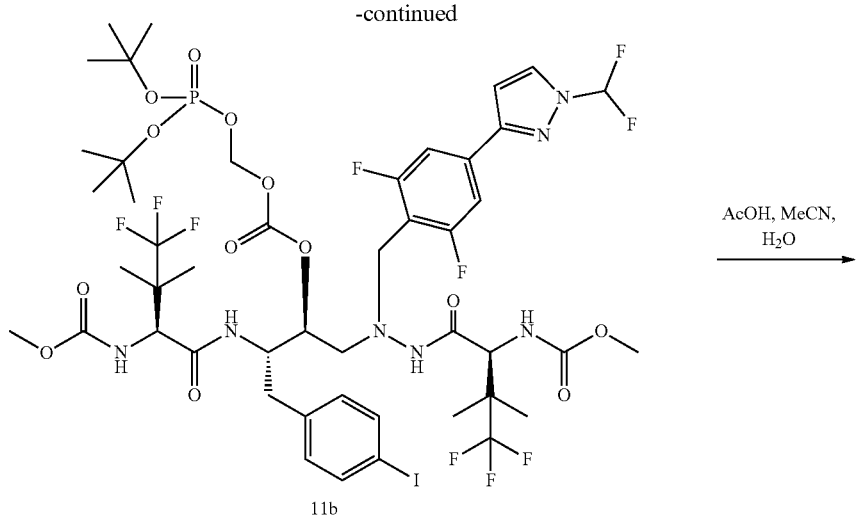
AcOH, MeCN, H₂O
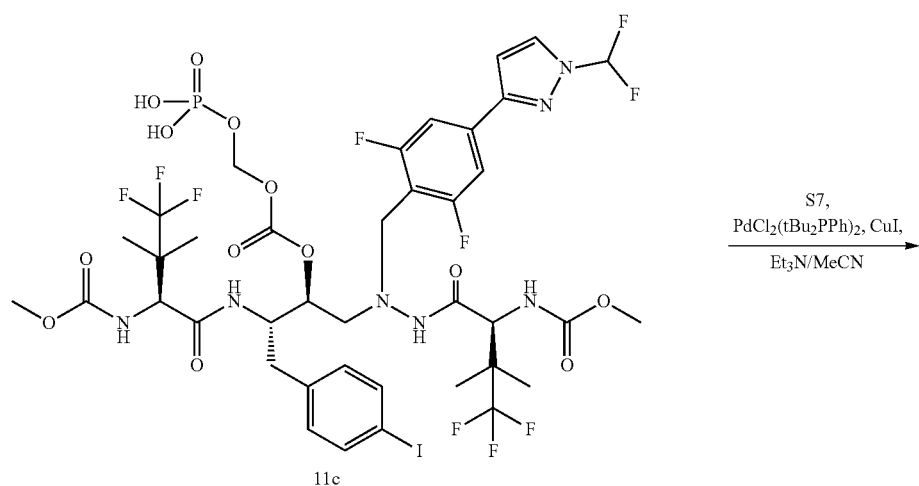
S7, PdCl₂(tBu₂PPh)₂, CuI, Et₃N/MeCN
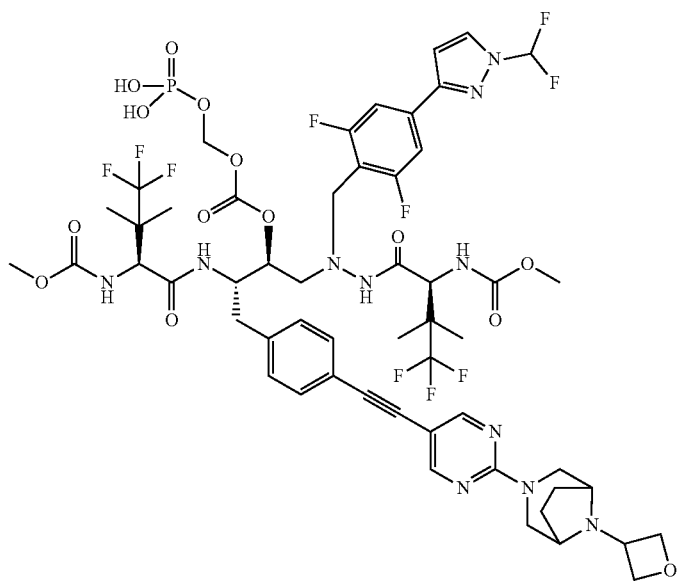

Example 11

Synthesis of methyl ((5S,10S,11S,14S)-10-(((chloromethoxy)carbonyl)oxy)-8-(4-(1-(difluoromethyl)-1H-pyrazol-3-yl)-2,6-difluorobenzyl)-16,16,16-trifluoro-11-(4-iodobenzyl)-15,15-dimethyl-3,6,13-trioxo-5-(1,1,1-trifluoro-2-methylpropan-2-yl)-2-oxa-4,7,8,12-tetraazahexadecan-14-yl)carbamate (11a)

To a solution of 112 (250 mg, 247 μmol) in pyridine (2.5 mL) at 0° C. was added chloromethyl chloroformate (0.24 mL, 2699 μmol). After 6 hours, the reaction was diluted with EtOAc and washed with sat'd NaHCO$_3$ and brine and dried over sodium sulfate to give 11a. MS (ESI) m/z 1106.0 [M]$^+$. $^1$H NMR (400 MHz, Methanol-d4) δ 8.61-8.43 (m, 2H), 8.10 (d, J=2.8 Hz, 1H), 7.95-7.74 (m, 1H), 7.52 (d, J=9.0 Hz, 3H), 7.48-7.35 (m, 4H), 7.14-6.87 (m, 3H), 5.91 (d, J=6.5 Hz, 1H), 5.78 (d, J=6.4 Hz, 1H), 4.45 (d, J=6.0 Hz, 1H), 4.28 (d, J=15.8 Hz, 2H), 4.04 (d, J=13.2 Hz, 1H), 3.69 (d, J=15.8 Hz, 6H), 2.99 (dd, J=13.7, 6.6 Hz, 1H), 2.94-2.70 (m, 1H), 2.70-2.53 (m, 1H), 1.30-0.99 (m, 11H). $^{19}$F NMR (377 MHz, Methanol-d4) δ −77.59 (d, J=52.8 Hz), −96.94 (dd, J=59.8, 6.5 Hz), −114.68.

Synthesis of methyl ((5S,10S,11S,14S)-10-(((((di-tert-butoxyphosphoryl)oxy)methoxy)carbonyl)oxy)-8-(4-(1-(difluoromethyl)-1H-pyrazol-3-yl)-2,6-difluorobenzyl)-16,16,16-trifluoro-11-(4-iodobenzyl)-15,15-dimethyl-3,6,13-trioxo-5-(1,1,1-trifluoro-2-methylpropan-2-yl)-2-oxa-4,7,8,12-tetraazahexadecan-14-yl)carbamate (11b)

To a solution of 1a (249.4 mg, 172.92 μmol) in DMF (2 mL), was added tetrabutylammonium iodide (67.4 mg, 182.48 μmol) and di-tert-butylphosphate, potassium salt (182.1 mg, 733.39 μmol). The reaction was stirred at 40° C. overnight. The reaction mixture was purified by HPLC to give 11b. MS (ESI) m/z 1280.2 [M]$^+$. $^1$H NMR (400 MHz, Methanol-d4) δ 8.40 (d, J=9.4 Hz, 1H), 8.10 (d, J=2.7 Hz, 1H), 7.52 (s, 1H), 7.71-7.35 (m, 2H), 7.45 (d, J=8.3 Hz, 2H), 7.07-6.96 (m, 3H), 6.94 (d, J=2.7 Hz, 1H), 5.61 (ddt, J=24.5, 12.7, 4.4 Hz, 2H), 4.61 (s, 2H), 4.48 (d, J=4.1 Hz, 1H), 4.37-4.21 (m, 3H), 4.04 (d, J=13.3 Hz, 1H), 3.71 (s, 3H), 3.67 (s, 3H), 3.25-3.14 (m, OH), 2.98 (dd, J=13.3, 5.9 Hz, 1H), 2.83 (dd, J=13.4, 5.5 Hz, 1H), 2.77-2.62 (m, 1H), 1.50 (t, J=1.8 Hz, 9H), 1.21 (s, 3H), 1.16 (s, 3H), 1.14 (s, 3H), 1.06 (s, 3H). $^{19}$F NMR (377 MHz, Methanol-d4) δ −77.43 (d, J=5.7 Hz), −77.73 (d, J=8.4 Hz), −78.20 (s), −96.93 (dd, J=59.7, 11.4 Hz), −114.59.

Synthesis of methyl ((5S,10S,11S,14S)-8-(4-(1-(difluoromethyl)-1H-pyrazol-3-yl)-2,6-difluorobenzyl)-16,16,16-trifluoro-11-(4-iodobenzyl)-15,15-dimethyl-3,6,13-trioxo-10-(((((phosphonooxy)methoxy)carbonyl)oxy)-5-(1,1,1-trifluoro-2-methylpropan-2-yl)-2-oxa-4,7,8,12-tetraazahexadecan-14-yl)carbamate (11c)

A solution of 11b (105 mg, 81.88 mol) in AcOH, CH$_3$CN, and water (1:1:1, 1.2 mL) was heated at 50° C. for 1 hr. The reaction mixture was then cooled and purified by HPLC to afford 11c. MS (ESI) m/z 1167.8 [M]$^+$. $^1$H NMR (400 MHz, Methanol-d4) δ 8.11 (d, J=2.5 Hz, 1H), 7.75-7.30 (m, 2H), 7.54-7.41 (m, 3H), 7.01 (d, J=8.1 Hz, 2H), 6.94 (s, 1H), 5.63 (ddd, J=27.3, 13.9, 5.5 Hz, 2H), 4.56 (s, 1H), 4.47 (s, 1H), 4.39-4.17 (m, 2H), 4.03 (d, J=13.3 Hz, 1H), 3.71 (s, 2H), 3.67 (s, 4H), 3.21 (s, 7H), 2.98 (d, J=7.5 Hz, 0H), 2.84 (d, J=13.3 Hz, 1H), 2.76-2.61 (m, 1H), 1.20 (s, 3H), 1.16 (s, 3H), 1.13 (s, 3H), 1.05 (s, 3H). $^{19}$F NMR (377 MHz, Methanol-d4) δ −77.48, −77.76, −78.21, −96.94 (dd, J=59.6, 9.7 Hz), −114.58.

Synthesis of methyl ((5S,10S,11S,14S)-8-(4-(1-(difluoromethyl)-1H-pyrazol-3-yl)-2,6-difluorobenzyl)-16,16,16-trifluoro-15,15-dimethyl-11-(4-((2-(8-(oxetan-3-yl)-3,8-diazabicyclo[3.2.1]octan-3-yl)pyrimidin-5-yl)ethynyl)benzyl)-3,6,13-trioxo-10-(((((phosphonooxy)methoxy)carbonyl)oxy)-5-(1,1,1-trifluoro-2-methylpropan-2-yl)-2-oxa-4,7,8,12-tetraazahexadecan-14-yl)carbamate (11)

A solution of 11c (93.4 mg, 0.07 mmol), S7 (29.5 mg, 0.109 mmol), cuprous iodide (6.9 mg, 0.036 mmol), Pd(tBu$_2$PPh)$_2$Cl$_2$ (10.8 mg, 0.015 mmol), triethylamine (0.4 mL, 2.87 mmol) and CH$_3$CN (3 mL) was degassed for 10 min with argon. The reaction was heated to 40° C. for 30 min. The reaction mixture was purified by HPLC to afford 11. MS (ESI) m/z 1311.1 [M+H]$^+$. $^1$H NMR (400 MHz, Methanol-d4) δ 8.51 (s, 2H), 8.09 (d, J=2.7 Hz, 1H), 7.52 (t, J=59.8 Hz, 1H), 7.44 (d, J=8.2 Hz, 2H), 7.34 (d, J=7.9 Hz, 2H), 7.24 (d, J=8.0 Hz, 2H), 6.98 (d, J=10.1 Hz, 1H), 6.93 (d, J=2.7 Hz, 1H), 6.78 (d, J=9.9 Hz, 0H), 5.62 (ddd, J=25.7, 13.8, 5.5 Hz, 2H), 4.95 (t, J=7.6 Hz, 2H), 4.75 (s, 1H), 4.62 (s, 1H), 4.47 (d, J=6.6 Hz, 1H), 4.33-4.19 (m, 2H), 4.13 (s, 2H), 4.04 (d, J=13.3 Hz, 1H), 3.67 (d, J=5.5 Hz, 6H), 3.49 (s, 1H), 3.46 (s, 1H), 3.21 (dd, J=13.6, 6.2 Hz, 1H), 3.05-2.85 (m, 2H), 2.84-2.72 (m, 1H), 2.27-2.15 (m, 2H), 1.98 (d, J=8.8 Hz, 2H), 1.27 (d, J=13.9 Hz, 1H), 1.20 (s, 3H), 1.16 (s, 3H), 1.13 (s, 3H), 1.04 (s, 3H). $^{19}$F NMR (376 MHz, Methanol-d4) δ −77.42, −77.74, −77.94, −96.95 (dd, J=59.8, 8.7 Hz), −114.59. 19F NMR (377 MHz, Methanol-d4) δ −77.29, −77.61, −96.94 (dd, J=59.8, 12.2 Hz), −114.42 (d, J=8.6 Hz).

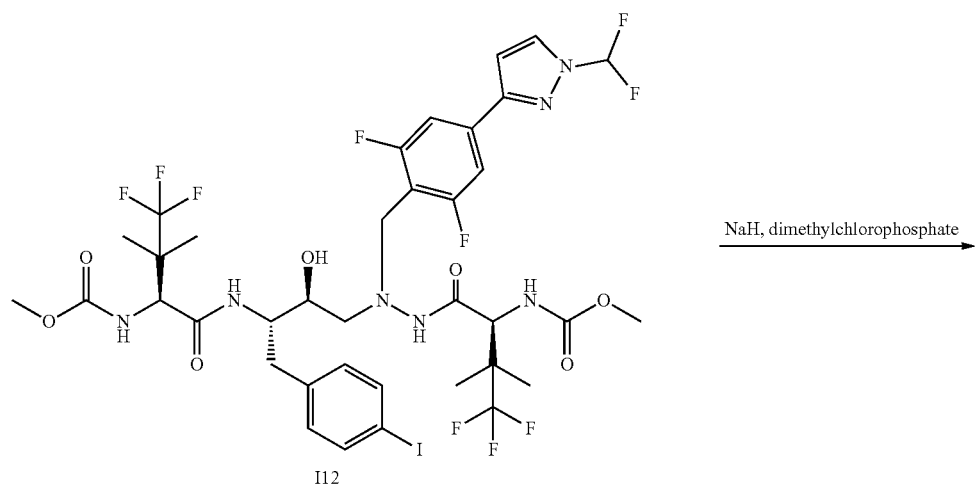
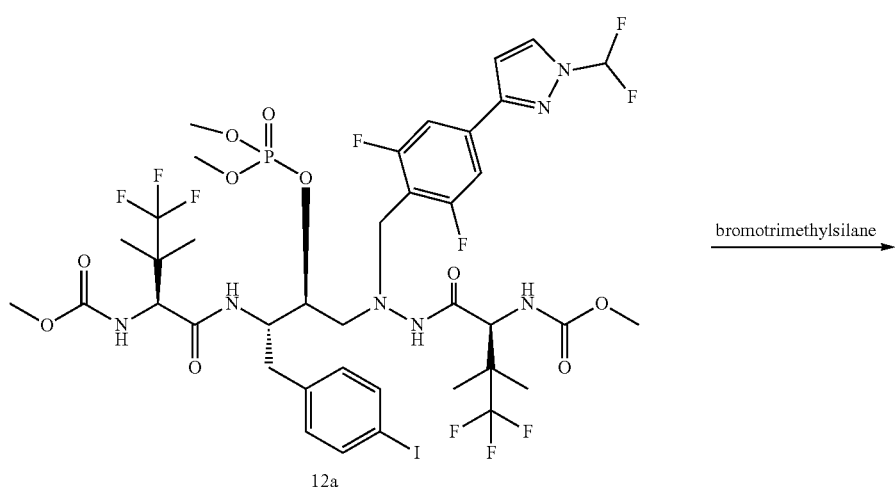
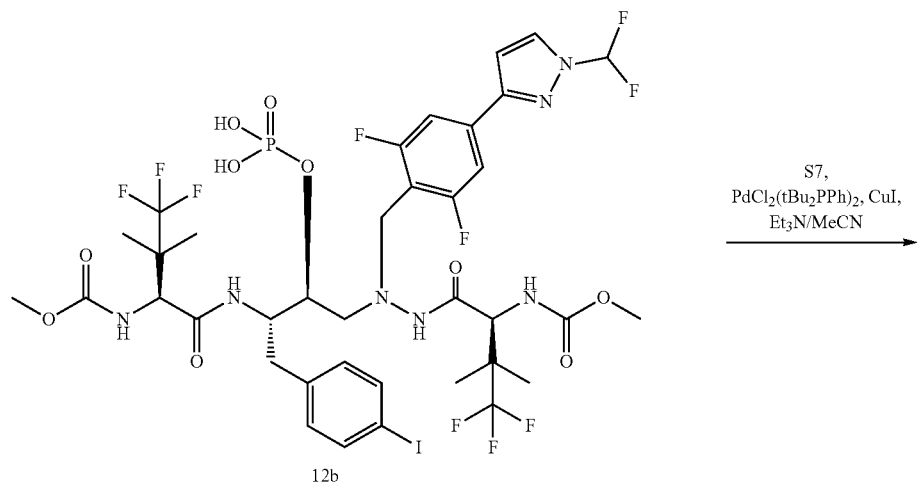

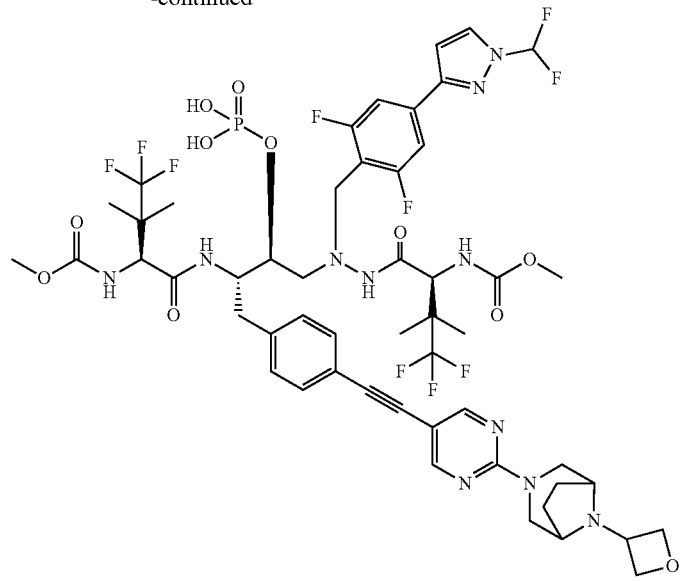

12

Example 12

Synthesis of methyl ((5S,10S,11S,14S)-8-(4-(1-(difluoromethyl)-1H-pyrazol-3-yl)-2,6-difluorobenzyl)-10-((dimethoxyphosphoryl)oxy)-16,16,16-trifluoro-1-(4-iodobenzyl)-15,15-dimethyl-3,6,13-trioxo-5-(1,1,1-trifluoro-2-methylpropan-2-yl)-2-oxa-4,7,8,12-tetraazahexadecan-14-yl)carbamate (12a)

To a solution of 112 (150 mg, 148 μmol) in THF (4 mL) at 0° C. was added a 60% dispersion of sodium hydride in oil (28 mg, 0.70 mmol). After 5 min, dimethyl chlorophosphate (40 μL, 0.371 mmol) was added. The reaction was stirred at room temperature overnight. The reaction was diluted with EtOAc and brine and the organic extract was dried over sodium sulfate. The crude residue was purified by silica gel chromatography (50% to 75% EtOAc/hexanes) to give 12a. MS (ESI) m/z 1121.9 [M+H]⁺. ¹H NMR (400 MHz, Methanol-d4) δ 8.01 (d, J=2.8 Hz, 1H), 7.62-7.27 (m, 2H), 7.44 (s, 1H), 7.36 (d, J=8.2 Hz, 1H), 6.96 (d, J=8.2 Hz, 2H), 6.85 (d, J=2.7 Hz, 1H), 4.43 (s, 1H), 4.28-4.15 (m, 2H), 4.13-3.90 (m, 2H), 3.72 (dd, J=11.2, 9.1 Hz, 5H), 3.60 (d, J=18.3 Hz, 5H), 3.08 (dd, J=13.1, 8.6 Hz, 1H), 2.96 (dd, J=13.0, 4.5 Hz, 1H), 2.72 (t, J=7.4 Hz, 2H), 1.11 (s, 2H), 1.07 (d, J=3.6 Hz, 5H), 0.96 (s, 2H), 0.80 (d, J=6.7 Hz, 1H). ¹⁹F NMR (377 MHz, Methanol-d4) δ −77.29, −77.61, −96.94 (dd, J=59.8, 12.2 Hz), −114.42 (d, J=8.6 Hz).

Synthesis of methyl ((5S,10S,11S,14S)-8-(4-(1-(difluoromethyl)-1H-pyrazol-3-yl)-2,6-difluorobenzyl)-16,16,16-trifluoro-11-(4-iodobenzyl)-15,15-dimethyl-3,6,13-trioxo-10-(phosphonooxy)-5-(1,1,1-trifluoro-2-methylpropan-2-yl)-2-oxa-4,7,8,12-tetraazahexadecan-14-yl)carbamate (12b)

To a solution of 12a (72.6 mg, 64.72 μmol) in CH₃CN (3 mL) was added bromotrimethylsilane (125 μL, 0.967 mmol). The reaction was stirred for 8 hr, then quenched with MeOH, stirred for 5 min, then concentrated to dryness. The residue was diluted with MeOH and reconcentrated. The crude residue was purified by HPLC to give 12b. MS (ESI) m/z 1093.7 [M+H]⁺. ¹H NMR (400 MHz, Methanol-d4) δ 8.11 (d, J=2.7 Hz, 1H), 7.54 (t, J=59.8 Hz, 1H), 7.53 (d, J=8.0 Hz, 1H), 7.47 (d, J=8.2 Hz, 2H), 7.20 (d, J=9.9 Hz, 1H), 7.03 (d, J=8.1 Hz, 2H), 6.95 (d, J=2.8 Hz, 1H), 6.83 (d, J=10.2 Hz, 1H), 4.62-4.44 (m, 1H), 4.39 (s, 2H), 4.36-4.25 (m, 1H), 4.17 (d, J=13.4 Hz, 1H), 4.03 (d, J=13.6 Hz, 1H), 3.72 (s, 3H), 3.66 (s, 3H), 3.08-2.76 (m, 4H), 1.20 (s, 3H), 1.13 (s, 3H), 1.12 (s, 3H), 1.09 (s, 3H). ¹⁹F NMR (377 MHz, Methanol-d4) δ −77.42, −77.76, −78.12, −96.95 (dd, J=59.7, 16.7 Hz), −114.12.

Synthesis of methyl ((5S,10S,11S,14S)-8-(4-(1-(difluoromethyl)-1H-pyrazol-3-yl)-2,6-difluorobenzyl)-16,16,16-trifluoro-15,15-dimethyl-11-(4-((2-(8-(oxetan-3-yl)-3,8-diazabicyclo[3.2.1]octan-3-yl)pyrimidin-5-yl)ethynyl)benzyl)-3,6,13-trioxo-10-(phosphonooxy)-5-(1,1,1-trifluoro-2-methylpropan-2-yl)-2-oxa-4,7,8,12-tetraazahexadecan-14-yl) carbamate (12)

A solution of 12b (39.6 mg, 0.033 mmol), S7 (13.3 mg, 0.049 mmol), cuprous iodide (3.9 mg, 0.020 mmol), Pd(tBu₂PPh)₂Cl₂ (5.4 mg, 0.01 mmol), triethylamine (0.2 mL, 1.435 mmol) and CH₃CN (2 mL) was degassed for 10 min with argon. The reaction was heated at 40° C. for 1 hr. The reaction was concentrated to dryness and purified by HPLC to give 12. MS (ESI) m/z 1236.1 [M]⁺. ¹H NMR (400 MHz, Methanol-d4) δ 8.36 (s, 2H), 8.02 (d, J=2.7 Hz, 1H), 7.45 (t, J=59.8 Hz, 1H), 7.38 (d, J=8.5 Hz, 3H), 7.22 (d, J=7.8 Hz, 3H), 7.11 (d, J=7.7 Hz, 3H), 6.86 (d, J=2.8 Hz, 1H), 6.61 (d, J=10.1 Hz, 1H), 4.84 (d, J=7.6 Hz, 3H), 4.36 (d, J=10.1 Hz, 1H), 4.25 (d, J=9.5 Hz, 1H), 4.09 (s, OH), 4.02 (s, 3H), 3.95 (d, J=13.6 Hz, 1H), 3.59 (d, J=4.5 Hz, 7H), 3.46-3.35 (m, 3H), 2.94-2.71 (m, 5H), 2.11 (d, J=9.4 Hz, 3H), 1.88 (d, J=8.9 Hz, 2H), 1.19 (d, J=13.9 Hz, 1H), 1.12 (s, 3H), 1.06-0.95 (m, 9H). ¹⁹F NMR (377 MHz, Methanol-d4) δ −77.42, −77.73, −77.76, −96.95 (dd, J=59.6, 13.6 Hz), −114.10.

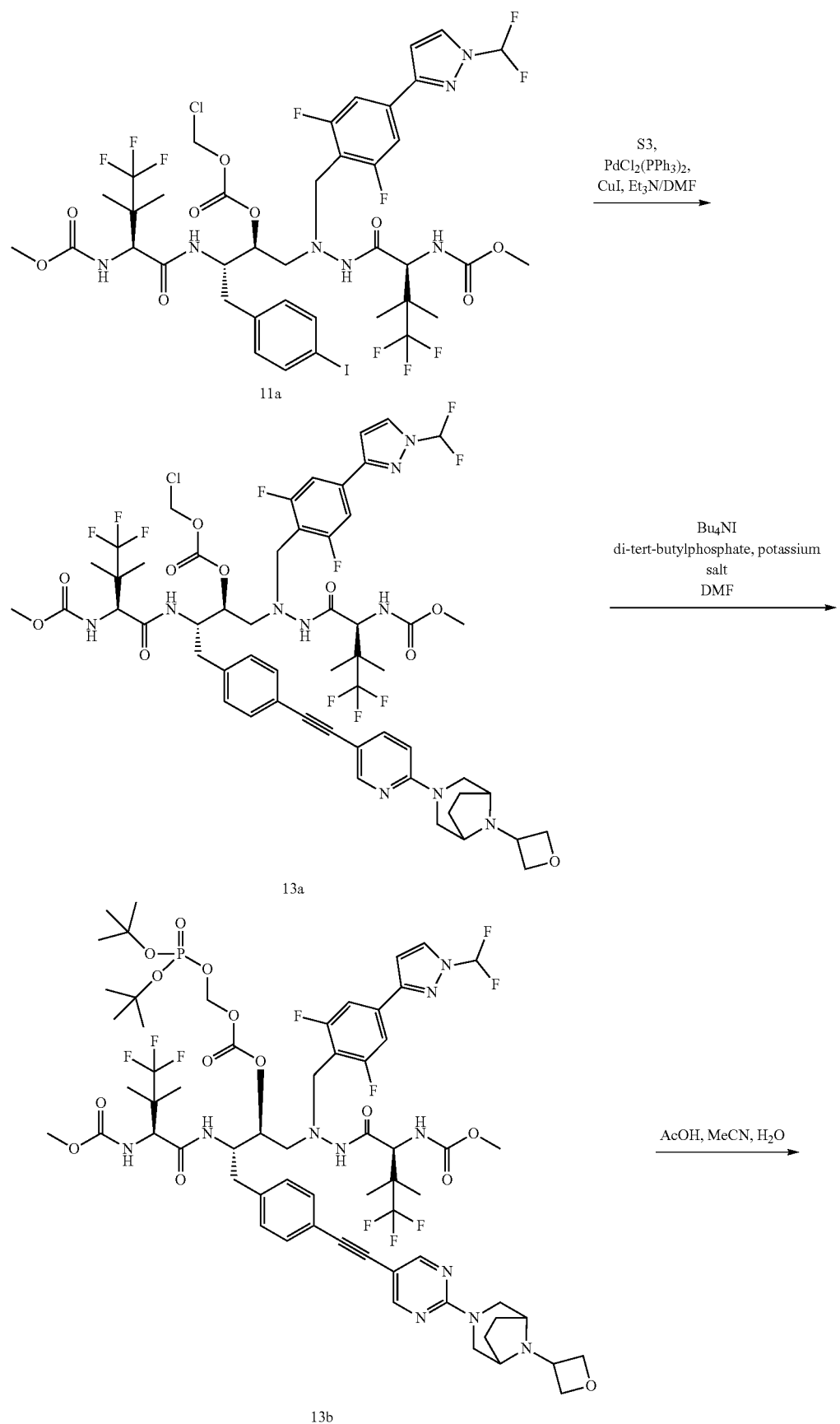

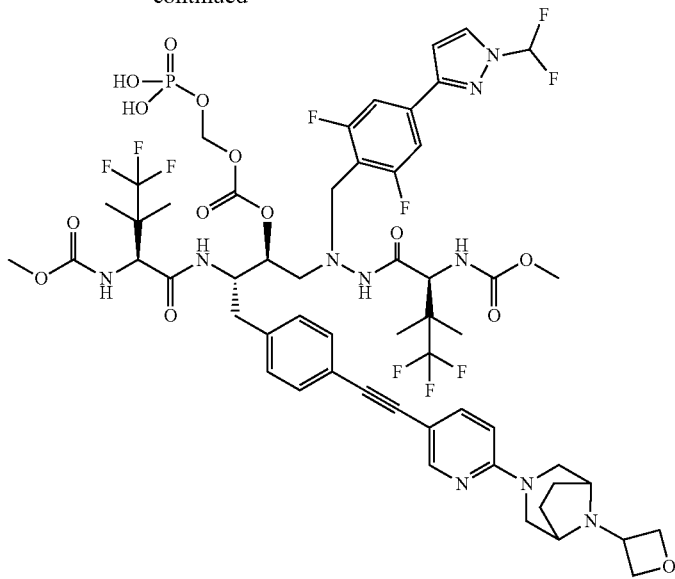

13

Example 13

Synthesis of methyl ((5S,10S,11S,14S)-10-(((chloromethoxy)carbonyl)oxy)-8-(4-(1-(difluoromethyl)-1H-pyrazol-3-yl)-2,6-difluorobenzyl)-16,16,16-trifluoro-15,15-dimethyl-11-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,8,12-tetraazahexadecan-14-yl)carbamate (13a)

A solution of 11a (272.8 mg, 0.247 mmol), S3 (86.4 mg, 0.321 mmol), cuprous iodide (15.2 mg, 0.080 mmol), trans-dichlorobis(triphenylphosphine)palladium (II) (37.2 mg, 0.052 mmol), triethylamine (1 mL, 7.175 mmol) and DMF (4 mL) was degassed for 10 min with Ar. The reaction was stirred at room temperature overnight. The reaction mixture was concentrated to dryness and purified by HPLC to afford 13a. MS (ESI) m/z 1248.6 [M+H]$^+$. $^1$H NMR (400 MHz, Methanol-d4) δ 8.37 (d, J=9.3 Hz, 1H), 8.30 (dd, J=4.6, 2.2 Hz, 1H), 8.10 (dd, J=2.8, 1.6 Hz, 1H), 7.70 (dq, J=9.3, 2.3 Hz, 2H), 7.53 (s, 1H), 7.46 (dd, J=12.1, 8.1 Hz, 2H), 7.40-7.27 (m, 3H), 7.21 (d, J=8.1 Hz, 2H), 6.94 (dd, J=5.8, 2.7 Hz, 1H), 6.86 (d, J=8.9 Hz, 1H), 5.91 (d, J=6.4 Hz, 1H), 5.78 (d, J=6.4 Hz, 1H), 4.96 (t, J=7.6 Hz, 3H), 4.70-4.51 (m, 2H), 4.45 (d, J=6.6 Hz, 1H), 4.40-4.24 (m, 5H), 4.15 (s, 3H), 4.05 (d, J=13.1 Hz, 1H), 3.77-3.64 (m, 8H), 3.39 (d, J=13.9 Hz, 3H), 2.96 (ddd, J=25.2, 13.8, 6.1 Hz, 1H), 2.79-2.66 (m, 1H), 2.34-2.16 (m, 3H), 2.15-2.02 (m, 3H), 1.35-1.02 (m, 17H). $^{19}$F NMR (376 MHz, Methanol-d4) δ −77.50, −77.68, −77.91, −96.96 (dd, J=59.9, 5.4 Hz), −114.66.

Synthesis of methyl ((5S,10S,11S,14S)-10-(((((di-tert-butoxyphosphoryl)oxy)methoxy)carbonyl)oxy)-8-(4-(1-(difluoromethyl)-1H-pyrazol-3-yl)-2,6-difluorobenzyl)-16,16,16-trifluoro-15,15-dimethyl-11-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,8,12-tetraazahexadecan-14-yl)carbamate (13b)

To a solution of 13a (130 mg, 82.09 μmol) in DMF (3 mL), was added di-tert-butylphosphate, potassium salt (81.5 mg, 0.328 mmol) and tetrabutylammonium iodide (5.2 mg, 14.08 μmol). The reaction was stirred at 40° C. overnight. The reaction mixture was purified by HPLC to afford 13b. MS (ESI) m/z 1421.5 [M+H]$^+$. $^1$H NMR (400 MHz, Methanol-d4) δ 8.43 (d, J=9.4 Hz, 1H), 8.30 (d, J=2.2 Hz, 1H), 8.11 (d, J=2.7 Hz, 1H), 7.71 (d, J=2.3 Hz, 1H), 7.69 (s, 1H), 7.54 (s, 1H), 7.33 (d, J=7.9 Hz, 2H), 7.23 (d, J=8.1 Hz, 3H), 7.06 (d, J=10.1 Hz, 1H), 6.95 (d, J=2.8 Hz, 1H), 6.85 (dd, J=14.7, 9.4 Hz, 2H), 5.61 (ddd, J=24.9, 12.9, 5.5 Hz, 2H), 4.96 (t, J=7.6 Hz, 3H), 4.81 (dd, J=8.3, 5.0 Hz, 3H), 4.68 (s, 1H), 4.48 (t, J=5.1 Hz, 1H), 4.39-4.21 (m, 5H), 4.16 (s, 2H), 4.05 (d, J=13.4 Hz, 1H), 3.68 (d, J=5.9 Hz, 7H), 3.38 (d, J=13.9 Hz, 3H), 3.26-3.16 (m, 1H), 2.94 (ddd, J=25.3, 13.2, 5.5 Hz, 2H), 2.85-2.69 (m, 1H), 2.32-2.15 (m, 2H), 2.08 (d, J=8.6 Hz, 2H), 1.51 (d, J=2.0 Hz, 19H), 1.21 (s, 4H), 1.17 (s, 3H), 1.15 (s, 3H), 1.05 (s, 3H). $^{19}$F NMR (377 MHz, Methanol-d4) δ −77.45, −77.78, −77.94, −96.93 (dd, J=59.7, 12.0 Hz), −114.59.

Synthesis of methyl ((5S,10S,11S,14S)-8-(4-(1-(difluoromethyl)-1H-pyrazol-3-yl)-2,6-difluorobenzyl)-16,16,16-trifluoro-15,15-dimethyl-11-(4-((6-(8-(oxetan-3-yl)-3,8-diazabicyclo[3.2.1]octan-3-yl)pyridin-3-yl)ethynyl)benzyl)-3,6,13-trioxo-10-(((((phosphonooxy)methoxy)carbonyl)oxy)-5-(1,1,1-trifluoro-2-methylpropan-2-yl)-2-oxa-4,7,8,12-tetraazahexadecan-14-yl)carbamate (13)

A solution of 13b (23.2 mg, 14.07 mol) in AcOH, CH$_3$CN, and water (1:1:1, 1 mL) was heated at 50° C. for 3 hr. The reaction mixture was purified by HPLC to afford 13. MS (ESI) m/z 1309.1 [M]$^+$. $^1$H NMR (400 MHz, Methanol-d4) δ 8.20 (d, J=2.3 Hz, 1H), 8.01 (d, J=2.7 Hz, 1H), 7.61 (d, J=2.3 Hz, 1H), 7.59 (s, 1H), 7.44 (s, 1H), 7.36 (d, J=8.2 Hz, 2H), 7.24 (d, J=7.9 Hz, 2H), 7.14 (d, J=8.0 Hz, 2H), 6.95 (d, J=10.1 Hz, 1H), 6.85 (d, J=2.8 Hz, 1H), 6.77 (d, J=9.1 Hz, 2H), 6.73 (s, OH), 5.53 (ddd, J=25.4, 13.7, 5.4 Hz, 2H), 4.87 (t, J=7.6 Hz, 3H), 4.72 (dd, J=8.3, 5.0 Hz, 2H), 4.54 (s, 1H), 4.38 (d, J=9.8 Hz, 1H), 4.34-4.13 (m, 3H), 4.06 (s, 2H), 3.94 (d, J=13.3 Hz, 1H), 3.59 (d, J=5.9 Hz, 6H), 3.28 (d, J=13.9 Hz, 3H), 2.99-2.76 (m, 2H), 2.76-2.62 (m, 1H), 2.13 (d, J=9.7 Hz, 2H), 1.98 (d, J=8.7 Hz, 2H), 1.11 (s, 4H), 1.07 (s, 3H), 1.05 (s, 3H), 0.94 (s, 3H). $^{19}$F NMR (377 MHz, Methanol-d4) δ −77.47, −77.82, −77.88, −96.92 (d, J=59.7 Hz), −114.54.

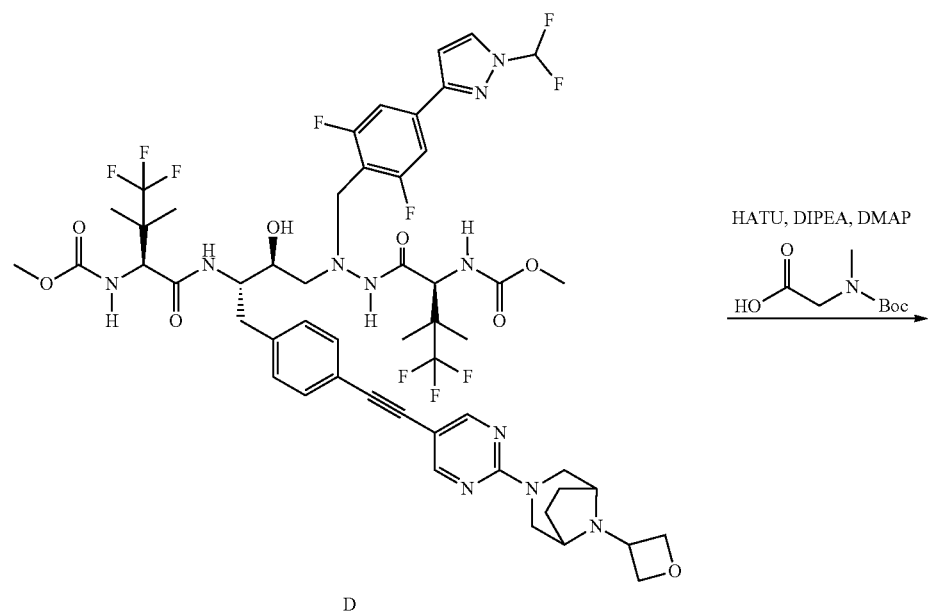
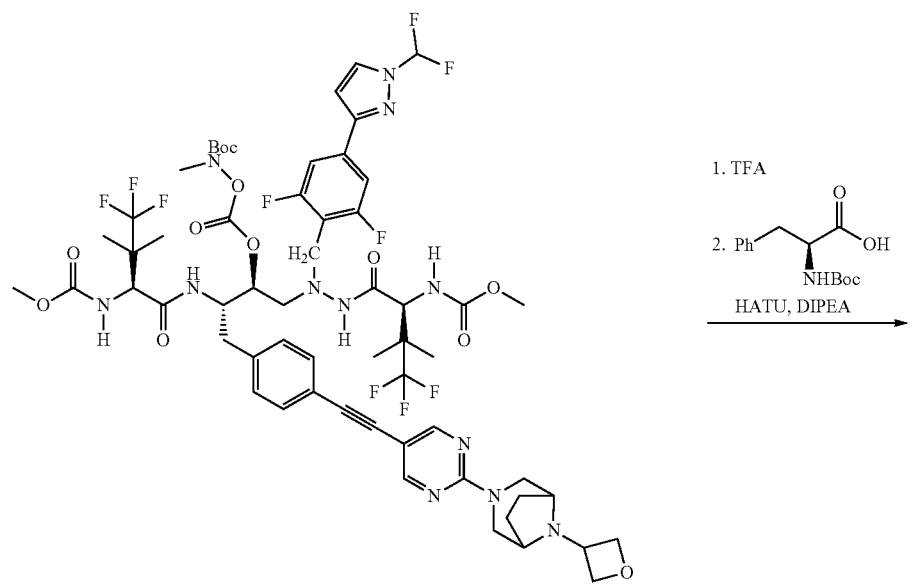

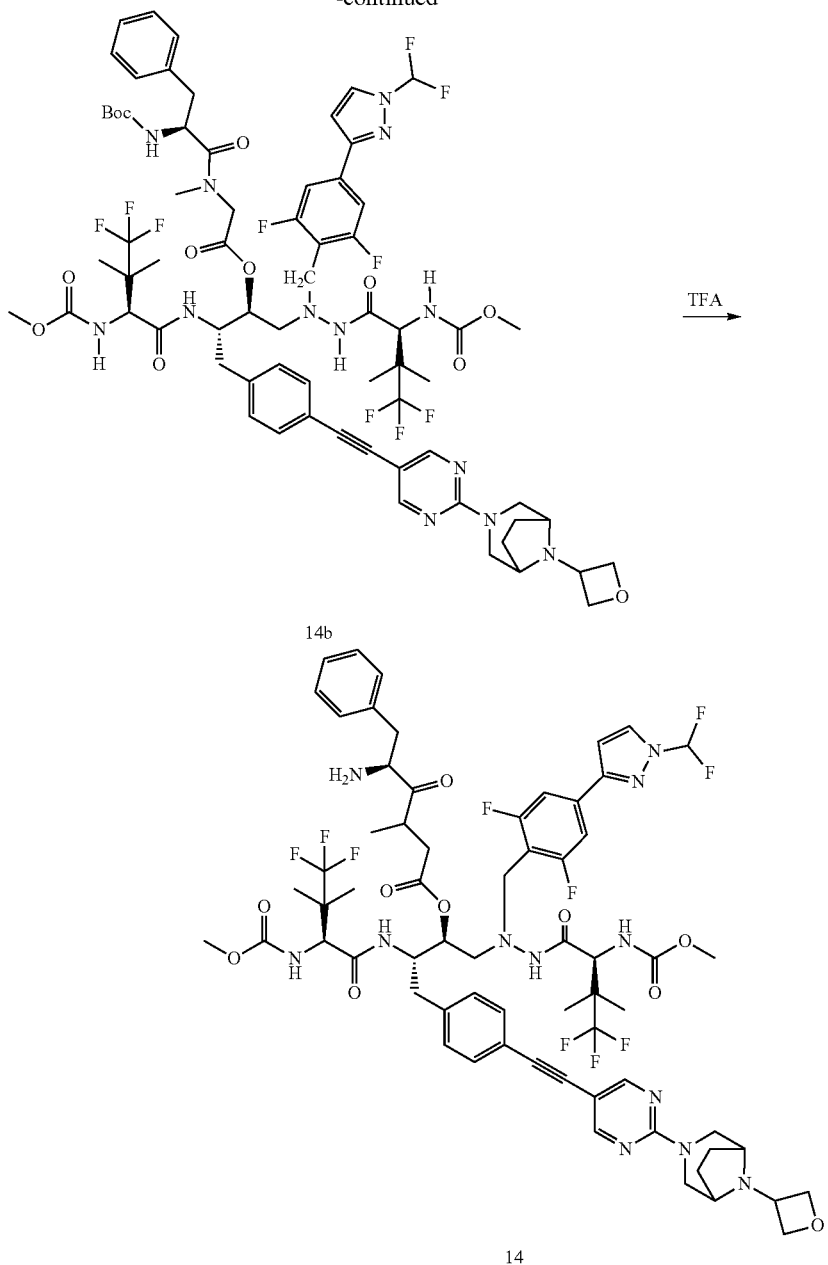

Example 14

Synthesis of (2S,3S)-1-(1-(4-(1-(difluoromethyl)-1H-pyrazol-3-yl)-2,6-difluorobenzyl)-2-((S)-4,4,4-trifluoro-2-((methoxycarbonyl)amino)-3,3-dimethylbutanoyl)hydrazinyl)-4-(4-((2-(8-(oxetan-3-yl)-3,8-diazabicyclo[3.2.1]octan-3-yl)pyrimidin-5-yl)ethynyl)phenyl)-3-((S)-4,4,4-trifluoro-2-((methoxycarbonyl)amino)-3,3-dimethylbutanamido)butan-2-yl N-(tert-butoxycarbonyl)-N-methylglycinate (14a)

2-[tert-butoxycarbonyl(methyl)amino]acetic acid (0.16 g, 0.87 mmol) was combined with HATU (0.30 g, 0.80 mol) in DCM (3 mL). After 5 minutes, DIPEA (0.17 mL, 0.95 mmol), compound D (200 mg, 0.173 mmol), and 4-DMAP (42 mg, 0.35 mmol) were added sequentially. The mixture was stirred at room temperature. After 10 minutes, the reaction was rinsed twice with 1 M HCl, rinsed once with aqueous sodium bicarbonate, dried over sodium sulfate, filtered and concentrated to yield crude (2S,3 S)-1-(1-(4-(1-(difluoromethyl)-1H-pyrazol-3-yl)-2,6-difluorobenzyl)-2-((S)-4,4,4-trifluoro-2-((methoxycarbonyl)amino)-3,3-dimethylbutanoyl)hydrazinyl)-4-(4-((2-(8-(oxetan-3-yl)-3,8-diazabicyclo[3.2.1]octan-3-yl)pyrimidin-5-yl)ethynyl)phenyl)-3-((S)-4,4,4-trifluoro-2-((methoxycarbonyl)amino)-3,3-dimethylbutanamido)butan-2-yl N-(tert-butoxycarbonyl)-N-methylglycinate. MS (ESI) m/z 1328.3 [M+H]+.

Synthesis of (2S,3S)-1-(1-(4-(1-(difluoromethyl)-1H-pyrazol-3-yl)-2,6-difluorobenzyl)-2-((S)-4,4,4-trifluoro-2-((methoxycarbonyl)amino)-3,3-dimethylbutanoyl)hydrazinyl)-4-(4-((2-(8-(oxetan-3-yl)-3,8-diazabicyclo[3.2.1]octan-3-yl)pyrimidin-5-yl)ethynyl)phenyl)-3-((S)-4,4,4-trifluoro-2-((methoxycarbonyl)amino)-3,3-dimethylbutanamido)butan-2-yl N-((tert-butoxycarbonyl)-L-phenylalanyl)-N-methylglycinate (14b)

Crude 14a from the reaction above was dissolved in DCM (4 mL) and treated with TFA (0.7 mL). After 15 minutes, the reaction was cooled to 5° C., poured slowly into aqueous sodium bicarbonate, and extracted with DCM (15 mL). The DCM layer was rinsed twice with aqueous sodium bicarbonate, dried over sodium sulfate and filtered. MS (ESI) m/z 1227.6 [M+H]$^+$. To this solution was added (2S)-2-(tert-butoxycarbonylamino)-3-phenyl-propanoic acid (60 mg, 0.22 mmol), followed by concentration in vacuo to dryness. This crude material was dissolved in DCM (3 mL) and treated with HATU (79 mg, 0.21 mmol) and DIPEA (0.17 mL, 0.95 mmol). After 10 minutes, the reaction was rinsed twice with 1 M HCl, rinsed once with aqueous sodium bicarbonate, dried over sodium sulfate, filtered, concentrated, and purified by HPLC to afford 14b as a TFA salt. MS (ESI) m/z 1475.3 [M+H]$^+$.

Synthesis of (2S,3S)-1-(1-(4-(1-(difluoromethyl)-1H-pyrazol-3-yl)-2,6-difluorobenzyl)-2-((S)-4,4,4-trifluoro-2-((methoxycarbonyl)amino)-3,3-dimethylbutanoyl)hydrazinyl)-4-(4-((2-(8-(oxetan-3-yl)-3,8-diazabicyclo[3.2.1]octan-3-yl)pyrimidin-5-yl)ethynyl)phenyl)-3-((S)-4,4,4-trifluoro-2-((methoxycarbonyl)amino)-3,3-dimethylbutanamido)butan-2-yl N-(L-phenylalanyl)-N-methylglycinate (14)

14b (270 mg, 0.17 mmol) was dissolved in DCM (3 mL) and treated with TFA (0.5 mL). After 30 minutes, the reaction was diluted with ice (0.5 g) and DMF (1 mL). The DCM was removed in vacuo and the residue was purified by HPLC to afford 14 as a TFA salt. 1H NMR (400 MHz, Methanol-d4) δ 8.54 (d, J=1.4 Hz, 2H), 8.31 (d, J=9.3 Hz, 1H), 8.19 (d, J=9.4 Hz, 0H), 8.16 (d, J=2.7 Hz, 0H), 8.14 (d, J=2.8 Hz, 1H), 7.74-7.68 (m, 0H), 7.60-7.52 (m, 1H), 7.51-7.30 (m, 9H), 7.25 (d, J=8.0 Hz, 2H), 7.18 (d, J=8.0 Hz, 1H), 7.09-6.94 (m, 2H), 6.93-6.81 (m, 1H), 5.33-5.21 (m, 0H), 5.21-5.07 (m, 1H), 5.03-4.94 (m, 2H), 4.88-4.71 (m, 5H), 4.61-4.45 (m, 3H), 4.45-4.23 (m, 2H), 4.18-4.14 (m, 2H), 4.10-3.96 (m, 2H), 3.72 (s, 2H), 3.70 (s, 1H), 3.69 (s, 2H), 3.51 (d, J=14.8 Hz, 2H), 3.26-3.11 (m, 2H), 2.98-2.85 (m, 3H), 2.78-2.68 (m, 1H), 2.30-2.15 (m, 2H), 2.04-1.92 (m, 2H), 1.25-1.14 (m, 9H), 1.14-1.03 (m, 3H). MS (ESI) m/z 1375.5 [M+H]$^+$.

4. Biological Assays

MT-4 HIV Assay

Compounds were tested in a high-throughput 384-well assay format for their ability to inhibit the replication of HIV-1 (IIIB) in MT-4 cells. Compounds were serially diluted (1:3) in DMSO on 384-well polypropylene plates and further diluted 200-fold into complete RPMI media (10% FBS, 1% P/S) using the Biotek Micro Flow and Agilent ECHO acoustic dispenser. Each plate contained up to 8 test compounds, with negative (No Drug Control) and 5 μM AZT positive controls. MT-4 cells were pre-infected with 10 μL of either RPMI (mock-infected) or a fresh 1:250 dilution of an HIV-1 (IIIB) concentrated virus stock. Infected and uninfected MT-4 cells were further diluted in complete RPMI media and added to each plate using a Micro Flow dispenser. After 5 days incubation in a humidified and temperature controlled incubator (37° C.), Cell Titer Glo (Promega) was added to the assay plates to quantify the amount of luciferase. EC$_{50}$ values were defined as the compound concentration that causes a 50% decrease in luminescence signal, and were calculated using a sigmoidal dose-response model to generate curve fits. Data for certain compounds is reported in Table 1 below.

Liver Microsomal Stability Protocol

Test compounds and one control compound (verapamil) were tested in 3 different species in duplicate sets.

General Conditions:

Test compound concentration: 1 μM; Protein concentration: 0.5 mg/mL (for rat and human liver microsomes); Cofactor: NADPH-Regenerating system (NRS) solution. Time-points: 2, 12, 25, 45, and 65 minutes.

Reaction composition (in each incubation well) contains:

5 μL compound (50 uM stock solution, 50:50 ACN:H2O)
25 μL NRS solution
6.25 μL 20 mg/mL liver microsomes
213.75 μL 100 mM KPO4, pH 7.4

250 μL total volume

At an incubation temperature of 37° C., the reaction was started with addition of NADPH Regeneration System, at each time point, 25 μL of the reaction mixture was removed and added to a plate with 225 μL quenching solution (50% MeOH, 25% ACN, 25% H$_2$O, and 200 nM labetalol as internal standard). After plates were vortexed, they were centrifuged for 30 minutes to remove proteins. About 100 μL supernatant was removed to a new plate and diluted with 150 μL water. About 20 μL of the mixture was injected into an LC/MS/MS system to monitor the compound's response. In vitro measured t$_{1/2}$ was used to calculate Clint values. Data is presented in Table 1 below.

TABLE 1

| Cmpd | EC$_{50}$ (nM) | Rat. Pred. Cl. (L/H/kg) | Human Pred Cl. (L/H/kg) |
|---|---|---|---|
| 1 | 4.62 | <0.4 | 0.37 |
| 2 | 56.615 | 0.84 | 0.53 |
| 3 | 602.77 | — | — |
| 4 | 5714.3 | — | — |
| 5 | 1140 | 0.58 | 0.28 |
| 6 | 277.53 | <0.4 | 0.29 |
| 7 | 247.08 | — | — |
| 8 | 102.18 | — | — |
| 9 | 20.57 | — | — |
| 12 | — | 0.91 | 0.47 |
| 14 | 6.54 | — | — |

Kinetic Solubility Analysis (CLND)

Buffer Preparation:

0.1N HCl: Hydrochloric acid, 0.1N standardized solution.

1×PBS, 7.4: Phosphate Buffered Saline solution 10×, PBS 50 mL was added to approximately 450 mL HPLC grade H$_2$O. The volume of the solution was then adjusted to 500 mL for a total dilution factor of 1:10 and a final PBS concentration of IX. The pH of the final solution was measured and found to be 7.4.

Kinetic Solubility from DMSO Stocks:

100-fold dilutions of each DMSO stock solution were prepared in singleton by combining 3 μL of DMSO stock with 297 μL of the appropriate media in a Millipore solubility filter plate with a 0.45 μM polycarbonate filter membrane using Hamilton Starlet liquid handling. The final DMSO concentration is 1.0% and maximum theoretical compound concentration is 100 μM (assuming stock concentration of 10 mM). The filter plate was sealed. Following 24-hour incubation at ambient temperature (24.2-27.5° C.), the samples were vacuum filtered and the filtrates were collected in a 96 well polypropylene plate for analysis. The collection plate was sealed for analysis. Filtrates were injected into the nitrogen detector for quantification. The results are reported here in M.

Calculation of Results:

The equimolar nitrogen response of the detector was calibrated using standards which spanned the dynamic range of the instrument from 0.08 to 4500 g/mL nitrogen. The filtrates were quantified with respect to this calibration curve. The calculated solubility values were corrected for background nitrogen present in the DMSO and the media used to prepare the samples. All reported values for compounds containing adjacent nitrogen atoms in a ring structure should be increased by 25%. A comments field contains notes pertinent to the assay of each compound, such as, measured solubility is greater than 75% of the dose concentration, actual solubility may be higher. The solubility results presented assume that the samples were free of nitrogen containing impurities and were stable under the assay conditions.

TABLE 2

| Example # | Solubility, μM | |
|---|---|---|
| | PBS, pH 7.4, RT | HCl, pH 1.0, RT |
| Compound D | <1 | 19.5 |
| 1 | <1 | 20.0 |
| 2 | <1 | 81.0 |
| 3 | <1 | 25.2 |
| 4 | <1 | 99.2 |
| 5 | <1 | 89.2 |
| 6 | <1 | 38.5 |
| 7 | 9.3 | >100 |
| 8 | <1 | 90.0 |
| 9 | 6.8 | 86.8 |
| 10 | <1 | 79.3 |
| 12 | 84.6 | 13.1 |
| 13 | <1 | 67.4 |

Pharmacokinetic Profiling

Dog PK

Compound 11 was formulated in a suspension formulation (1% HPMC and 0.05% Tween 20 in DI Water) and administered orally at 10 mg-eq/kg to a dosing group consisting of three non-naïve male beagle dogs. At dosing, the animals weighed between 9 to 12 kg. The animals were fasted overnight prior to dose administration and up to four hours after dosing. Serial venous blood samples (approximately 1.0 mL each) were obtained at pre-dose, 0.25, 0.50, 1, 2, 4, 6, 8, 12, and 24 hours post-dose. The blood samples were collected into Vacutainer™ tubes containing EDTA-K2 as the anti-coagulant and were immediately placed on wet ice pending centrifugation for plasma. An LC/MS/MS method was used to measure the concentration of compound 11 and compound D in plasma. Compound 11 was not detected in plasma. The bioavailability of compound D was estimated to be 5.5±2.6% based on previous IV data. In a second experiment, compound D was dosed orally as a suspension using the same formulation and dose level. In this case, the bioavailability of compound D was estimated to be 2.6±1.1%.

Rat PK

Compound 14 was formulated in a solution formulation (84% 10 mM HCl; 15% 2-Hydroxypropyl-β-Cyclodextrin; 1% Dimethyl sulfoxide pH 2.0) and administered orally at 2.5 and 75 mg-eq/kg to a dosing groups consisting of three male SD rats. At dosing, the animals weighed between 270 and 350 g. The animals were fasted overnight prior to dose administration and up to four hours after dosing. Serial venous blood samples were obtained at pre-dose, 0.25, 0.50, 1, 2, 4, 6, 8, 12, and 24 hours post-dose. The blood samples were collected into Vacutainer™ tubes containing EDTA-K2 as the anti-coagulant and were immediately placed on wet ice pending centrifugation for plasma. An LC/MS/MS method was used to measure the concentration of compound 14 and compound D in plasma. Trace amounts of compound 14 were detected in plasma in the 75 mg-eq/kg dose group. The bioavailability of compound D was estimated to be 13±4%, 6.6±1.2% in the 2.5 and 75 mg-eq/kg dose groups, respectively, based on previous IV data.

What is claimed is:

1. A compound of Formula (I):

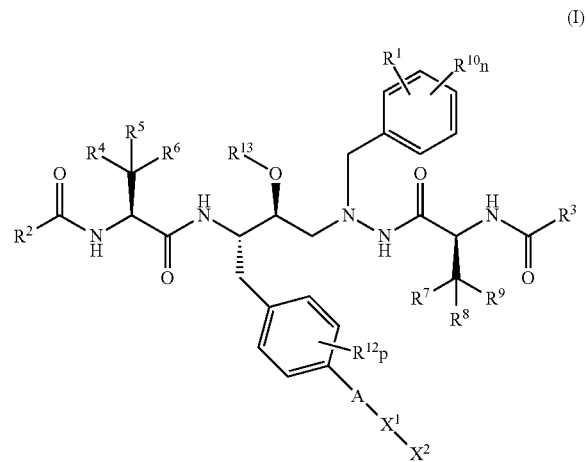

or a pharmaceutically acceptable salt thereof, wherein:

$R^1$ is a 5 to 10-membered heterocycle having 1 to 5 heteroatoms selected from N, O, and S, or a 5 to 10-membered heteroaryl having 1 to 5 heteroatoms selected from N, O, and S, wherein the 5 to 10-membered heterocycle or 5 to 10-membered heteroaryl is optionally substituted with 1 to 5 $R^a$ groups;

$R^2$ and $R^3$ are each independently $C_{1-4}$ alkyl, $C_{3-6}$ cycloalkyl, O—$R^{2A}$, $C_{1-2}$ alkyl-O—$R^{2A}$, N—$(R^{3A})_2$, or $C_{1-2}$ alkyl-N—$(R^{3A})_2$, wherein each $R^{2A}$ is independently $C_{1-4}$ alkyl, $C_{3-6}$ cycloalkyl, or a 4 to 10-membered heterocyclyl having 1 to 5 heteroatoms selected from N, O, and S, wherein each $R^{3A}$ is independently hydrogen, $C_{1-4}$ alkyl, $C_{3-6}$ cycloalkyl, or COO($R^e$), wherein each $R^e$ is independently hydrogen or $C_{1-4}$ alkyl, and wherein each $C_{3-6}$ cycloalkyl or 4 to 10-membered heterocyclyl is optionally substituted by 1 to 3 $R^f$ groups, wherein each $R^f$ is independently $C_{1-2}$ alkyl or halogen;

$R^4$ is hydrogen, halo, $C_{1-4}$ alkyl, $C_{1-4}$haloalkyl, $C_{3-6}$ cycloalkyl, $C_{1-4}$ alkoxy, or $C_{1-4}$haloalkoxy;

$R^7$ is hydrogen, halo, $C_{1-4}$ alkyl, $C_{1-4}$haloalkyl, $C_{3-6}$ cycloalkyl, $C_{1-4}$ alkoxy, or $C_{1-4}$haloalkoxy;

$R^5$, $R^6$, $R^8$, and $R^9$ are each independently hydrogen, halo, $C_{1-2}$ alkyl, $C_{1-2}$ haloalkyl, or $C_{3-6}$ cycloalkyl;

and wherein two or more of $R^4$, $R^5$ and $R^6$ or two or more of $R^7$, $R^8$, and $R^9$ optionally join together to form one or more $C_{3-6}$ cycloalkyl groups that are optionally substituted with 1 to 4 groups selected from halogen, $C_{1-2}$ alkyl, and $C_{1-2}$ haloalkyl;

each $R^{10}$ is independently halogen, cyano, $C_{1-4}$ alkoxy, $C_{1-6}$ alkyl, or $C_{3-6}$ cycloalkyl;

n is 0 to 4;

each $R^a$ is independently halogen, $C_{1-4}$ alkyl, $C_{1-4}$ alkyl with 1 to 2 groups selected from hydroxyl and $C_{1-4}$ alkoxy, $C_{1-4}$ haloalkyl, $C_{1-4}$ alkoxy, $C_{3-6}$ cycloalkyl, 4 to 10-membered heterocyclyl having 1 to 5 heteroatoms selected from N, O, and S which is optionally substituted with $R^{a1}$, or O—$R^{3B}$, wherein $R^{3B}$ is $C_{3-6}$ cycloalkyl optionally substituted with $R^a$ or a 4 to 10-membered heterocyclyl having 1 to 5 heteroatoms selected from N, O, and S optionally substituted with $R^{a1}$, wherein each $R^{a1}$ is independently $C_{1-4}$ alkyl, $C_{3-6}$ cycloalkyl, $C_{1-4}$ haloalkyl, or 4 to 8-membered heterocyclyl having 1 to 3 heteroatoms selected from N, O, and S;

A is ethynyl or a bond;

$X^1$ is a 6 to 10-membered aryl or a 5 to 10-membered heteroaryl having 1 to 3 heteroatoms selected from N, O, and S, wherein each 6 to 10-membered aryl or 5 to 10-membered heteroaryl is optionally substituted with 1 to 4 $R^b$ groups;

$X^2$ is hydrogen or a 4 to 10-membered heterocyclyl having 1 to 5 heteroatoms selected from N, O, and S, wherein the 4 to 10-membered heterocyclyl is optionally substituted with one $R^{11}$ and optionally substituted with 1 to 5 $R^b$ groups;

$R^{11}$ is —C=O($R^c$), $CH_2(R^d)$, $S(O)_{1-2}(C_{1-4}$ alkyl), $S(O)_{1-2}$—($C_{3-6}$ cycloalkyl), a 4 to 10-membered heterocyclyl having 1 to 5 heteroatoms selected from N, O, and S, or a 5 to 9-membered heteroaryl having 1 to 5 heteroatoms selected from N, O, and S, wherein each 4 to 10-membered heterocyclyl or 5 to 9-membered heteroaryl is optionally substituted with 1 to 5 $R^b$ groups;

each $R^b$ is independently halogen, oxo, $C_{1-4}$ alkyl, $C_{1-4}$ alkyl with 1 to 2 groups selected from hydroxyl and $C_{1-4}$ alkoxy, $C_{1-4}$ haloalkyl, $C_{1-4}$ alkoxy, or COO($R^e$);

$R^c$ is $C_{1-4}$alkyl, $C_{1-4}$haloalkyl, $C_{1-4}$ alkoxy, $N(R^e)_2$, $C_{3-6}$ cycloalkyl, or a 4 to 6-membered heterocyclyl having 1 to 3 heteroatoms selected from N, O, and S, wherein the $C_{3-6}$ cycloalkyl and the 4 to 6-membered heterocyclyl are optionally substituted by 1 to 5 $R^b$ groups;

$R^d$ is COO($R^e$), $N(R^e)_2$, $C_{3-6}$ cycloalkyl, or a 4 to 6-membered heterocyclyl having 1 to 3 heteroatoms selected from N, O, and S, wherein the $C_{3-6}$ cycloalkyl and the 4 to 6-membered heterocyclyl is optionally substituted by 1 to 5 $R^b$ groups;

each $R^{12}$ is $C_{1-2}$ alkyl, halo, —$OC_{1-2}$ alkyl, or cyano;

each p is 0 to 4;

$R^{13}$ is —C(=O)$R^{g1}$, —C(=O)O$R^{g2}$, or —P(=O)(O$R^h)_2$;

$R^{g1}$ is H, $C_{1-6}$ alkyl, $C_{3-6}$ cycloalkyl, or 5- to 6-membered heteroaryl having 1 to 3 heteroatoms selected from N, O, and S;

wherein the $C_{1-6}$ alkyl of $R^{g1}$ is optionally substituted with 1, 2, 3, or 4 substituents independently selected from halogen, $C_{1-4}$ alkoxy, —$N(R^i)_2$, —$C_{1-4}$ alkyl-$N(R^i)_2$, —$N(R^i)_3^+$, and 4- to 6-membered heterocyclyl having 1 to 3 heteroatoms selected from N, O, and S, wherein the 4- to 6-membered heterocyclyl is optionally substituted with 1, 2, 3, or 4 substituents independently selected from halogen, $C_{1-4}$ alkyl, $C_{1-4}$ alkoxy, $N(R^i)_2$, and —$C_{1-4}$ alkyl-$N(R^i)_2$;

wherein the 5- to 6-membered heteroaryl and $C_{3-6}$ cycloalkyl of $R^{g1}$ are each optionally substituted with 1, 2, 3, or 4 substituents independently selected from halogen, $C_{1-6}$ alkyl, $C_{1-4}$ alkoxy, —$N(R^i)_2$, and —$C_{1-4}$ alkyl-$N(R^i)_2$;

$R^{g2}$ is $C_{1-6}$ alkyl optionally substituted with 1, 2, 3, or 4 substituents independently selected from halogen, $C_{1-6}$ alkyl, $C_{1-4}$ alkoxy, —$N(R^i)_2$, —$C_{1-4}$ alkyl-$N(R^i)_2$, and —O—P(=O)(O$R^h)_2$; and $R^h$ and $R^i$ are each independently selected from H and $C_{1-3}$ alkyl.

2. The compound of claim 1, or a pharmaceutically acceptable salt thereof, wherein $R^2$ and $R^3$ are each independently $C_{1-4}$ alkyl, $C_{3-6}$ cycloalkyl, or O—$R^{2A}$, wherein $R^{2A}$ is $C_{1-4}$ alkyl, $C_{3-6}$ cycloalkyl, or a 4 to 10-membered heterocyclyl having 1 to 5 heteroatoms selected from N, O, and S.

3. The compound of claim 1, or a pharmaceutically acceptable salt thereof, wherein $R^2$ and $R^3$ are each independently:

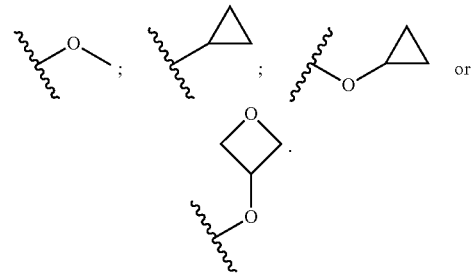

4. The compound of claim 3, or a pharmaceutically acceptable salt thereof, wherein $R^2$ and $R^3$ are each methoxy.

5. The compound of claim 1, or a pharmaceutically acceptable salt thereof, wherein $R^4$ is hydrogen, $C_{1-4}$ alkyl, or $C_{1-4}$ haloalkyl.

6. The compound of claim 5, or a pharmaceutically acceptable salt thereof, wherein $R^4$ is $C_{1-4}$ haloalkyl.

7. The compound of claim 6, or a pharmaceutically acceptable salt thereof, wherein $R^4$ is $CF_3$.

8. The compound of claim 1, or a pharmaceutically acceptable salt thereof, wherein $R^7$ is hydrogen, $C_{1-4}$ alkyl, or $C_{1-4}$ haloalkyl.

9. The compound of claim 8, or a pharmaceutically acceptable salt thereof, wherein $R^7$ is $C_{1-4}$ haloalkyl.

10. The compound of claim 9, or a pharmaceutically acceptable salt thereof, wherein $R^7$ is $CF_3$.

11. The compound of claim 1, or a pharmaceutically acceptable salt thereof, wherein $R^5$ and $R^6$ are $C_{1-2}$ alkyl.

12. The compound of claim 11, or a pharmaceutically acceptable salt thereof, wherein $R^5$ and $R^6$ are methyl.

13. The compound of claim 1, or a pharmaceutically acceptable salt thereof, wherein $R^8$ and $R^9$ are $C_{1-2}$ alkyl.

14. The compound of claim 13, or a pharmaceutically acceptable salt thereof, wherein $R^8$ and $R^9$ are methyl.

15. The compound of claim 1, or a pharmaceutically acceptable salt thereof, wherein n is 2.

16. The compound of claim 1, or a pharmaceutically acceptable salt thereof, wherein each $R^{10}$ is halogen.

17. The compound of claim 16, or a pharmaceutically acceptable salt thereof, wherein each $R^{10}$ is fluoro.

18. The compound of claim 1, or a pharmaceutically acceptable salt thereof, wherein A is ethynyl.

19. The compound of claim 1, or a pharmaceutically acceptable salt thereof, wherein $R^1$ is a 5 to 6-membered heterocycle having 1 to 3 heteroatoms selected from N, O, and S, or a 5 to 6-membered heteroaryl having 1 to 3 heteroatoms selected from N, O, and S, wherein the 5 to 6-membered heterocycle or 5 to 6-membered heteroaryl is optionally substituted with 1 to 3 $R^a$ groups.

20. The compound of claim 19, or a pharmaceutically acceptable salt thereof, wherein $R^1$ is a 5 to 6-membered heteroaryl having 1 to 3 heteroatoms selected from N, O, and S and is optionally substituted with 1 to 3 $R^a$ groups.

21. The compound of claim 19, or a pharmaceutically acceptable salt thereof, wherein $R^1$ is independently:

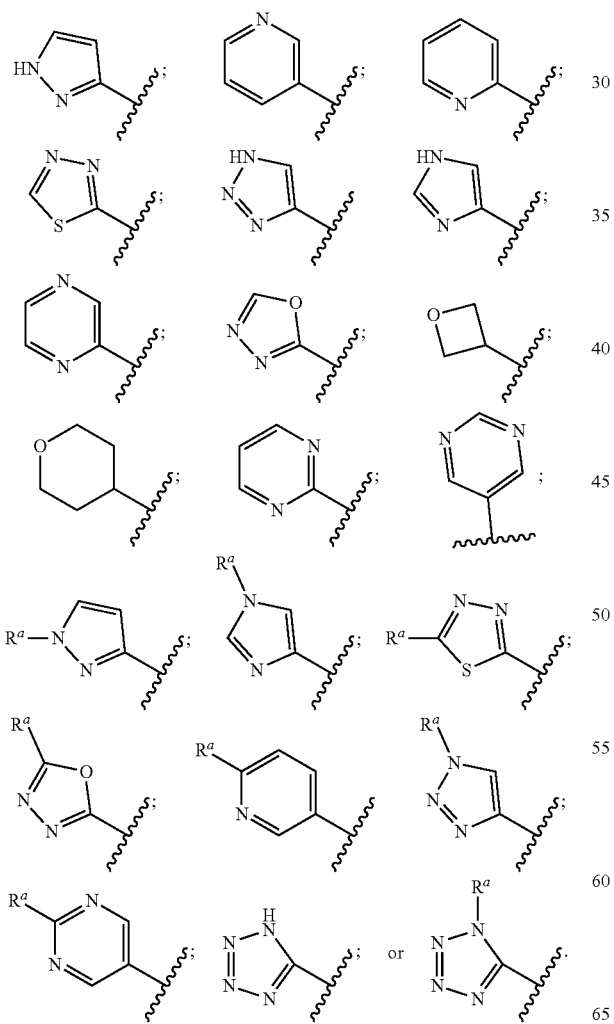

22. The compound of claim 19, or a pharmaceutically acceptable salt thereof, wherein $R^1$ is:

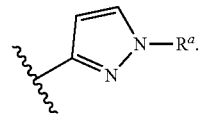

23. The compound of claim 19, or a pharmaceutically acceptable salt thereof, wherein $R^a$ is $C_{1-4}$ haloalkyl.

24. The compound of claim 19, or a pharmaceutically acceptable salt thereof, wherein $R^a$ is:

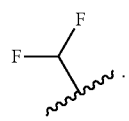

25. The compound of claim 1, or a pharmaceutically acceptable salt thereof, wherein $X^1$ is a 6 membered aryl or a 5 to 6-membered heteroaryl having 1 to 3 heteroatoms selected from N, O, and S, wherein each 6-membered aryl or 5 to 6-membered heteroaryl is optionally substituted with 1 to 4 $R^b$ groups.

26. The compound of claim 25, or a pharmaceutically acceptable salt thereof, wherein $X^1$ is:

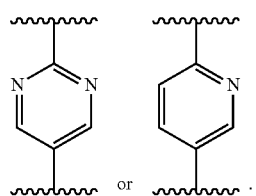 [SMILES: *c1cnc(*)nc1 ; *c1ccc(*)nc1]

27. The compound of claim 25, or a pharmaceutically acceptable salt thereof, wherein $X^1$ is

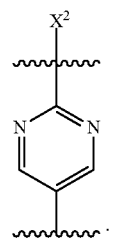

28. The compound of claim 1, or a pharmaceutically acceptable salt thereof, wherein $X^2$ is a 4 to 10-membered heterocyclyl having 1 to 3 heteroatoms selected from N, O, and S and is optionally substituted with one $R^{11}$ and optionally substituted with 1 to 5 $R^b$ groups.

29. The compound of claim 28, or a pharmaceutically acceptable salt thereof, wherein $X^2$ is:

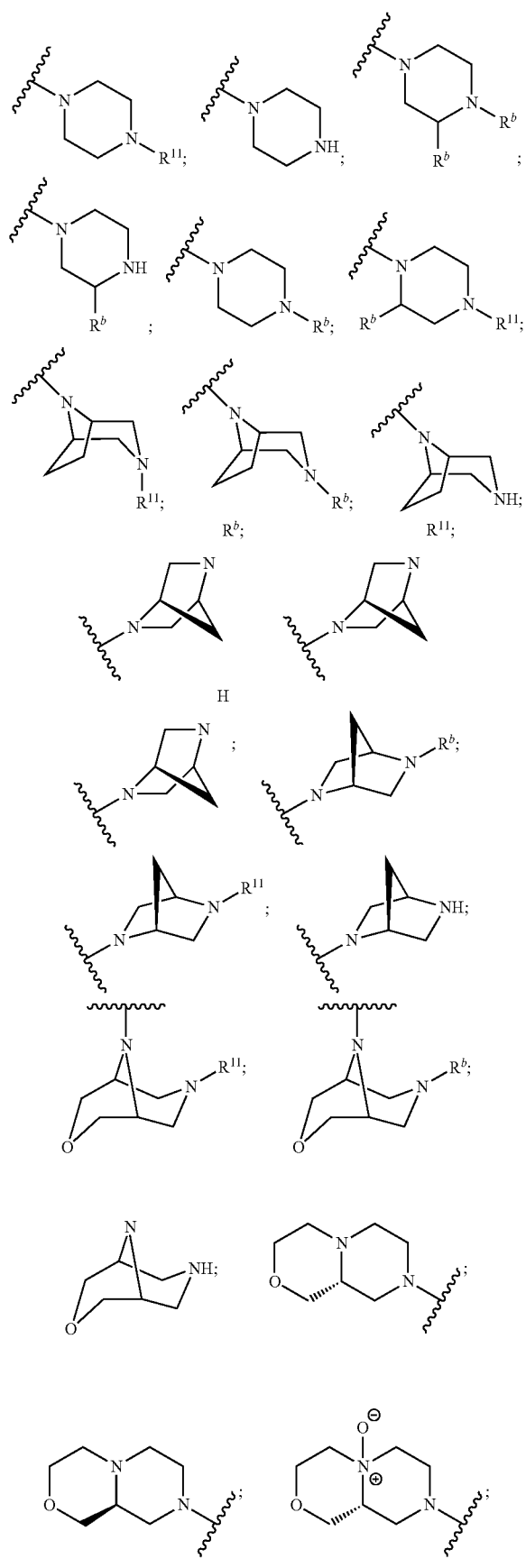
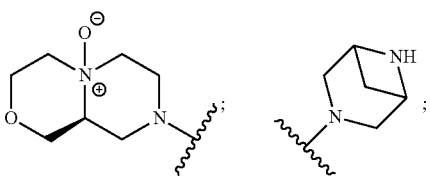
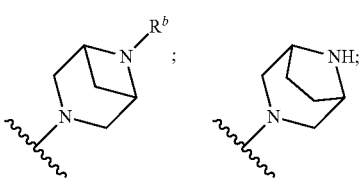
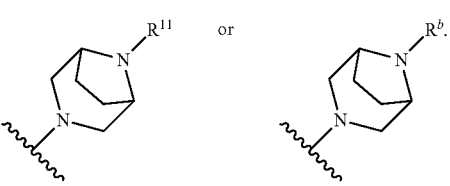
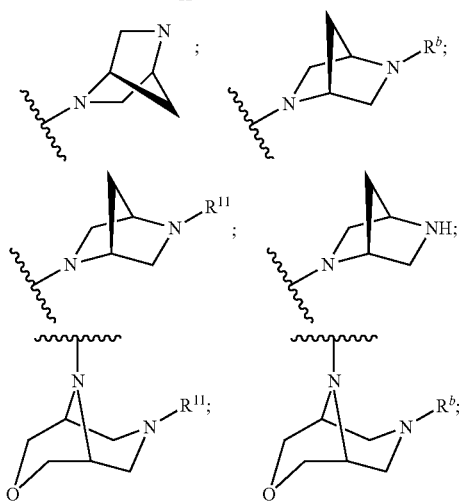

30. The compound of claim 28, or a pharmaceutically acceptable salt thereof, wherein $X^2$ is:

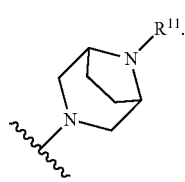

31. The compound of claim 28, or a pharmaceutically acceptable salt thereof, wherein $R^{11}$ is 4 to 10-membered heterocyclyl having 1 to 3 heteroatoms selected from N, O, and S.

32. The compound of claim 31, or a pharmaceutically acceptable salt thereof, wherein $R^{11}$ is a 4 to 6-membered heterocycle having one oxygen.

33. The compound of claim 32, or a pharmaceutically acceptable salt thereof, wherein $R^{11}$ is oxetan-3-yl.

34. The compound of claim 1, or a pharmaceutically acceptable salt thereof, wherein p is 0.

35. The compound of claim 1, or a pharmaceutically acceptable salt thereof, wherein $R^{13}$ is —C(=O)$R^{g1}$, wherein $R^{g1}$ is (i) H, (ii) a 6-membered heteroaryl having 1 or 2 nitrogen atoms, or (iii) $C_{1-6}$ alkyl optionally substituted with 1 or 2 substituents independently selected from $NH_2$, $N(CH_3)_2$, $N(CH_3)_3^+$, and a 6-membered heterocyclyl having 1 to 2 heteroatoms selected from N and O.

36. The compound of claim 1, or a pharmaceutically acceptable salt thereof, wherein $R^{13}$ is —C(=O)O$R^{g2}$ or —P(=O)(OH)$_2$, wherein $R^{g2}$ is $C_{1-3}$ alkyl optionally substituted with —O—P(=O)(OH)$_2$.

37. The compound of claim 1 having Formula (II):

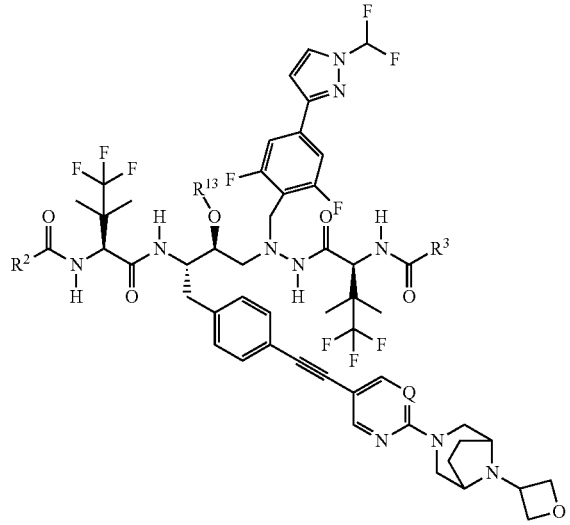

or a pharmaceutically acceptable salt thereof, wherein Q is N or CH.

38. The compound of claim 37, or a pharmaceutically acceptable salt thereof, wherein $R^2$ and $R^3$ are each independently $C_{1-4}$ alkyl, $C_{3-6}$ cycloalkyl, or O—$R^{2A}$, wherein $R^{2A}$ is $C_{1-4}$ alkyl, $C_{3-6}$ cycloalkyl, or a 4 to 10-membered heterocyclyl having 1 to 5 heteroatoms selected from N, O, and S.

39. The compound of claim 37, or a pharmaceutically acceptable salt thereof, wherein $R^2$ and $R^3$ are each independently:

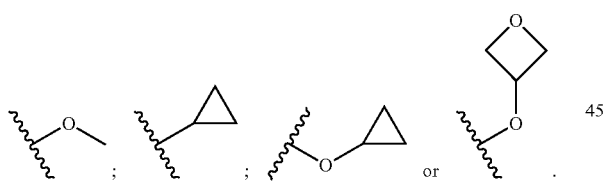

40. The compound of claim 37, or a pharmaceutically acceptable salt thereof, wherein $R^2$ and $R^3$ are each methoxy.

41. The compound of claim 37, or a pharmaceutically acceptable salt thereof, wherein $R^{13}$ is:

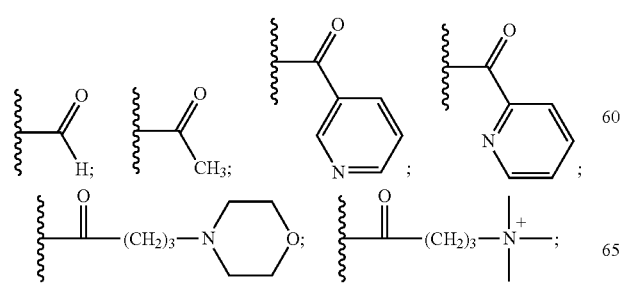

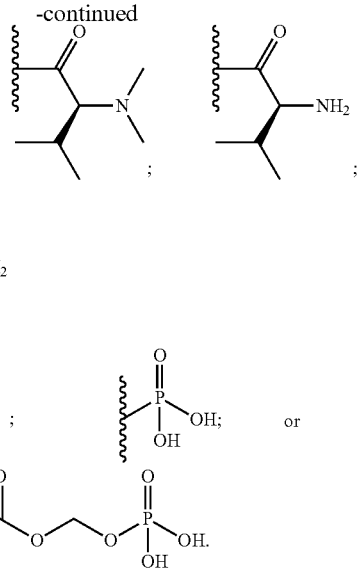

42. The compound of claim 1, selected from:

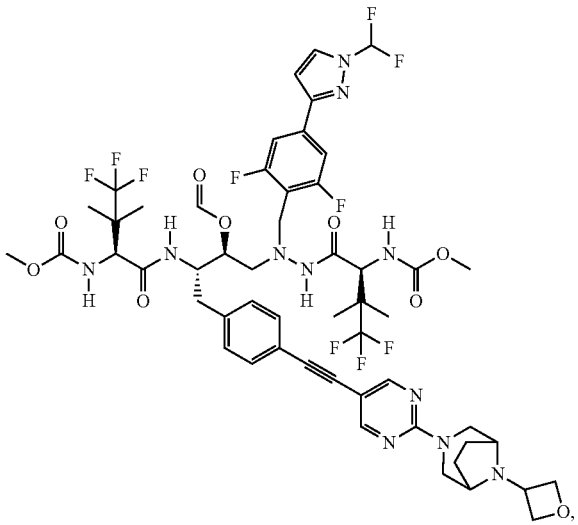

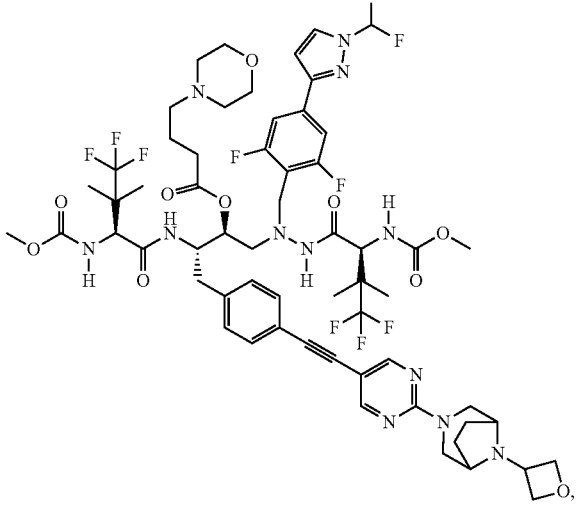

131
-continued
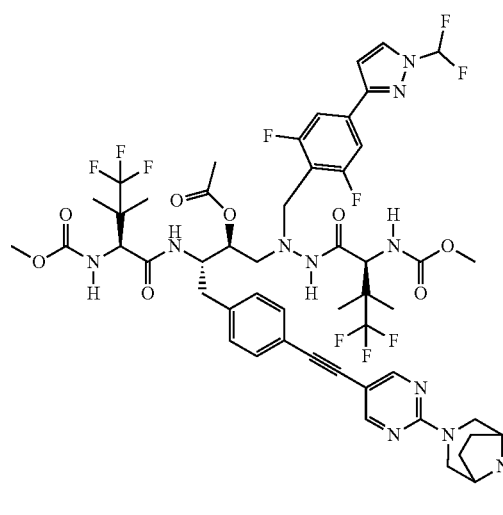
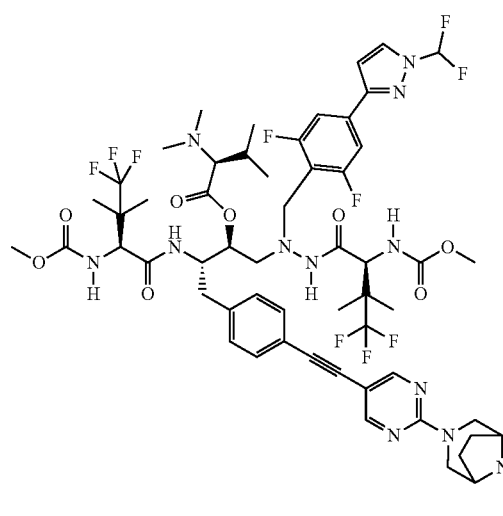
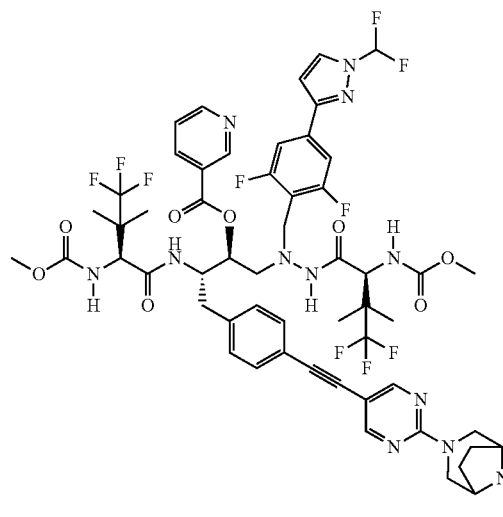
132
-continued
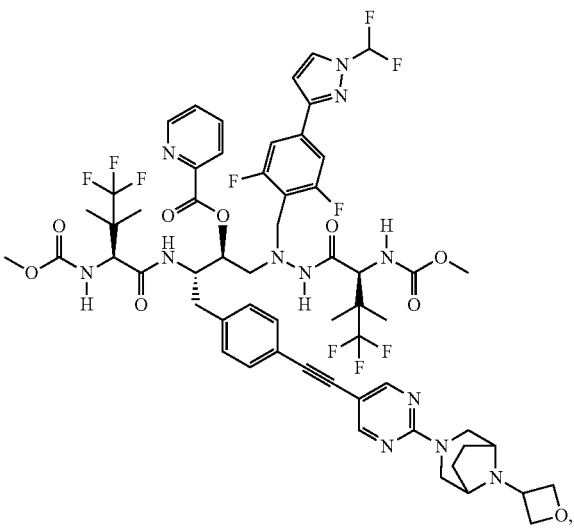
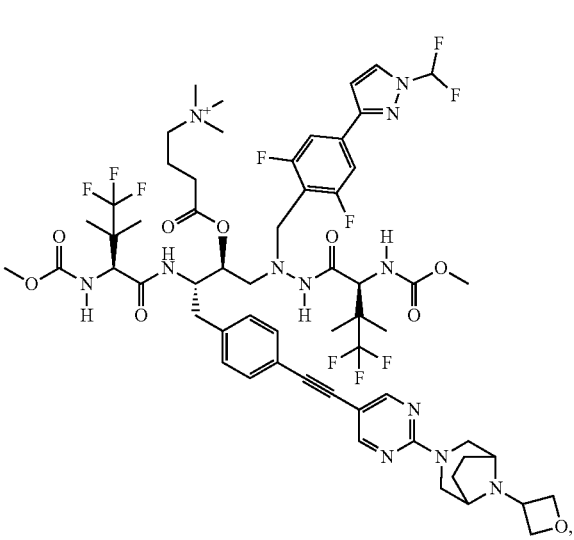
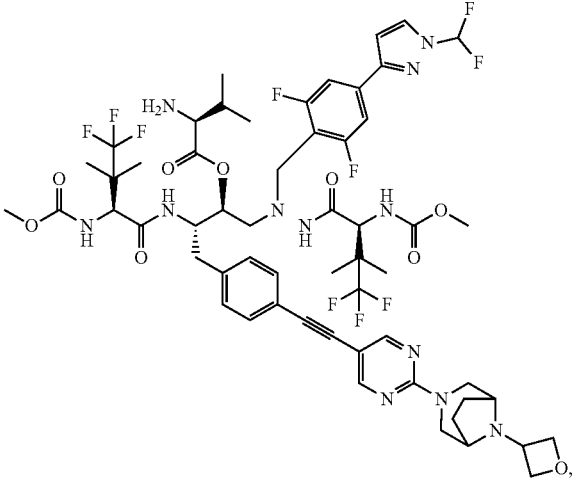 [SMILES: COC(=O)N[C@H](C(=O)N[C@@H](Cc1ccc(C#Cc2ccc(N3CC4CCC(C3)N4C3COC3)nc2)cc1)[C@H](CN(Cc1c(F)cc(C(=N)/C=C\NC(F)F)cc1F)NC(=O)[C@@H](NC(=O)OC)C(C)(C)C(F)(F)F)OC(=O)OCOP(=O)(O)O)C(C)(C)C(F)(F)F]

133
-continued
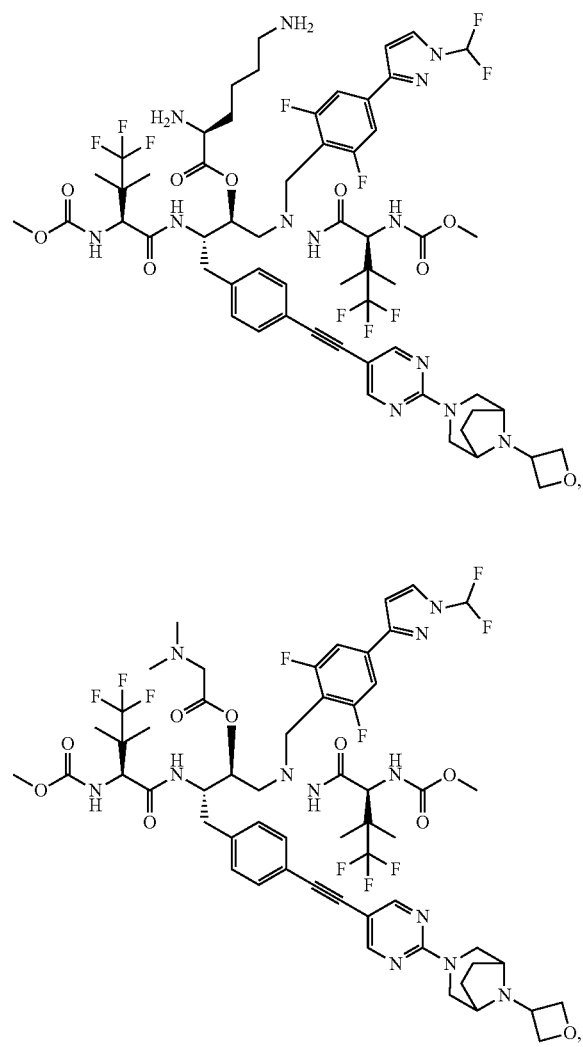
134
-continued
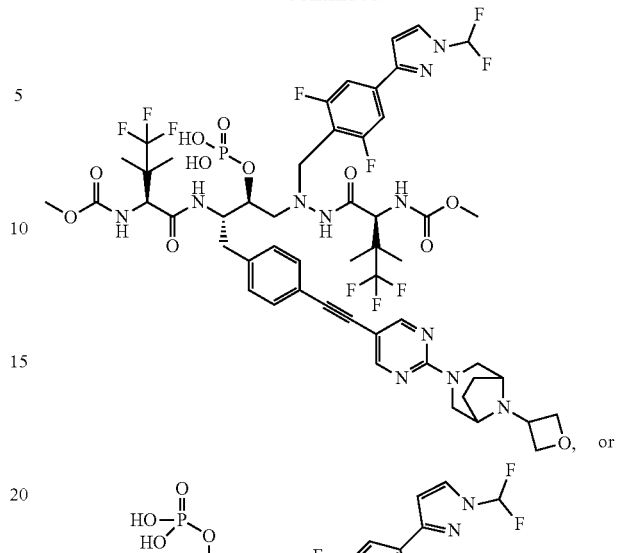
or a pharmaceutically acceptable salt thereof.
43. The compound of claim 1, which is
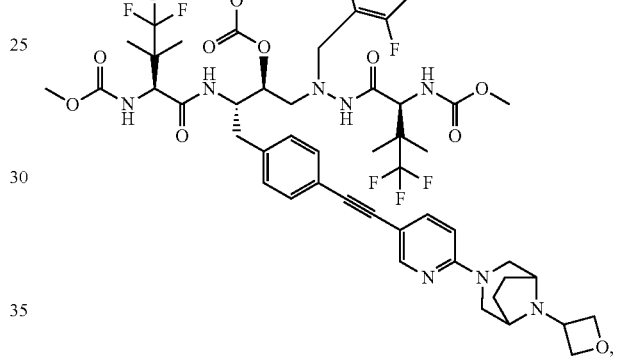
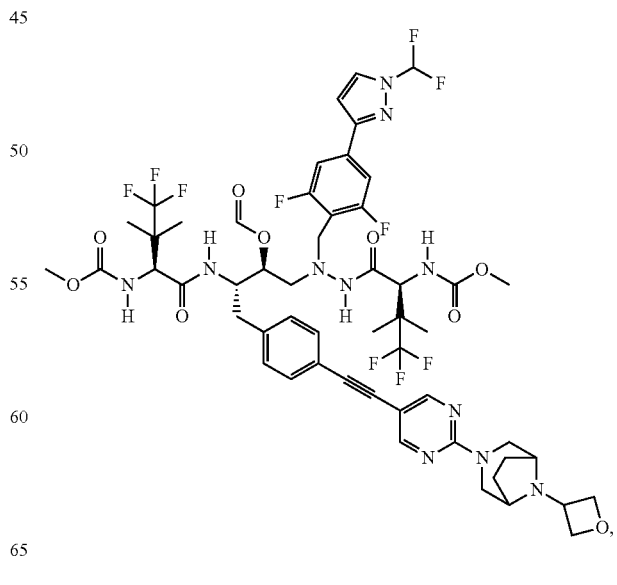
or a pharmaceutically acceptable salt thereof.

44. The compound of claim 1, which is
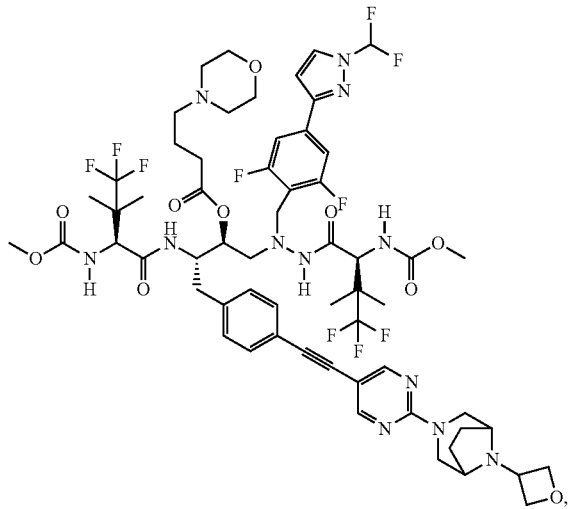 [SMILES: COC(=O)N[C@H](C(=O)N[C@@H](Cc1ccc(C#Cc2cnc(N3CC4CCC(C3)N4C3COC3)nc2)cc1)[C@H](CN(Cc1c(F)cc(-c2ccn(C(F)F)n2)cc1F)NC(=O)[C@@H](NC(=O)OC)C(C)(C)C(F)(F)F)OC(=O)CCCN1CCOCC1)C(C)(C)C(F)(F)F]
or a pharmaceutically acceptable salt thereof.
45. The compound of claim 1, which is
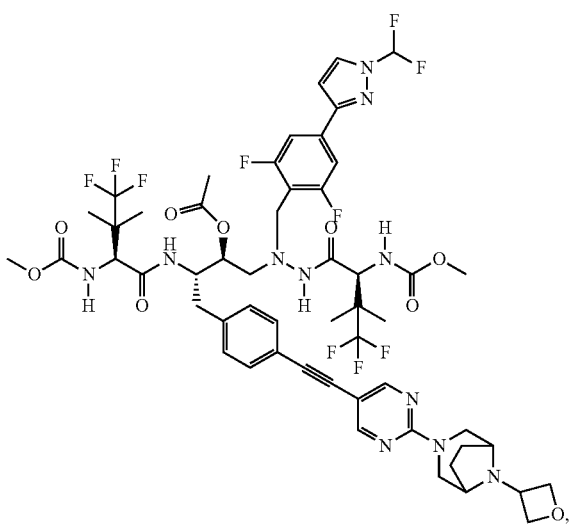 [SMILES: COC(=O)N[C@H](C(=O)N[C@@H](Cc1ccc(C#Cc2cnc(N3CC4CCC(C3)N4C3COC3)nc2)cc1)[C@H](CN(Cc1c(F)cc(-c2ccn(C(F)F)n2)cc1F)NC(=O)[C@@H](NC(=O)OC)C(C)(C)C(F)(F)F)OC(C)=O)C(C)(C)C(F)(F)F]
or a pharmaceutically acceptable salt thereof.
46. The compound of claim 1, which is
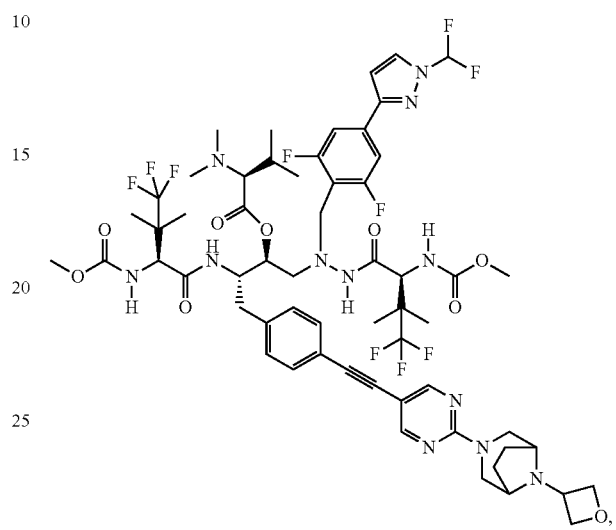
or a pharmaceutically acceptable salt thereof.
47. The compound of claim 1, which is
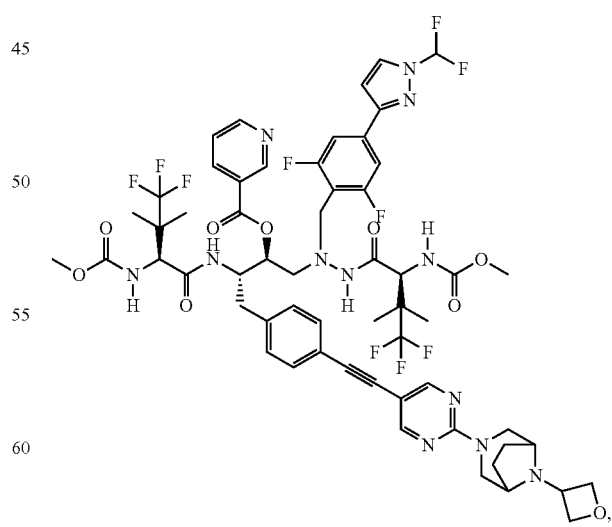
or a pharmaceutically acceptable salt thereof.

48. The compound of claim 1, which is
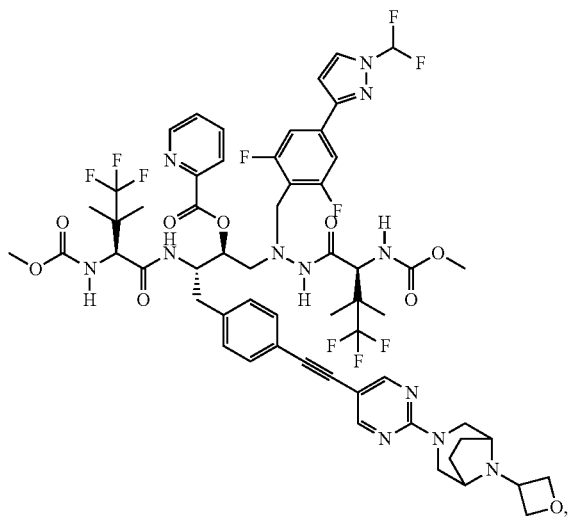 [SMILES: COC(=O)N[C@H](C(=O)N[C@@H](Cc1ccc(C#Cc2cnc(N3CC4CCC(C3)N4C3COC3)nc2)cc1)[C@H](CN(Cc1c(F)cc(-c2ccn(C(F)F)n2)cc1F)NC(=O)[C@@H](NC(=O)OC)C(C)(C)C(F)(F)F)OC(=O)c1ccccn1)C(C)(C)C(F)(F)F]
or a pharmaceutically acceptable salt thereof.
49. The compound of claim 1, which is
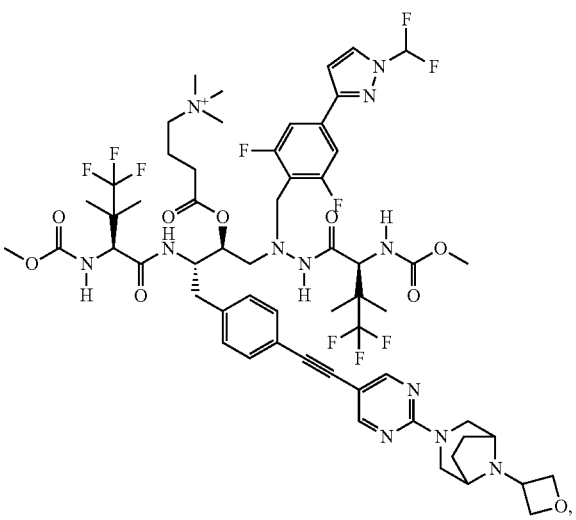 [SMILES: COC(=O)N[C@H](C(=O)N[C@@H](Cc1ccc(C#Cc2cnc(N3CC4CCC(C3)N4C3COC3)nc2)cc1)[C@H](CN(Cc1c(F)cc(-c2ccn(C(F)F)n2)cc1F)NC(=O)[C@@H](NC(=O)OC)C(C)(C)C(F)(F)F)OC(=O)CCC[N+](C)(C)C)C(C)(C)C(F)(F)F]
or a pharmaceutically acceptable salt thereof.
50. The compound of claim 1, which is
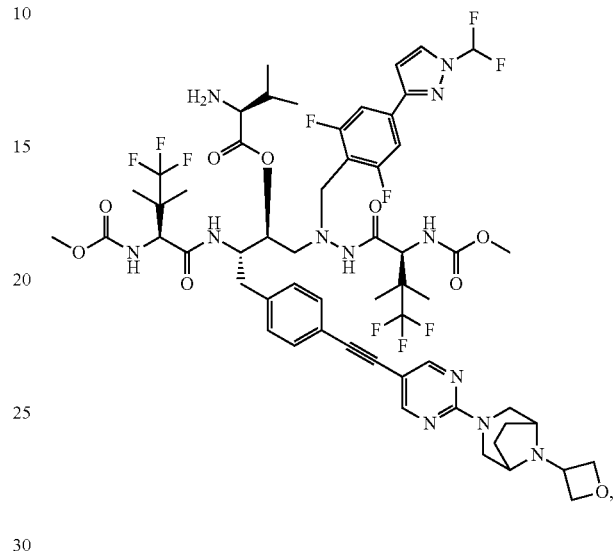
or a pharmaceutically acceptable salt thereof.
51. The compound of claim 1, which is
or a pharmaceutically acceptable salt thereof.

52. The compound of claim 1, which is
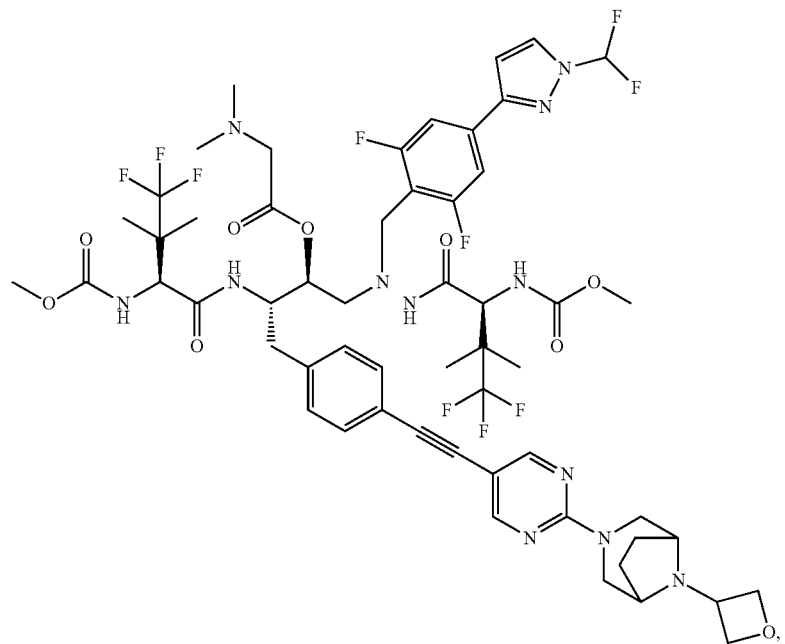
or a pharmaceutically acceptable salt thereof.
53. The compound of claim 1, which is
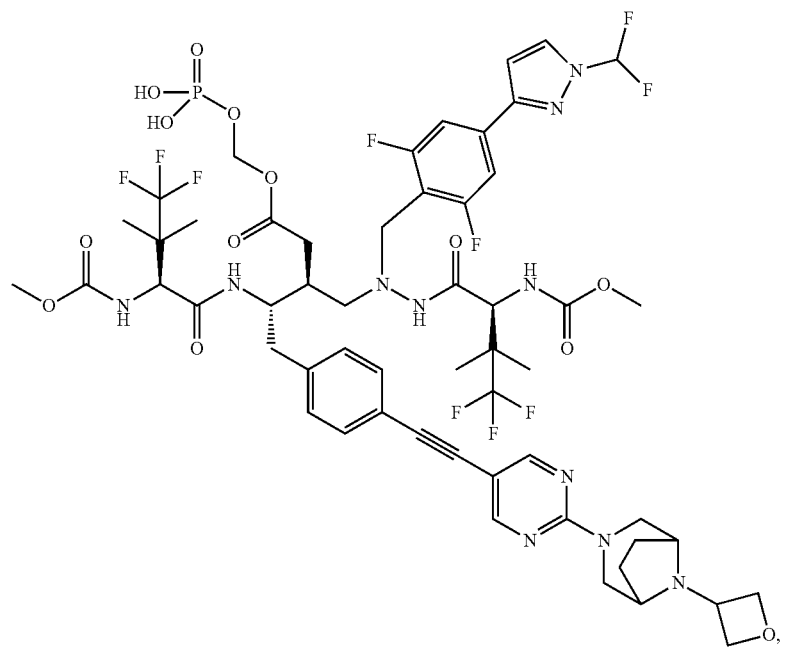 [SMILES: COC(=O)N[C@H](C(=O)N[C@@H](Cc1ccc(C#Cc2cnc(N3CC4CCC(C3)N4C3COC3)nc2)cc1)[C@@H](CC(=O)OCOP(=O)(O)O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]
or a pharmaceutically acceptable salt thereof.

54. The compound of claim 1, which is

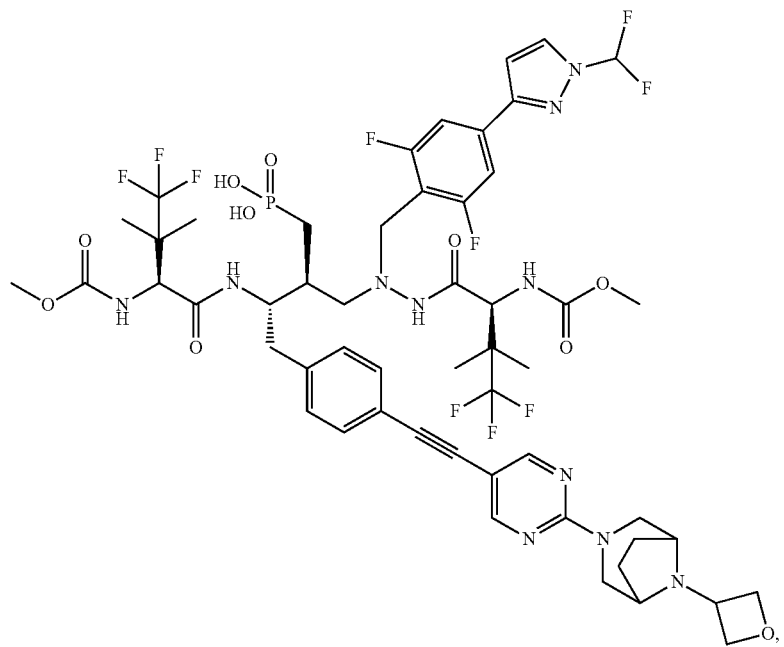

or a pharmaceutically acceptable salt thereof.

55. The compound claim 1, which is

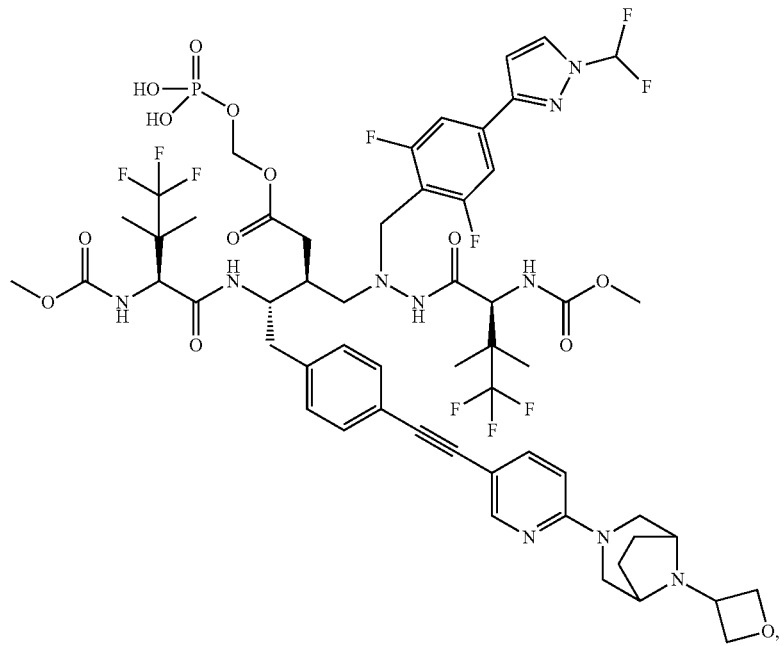 [SMILES: COC(=O)N[C@H](C(=O)N[C@@H](Cc1ccc(C#Cc2ccc(N3CC4CCC(C3)N4C3COC3)nc2)cc1)[C@@H](CC(=O)OCOP(=O)(O)O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

or a pharmaceutically acceptable salt thereof.

56. A pharmaceutical composition comprising a therapeutically effective amount of a compound of claim 1, or a pharmaceutically acceptable salt thereof, and a pharmaceutically acceptable excipient.

57. The pharmaceutical composition of claim 56, further comprising one, two, three, or four additional therapeutic agents.

58. The pharmaceutical composition of claim 57, wherein the additional therapeutic agents are selected from the group consisting of combination drugs for HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof.

59. The pharmaceutical composition of claim 57, wherein the additional therapeutic agents are selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and pharmacokinetic enhancers, or any combinations thereof.

60. The pharmaceutical composition of claim 57, wherein the additional therapeutic agents are selected from the group consisting of abacavir sulfate, bictegravir, tenofovir, tenofovir disoproxil, tenofovir disoproxil fumarate, tenofovir disoproxil hemifumarate, tenofovir alafenamide, and tenofovir alafenamide hemifumarate.

61. The pharmaceutical composition of claim 57, wherein the additional therapeutic agents are selected from the group consisting of tenofovir alafenamide, tenofovir alafenamide fumarate and tenofovir alafenamide hemifumarate.

62. A method of treating a human immunodeficiency virus (HIV) infection comprising administering a therapeutically effective amount of a compound of claim 1, or a pharmaceutically acceptable salt thereof, to a subject in need thereof.

63. The method of claim 62, wherein the method comprises administering the compound, or a pharmaceutically acceptable salt thereof, in combination with one, two, three, or four additional therapeutic agents.

64. The method of claim 63, wherein the additional therapeutic agents are selected from the group consisting of combination drugs for HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof.

65. The method of claim 63, wherein the additional therapeutic agents are selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and pharmacokinetic enhancers, or any combinations thereof.

66. The method of claim 63, wherein the additional therapeutic agents are selected from the group consisting of abacavir sulfate, bictegravir, tenofovir, tenofovir disoproxil, tenofovir disoproxil fumarate, tenofovir disoproxil hemifumarate, tenofovir alafenamide, and tenofovir alafenamide hemifumarate.

67. The method of claim 63, wherein the additional therapeutic agents are selected from the group consisting of tenofovir alafenamide, tenofovir alafenamide fumarate and tenofovir alafenamide hemifumarate.

68. The method of claim 63, wherein the additional therapeutic agents are administered simultaneously with the compound of Formula I, or a pharmaceutically acceptable salt thereof.

69. The method of claim 63, wherein the compound of Formula I is combined with the additional therapeutic agents in a unitary dosage form for simultaneous administration.

70. The method of claim 63, wherein the compound of Formula I is administered and the additional therapeutic agents are administered sequentially.

71. The method of claim 63, wherein the compound of Formula I is combined with tenofovir disoproxil, tenofovir disoproxil hemifumarate or tenofovir disoproxil fumarate.

72. The method of claim 63, wherein the compound of Formula I is combined with a first additional therapeutic agent selected from the group consisting of abacavir sulfate, bictegravir, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

73. The method of claim 63, wherein the compound of Formula I is combined with a first additional therapeutic agent selected from the group consisting of tenofovir alafenamide fumarate, tenofovir alafenamide, and tenofovir alafenamide hemifumarate, and a second additional therapeutic agent, wherein the second additional therapeutic agent is emtricitabine.

74. The method of claim 63, wherein the compound of Formula I is combined with a first additional therapeutic agent selected from the group consisting of tenofovir disoproxil fumarate, tenofovir disoproxil, and tenofovir disoproxil hemifumarate, and a second additional therapeutic agent, wherein the second additional therapeutic agent is emtricitabine.

75. The pharmaceutical composition of claim 57, wherein the additional therapeutic agents are selected from the group consisting of:

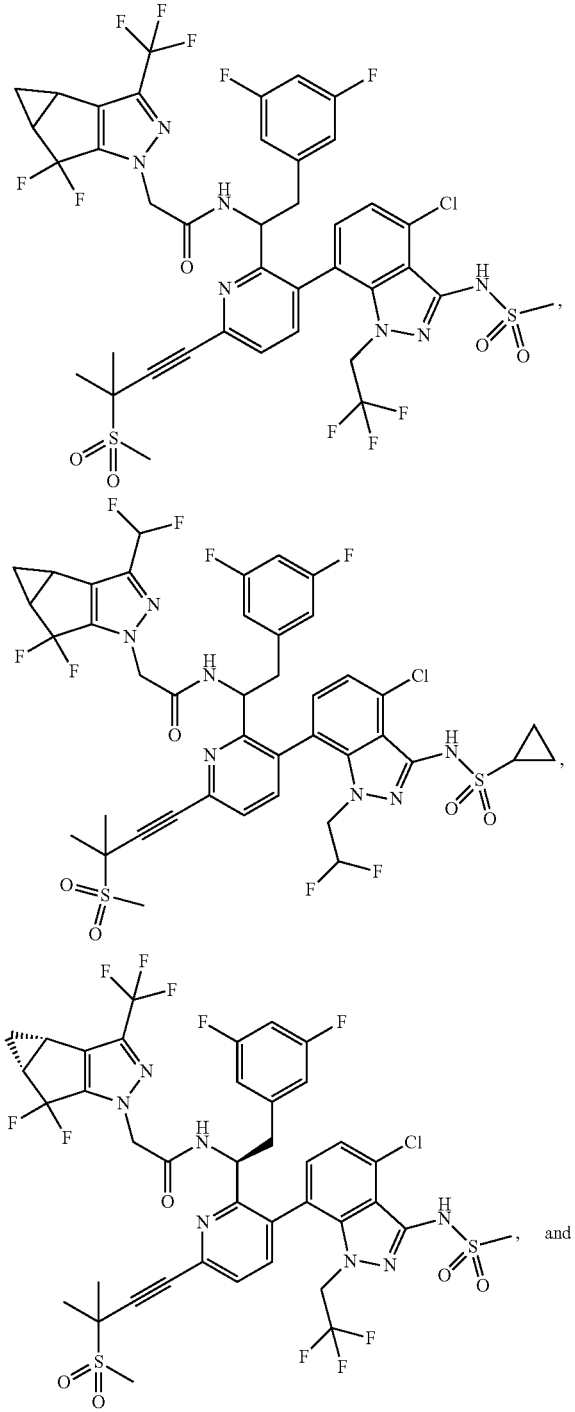

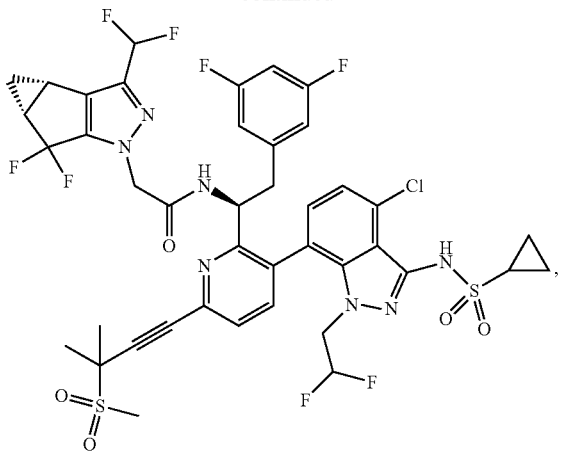

or a pharmaceutically acceptable salt thereof.

76. The pharmaceutical composition of claim 57, wherein the additional therapeutic agents are selected from the group consisting of:

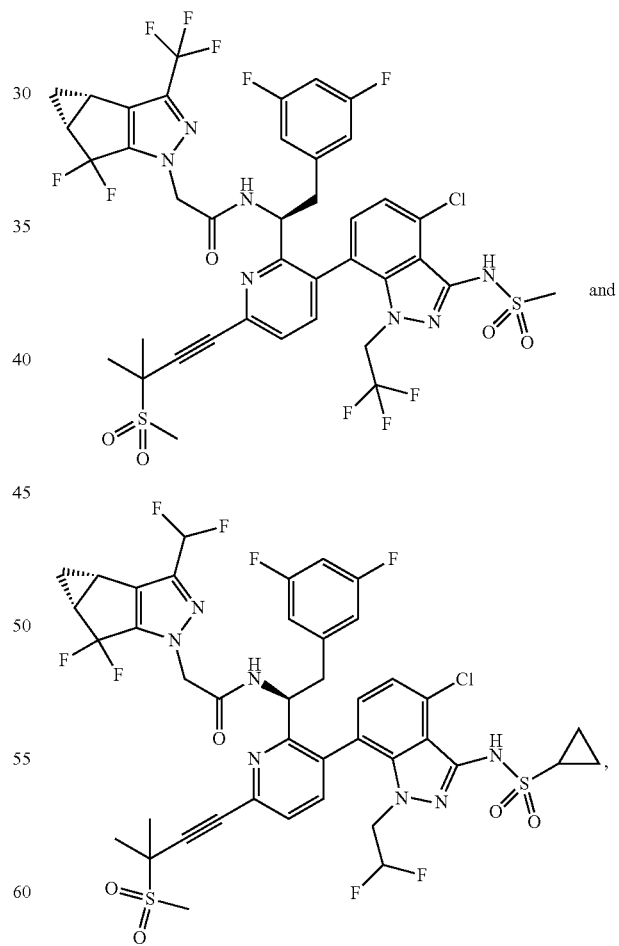

or a pharmaceutically acceptable salt thereof.

77. The pharmaceutical composition of claim 57, wherein the additional therapeutic agent is:

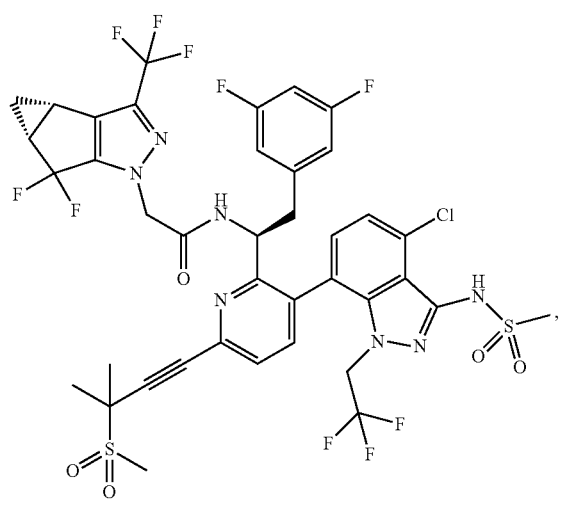 [SMILES: CC(C)(C#Cc1ccc(-c2ccc(Cl)c3c(NS(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]

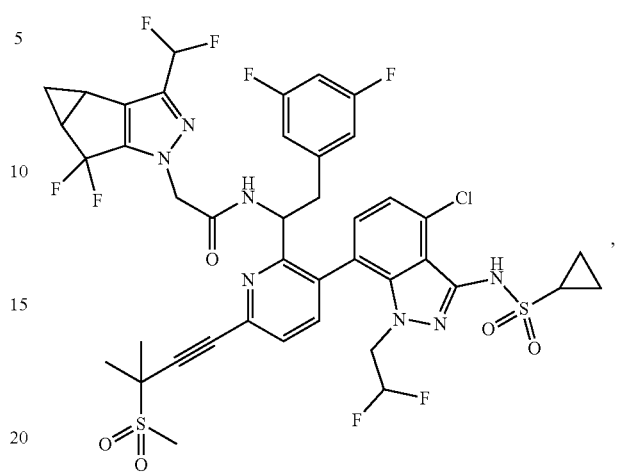

or a pharmaceutically acceptable salt thereof.

78. The pharmaceutical composition of claim 57, wherein the additional therapeutic agent is:

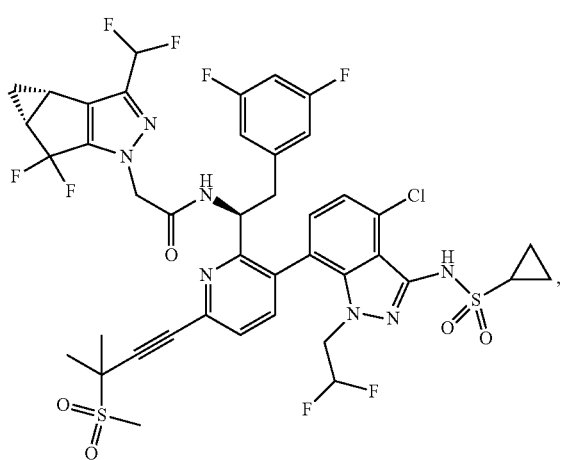 [SMILES: CC(C)(C#Cc1ccc(-c2ccc(Cl)c3c(NS(=O)(=O)C4CC4)nn(CC(F)F)c23)c([C@H](Cc2cc(F)cc(F)c2)NC(=O)Cn2nc(C(F)F)c3c2C(F)(F)[C@@H]2C[C@H]32)n1)S(C)(=O)=O]

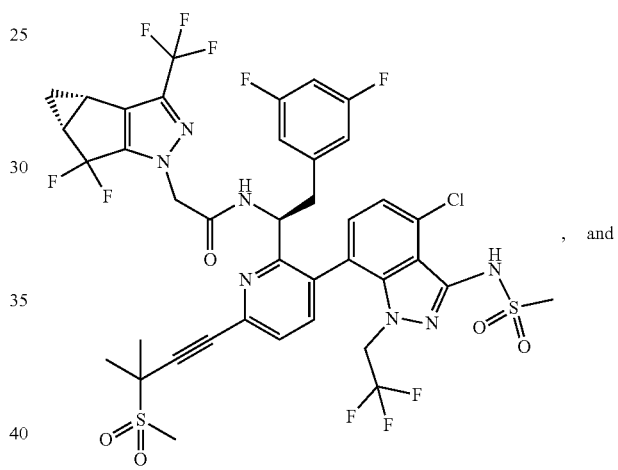

, and or a pharmaceutically acceptable salt thereof.

79. The method of claim 63, wherein the additional therapeutic agents are selected from the group consisting of:

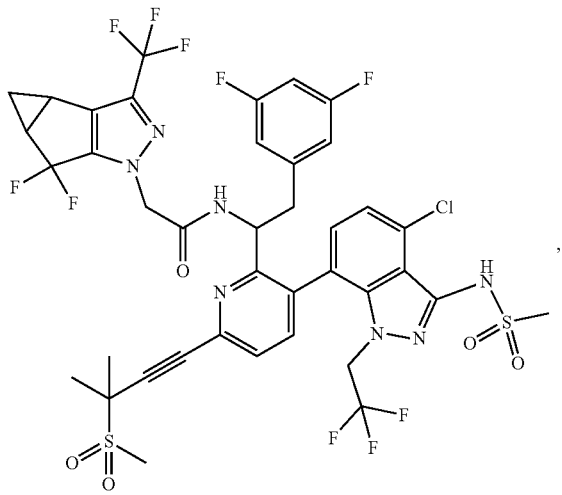

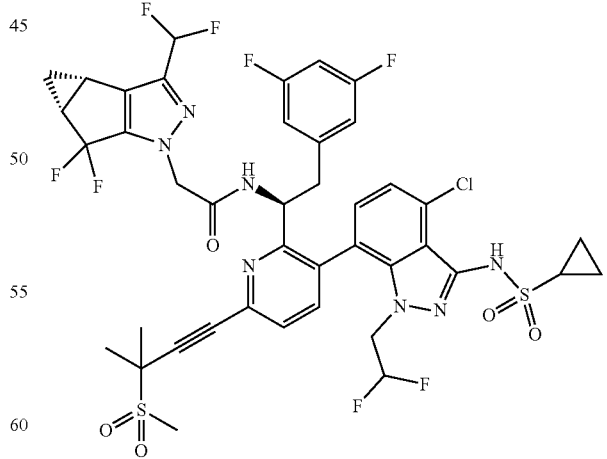

or a pharmaceutically acceptable salt thereof.

80. The method of claim 63, wherein the additional therapeutic agents are selected from the group consisting of:

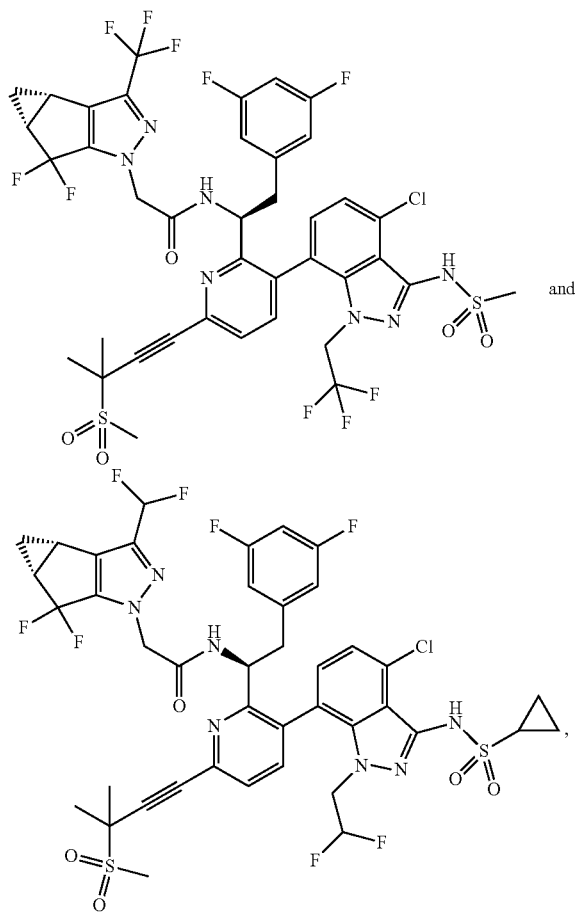

or a pharmaceutically acceptable salt thereof.

81. The method of claim 63, wherein the additional therapeutic agent is:

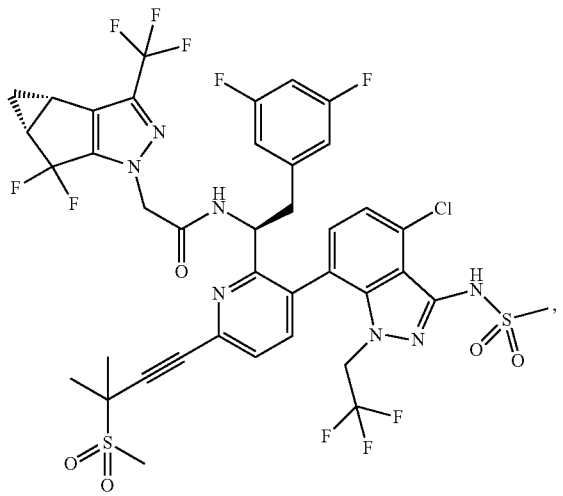 [SMILES: CC(C)(C#Cc1ccc(-c2ccc(Cl)c3c(NS(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]

or a pharmaceutically acceptable salt thereof.

82. The method of claim 63, wherein the additional therapeutic agent is:

or a pharmaceutically acceptable salt thereof.

83. The pharmaceutical composition of claim 57, wherein the additional therapeutic agents are selected from the group consisting of abacavir sulfate, bictegravir, tenofovir, tenofovir disoproxil, tenofovir disoproxil fumarate, tenofovir disoproxil hemifumarate, tenofovir alafenamide, tenofovir alafenamide hemifumarate, emtricitabine, lamivudine, GS-9131, dolutegravir, and cabotegravir.

84. The pharmaceutical composition of claim 57, wherein the additional therapeutic agents are selected from the group consisting of bictegravir, emtricitabine, and GS-9131.

85. The method of claim 63, wherein the additional therapeutic agents are selected from the group consisting of abacavir sulfate, bictegravir, tenofovir, tenofovir disoproxil, tenofovir disoproxil fumarate, tenofovir disoproxil hemifumarate, tenofovir alafenamide, tenofovir alafenamide hemifumarate, emtricitabine, lamivudine, GS-9131, dolutegravir, and cabotegravir.

86. The method of claim 63, wherein the additional therapeutic agents are selected from the group consisting of bictegravir, emtricitabine, and GS-9131.

* * * * *

UNITED STATES PATENT AND TRADEMARK OFFICE
CERTIFICATE OF CORRECTION

PATENT NO.       : 11,052,087 B2
APPLICATION NO.  : 16/525203
DATED            : July 6, 2021
INVENTOR(S)      : Chin et al.

Page 1 of 14

It is certified that error appears in the above-identified patent and that said Letters Patent is hereby corrected as shown below:

In the Specification

Column 20, Lines 1-7, delete " 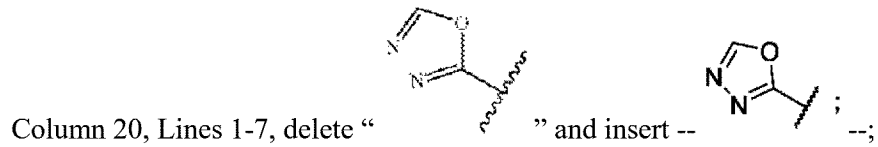 " and insert -- --;

Column 20, Lines 17-24, delete " 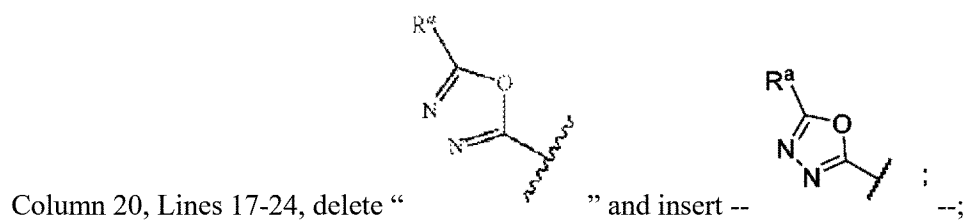 " and insert -- --;

Column 20, Lines 17-24, delete " 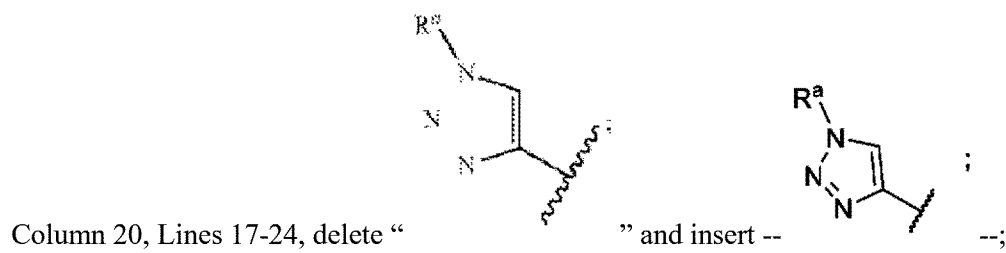 " and insert -- --;

Signed and Sealed this
Fourteenth Day of June, 2022

Katherine Kelly Vidal
*Director of the United States Patent and Trademark Office*

Column 32, Lines 1-23, delete " 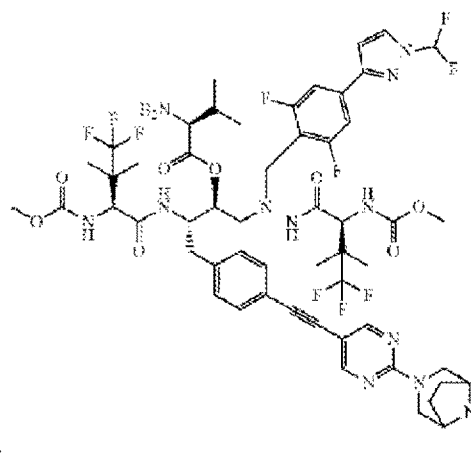 " and insert
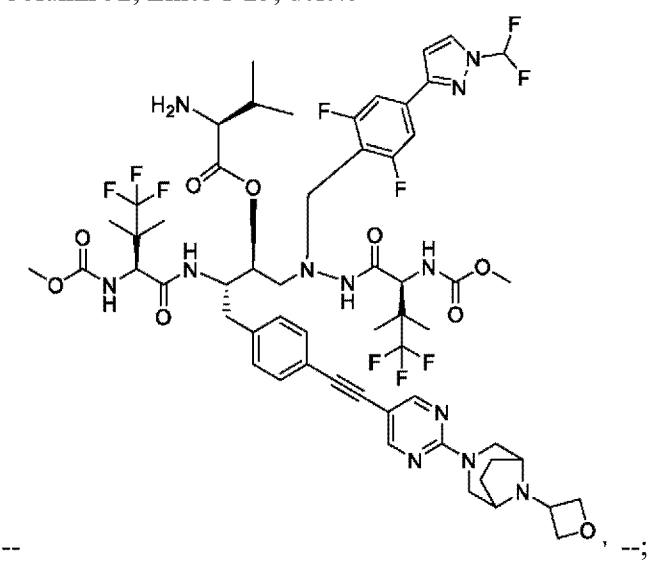
, --;
Column 32, Lines 25-45, delete " 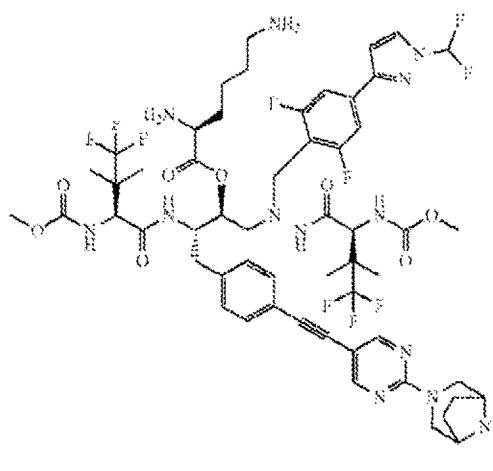 " and insert

CERTIFICATE OF CORRECTION (continued)
U.S. Pat. No. 11,052,087 B2

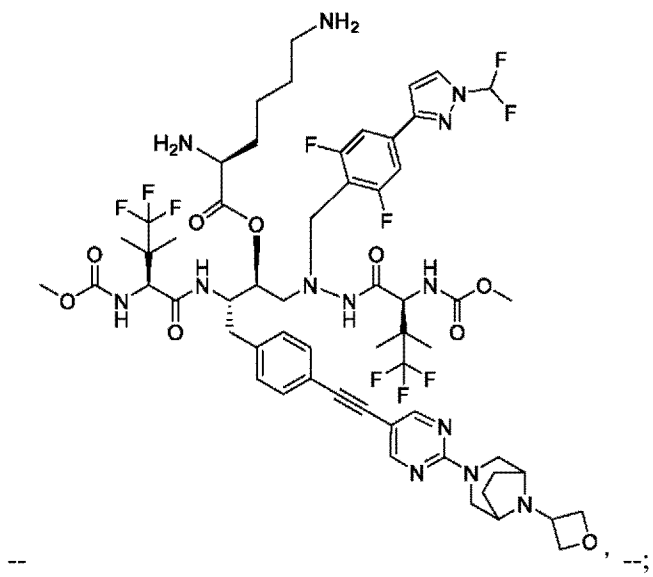

--,

Column 32, Lines 47-67, delete " 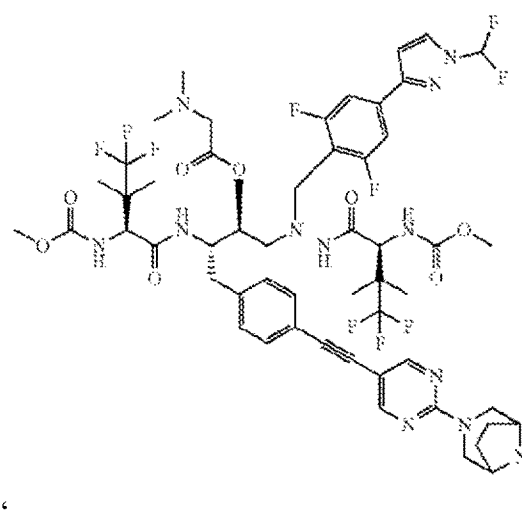 " and insert

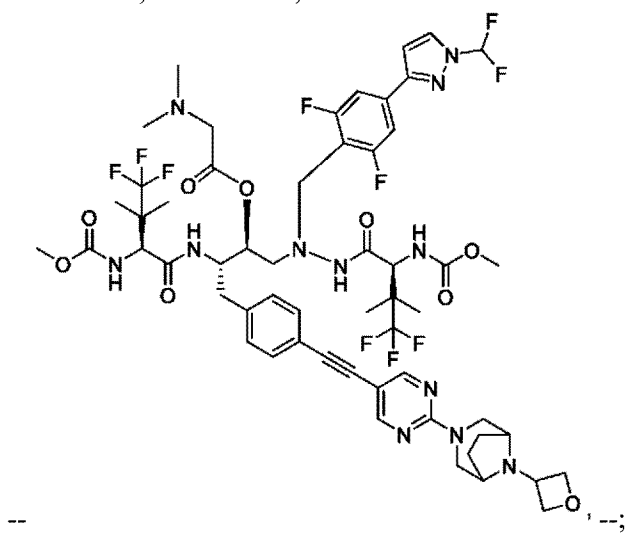

--;

CERTIFICATE OF CORRECTION (continued)
U.S. Pat. No. 11,052,087 B2

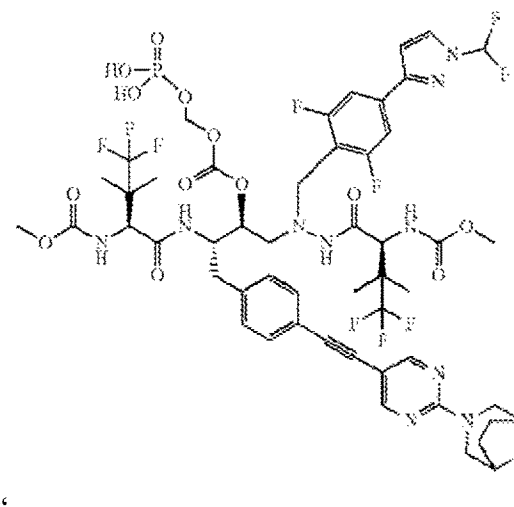

Column 33, Lines 1-19, delete " " and insert

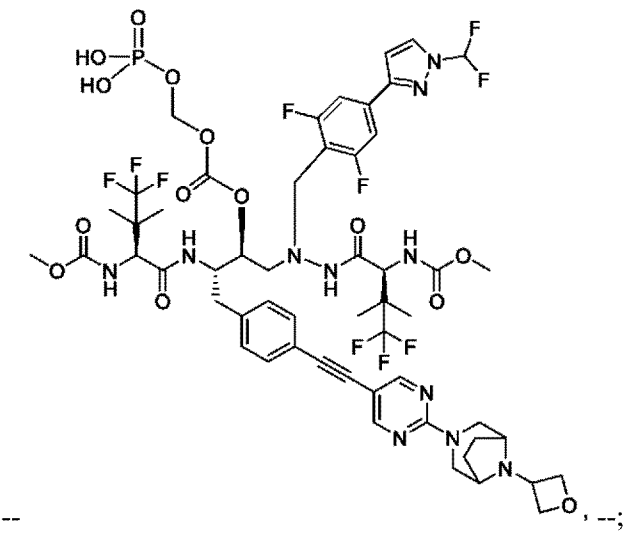

--

Column 33, Lines 20-36, delete " 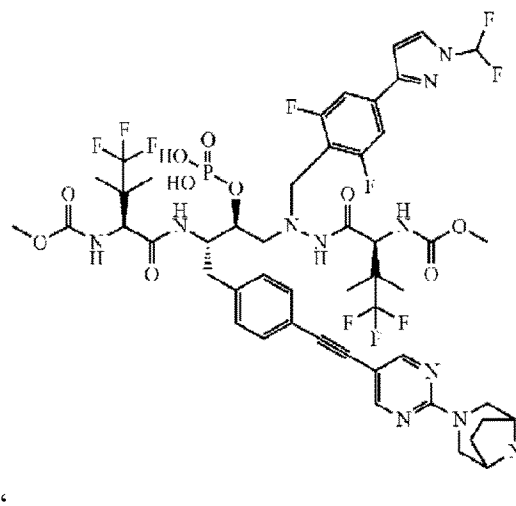 " and insert

CERTIFICATE OF CORRECTION (continued)
U.S. Pat. No. 11,052,087 B2

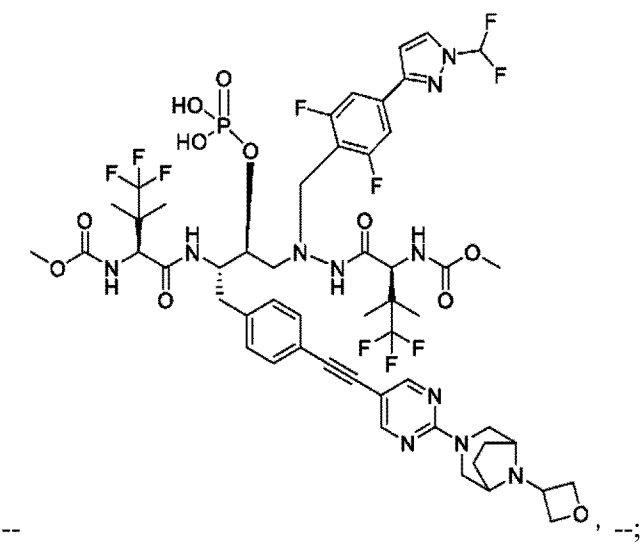

Column 39, Lines 26-42, delete " 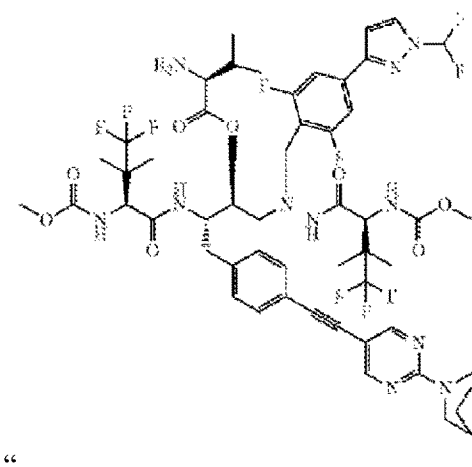 " and insert

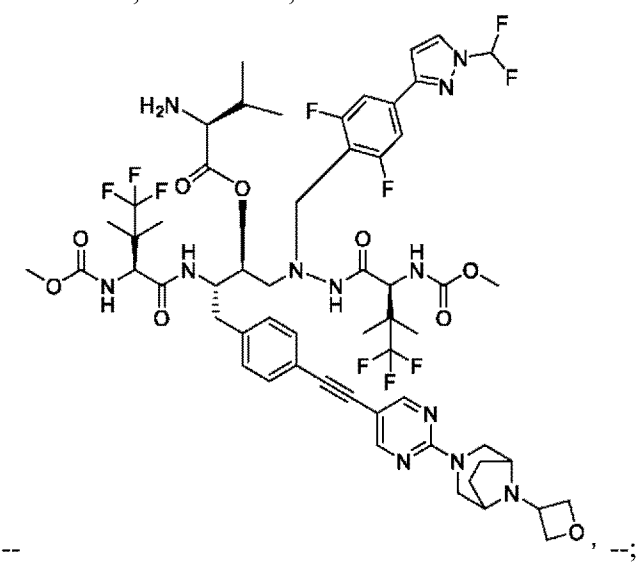

--;

CERTIFICATE OF CORRECTION (continued)
U.S. Pat. No. 11,052,087 B2

Column 39, Lines 47-64, delete " 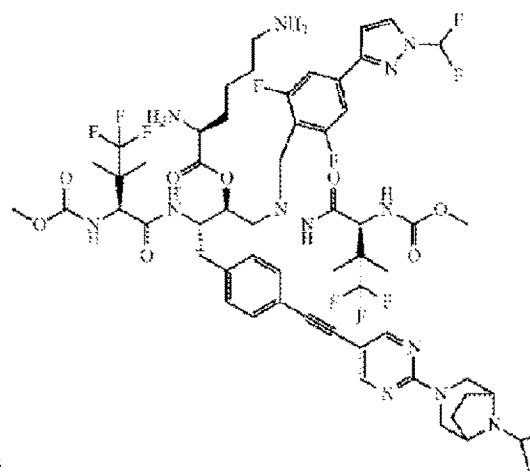 " and insert

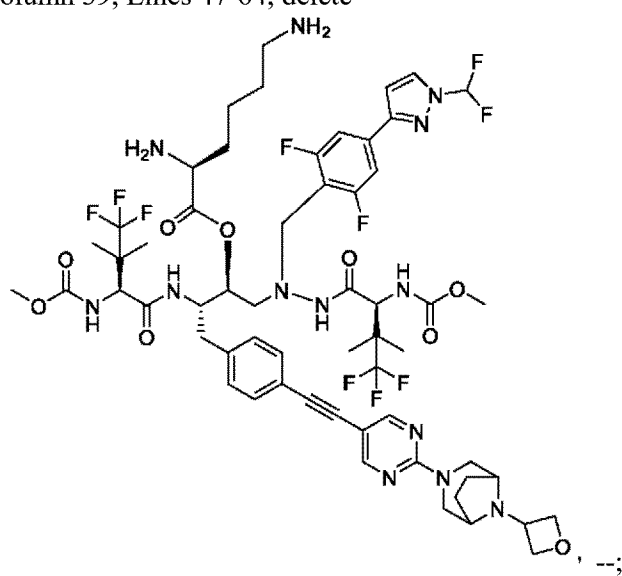

-- , --;

Column 40, Lines 2-21, delete " 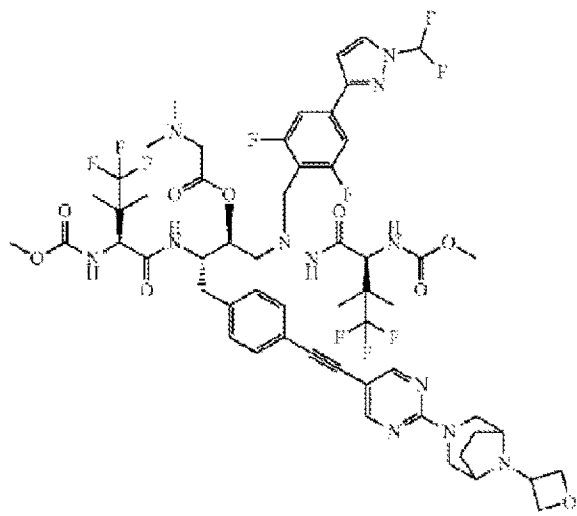 " and insert

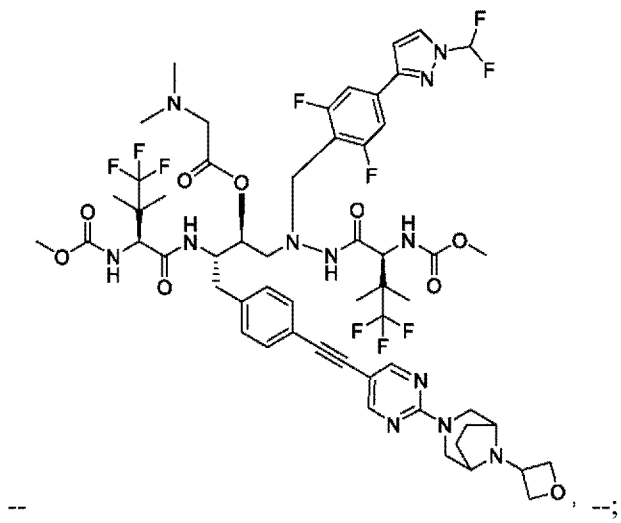
-- ;

Column 65, Lines 44-47, delete " 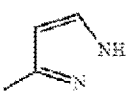 " and insert -- 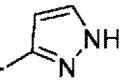 --;

Column 65, Lines 51-60, delete " 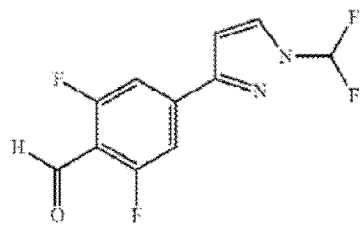 " and insert

-- 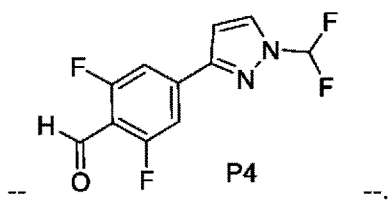 --.

In the Claims

Column 123, Line 1, Claim 1, delete "$C_{1-4}$haloalkyl" and insert -- $C_{1-4}$ haloalkyl --;

Column 123, Line 2, Claim 1, delete "$C_{1-4}$haloalkoxy" and insert -- $C_{1-4}$ haloalkoxy --;

Column 123, Line 3, Claim 1, delete "$C_{1-4}$haloalkyl" and insert -- $C_{1-4}$ haloalkyl --;

Column 123, Line 4, Claim 1, delete "$C_{1-4}$haloalkoxy" and insert -- $C_{1-4}$ haloalkoxy --;

Column 123, Line 23, Claim 1, delete "$R^{a}$" and insert -- $R^{a1}$ --;

Column 123, Line 53, Claim 1, delete "C$_{1-4}$alkyl" and insert -- C$_{1-4}$ alkyl --;
Column 123, Line 53, Claim 1, delete "C$_{1-4}$haloalkyl" and insert -- C$_{1-4}$ haloalkyl --;
Column 125, Lines 33-37, Claim 21, after " 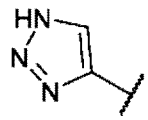 " insert -- ; --;
Column 125, Lines 54-59, Claim 21, after " 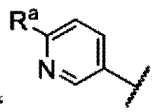 " insert -- ; --;
Column 126, Line 25, Claim 25, delete "6 membered" and insert -- 6-membered --;
Column 132, Lines 48-66, Claim 42, delete " 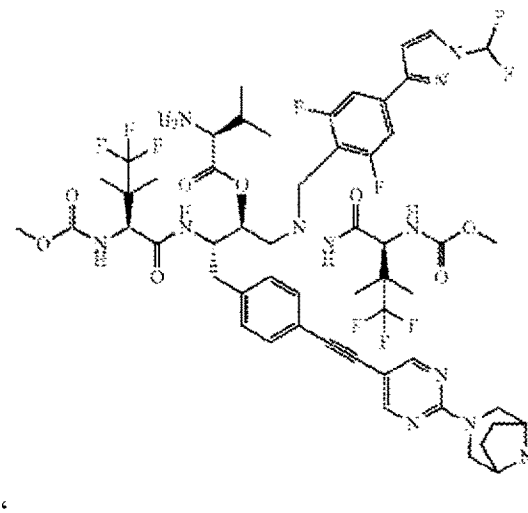 " and insert -- 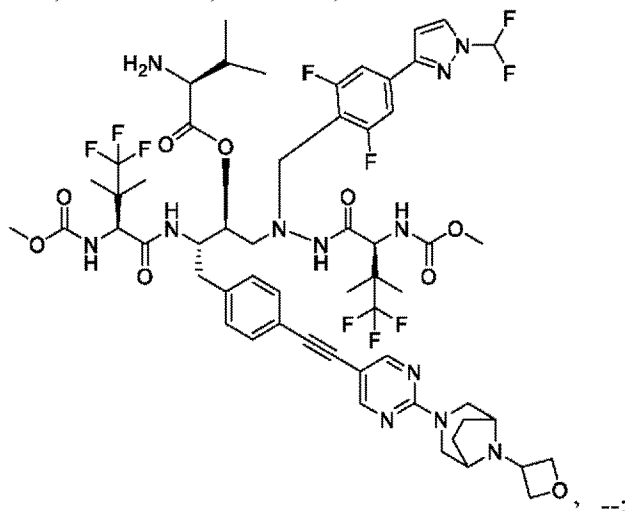, --;

Column 133, Lines 4-23, Claim 42, delete " 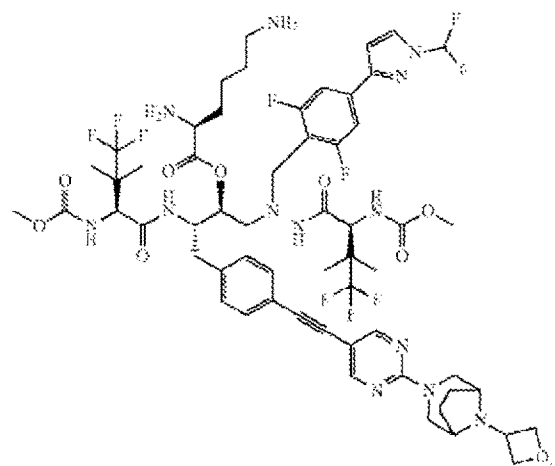 " and insert -- 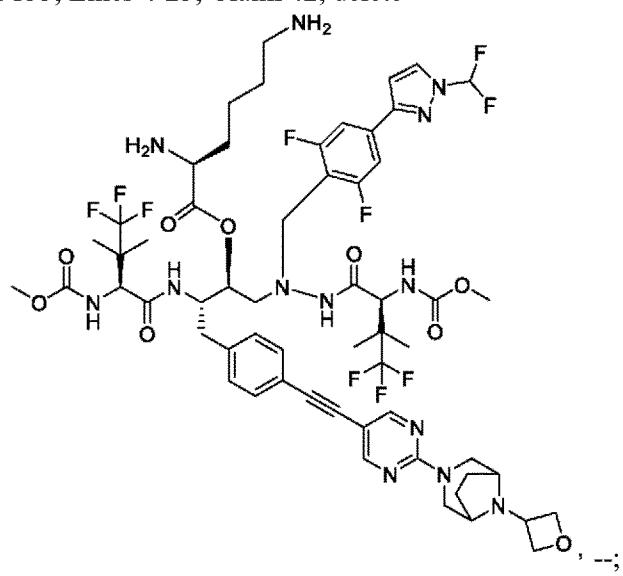 --;
Column 133, Lines 25-43, Claim 42, delete " 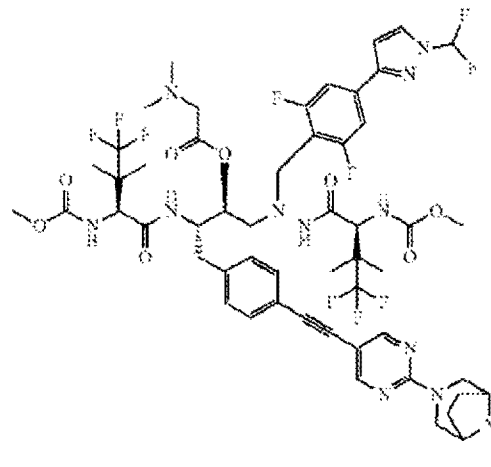 " and insert -- 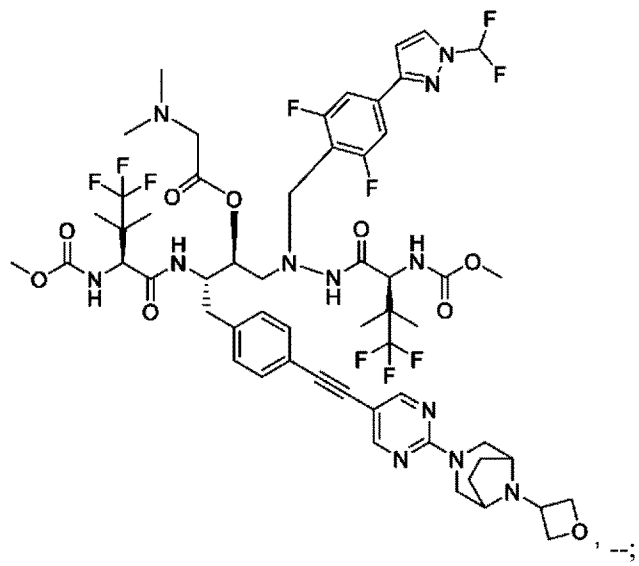 --;
Column 133, Lines 47-66, Claim 42, delete " 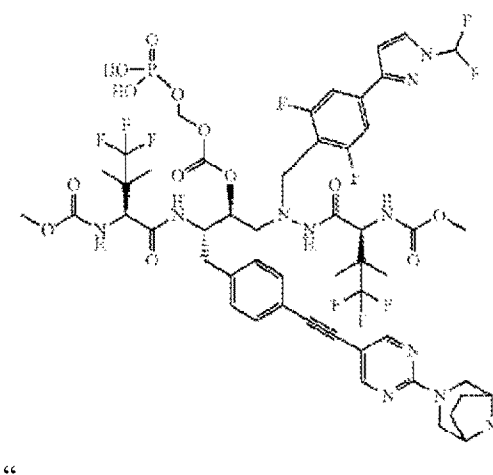 " and
insert -- 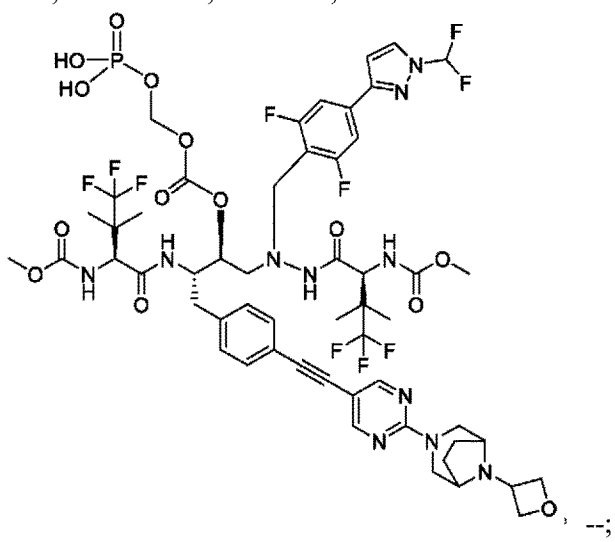 --;

CERTIFICATE OF CORRECTION (continued)
U.S. Pat. No. 11,052,087 B2

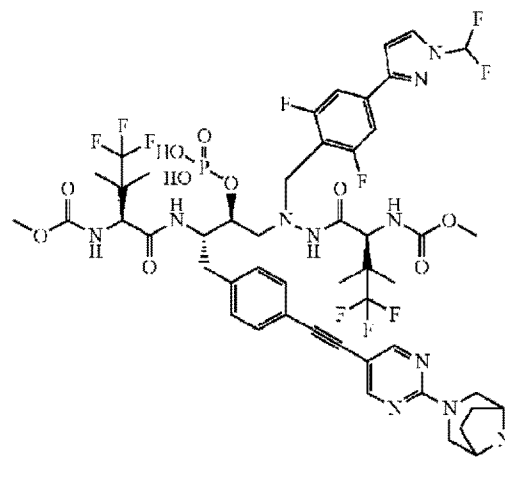

Column 134, Lines 1-18, Claim 42, delete "  " and insert -- 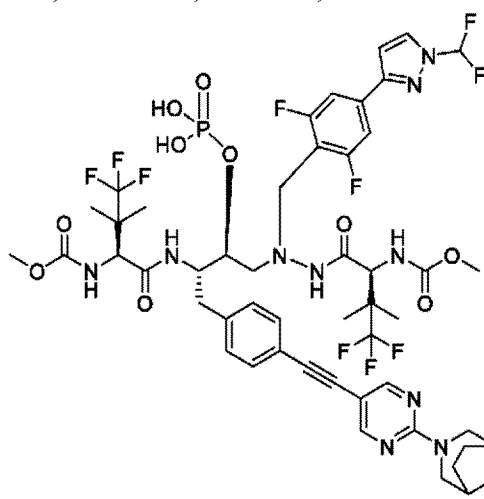 , --;

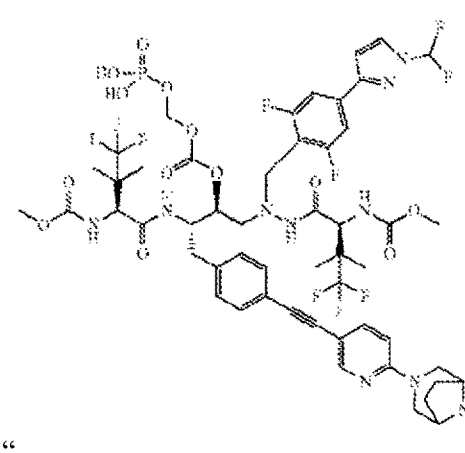

Column 134, Lines 18-37, Claim 42, delete "  " and insert

CERTIFICATE OF CORRECTION (continued)
U.S. Pat. No. 11,052,087 B2

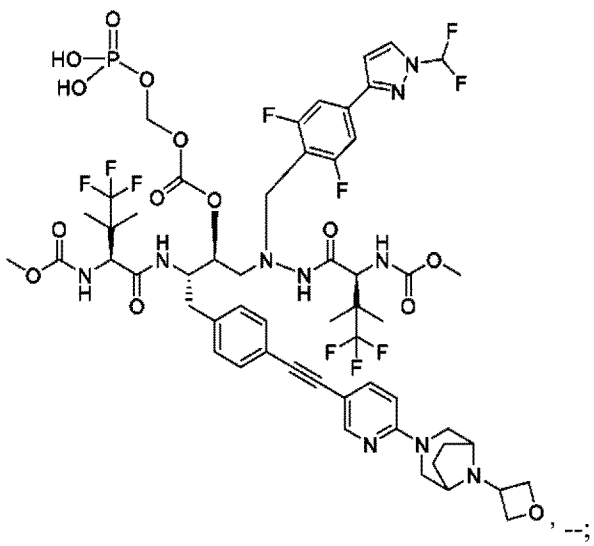

-- --

Column 137, Line 34, Claim 48, delete "Dr" and insert -- or --;

Column 139-140, Claim 52, delete " 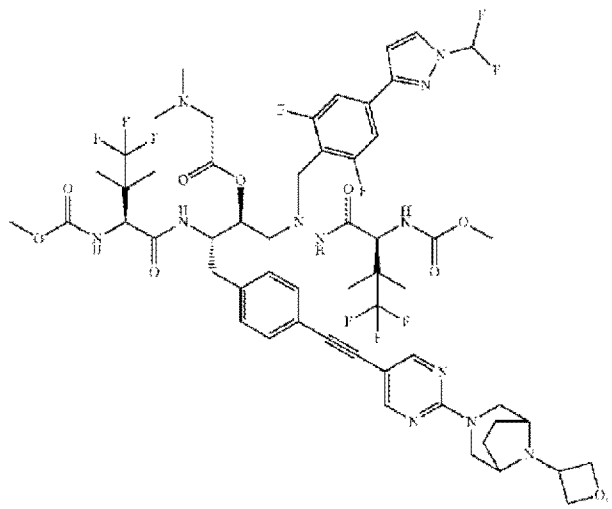 " and insert

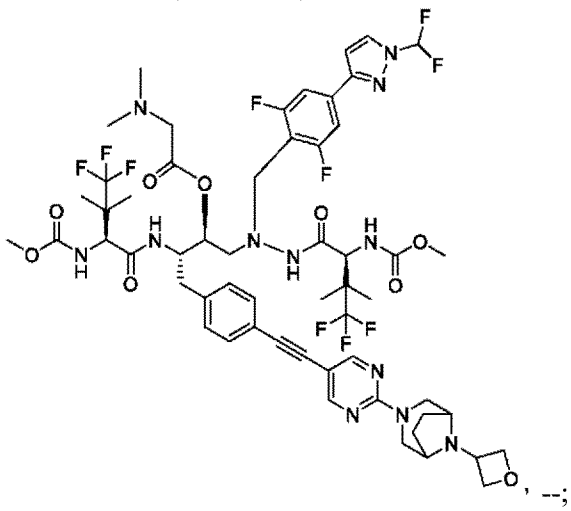

-- --;

CERTIFICATE OF CORRECTION (continued)
U.S. Pat. No. 11,052,087 B2

Column 139-140, Claim 53, delete " 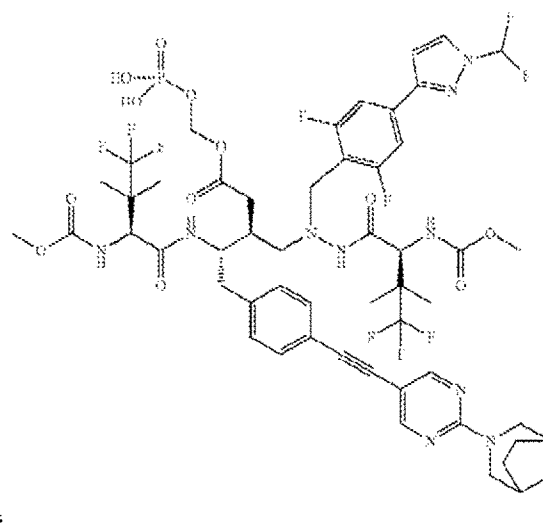 " and insert

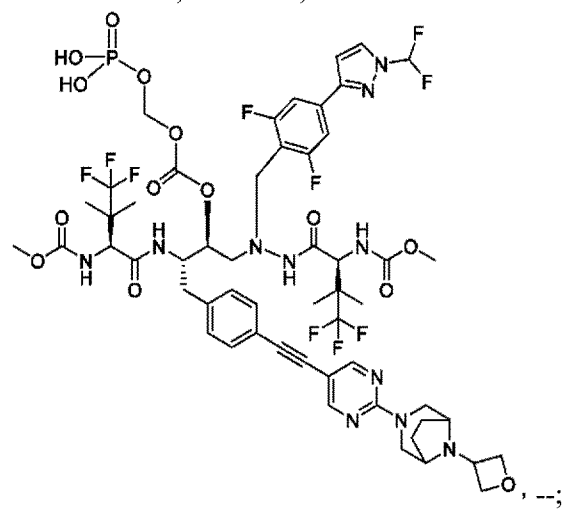

-- , --;

Column 141-142, Claim 54, delete " 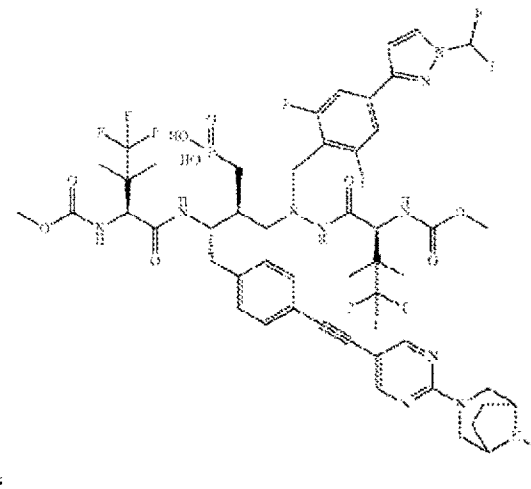 " and insert

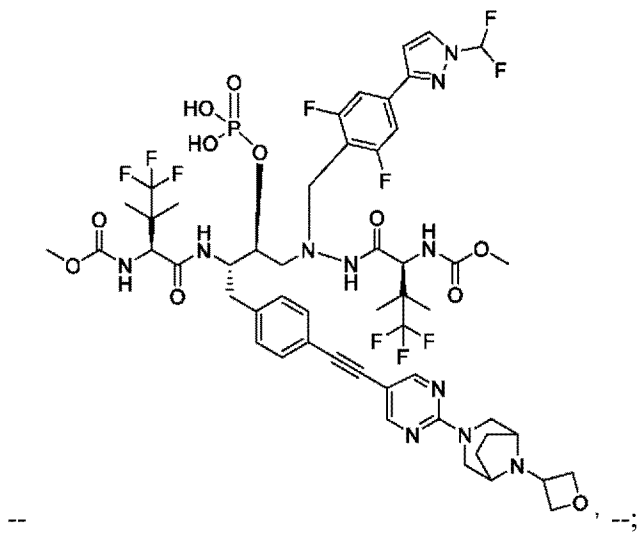
-- --;
Column 141, Claim 55, after "compound" insert -- of --.